United States Patent
Rector et al.

(10) Patent No.: US 11,278,288 B2
(45) Date of Patent: Mar. 22, 2022

(54) METHOD OF USING LOCKOUT FEATURES FOR SURGICAL STAPLER CARTRIDGE

(71) Applicant: Ethicon LLC, Guaynabo, PR (US)

(72) Inventors: Jason M. Rector, Maineville, OH (US); Douglas B. Hoffman, Harrison, OH (US); Robert J. Simms, Liberty Township, OH (US); John C. Schuckmann, Cincinnati, OH (US); Ryan J. Laurent, Loveland, OH (US); Frederick E. Shelton, IV, Hillsboro, OH (US); Jeffrey C. Gagel, Loveland, OH (US); Nicholas Fanelli, Morrow, OH (US)

(73) Assignee: Cilag GmbH International, Zug (CH)

( * ) Notice: Subject to any disclaimer, the term of this patent is extended or adjusted under 35 U.S.C. 154(b) by 330 days.

(21) Appl. No.: 16/401,230

(22) Filed: May 2, 2019

(65) Prior Publication Data
US 2019/0314019 A1   Oct. 17, 2019

Related U.S. Application Data

(63) Continuation of application No. 14/314,108, filed on Jun. 25, 2014, now Pat. No. 10,335,147.

(51) Int. Cl.
*A61B 17/10* (2006.01)
*A61B 17/072* (2006.01)
(Continued)

(52) U.S. Cl.
CPC .......... *A61B 17/105* (2013.01); *A61B 17/068* (2013.01); *A61B 17/0644* (2013.01);
(Continued)

(58) Field of Classification Search
CPC . A61B 17/105; A61B 17/0644; A61B 17/068; A61B 17/07207;
(Continued)

(56) References Cited

U.S. PATENT DOCUMENTS

| 4,805,823 A | 2/1989 | Rothfuss |
| 5,129,570 A | 7/1992 | Schulze et al. |

(Continued)

*Primary Examiner* — Dariush Seif
(74) *Attorney, Agent, or Firm* — Frost Brown Todd LLC

(57) ABSTRACT

A surgical instrument comprises a body, shaft, and end effector. The shaft couples the end effector and body together. The end effector comprises an anvil and lower jaw configured to receive a surgical staple cartridge. The anvil is configured to pivot toward and away from the staple cartridge and lower jaw. The shaft assembly comprises a knife member configured to longitudinally translate to thereby substantially simultaneously cut clamped tissue and staple the severed tissue. The end effector may comprise lockout features configure to prevent longitudinal translation of the knife member. The end effector or staple cartridge may comprise lockout bypass features configured to prevent lockout of the knife member. These lockout bypass features may operate to permit longitudinal translation of the knife member once or multiple times. The end effector may comprise features configured to ensure proper alignment of the anvil relative to the staple cartridge.

20 Claims, 161 Drawing Sheets

(51) Int. Cl.
  *A61B 17/064*   (2006.01)
  *A61B 17/068*   (2006.01)
  *A61B 17/00*    (2006.01)
  *A61B 17/29*    (2006.01)
  *A61B 90/00*    (2016.01)

(52) U.S. Cl.
  CPC .............. *A61B 17/07207* (2013.01); *A61B 2017/00017* (2013.01); *A61B 2017/00398* (2013.01); *A61B 2017/00477* (2013.01); *A61B 2017/07271* (2013.01); *A61B 2017/2927* (2013.01); *A61B 2090/0814* (2016.02)

(58) Field of Classification Search
  CPC ........... A61B 2017/00017; A61B 2017/00398; A61B 2017/00477; A61B 2017/07271; A61B 2017/2927
  USPC ....................................... 227/175.1
  See application file for complete search history.

(56) References Cited

U.S. PATENT DOCUMENTS

| | | | |
|---|---|---|---|
| 5,415,334 A | | 5/1995 | Williamson et al. |
| 5,465,895 A | | 11/1995 | Knodel et al. |
| 5,485,947 A | * | 1/1996 | Olson ............ A61B 17/07207 227/176.1 |
| 5,584,425 A | * | 12/1996 | Savage ........... A61B 17/07207 227/175.2 |
| 5,597,107 A | | 1/1997 | Knodel et al. |
| 5,632,432 A | * | 5/1997 | Schulze ........... A61B 17/07207 227/176.1 |
| 5,669,544 A | * | 9/1997 | Schulze ........... A61B 17/07207 227/176.1 |
| 5,673,840 A | * | 10/1997 | Schulze ........... A61B 17/07207 227/175.1 |
| 5,704,534 A | | 1/1998 | Huitema et al. |
| 5,785,232 A | * | 7/1998 | Vidal ............. A61B 17/07207 227/176.1 |
| 5,792,135 A | | 8/1998 | Madhani et al. |
| 5,814,055 A | | 9/1998 | Knodel et al. |
| 5,817,084 A | | 10/1998 | Jensen |
| 5,878,193 A | | 3/1999 | Wang et al. |
| 5,878,938 A | * | 3/1999 | Bittner .......... A61B 17/07207 227/175.4 |
| 6,231,565 B1 | | 5/2001 | Tovey et al. |
| 6,364,888 B1 | | 4/2002 | Niemeyer et al. |
| 6,783,524 B2 | | 8/2004 | Anderson et al. |
| 6,978,921 B2 | | 12/2005 | Shelton et al. |
| 7,000,818 B2 | | 2/2006 | Shelton et al. |
| 7,143,923 B2 | | 12/2006 | Shelton et al. |
| 7,303,108 B2 | | 12/2007 | Shelton |
| 7,367,485 B2 | | 5/2008 | Shelton et al. |
| 7,380,695 B2 | | 6/2008 | Doll et al. |
| 7,380,696 B2 | | 6/2008 | Shelton et al. |
| 7,404,508 B2 | | 7/2008 | Smith et al. |
| 7,434,715 B2 | | 10/2008 | Shelton et al. |
| 7,524,320 B2 | | 4/2009 | Tierney et al. |
| 7,644,848 B2 | | 1/2010 | Swayze et al. |
| 7,691,098 B2 | | 4/2010 | Wallace et al. |
| 7,721,930 B2 | | 5/2010 | McKenna et al. |
| 7,806,891 B2 | | 10/2010 | Nowlin et al. |
| 7,955,347 B2 | * | 6/2011 | Stout .............. A61B 5/150717 606/181 |
| 8,210,411 B2 | | 7/2012 | Yates et al. |
| 8,408,439 B2 | | 4/2013 | Huang et al. |
| 8,453,914 B2 | | 6/2013 | Laurent et al. |
| 8,479,969 B2 | | 7/2013 | Shelton |
| 8,573,461 B2 | | 11/2013 | Shelton et al. |
| 8,573,465 B2 | | 11/2013 | Shelton |
| 8,602,288 B2 | | 12/2013 | Shelton et al. |
| 8,616,431 B2 | | 12/2013 | Timm et al. |
| 8,783,541 B2 | | 7/2014 | Shelton et al. |
| 8,800,838 B2 | | 8/2014 | Shelton |
| 8,820,605 B2 | | 9/2014 | Shelton |
| 8,844,789 B2 | | 9/2014 | Shelton et al. |
| 10,064,620 B2 | | 9/2018 | Gettinger et al. |
| 10,292,701 B2 | | 5/2019 | Scheib et al. |
| 10,335,147 B2 | | 7/2019 | Rector et al. |
| 10,456,132 B2 | | 10/2019 | Gettinger et al. |
| 2004/0232200 A1 | * | 11/2004 | Shelton, IV ..... A61B 17/07207 227/176.1 |
| 2005/0222616 A1 | | 10/2005 | Rethy et al. |
| 2006/0081678 A1 | * | 4/2006 | Ehrenfels ......... A61B 17/07207 227/175.2 |
| 2007/0039995 A1 | * | 2/2007 | Schwemberger .... A61B 17/072 227/175.2 |
| 2009/0308909 A1 | * | 12/2009 | Nalagatla ......... A61B 17/07207 227/180.1 |
| 2010/0065604 A1 | * | 3/2010 | Weng ............. A61B 17/07207 227/175.2 |
| 2011/0290853 A1 | * | 12/2011 | Shelton, IV ........ A61B 17/072 227/177.1 |
| 2012/0199632 A1 | | 8/2012 | Spivey et al. |
| 2013/0274722 A1 | * | 10/2013 | Kostrzewski .......... A61B 17/29 606/1 |
| 2013/0277410 A1 | * | 10/2013 | Fernandez ........... A61B 17/068 227/175.2 |
| 2014/0239036 A1 | | 8/2014 | Zerkle et al. |
| 2014/0239037 A1 | | 8/2014 | Boudreaux et al. |
| 2014/0239038 A1 | | 8/2014 | Leimbach et al. |
| 2014/0239040 A1 | | 8/2014 | Fanelli et al. |
| 2014/0239041 A1 | | 8/2014 | Zerkle et al. |
| 2014/0239042 A1 | | 8/2014 | Simms et al. |
| 2014/0239043 A1 | | 8/2014 | Simms et al. |
| 2014/0239044 A1 | | 8/2014 | Hoffman |
| 2014/0243801 A1 | | 8/2014 | Fanelli et al. |
| 2015/0374373 A1 | * | 12/2015 | Rector ............. A61B 17/0644 606/219 |

\* cited by examiner

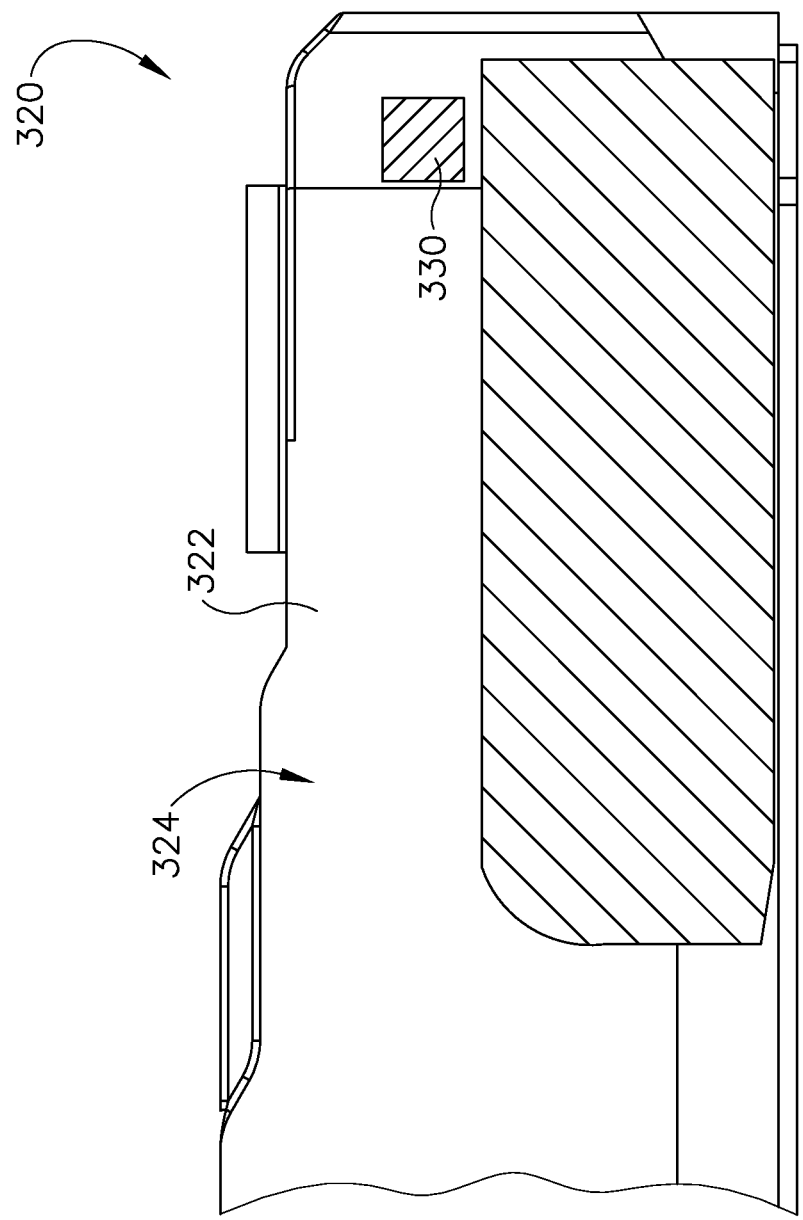

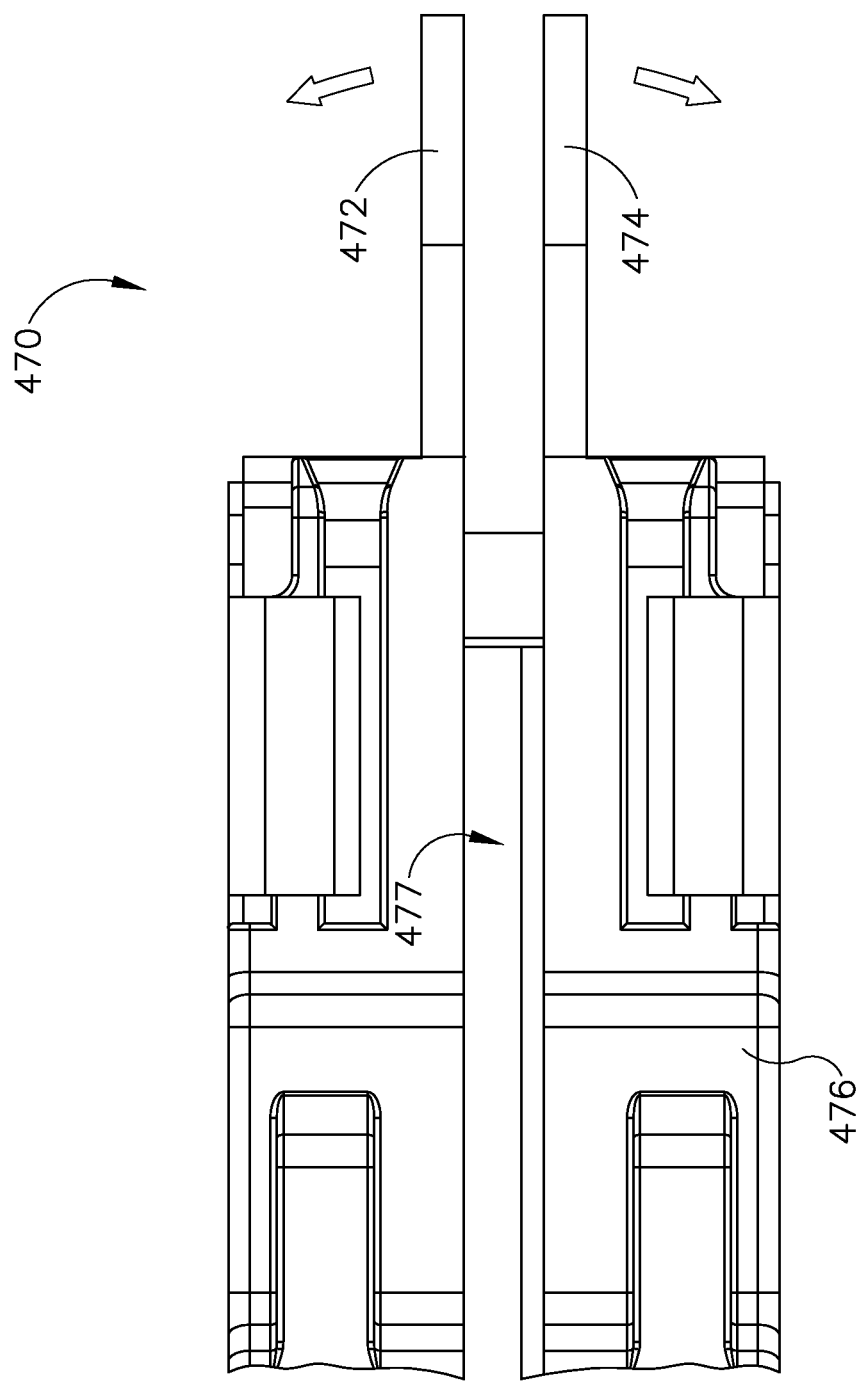

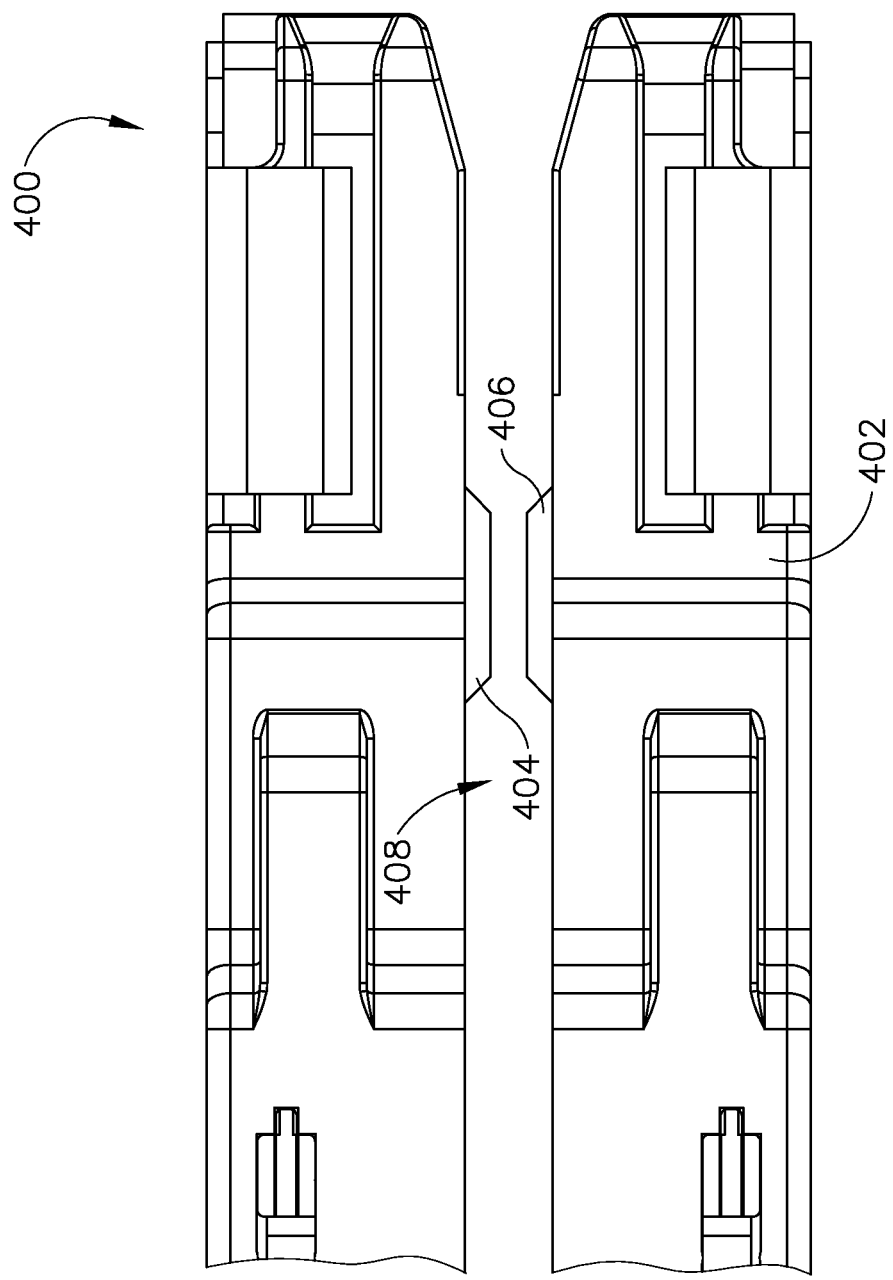

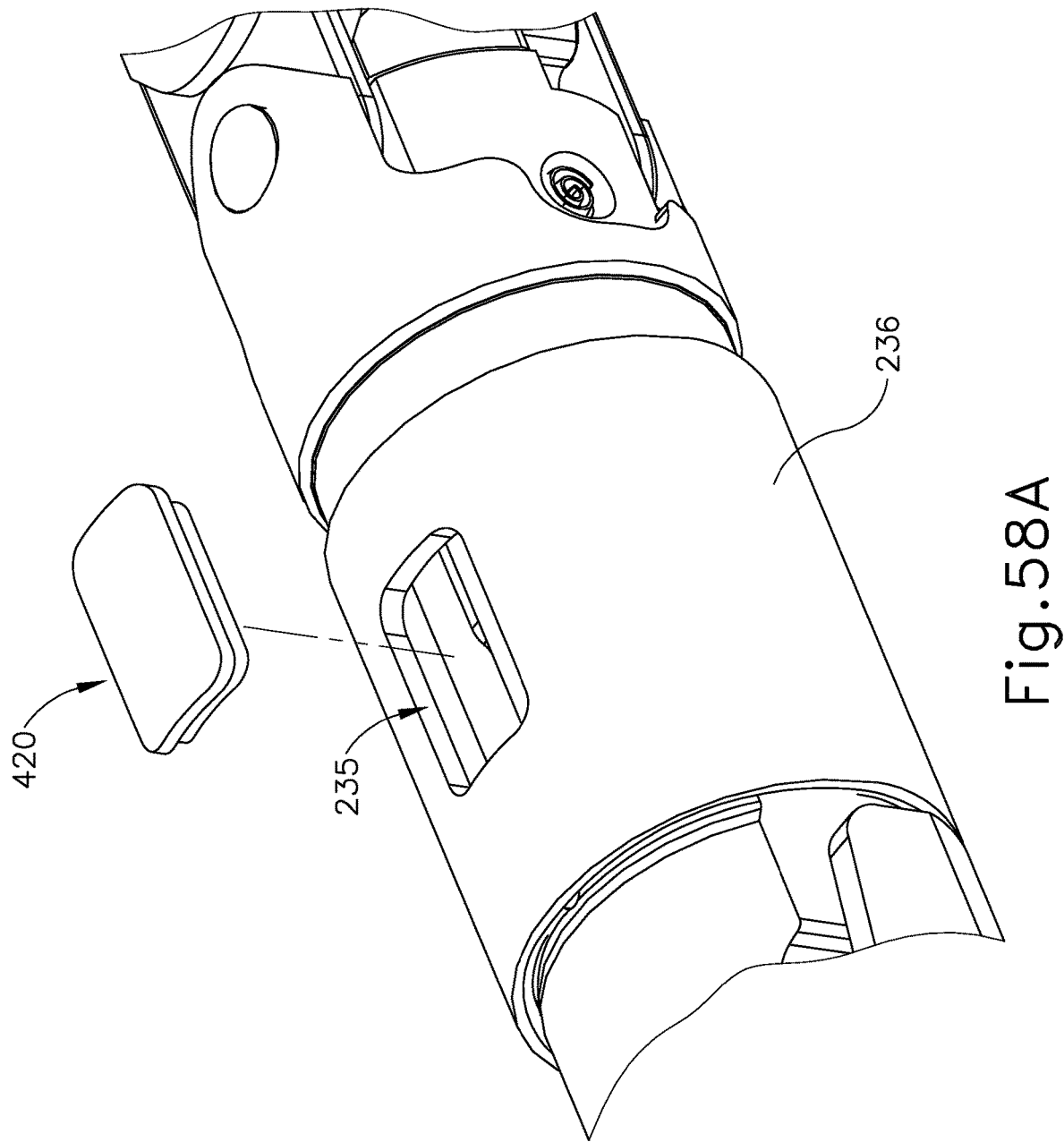

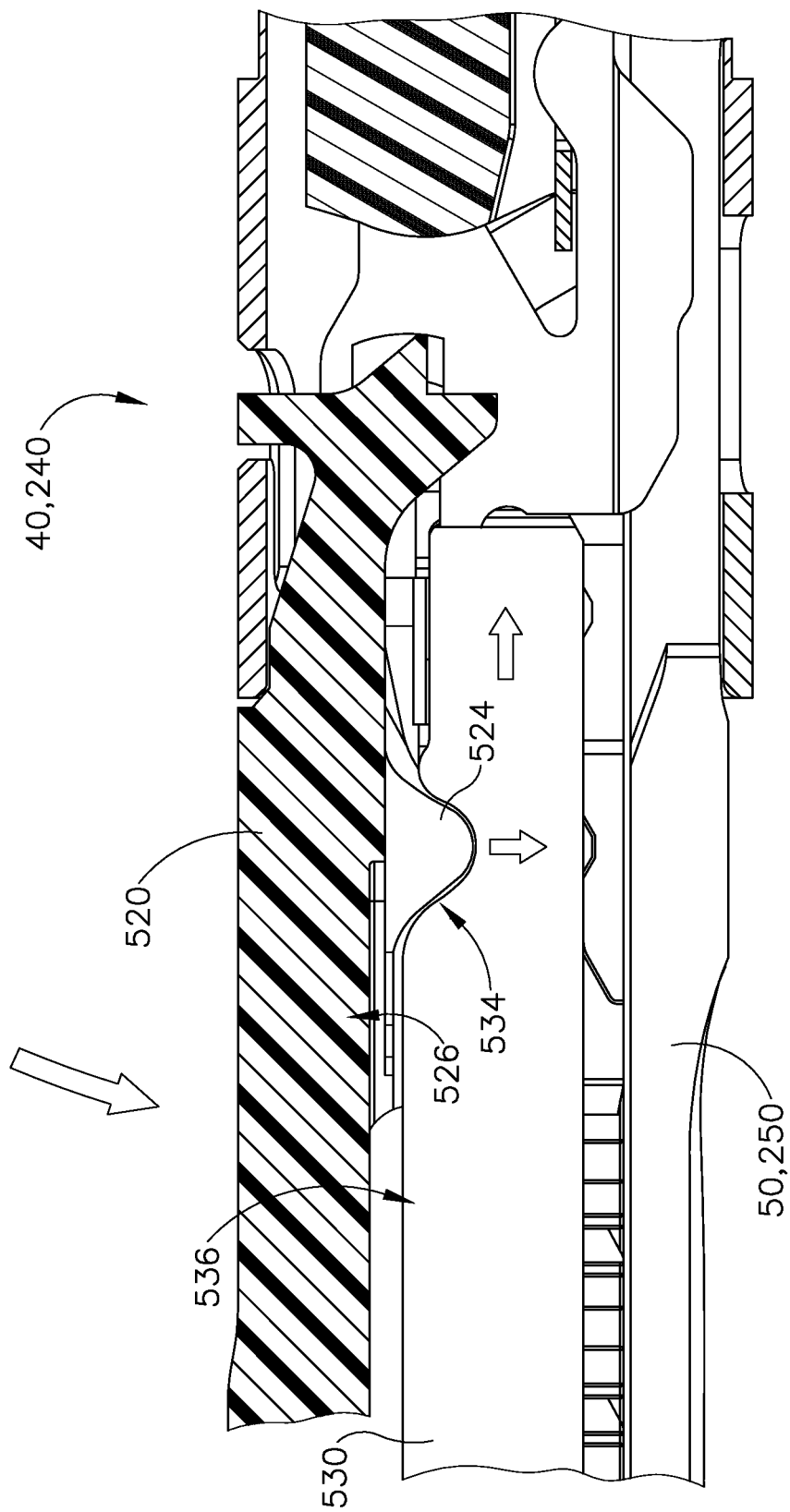

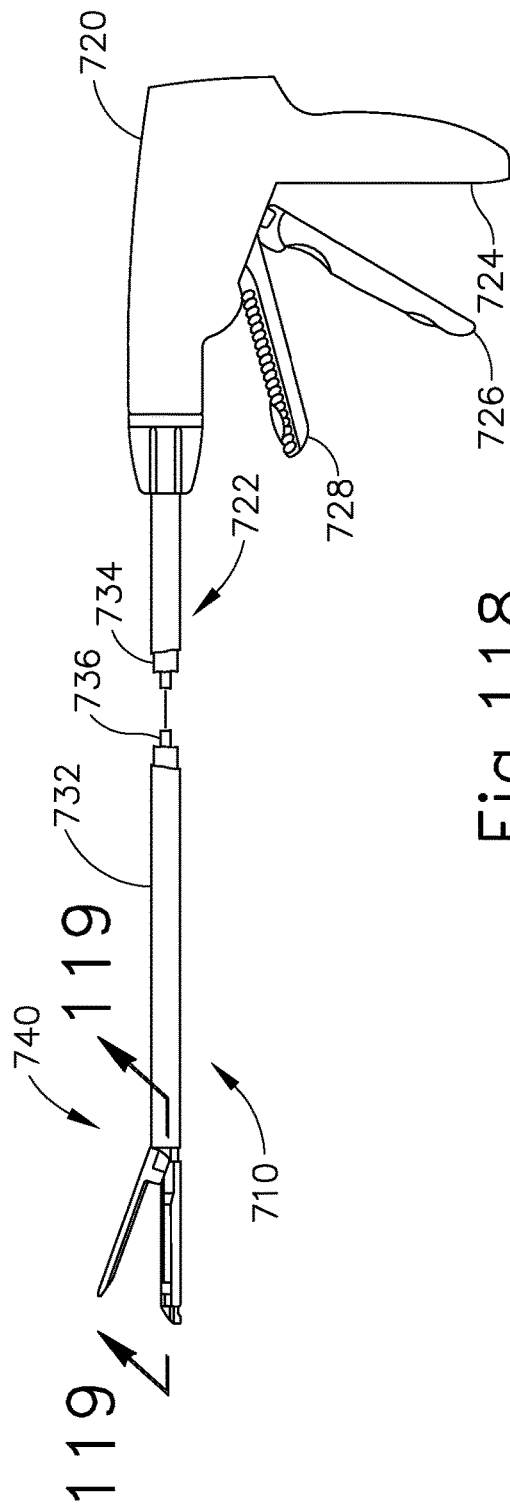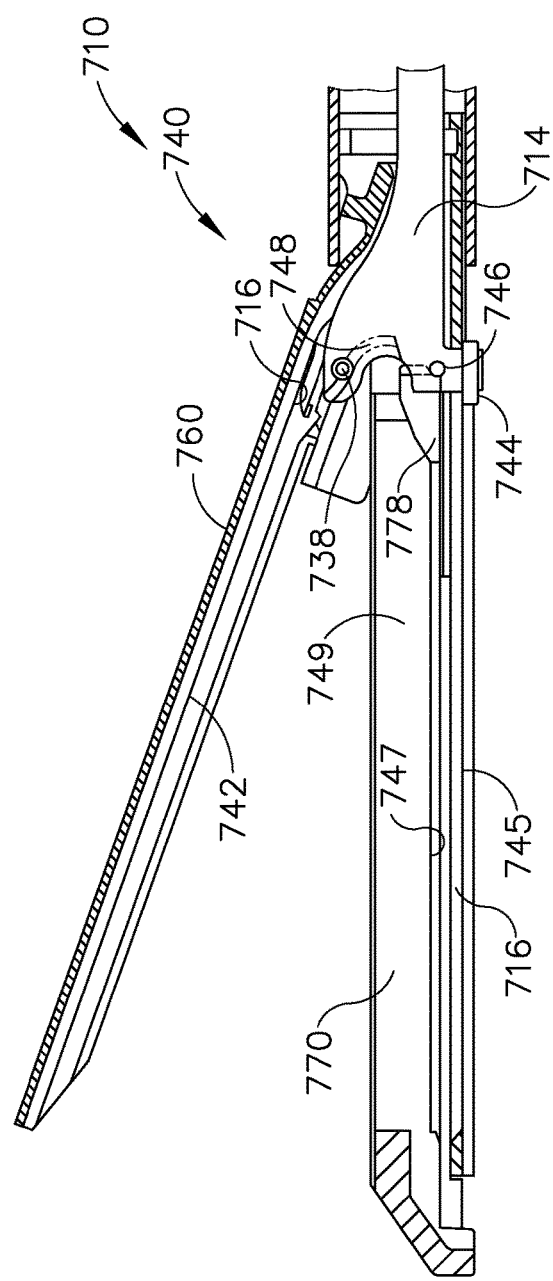
Fig.118
Fig.119

METHOD OF USING LOCKOUT FEATURES FOR SURGICAL STAPLER CARTRIDGE

This application is a continuation of U.S. patent application Ser. No. 14/314,108, filed Jun. 25, 2014 and issued as U.S. Pat. No. 10,335,147 on Jul. 2, 2019.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to cut and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015; U.S. patent application Ser. No. 13/780,082, entitled "Lockout Feature for Movable Cutting Member of Surgical Instrument," filed Feb. 28, 2013, issued as U.S. Pat. No. 9,717,497 Aug. 1, 2017; U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016; U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2107; U.S. patent application Ser. No. 13/780,162, entitled "Surgical Instrument with Articulation Lock having a Detenting Binary Spring," filed Feb. 28, 2013, issued as U.S. Pat. No. 9,867,615 on Jan. 16, 2018; U.S. patent application Ser. No. 13/780,171, entitled "Distal Tip Features for End Effector of Surgical Instrument," filed Feb. 28, 2013, issued as U.S. Pat. No. 9,622,746 on Apr. 18, 2017; U.S. patent application Ser. No. 13/780,379, entitled "Staple Forming Features for Surgical Stapling Instrument," filed Feb. 28, 2013, issued as U.S. Pat. No. 10,092,292 on Oct. 9, 2018; U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017; and U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 31 depicts a cross-sectional side view of the proximal end of the cartridge of FIG. 30;

FIG. 45B depicts a top view of the proximal end of the cartridge of FIG. 44A with the guide fins moved into the open position;

FIG. 51 depicts a top view of the proximal end of the cartridge of FIG. 50;

FIG. 58A depicts a perspective view of the end effector of FIG. 13, with the tab insert of FIG. 57 positioned to couple with the end effector;

FIG. 70B depicts a cross-sectional side view of the end effector of FIG. 3 with the cartridge of FIG. 69 moved into a second longitudinal position by movement of the anvil of FIG. 68 into a second rotational position;

FIG. 87 depicts a perspective view of an exemplary sled;

FIG. 88 depicts a side view of the sled of FIG. 87;

FIG. 89 depicts a top view of the self of FIG. 87;

FIG. 90 depicts a perspective view of the sled of FIG. 87 positioned within yet another exemplary alternative cartridge that may be incorporated into the end effector of FIG. 13;

FIG. 91 depicts a side view of the sled of FIG. 87 positioned within the proximal end of the cartridge of FIG. 90;

FIG. 92 depicts a top view of the sled of FIG. 87 positioned within the proximal end of the cartridge of FIG. 90;

FIG. 93 depicts a perspective view of the sled of FIG. 87 and the cartridge of FIG. 90 engaged with the lower jaw of FIG. 81;

FIG. 94 depicts a top view of the sled of FIG. 87 extending from the proximal end of the cartridge of FIG. 78 and engaged with the proximal end of the lower jaw of FIG. 81;

FIG. 95 depicts a cross-sectional perspective view of the sled of FIG. 87 extending from the proximal end of cartridge of FIG. 78 and engaged with the proximal end of the lower jaw of FIG. 81;

FIG. 96 depicts a perspective view of the proximal end of yet another exemplary alternative cartridge that may be incorporated into the end effector of FIG. 13;

FIG. 97 depicts a perspective view of the proximal end of the cartridge of FIG. 96 engaged with the proximal end of a lower jaw of the end effector of FIG. 3;

FIG. 98 depicts a rear view of the cartridge of FIG. 96 engaged with the lower jaw of FIG. 97;

Figure 1:
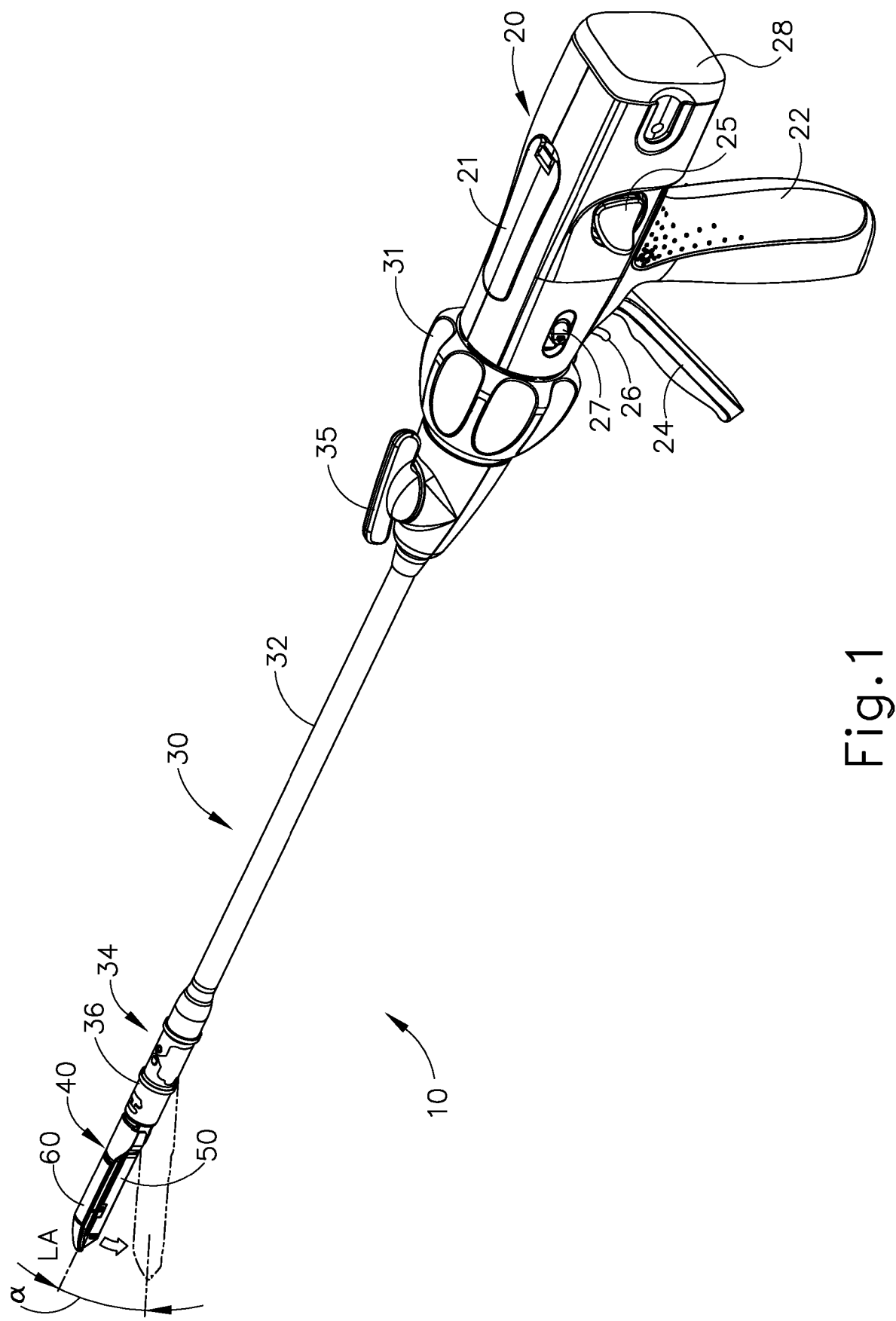
FIG. 1 depicts a perspective view of an exemplary articulating surgical stapling instrument.
Figure 3:
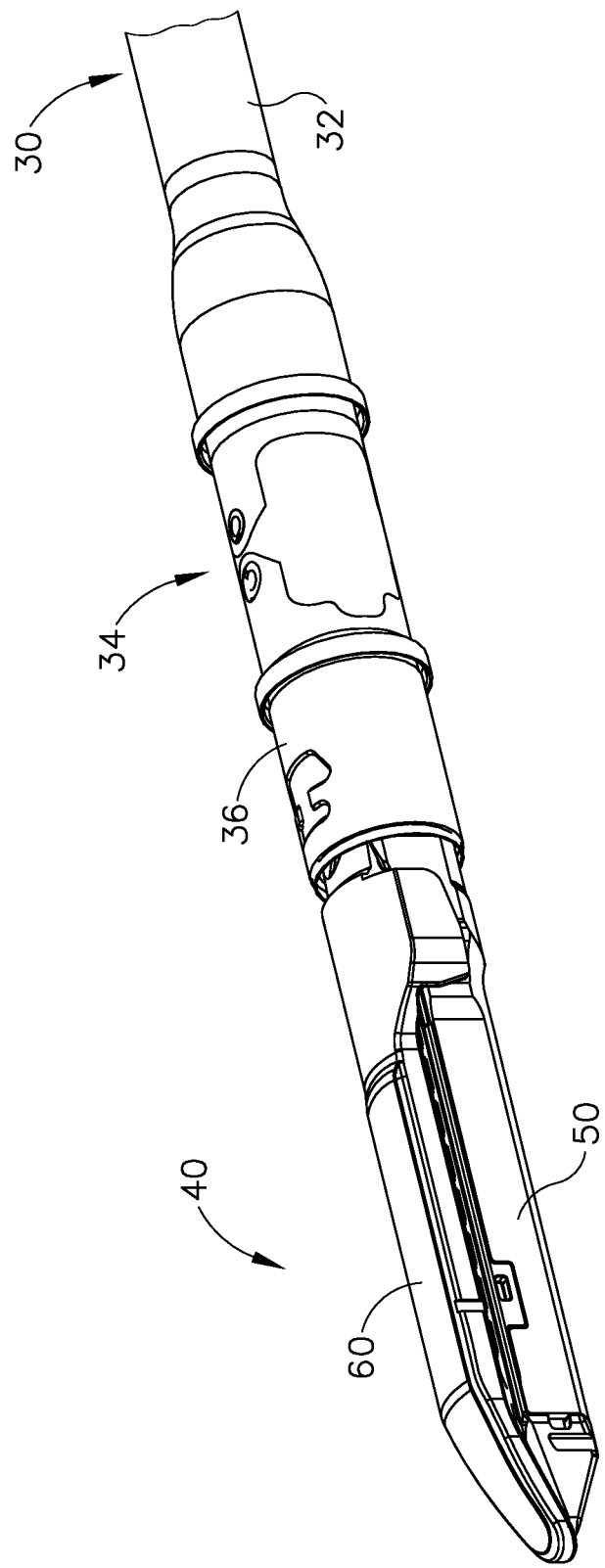
FIG. 3 depicts a perspective view of an end effector of the instrument of FIG. 1, with the end effector in a closed configuration.
Figure 13:
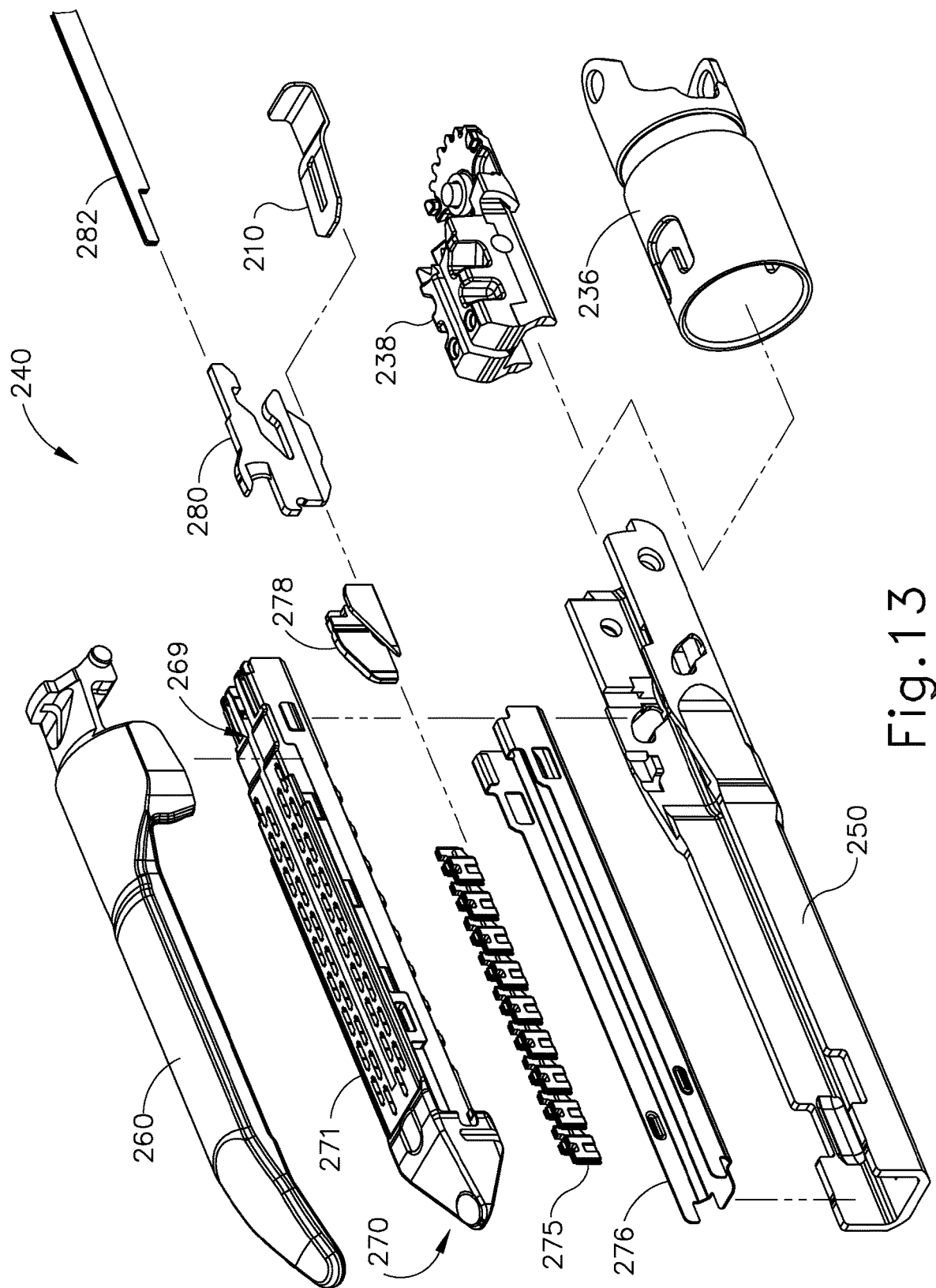
FIG. 13 depicts an exploded view of an exemplary alternative end effector that may be incorporated into the instrument of FIG. 1.
Figure 99:
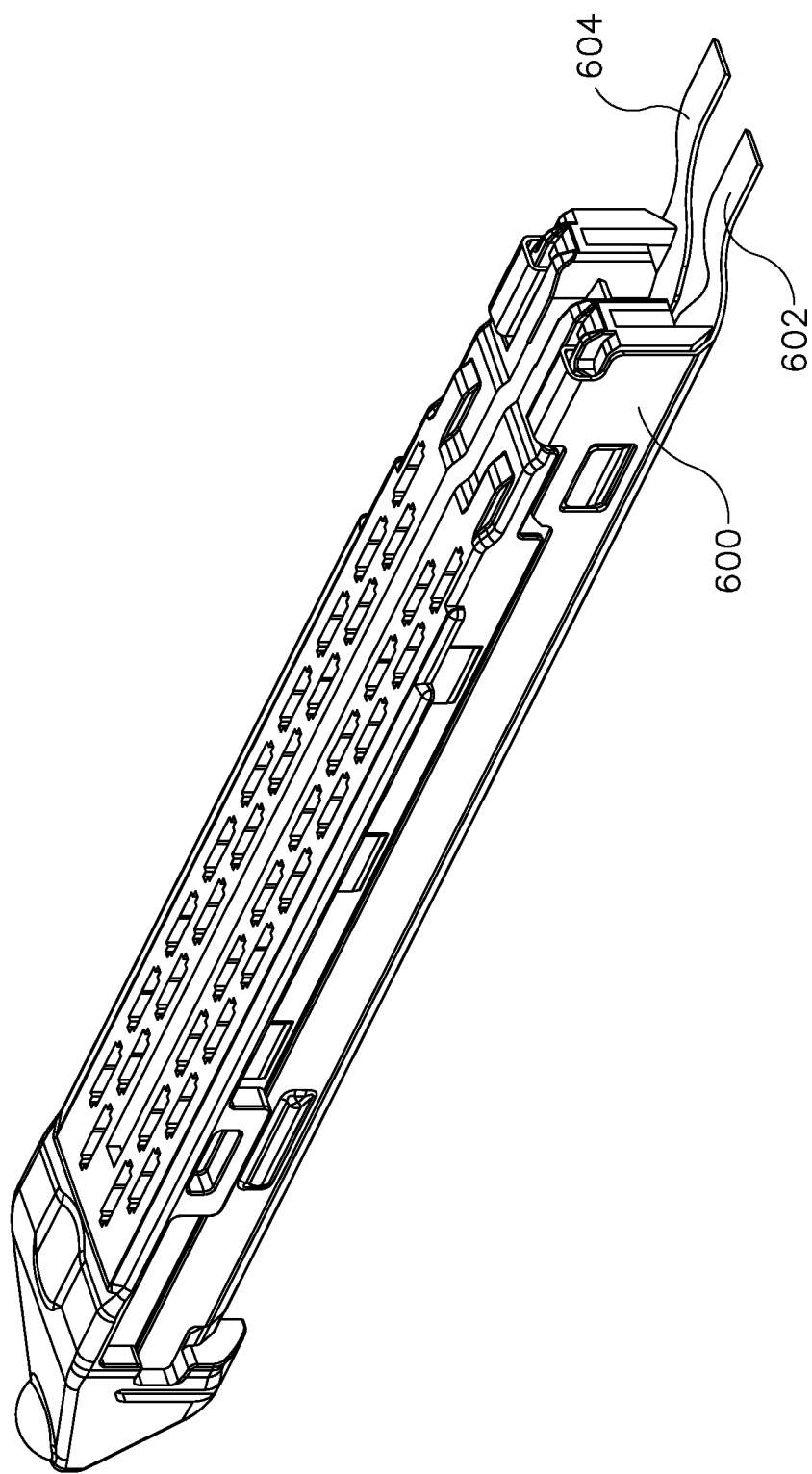
Figure 100:
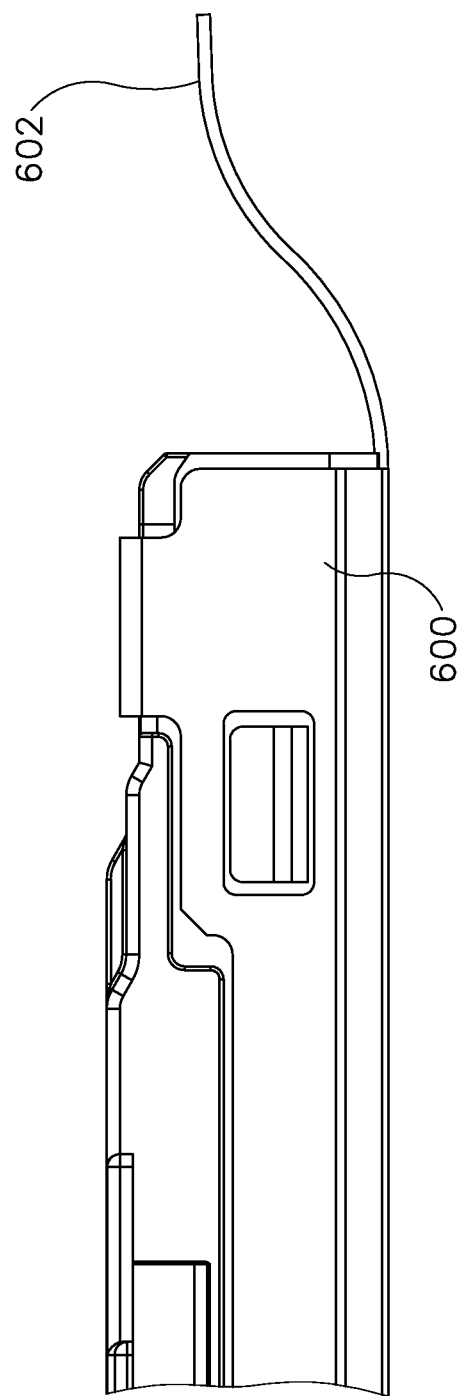
Figure 101:
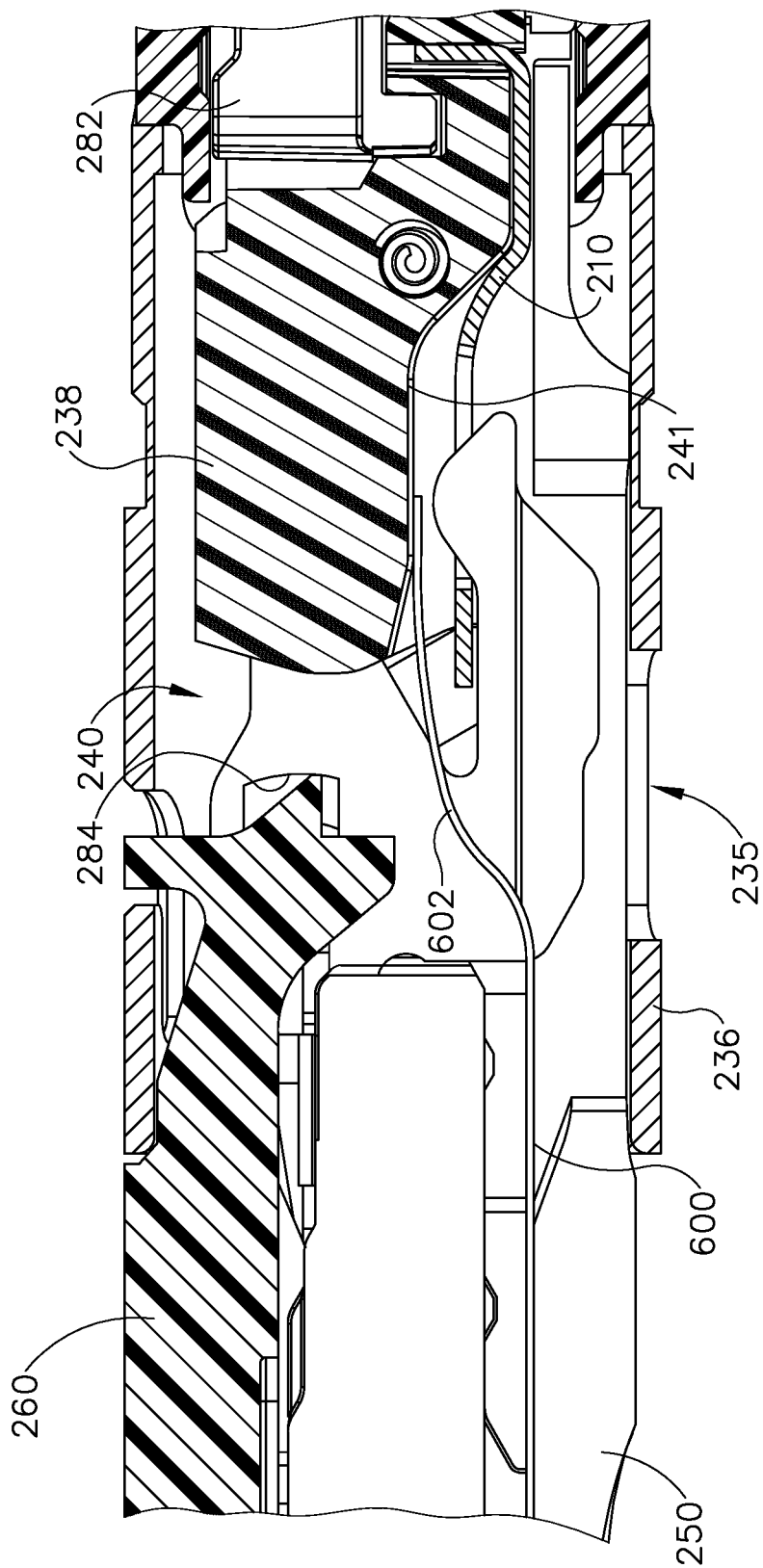
Figure 102:
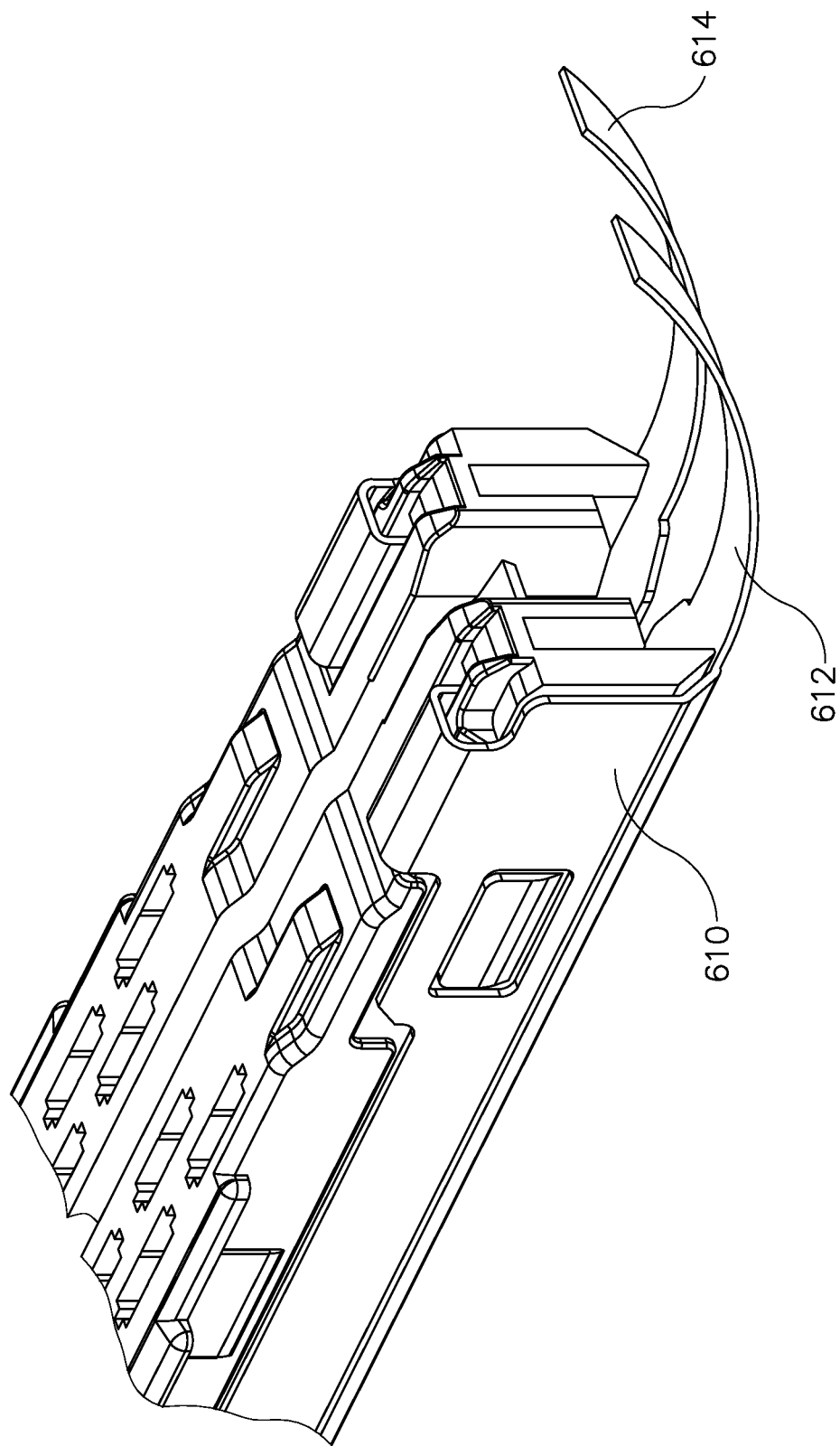
Figure 103:
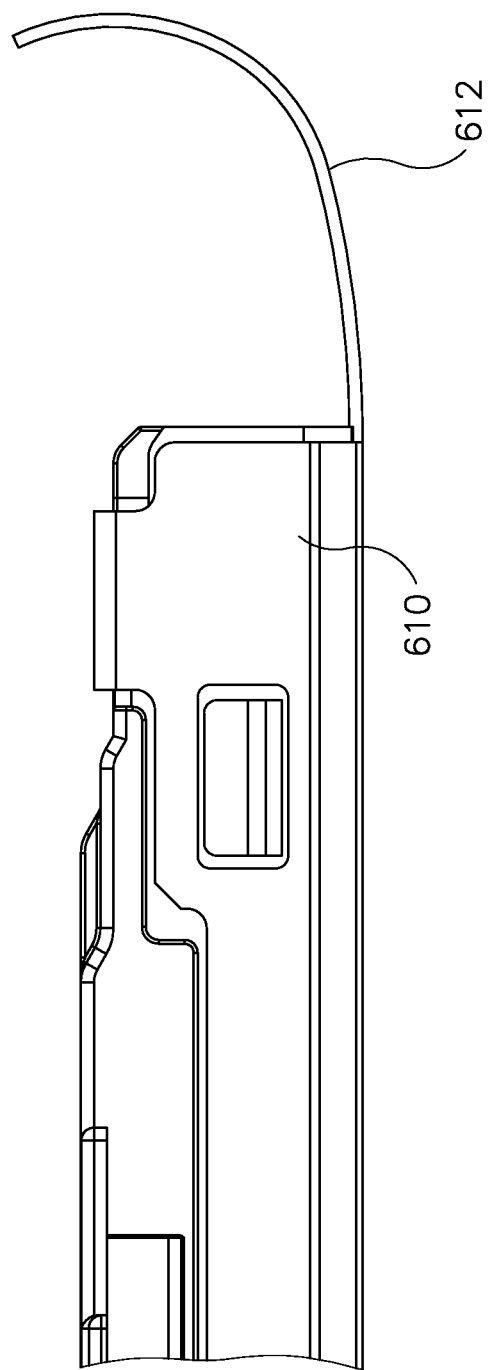
Figure 104:
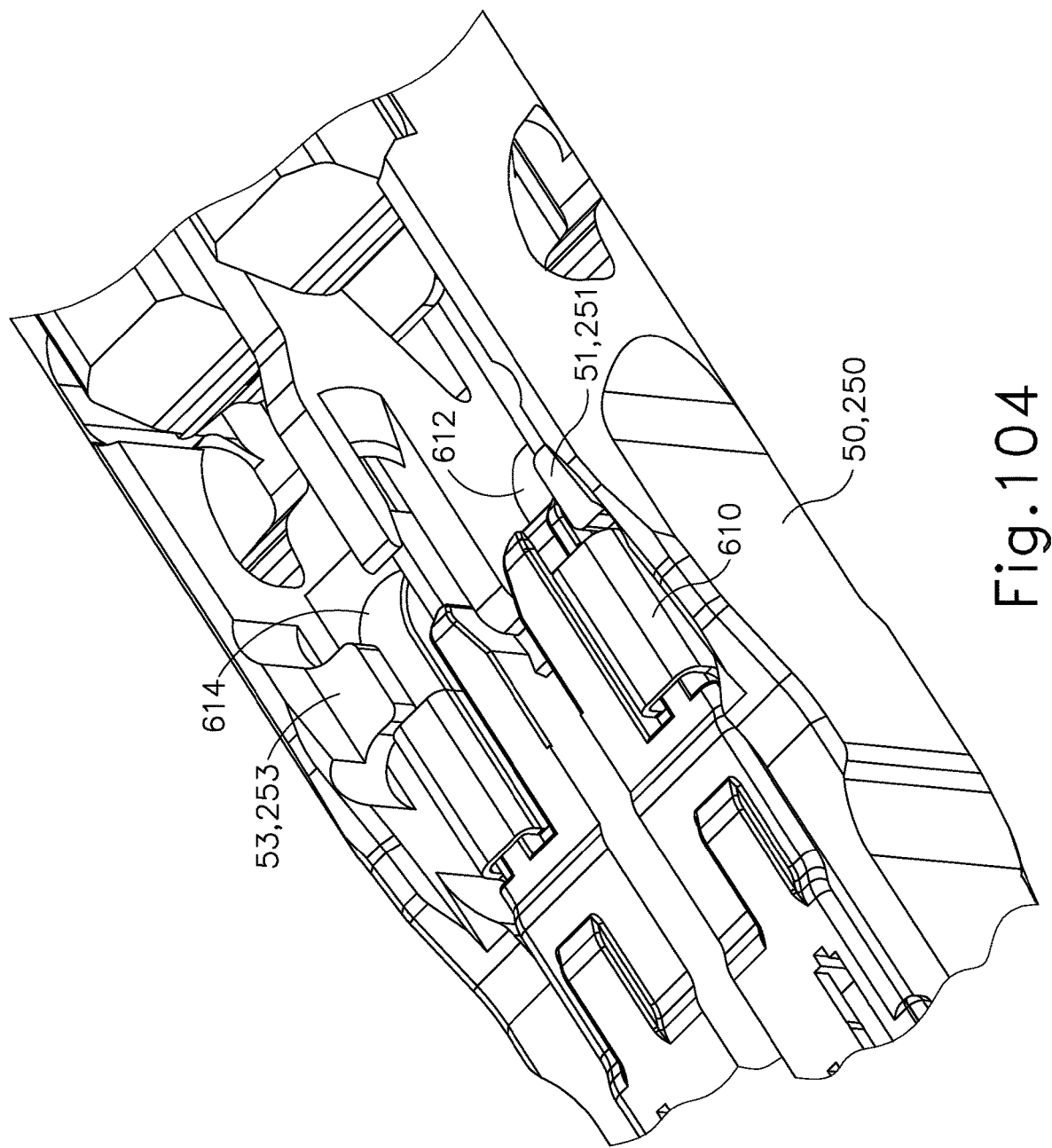
Figure 105:
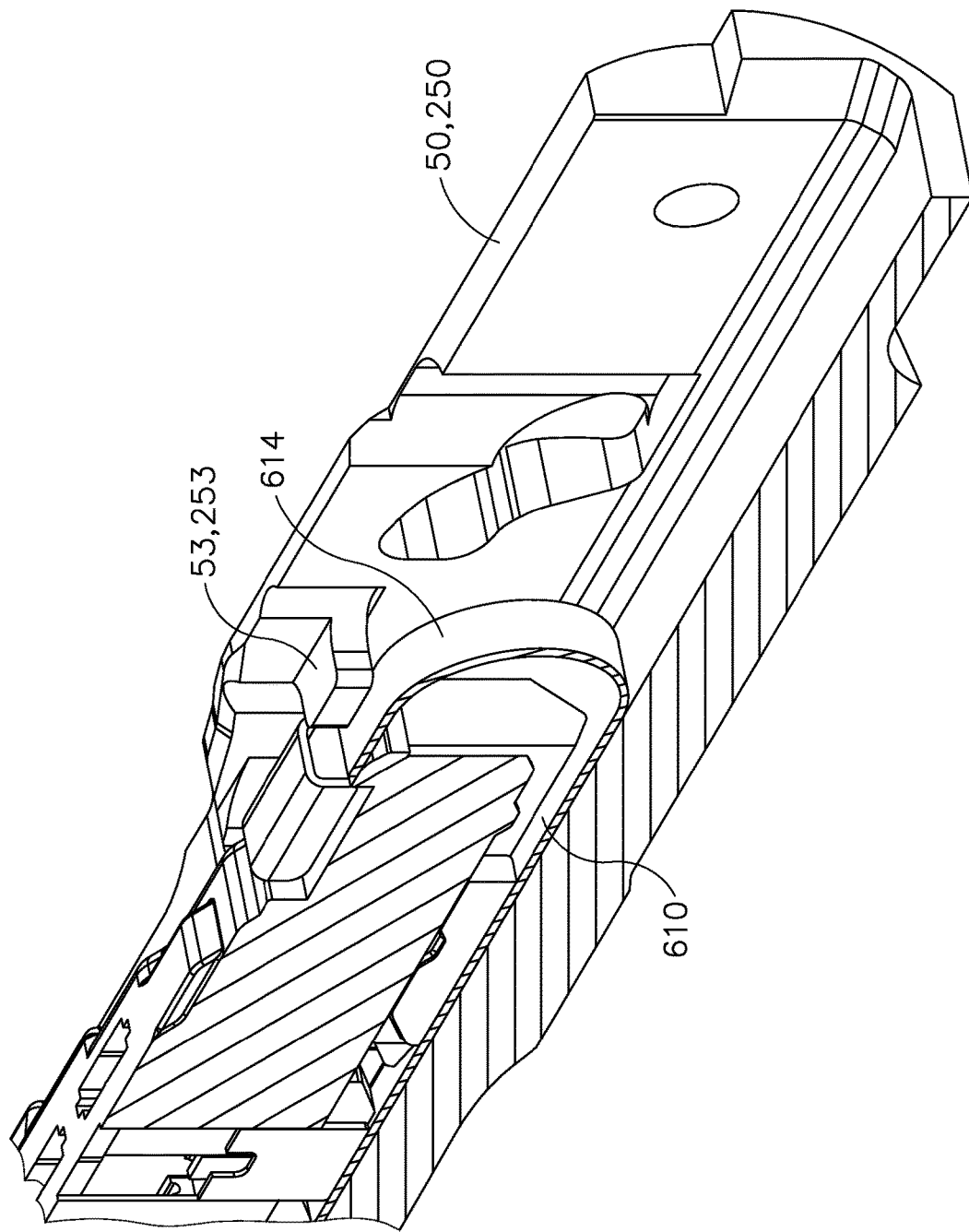
Figure 106:
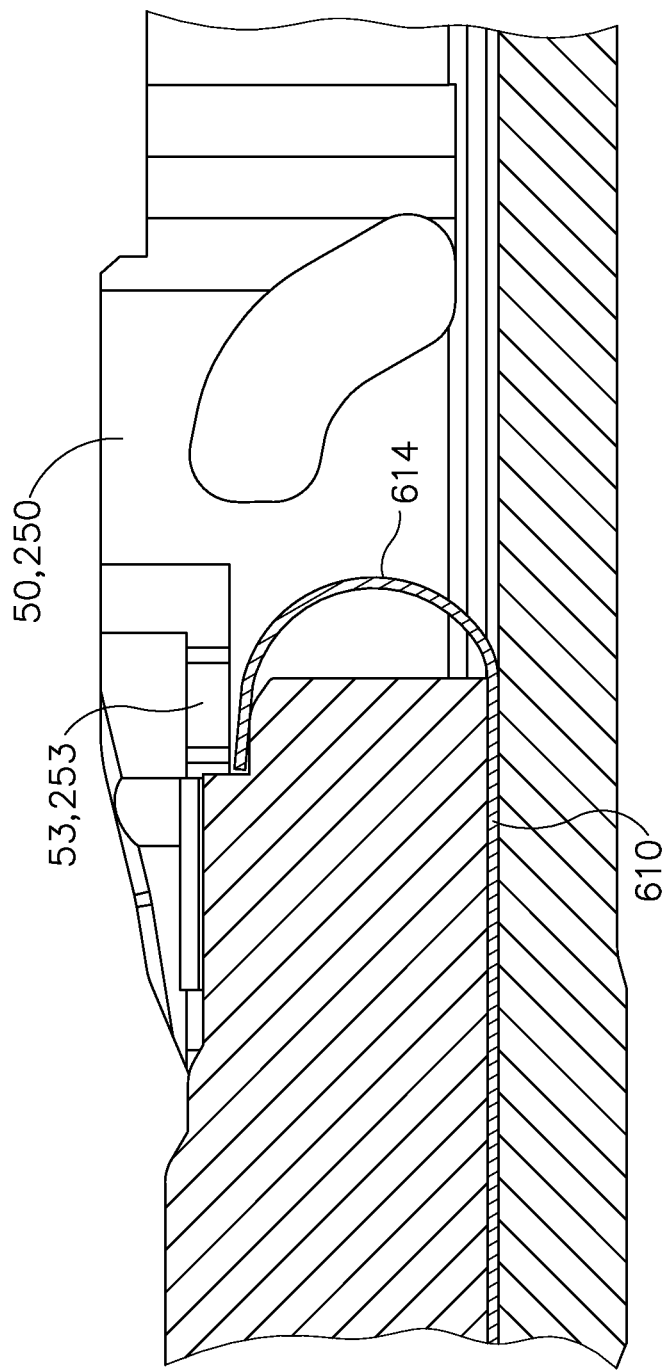
Figure 107:
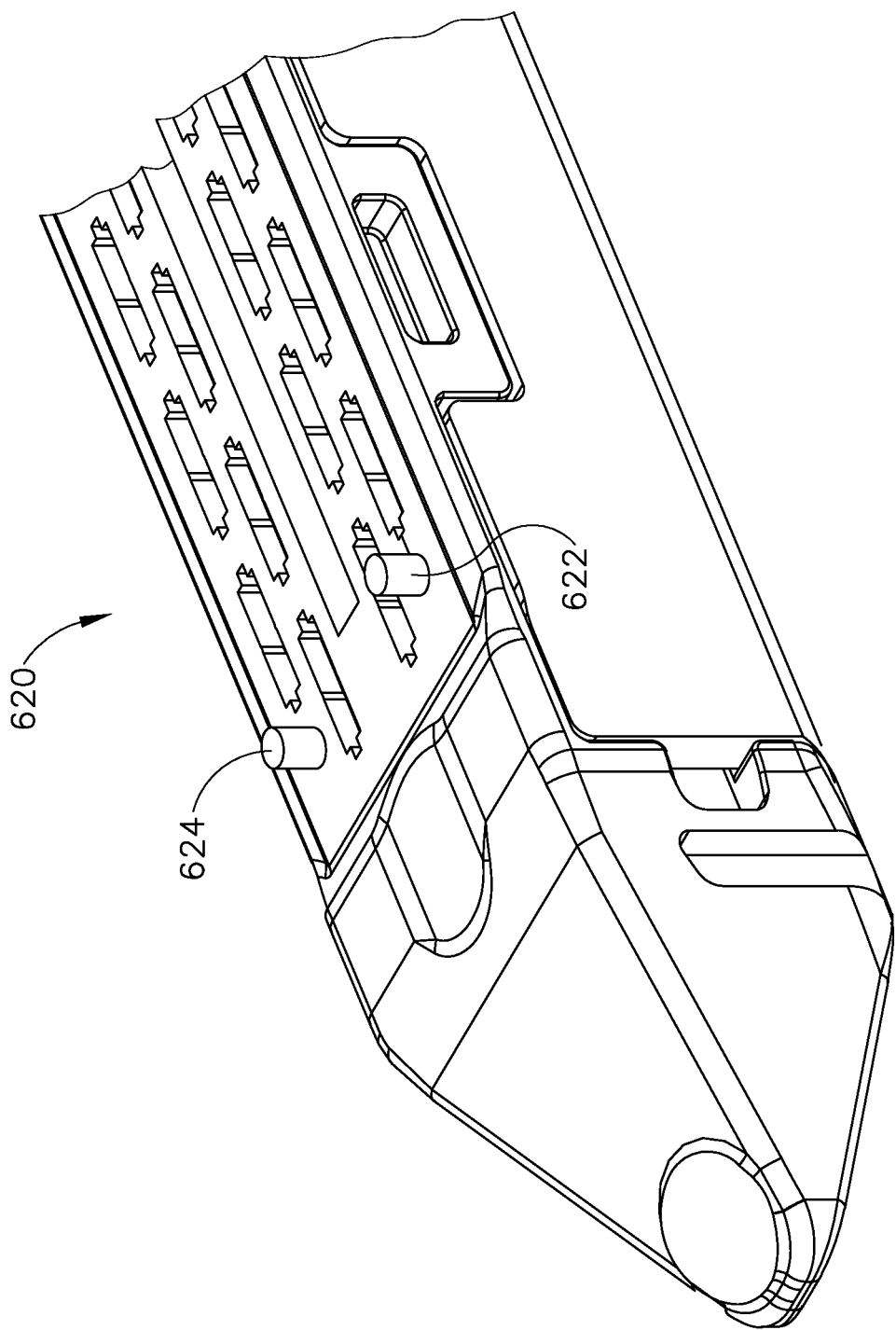
Figure 108:
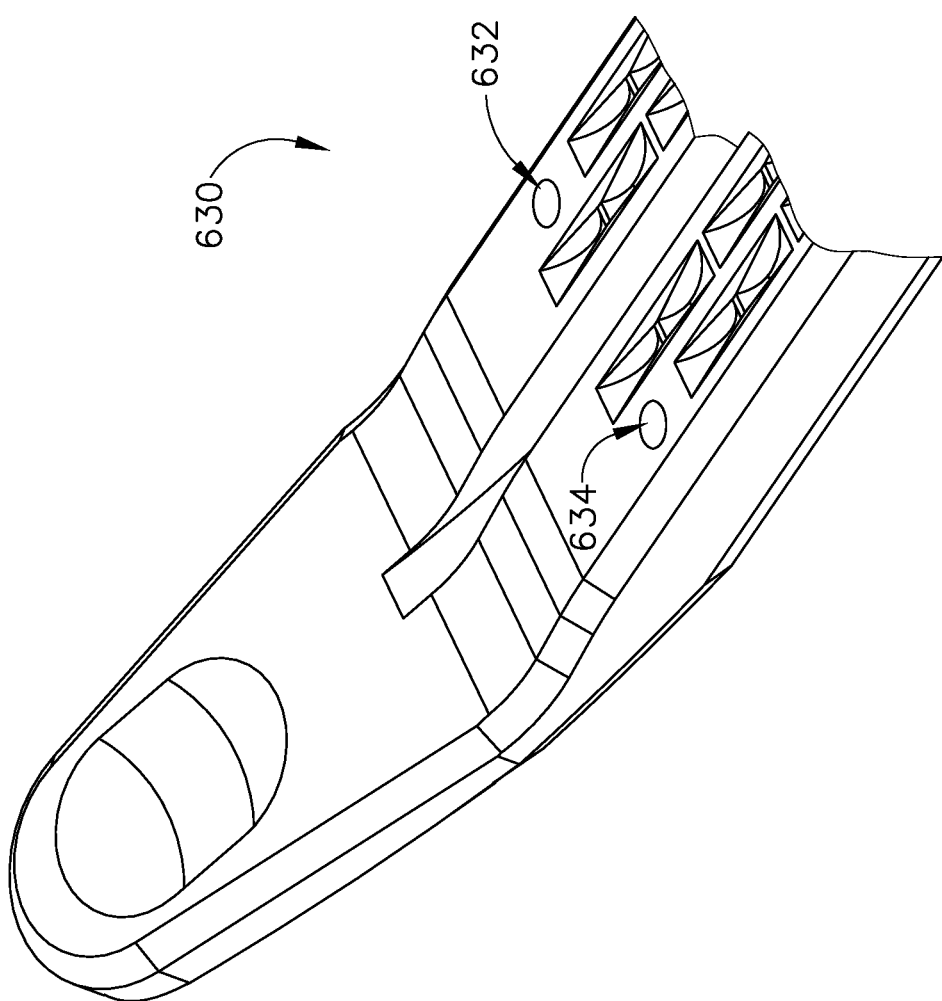
Figure 109:
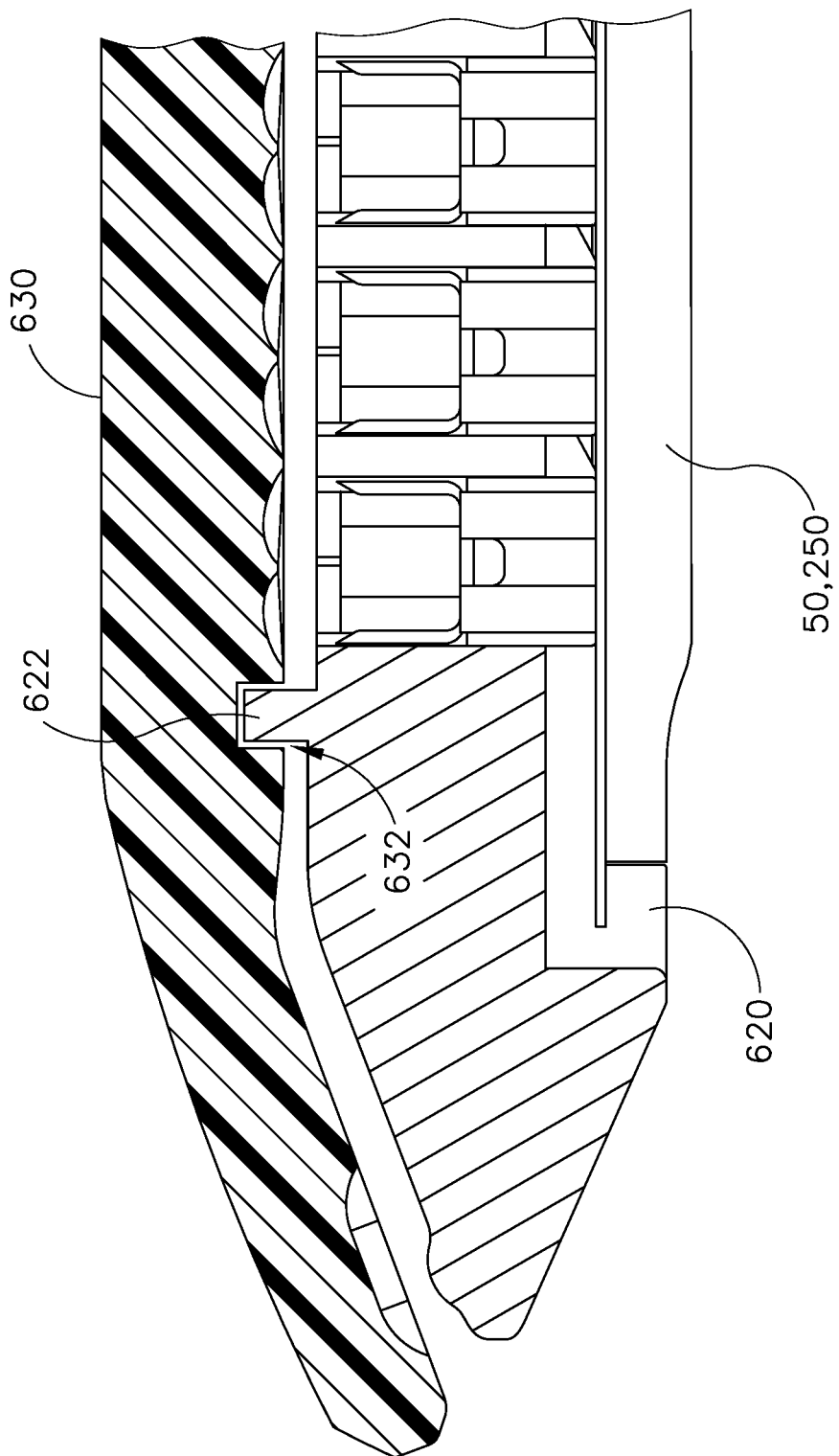
Figure 110:
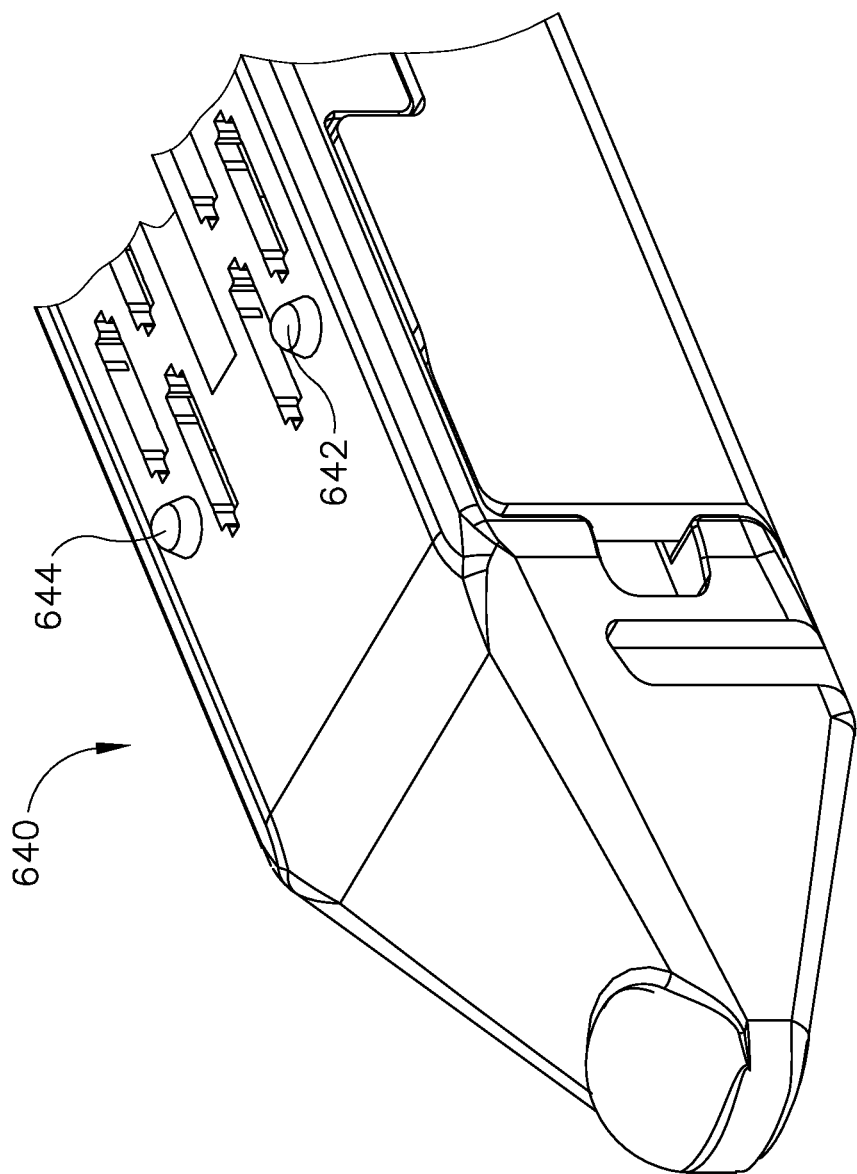
Figure 111:
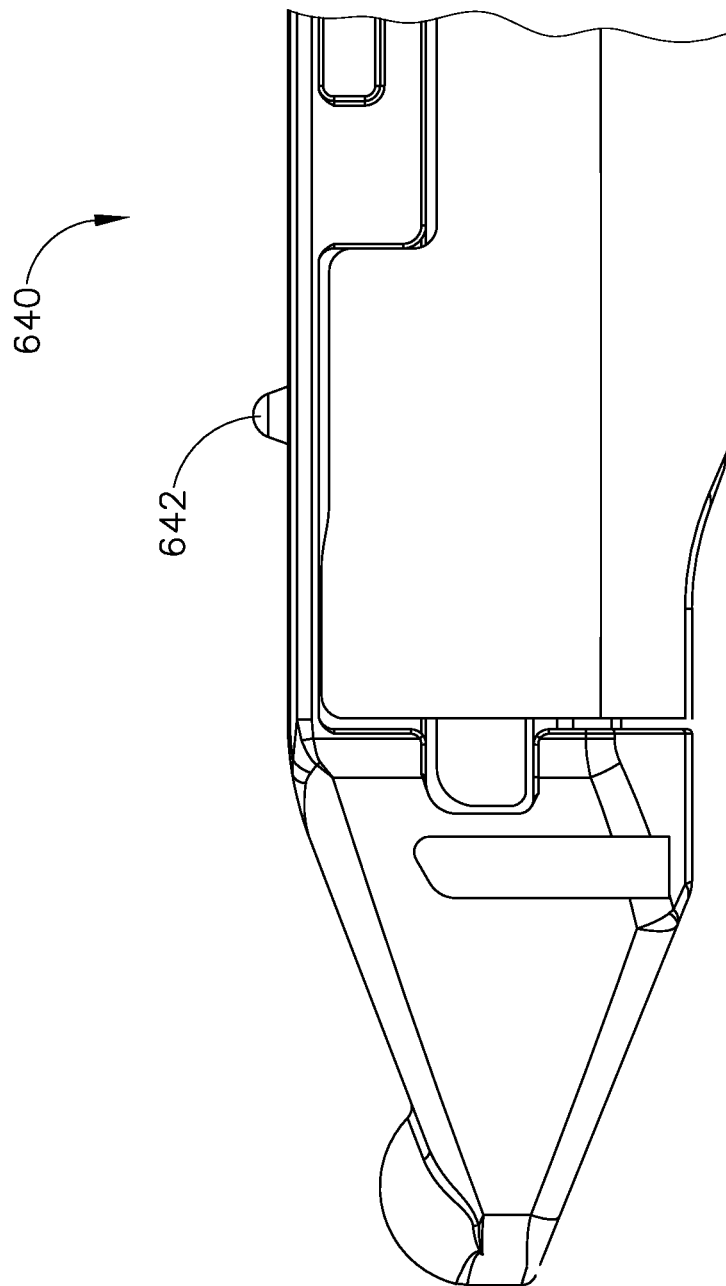
Figure 112:
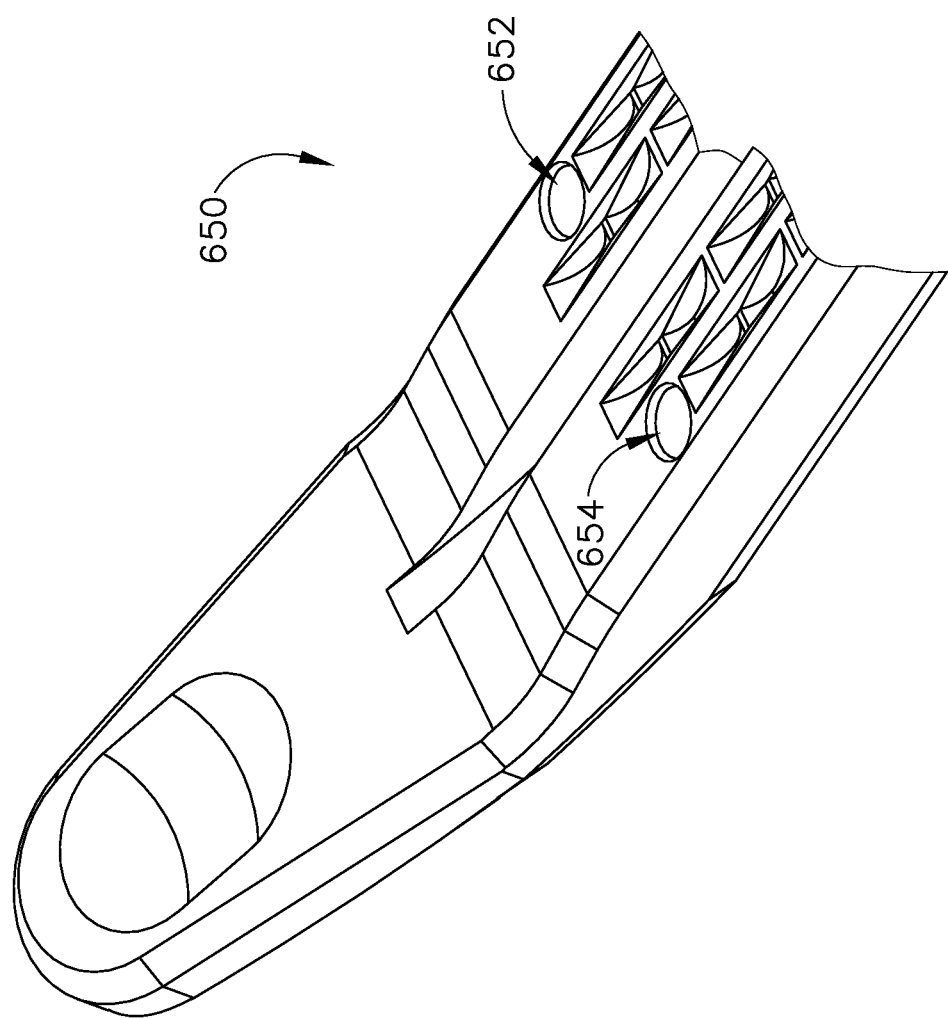
Figure 113:
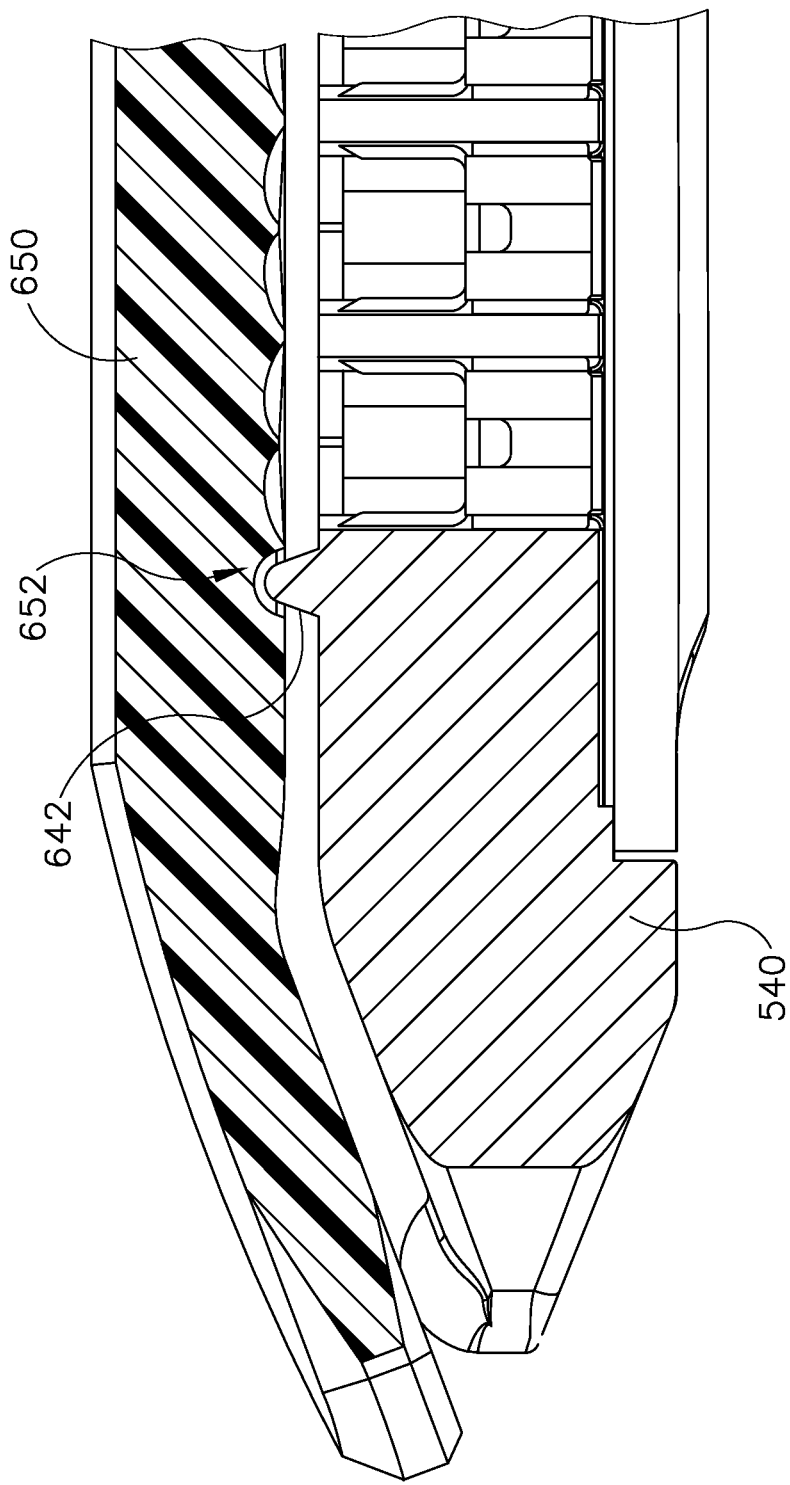
Figure 114:
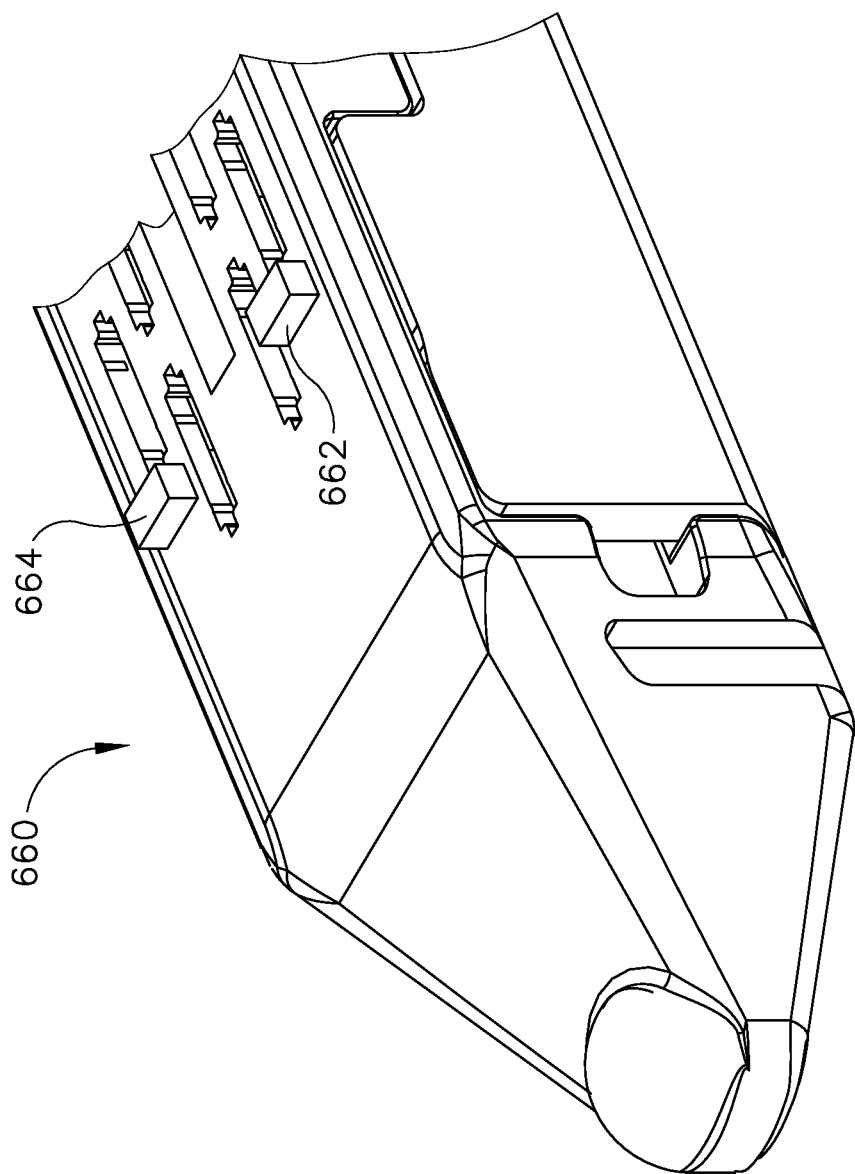
Figure 115:
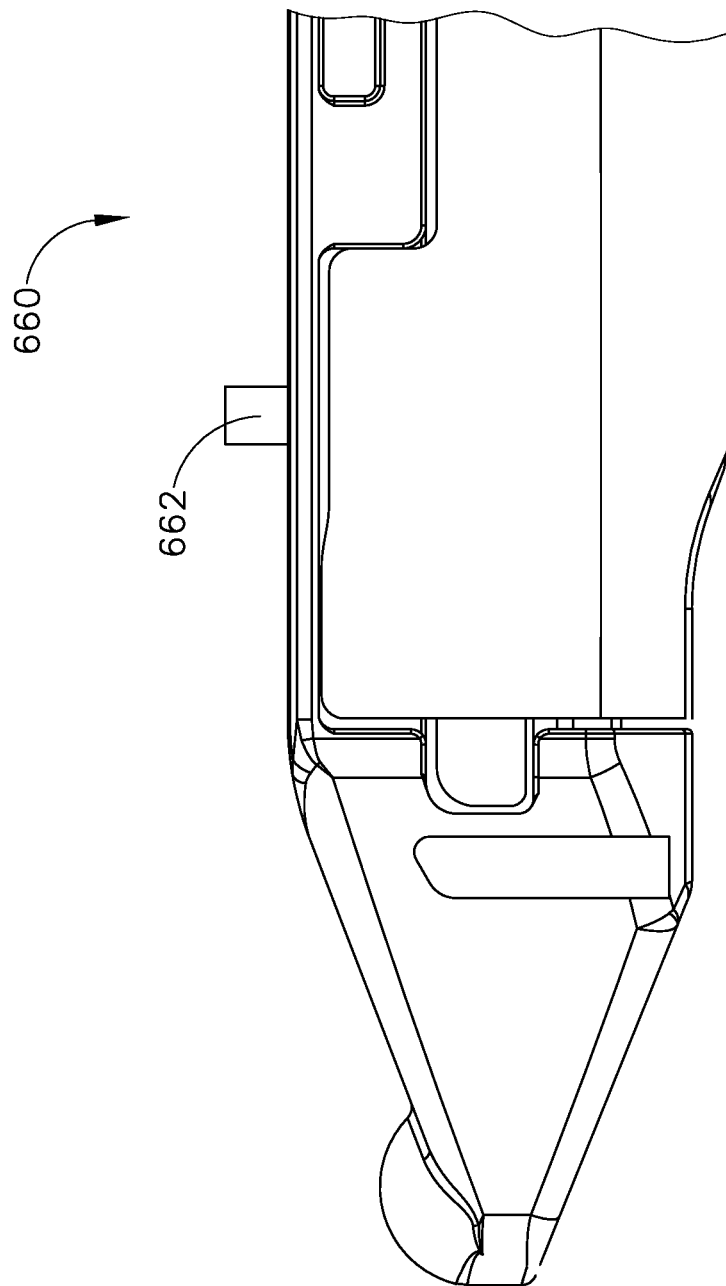
Figure 116:
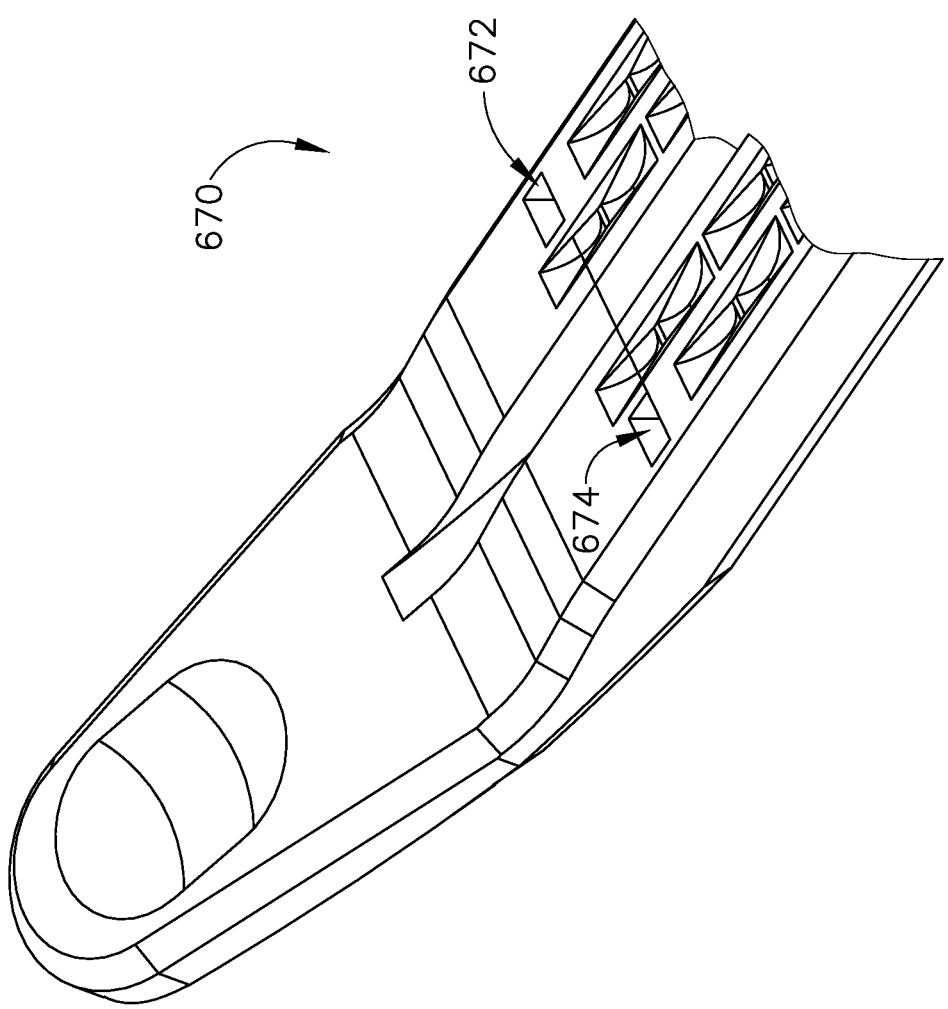
Figure 117:
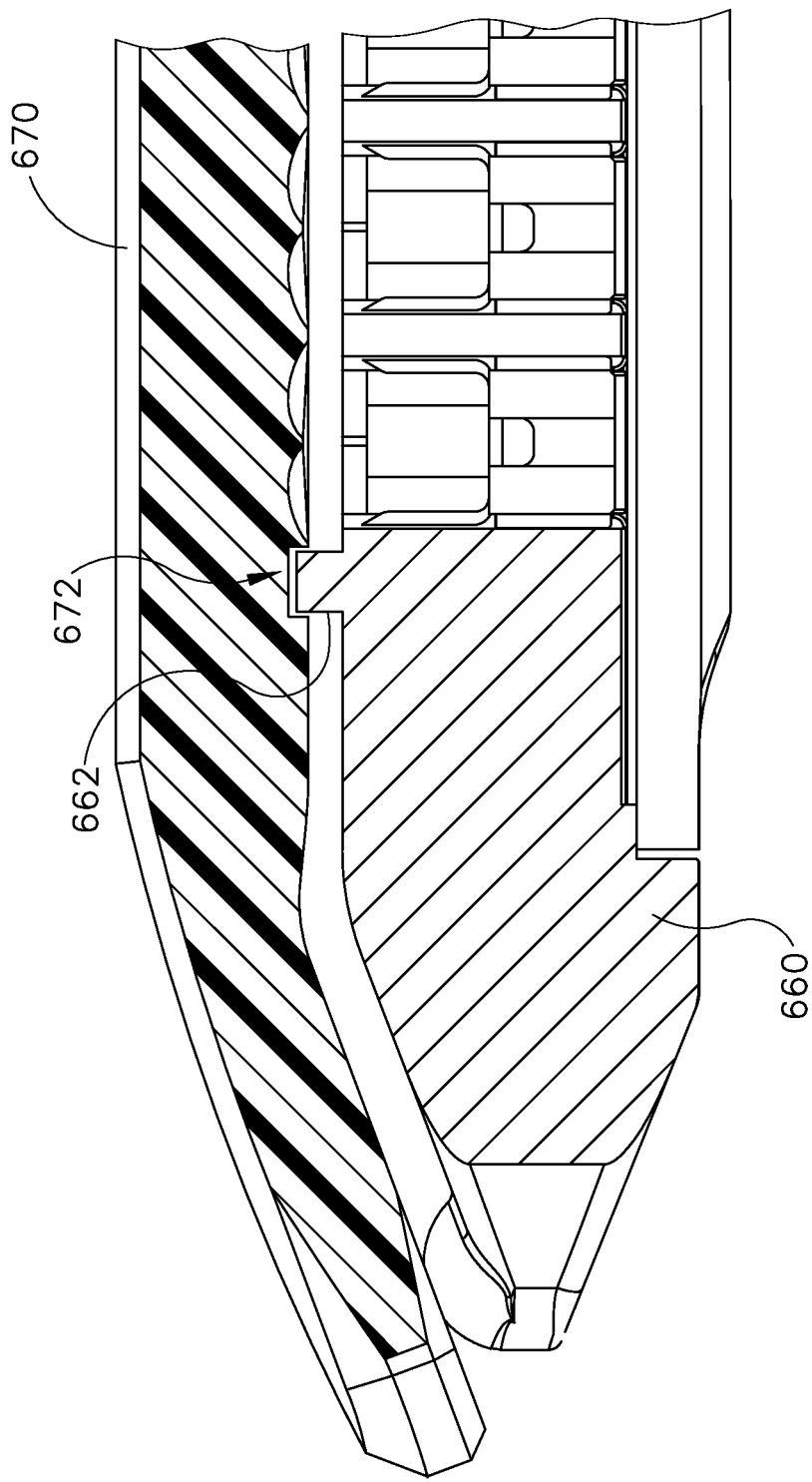
Figure 120:
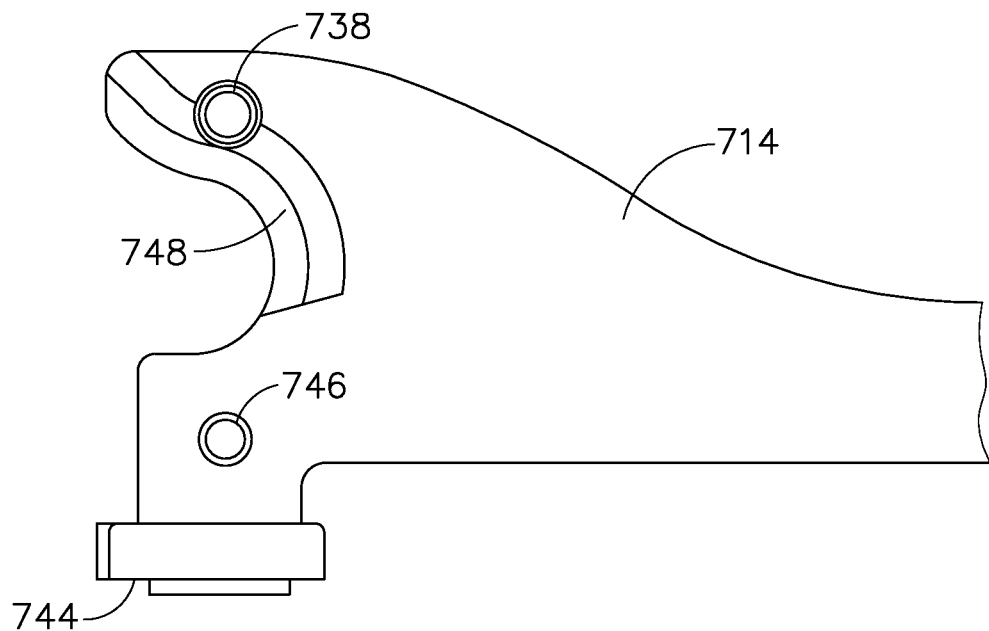
Figure 121:
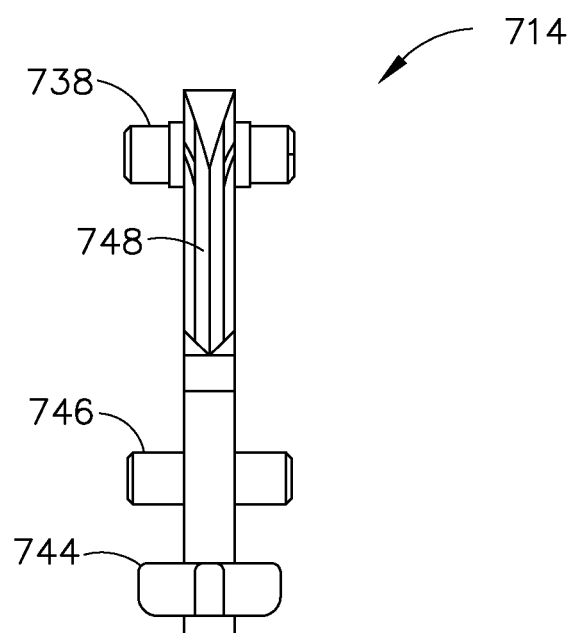
Figure 122:
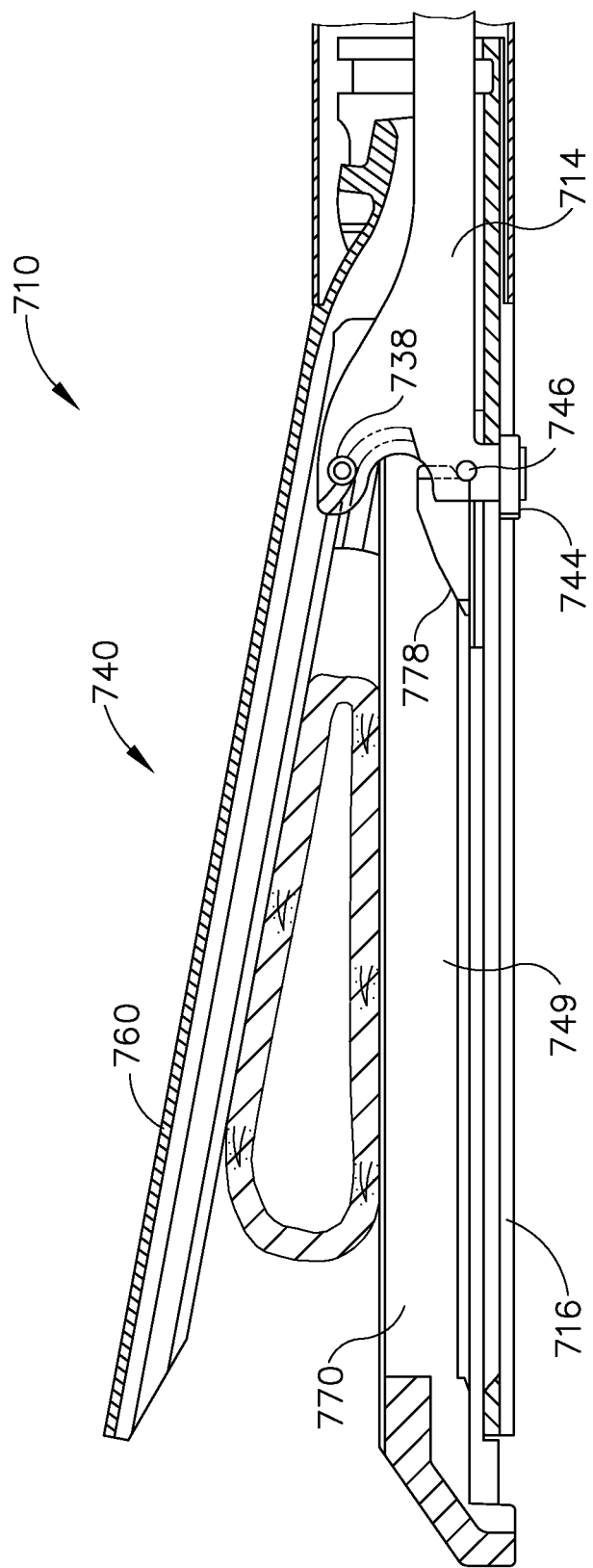
Figure 123:
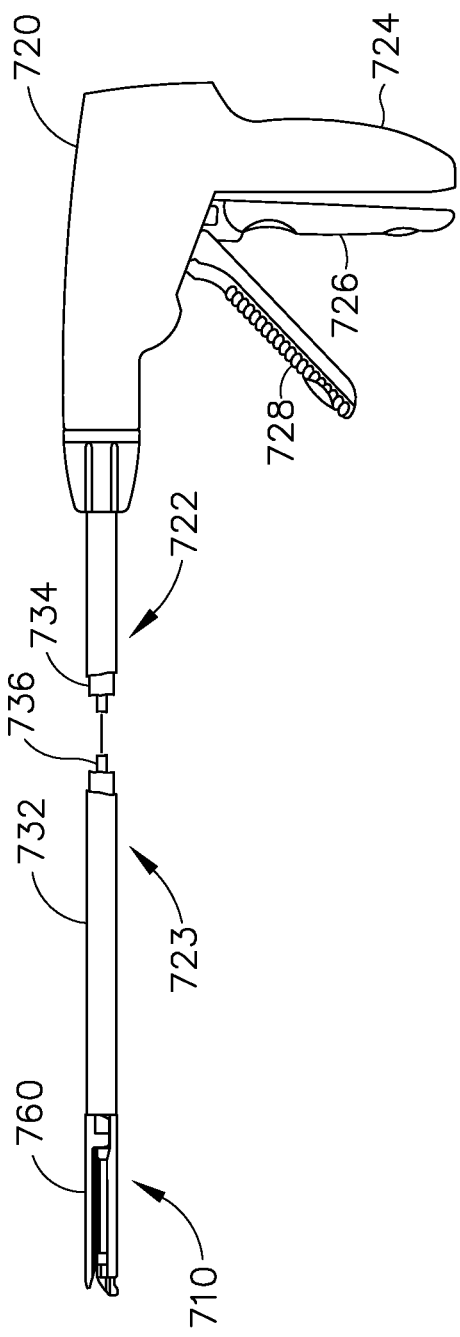
Figure 124:
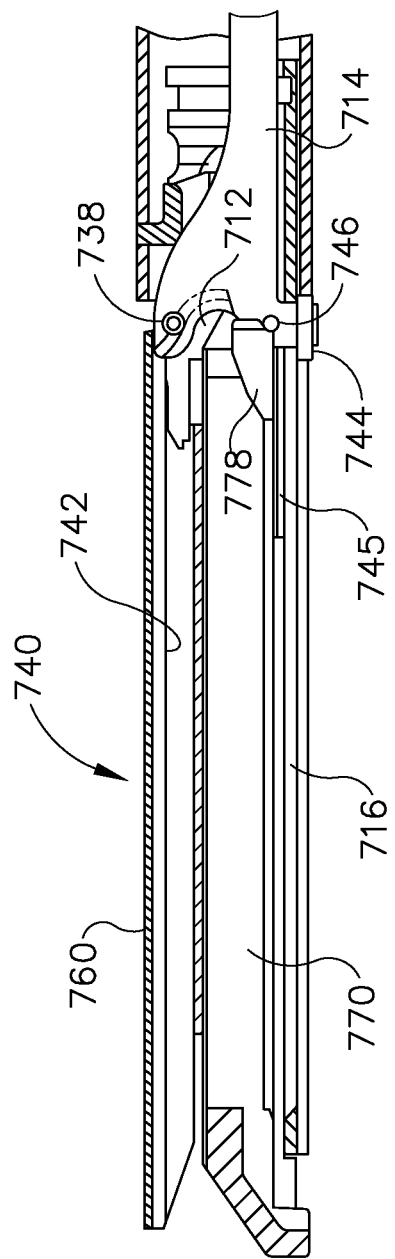
Figure 125:
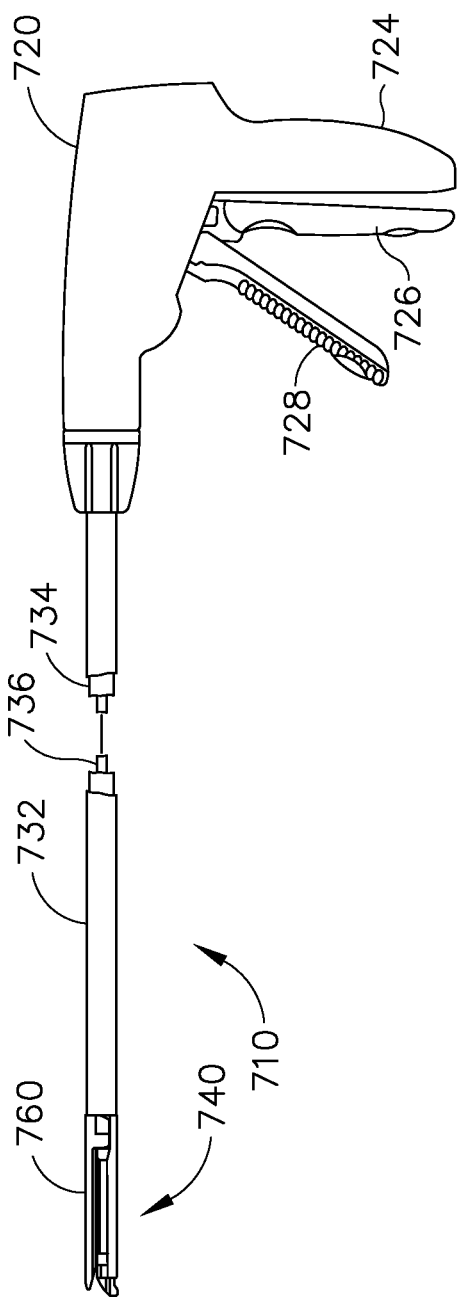
Figure 126:
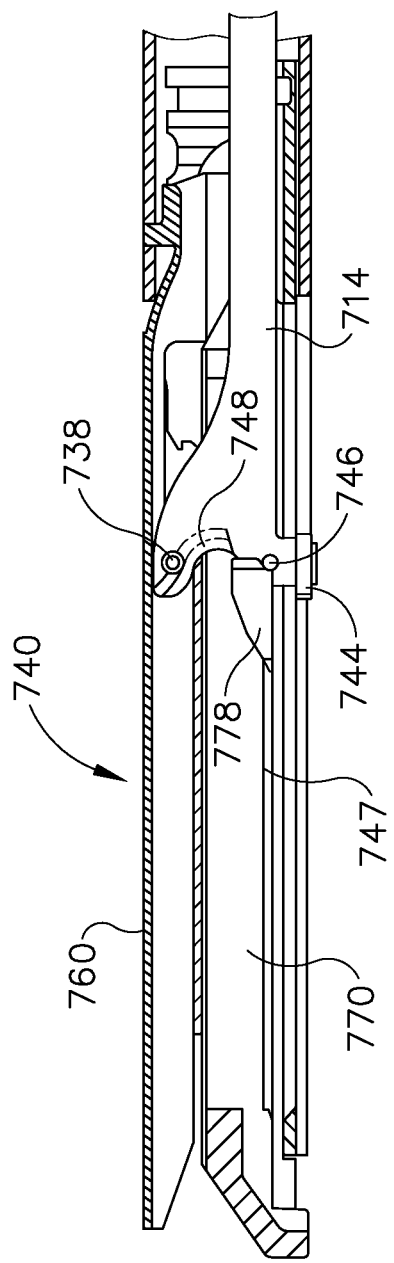
Figure 127:
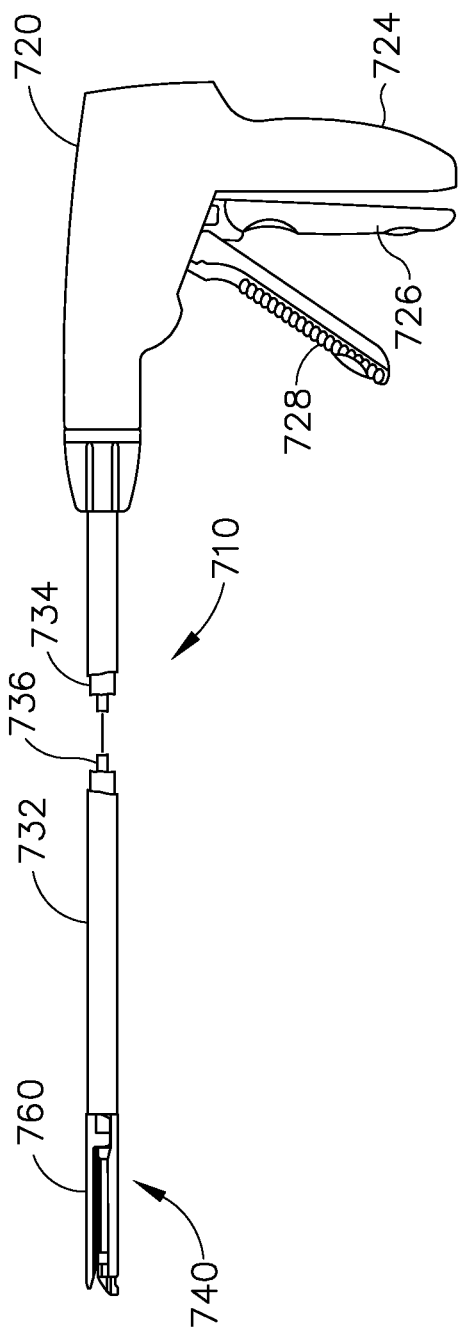
Figure 128:
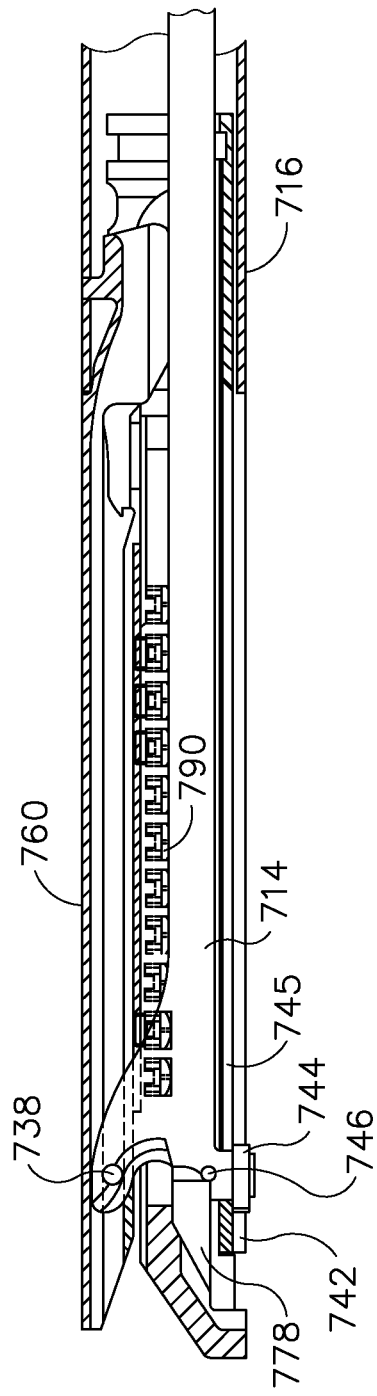
Figure 129:
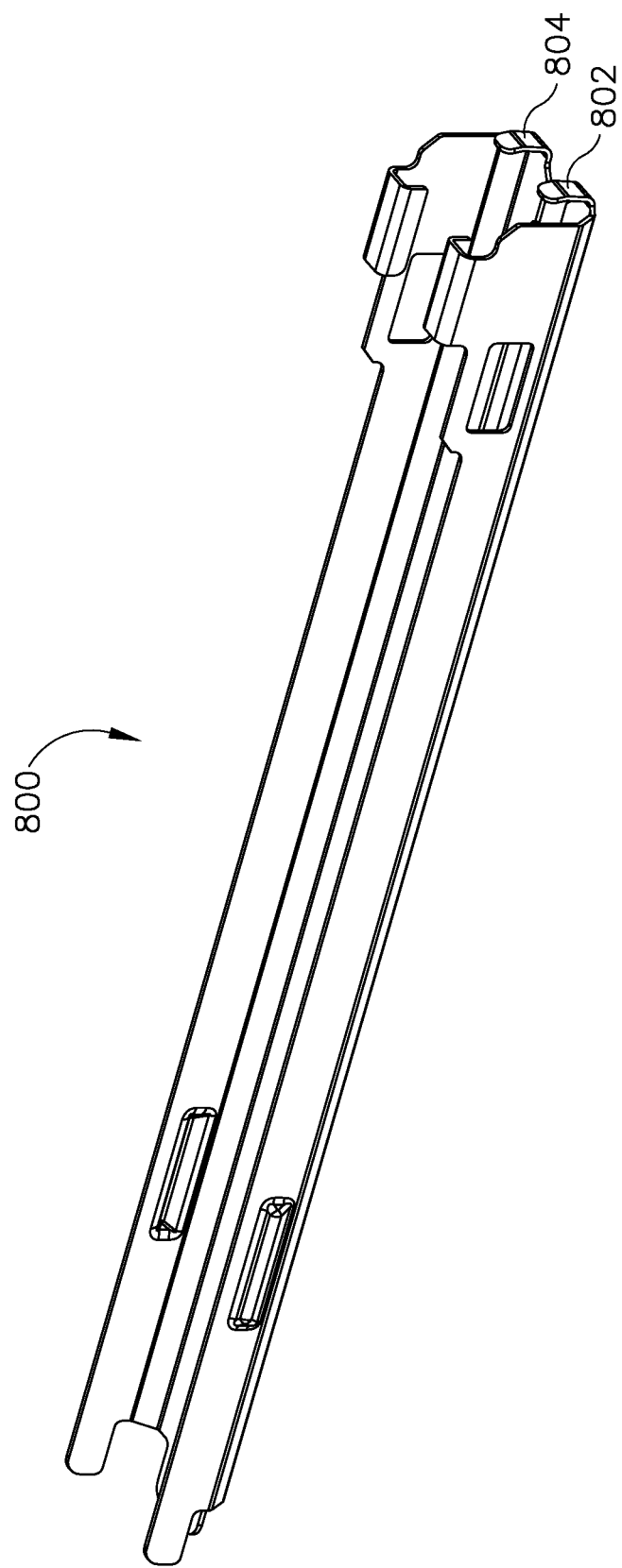
Figure 130:
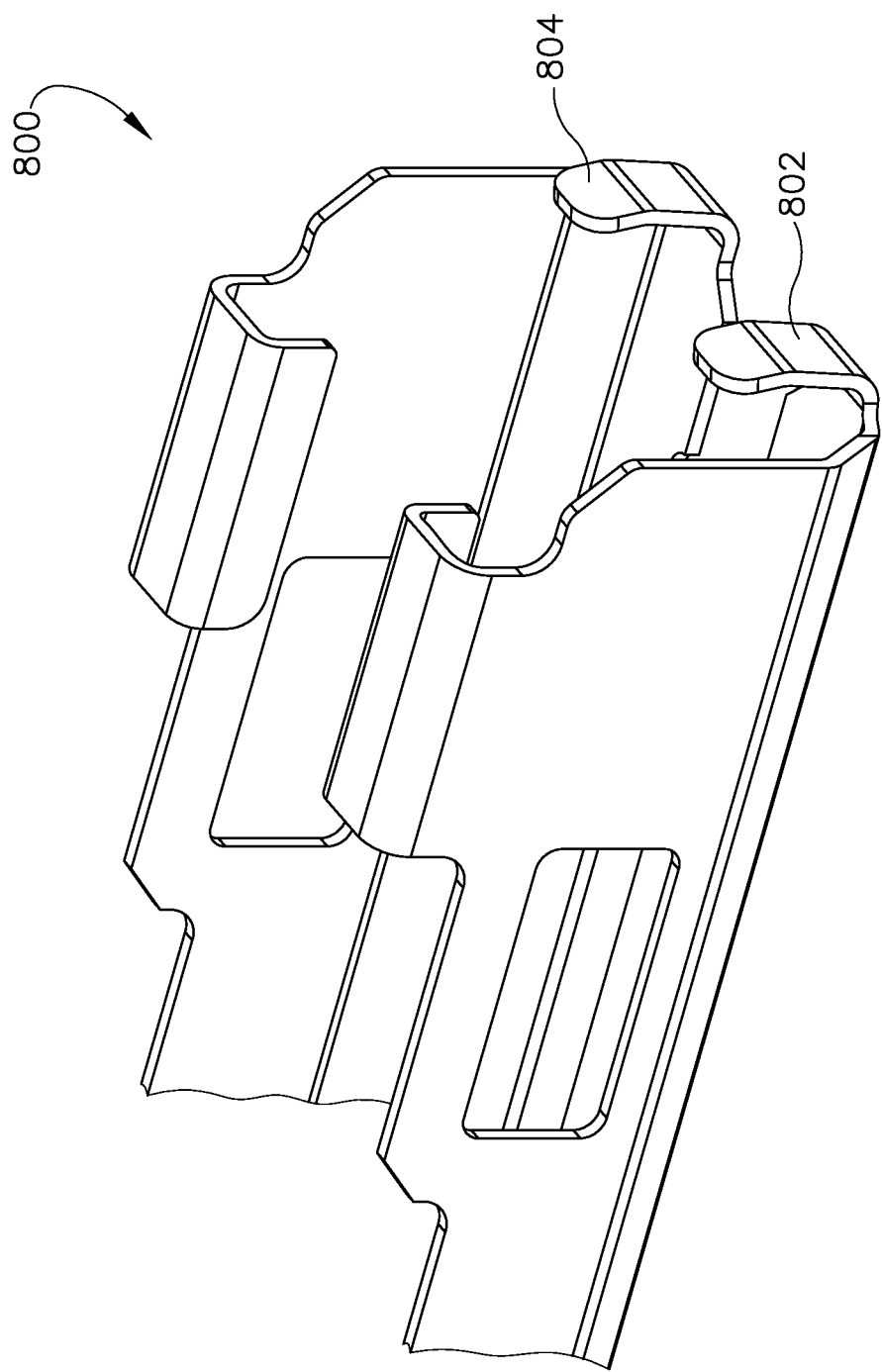
Figure 131:
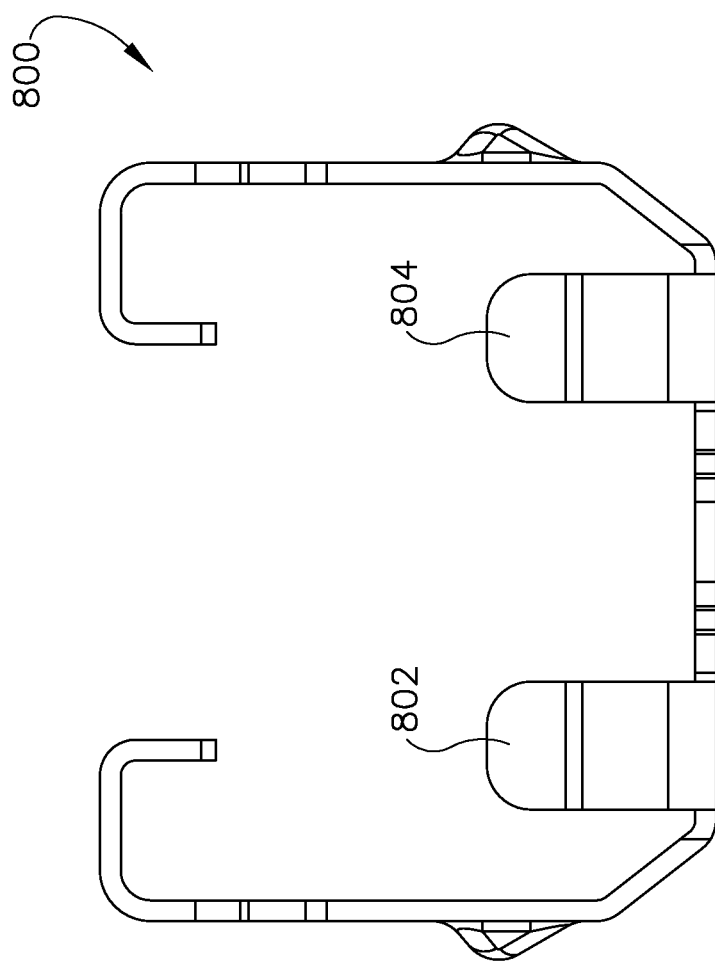
Figure 132:
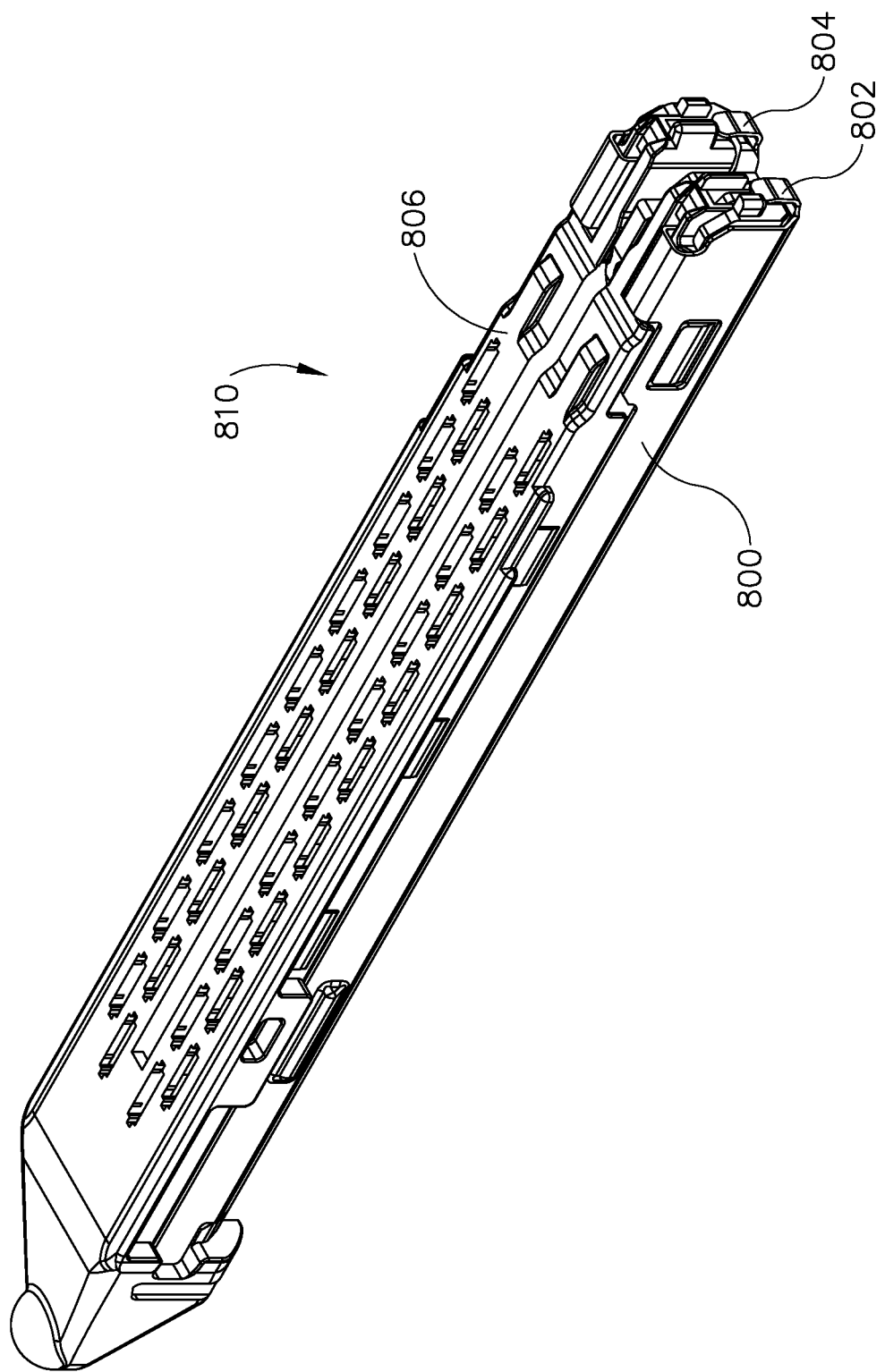
Figure 133:
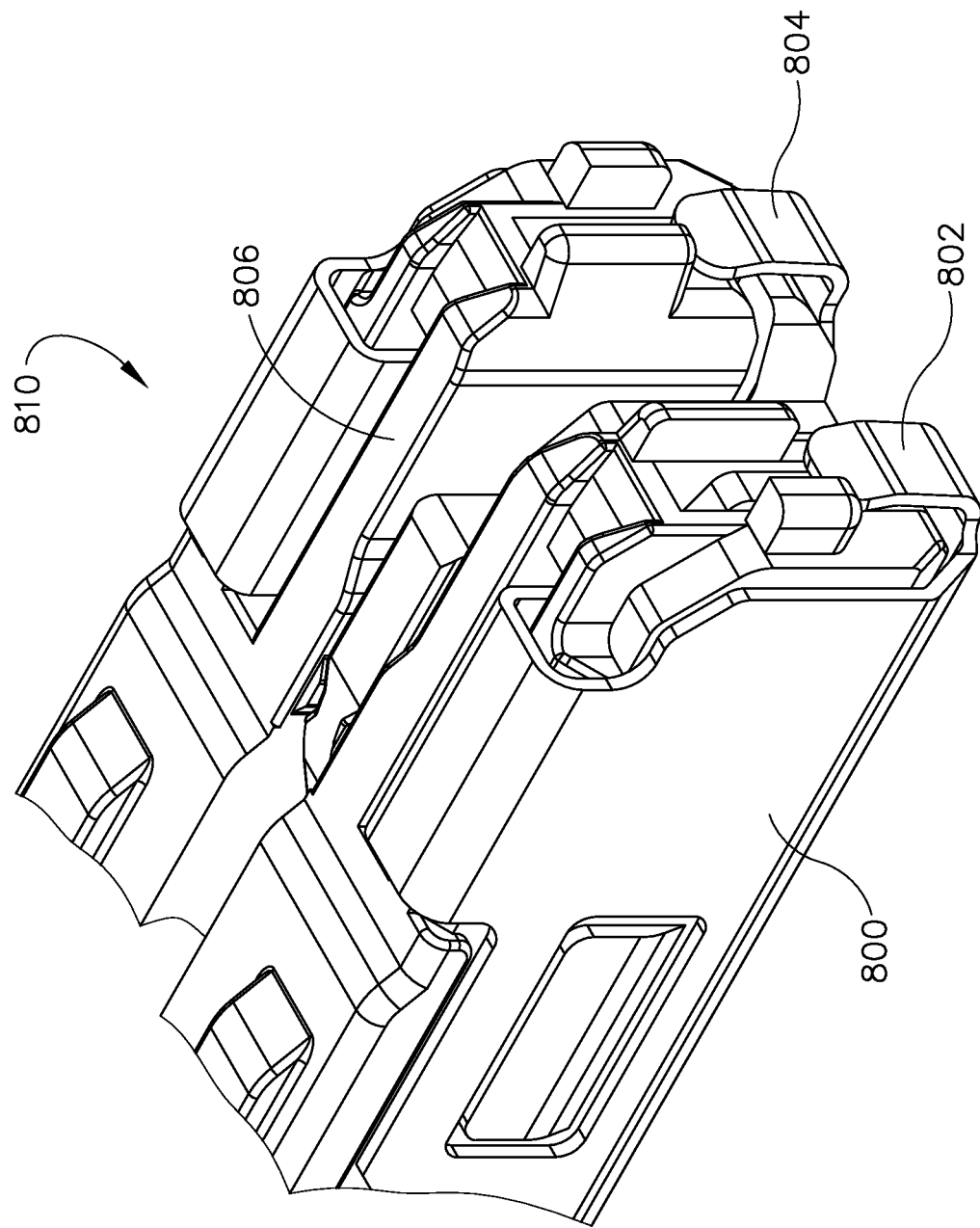
Figure 134:
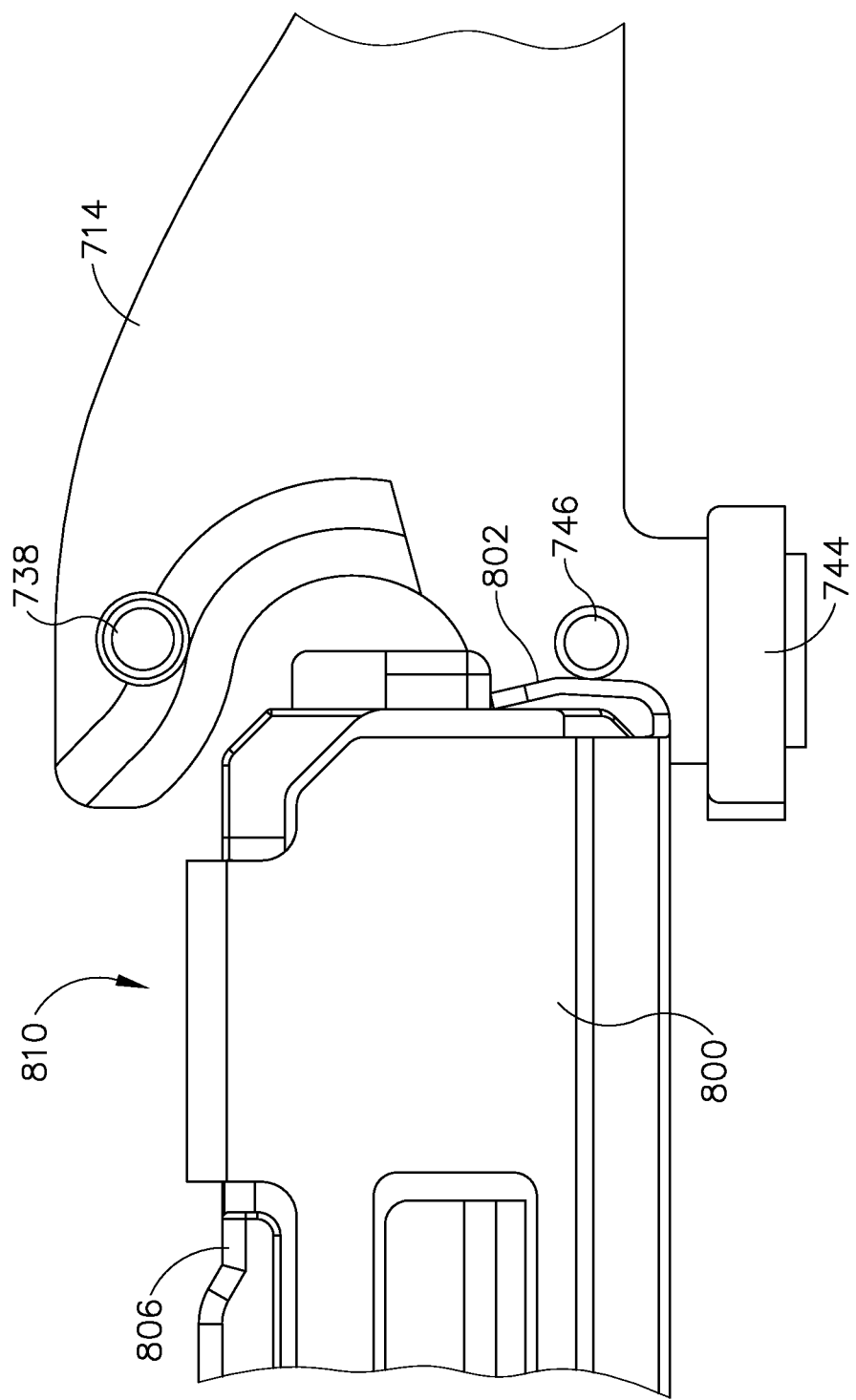
Figure 135:
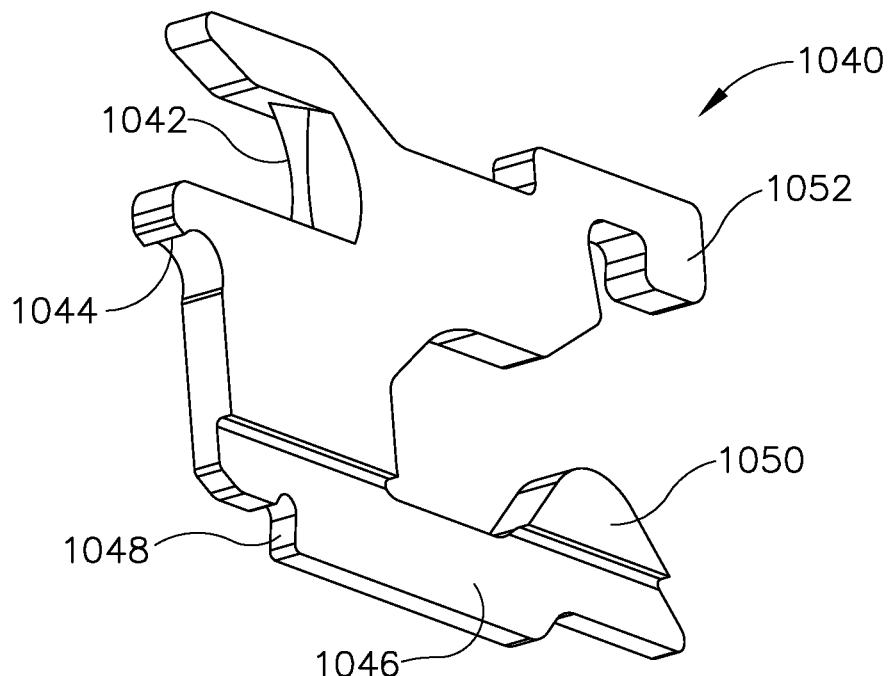
Figure 136:
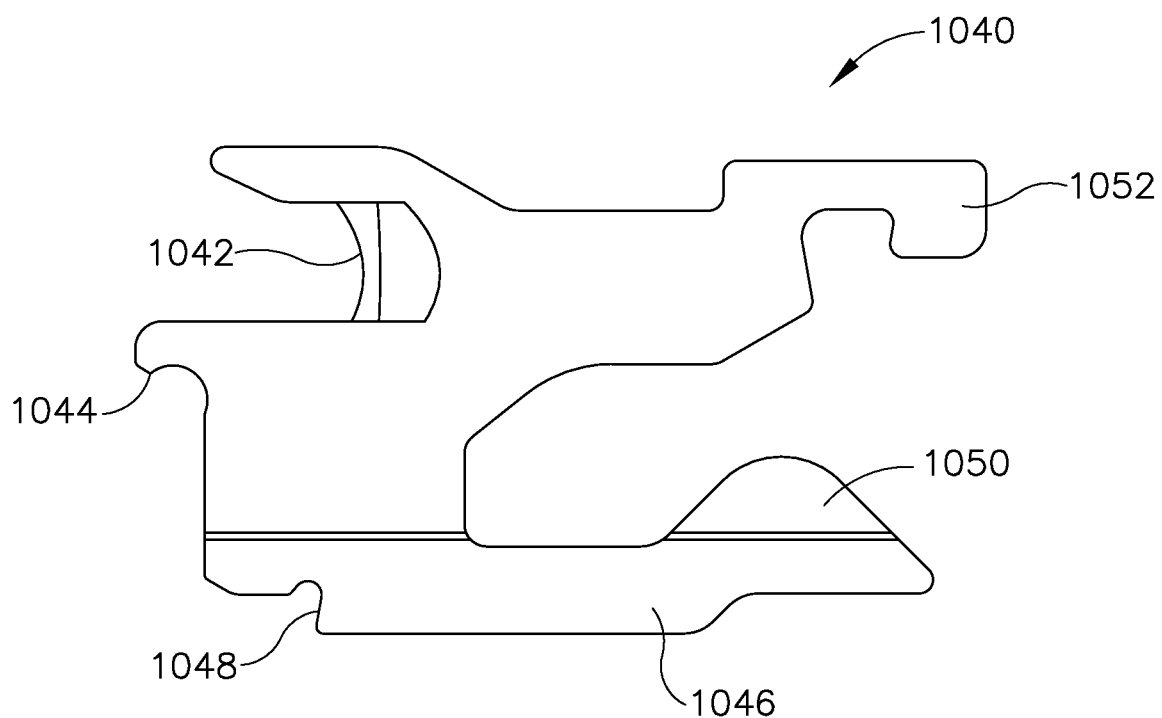
Figure 137:
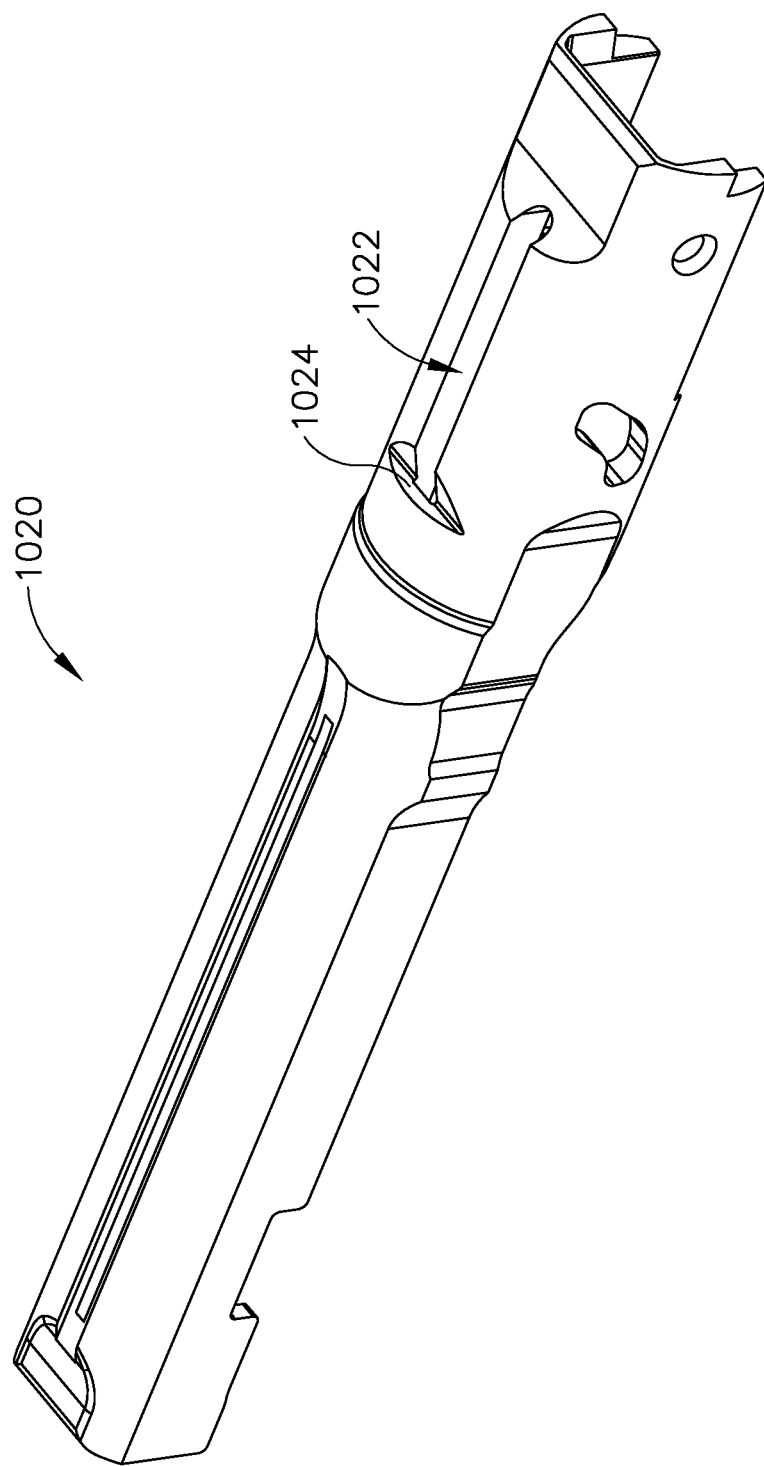
Figure 138:
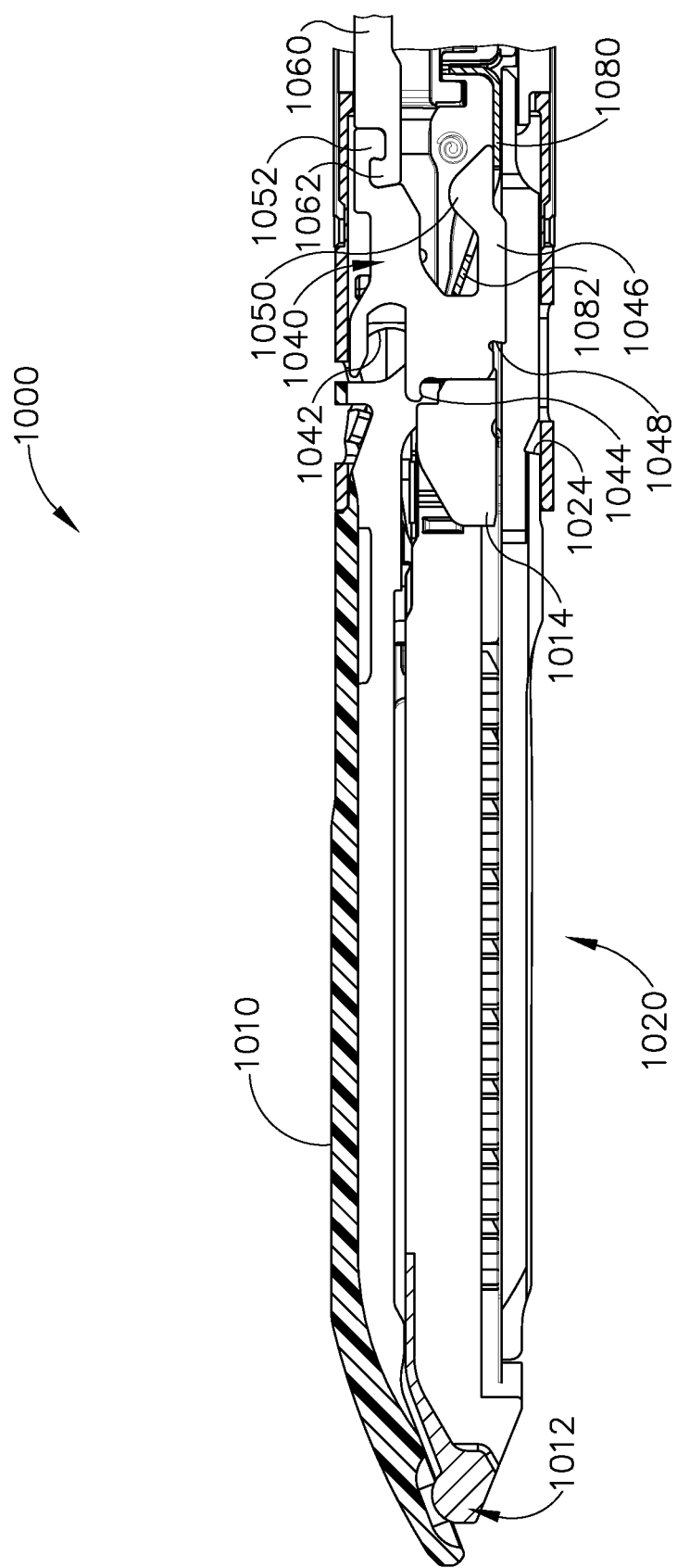
Figure 139:
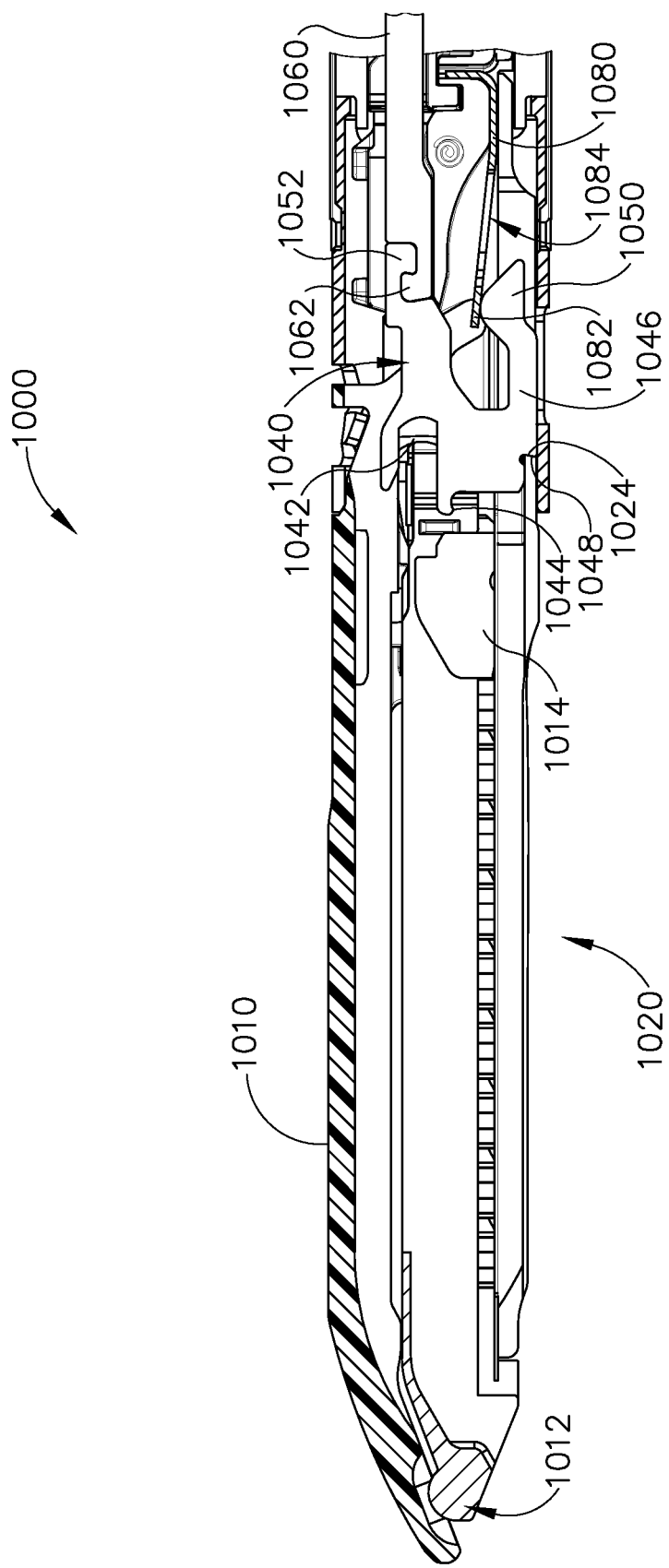

FIG. 99 depicts a perspective view of the proximal end of yet another exemplary alternative cartridge that may be incorporated into the end effector of FIG. 13;

FIG. 100 depicts a side view of the proximal end of the cartridge of FIG. 99;

FIG. 101 depicts a cross-sectional side view of the proximal end of the cartridge of FIG. 99 engaged with the end effector of FIG. 13;

FIG. 102 depicts a perspective view of the proximal end of yet another exemplary alternative cartridge that may be incorporated into the end effector of FIG. 13;

FIG. 103 depicts a side view of the proximal end of the cartridge of FIG. 102;

FIG. 104 depicts a perspective view of the proximal end of the cartridge of FIG. 102 engaged with the end effector of FIG. 13;

FIG. 105 depicts a cross-sectional perspective view of the proximal end of the cartridge of FIG. 102 engaged with the end effector of FIG. 13;

FIG. 106 depicts a cross-sectional side view of the proximal end of the cartridge of FIG. 102 engaged with the end effector of FIG. 13;

FIG. 107 depicts a perspective view of the distal end of an exemplary alternative cartridge that may be incorporated into the end effector of FIG. 3;

FIG. 108 depicts a perspective view of the distal end of another exemplary alternative anvil that may be incorporated into the end effector of FIG. 3;

FIG. 109 depicts a cross-sectional side view of the distal end of the cartridge of FIG. 107 engaged with the distal end of the anvil of FIG. 108;

FIG. 110 depicts a perspective view of the distal end of another exemplary alternative cartridge that may be incorporated into the end effector of FIG. 3;

FIG. 111 depicts a side view of the distal end of the cartridge of FIG. 110;

FIG. 112 depicts a perspective view of the distal end of yet another exemplary alternative anvil that may be incorporated into the end effector of FIG. 3;

FIG. 113 depicts a cross-sectional side view of the distal end of the cartridge of FIG. 110 engaged with the distal end of the anvil of FIG. 112;

FIG. 114 depicts a perspective view of the distal end of yet another exemplary alternative cartridge that may be incorporated into the end effector of FIG. 3;

FIG. 115 depicts a side view of the distal end of the cartridge of FIG. 114;

FIG. 116 depicts a perspective view of the distal end of yet another exemplary alternative anvil that may be incorporated into the end effector of FIG. 3;

FIG. 117 depicts a cross-sectional side view of the distal end of the cartridge of FIG. 114 engaged with the distal end of the anvil of FIG. 116;

FIG. 118 depicts a side elevation view of an exemplary alternative surgical stapling instrument;

FIG. 119 depicts a cross-sectional side view of an end effector of the instrument of FIG. 118;

FIG. 120 depicts a side elevation view of a firing bar of the surgical instrument of FIG. 118;

FIG. 121 depicts a front elevational view of the firing bar of FIG. 120;

FIG. 122 depicts a cross-sectional side view of the end effector of FIG. 119 in a partially closed but unclamped position gripping tissue;

FIG. 123 depicts a side view of the surgical stapling instrument of FIG. 118, with the end effector in the closed position;

FIG. 124 depicts a cross-sectional side view of the end effector of FIG. 119 in the closed position with tissue properly compressed;

FIG. 125 depicts a side view of the surgical stapling instrument of FIG. 118 in a partially fired position;

FIG. 126 depicts a cross-sectional side view of the end effector of FIG. 119 in the partially fired position;

FIG. 127 depicts a side view of the surgical stapling instrument of FIG. 118 in a fully fired position;

FIG. 128 depicts a cross-sectional side view of the end effector of FIG. 119 in the fully fired position;

FIG. 129 depicts a perspective view of an exemplary alternative cartridge tray that may be incorporated into the cartridge of the end effector of FIG. 13;

FIG. 130 depicts a detailed perspective view of the proximal end of the cartridge tray of FIG. 129;

FIG. 131 depicts a rear view of the cartridge tray of FIG. 129;

FIG. 132 depicts a perspective view of yet another exemplary cartridge having the cartridge tray of FIG. 129;

FIG. 133 depicts a perspective view of the proximal end of the cartridge of FIG. 132;

FIG. 134 depicts a side view of the firing bar of FIG. 120 contacting the proximal end of the cartridge tray of FIG. 129;

FIG. 135 depicts a perspective view of an exemplary alternative knife member that may be incorporated into an exemplary alternative end effector for the instrument of FIG. 1;

FIG. 136 depicts a side elevational view of the knife member of FIG. 135;

FIG. 137 depicts a perspective view showing the underside of an exemplary alternative lower jaw that may be combined with the knife member of FIG. 135 in an exemplary alternative end effector for the instrument of FIG. 1;

FIG. 138 depicts a cross-sectional side view of an exemplary alternative end effector incorporating the knife member of FIG. 135 and the lower jaw of FIG. 137, with the knife member in a proximal position; and FIG. 139 depicts a cross-sectional side view of the end effector of FIG. 138, with the knife member in a locked out position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and cutting instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
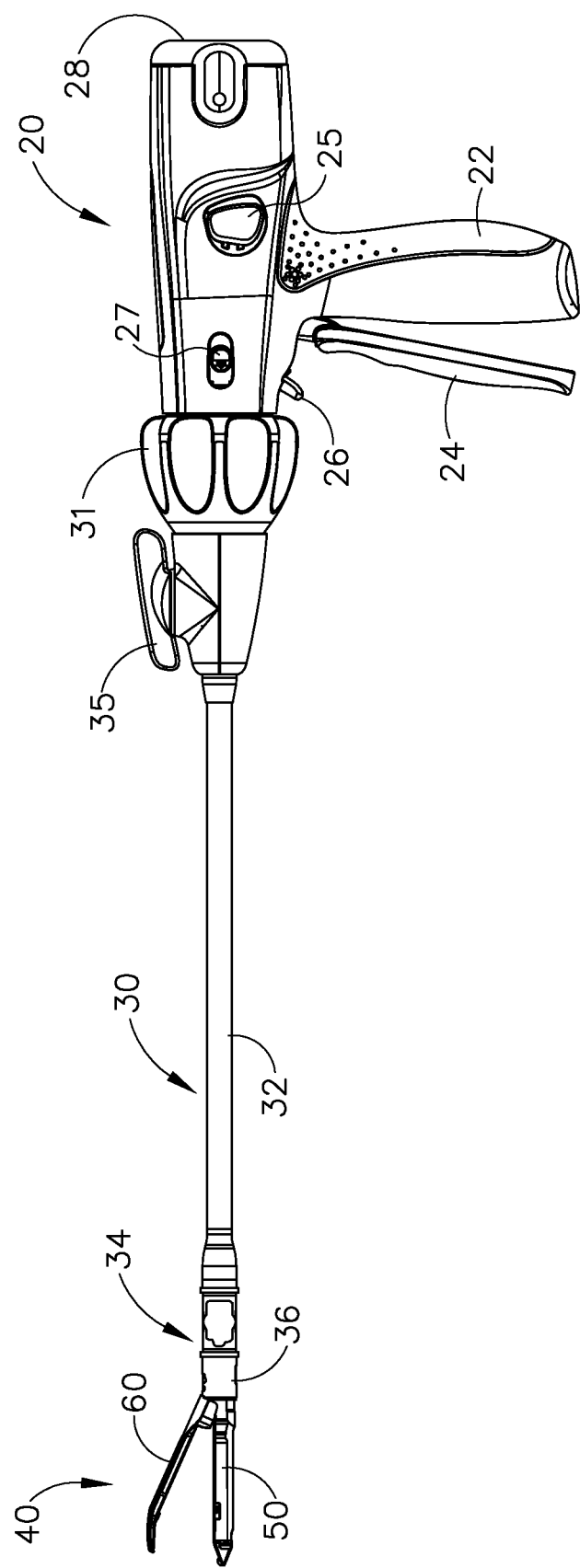
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. patent application Ser. No. 13/780,067, entitled "Surgical Instrument End Effector Articulation Drive with Pinion and Opposing Racks," filed Feb. 28, 2013, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed on even date herewith, published as U.S. Pub. No. 2015/0374360 on Dec. 31, 2015, issued as U.S. Pat. No. 10,292,701 on May 21, 2019, the disclosure of which is incorporated by reference herein; and/or U.S. patent application Ser. No. 14/314,276, entitled "Method of Unlocking Articulation Joint in Surgical Stapler," filed on even date herewith, issued as U.S. Pat. No. 10,064,620 on Sep. 4, 2018, the disclosure of which is incorporated by reference herein. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 4:
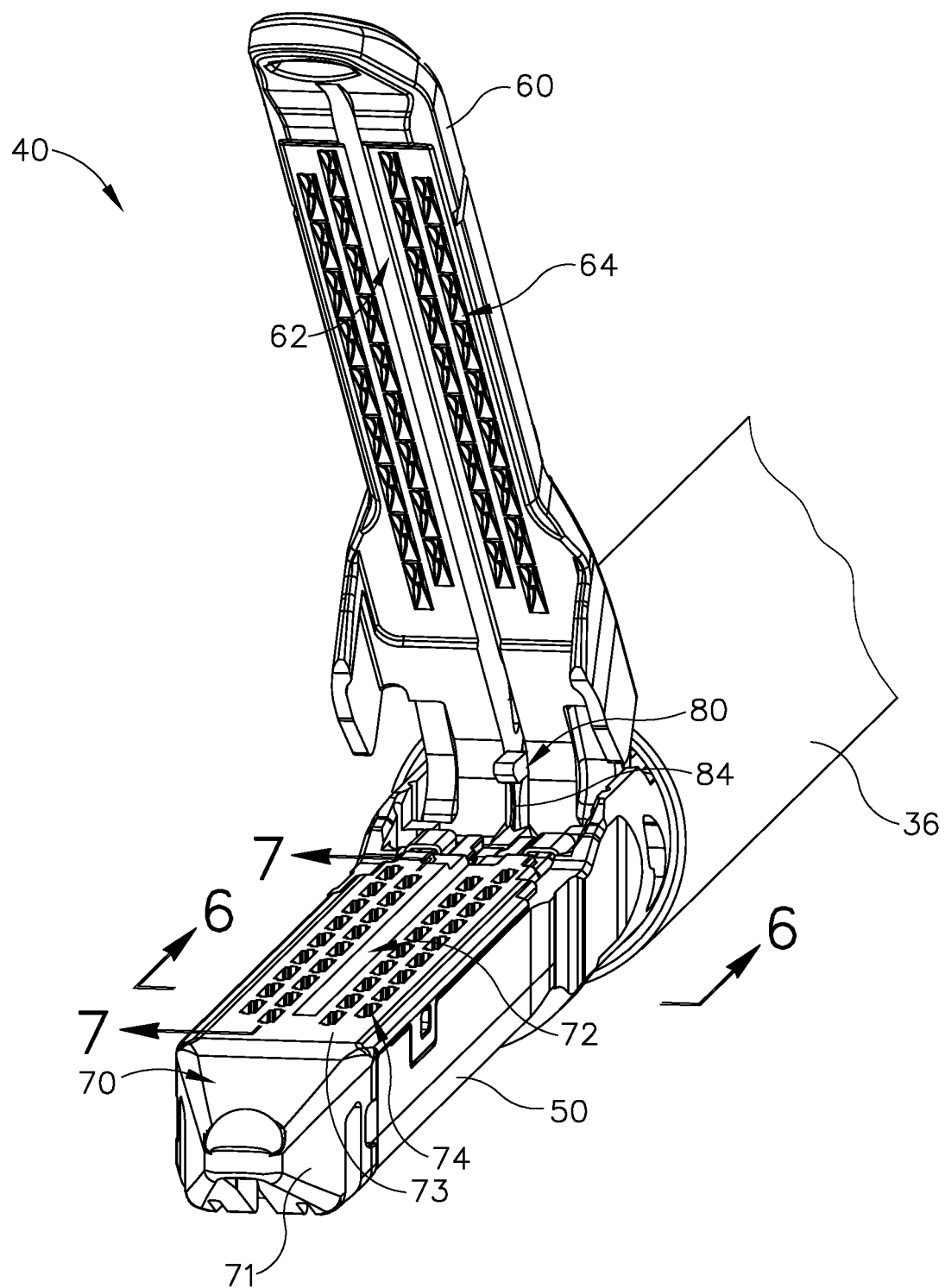
FIG. 4 depicts a perspective view of the end effector of FIG. 3, with the end effector in an open configuration.
Figure 5:
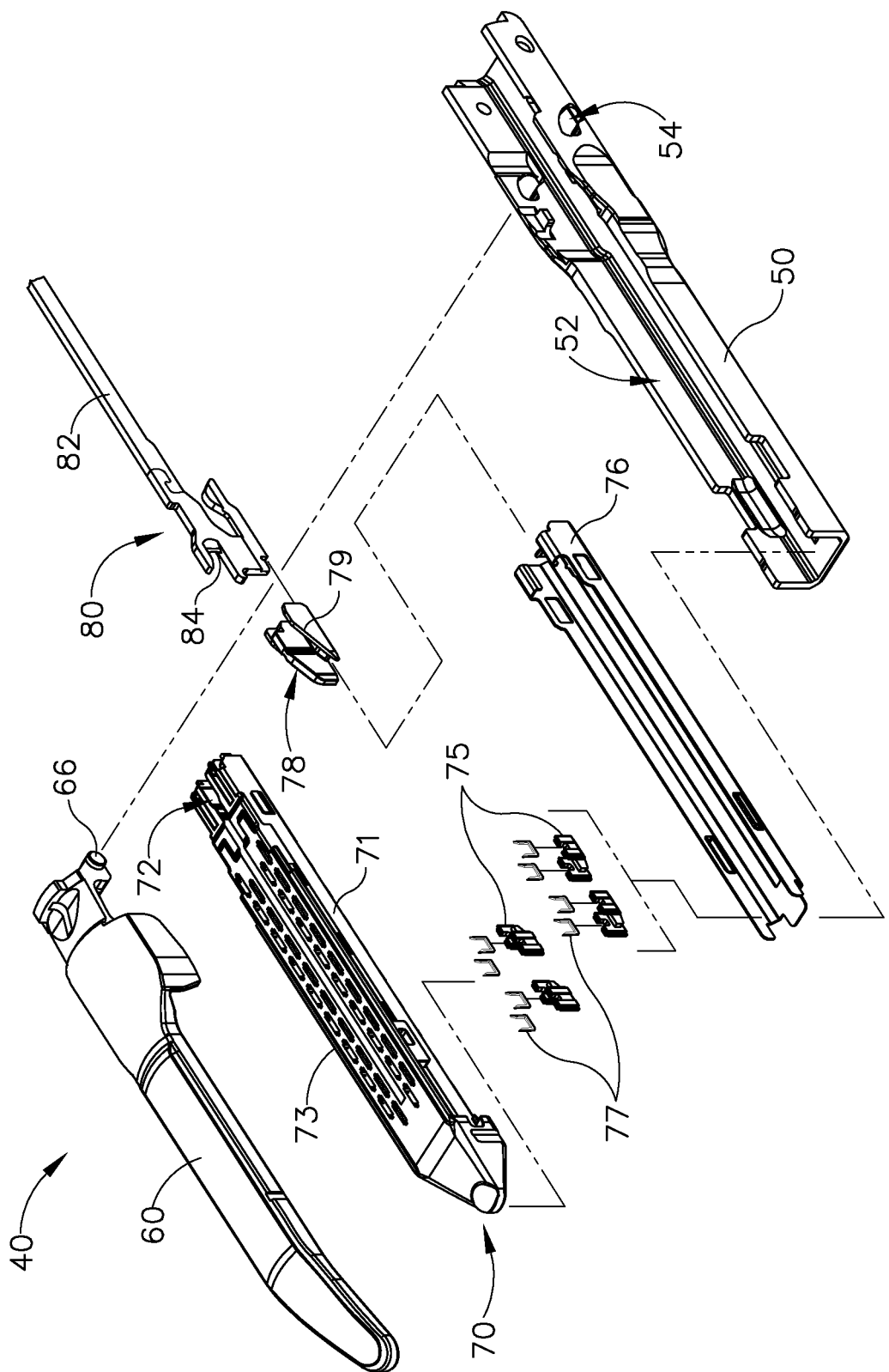
FIG. 5 depicts an exploded perspective view of the end effector of FIG. 3.
Figure 6:
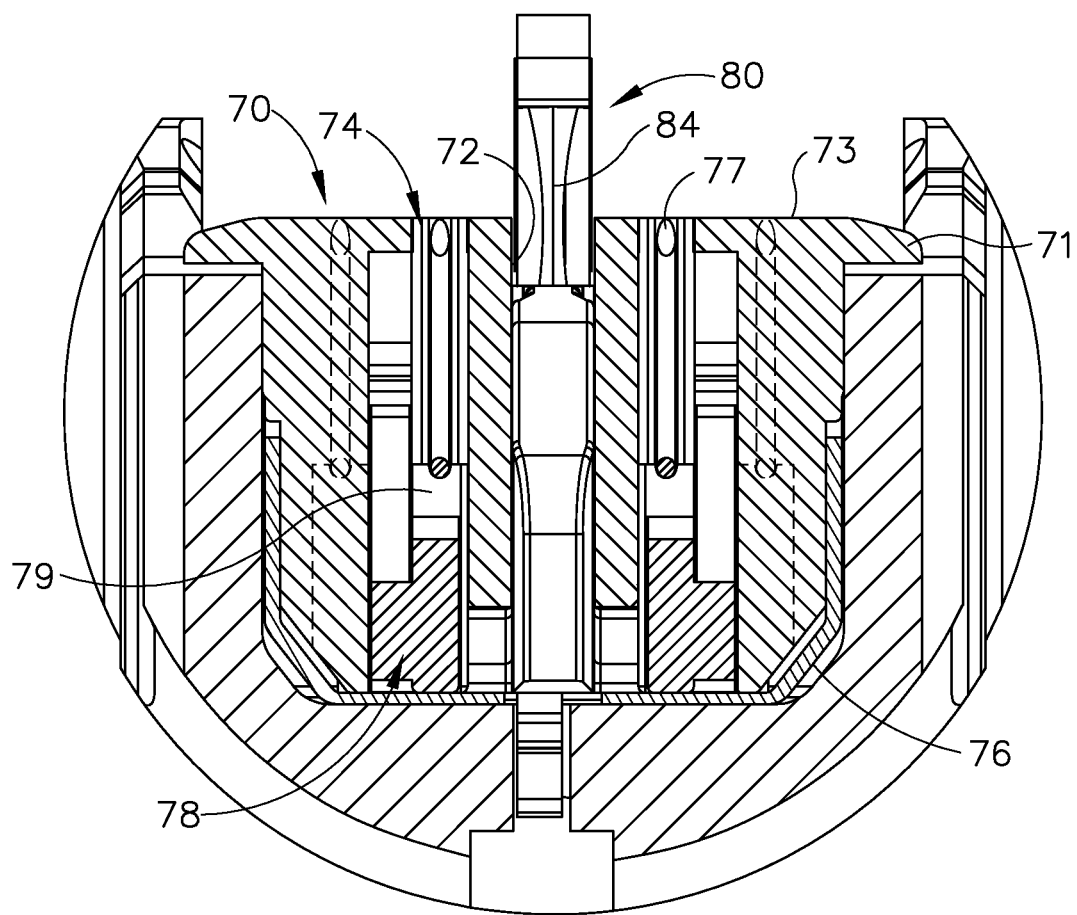
FIG. 6 depicts a cross-sectional end view of the end effector of FIG. 3, taken along line 6-6 of FIG. 4.
Figure 7A:
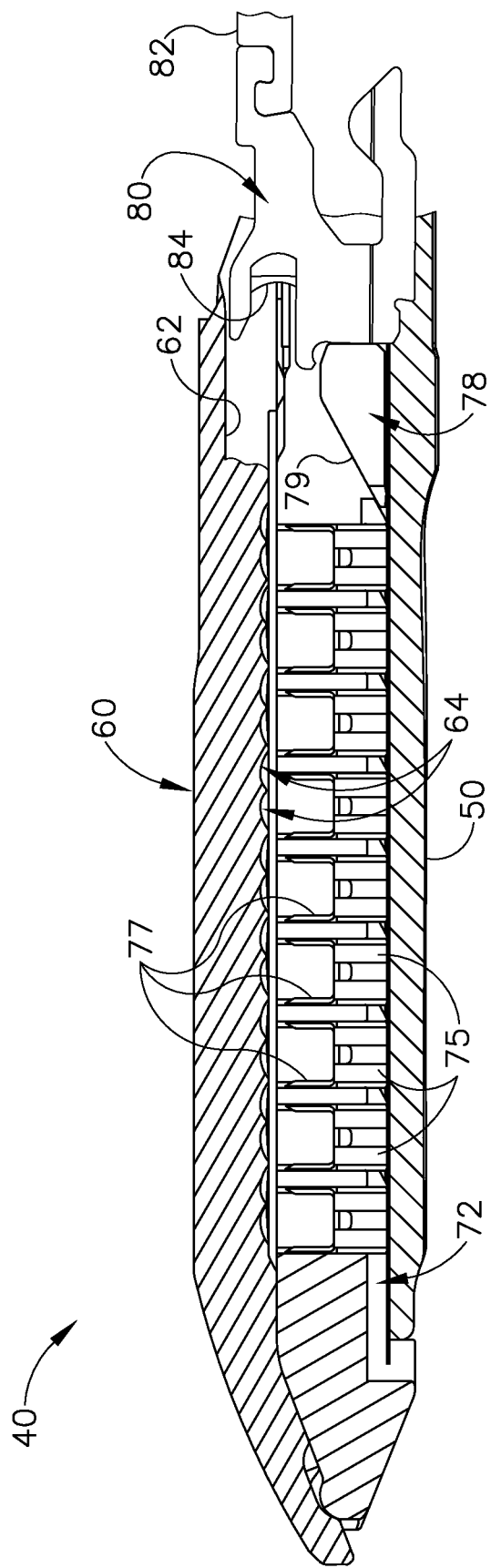
FIG. 7A depicts a cross-sectional side view of the end effector of FIG. 3, taken along line 7-7 of FIG. 4, with the firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (74) are located in staple pockets (74). As wedge sled (78) is driven to the distal position shown in FIG. 7B by a translating knife member (80), wedge sled (78) drives staple drivers (75) upwardly, thereby driving staples (74) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U. U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. patent application Ser. No. 13/780,417, entitled "Installation Features for Surgical Instrument End Effector Cartridge," filed Feb. 28, 2013, issued as U.S. Pat. No. 9,808, 248 on Nov. 1, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016; at least some of the teachings of U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017; and/or at least some of the teachings of U.S. patent application Ser. No. 13/780,379, entitled "Staple Forming Features for Surgical Stapling Instrument," filed Feb. 28, 2013, published as U.S. Pub. No. 2014/0239037 on Oct. 9, 2018, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
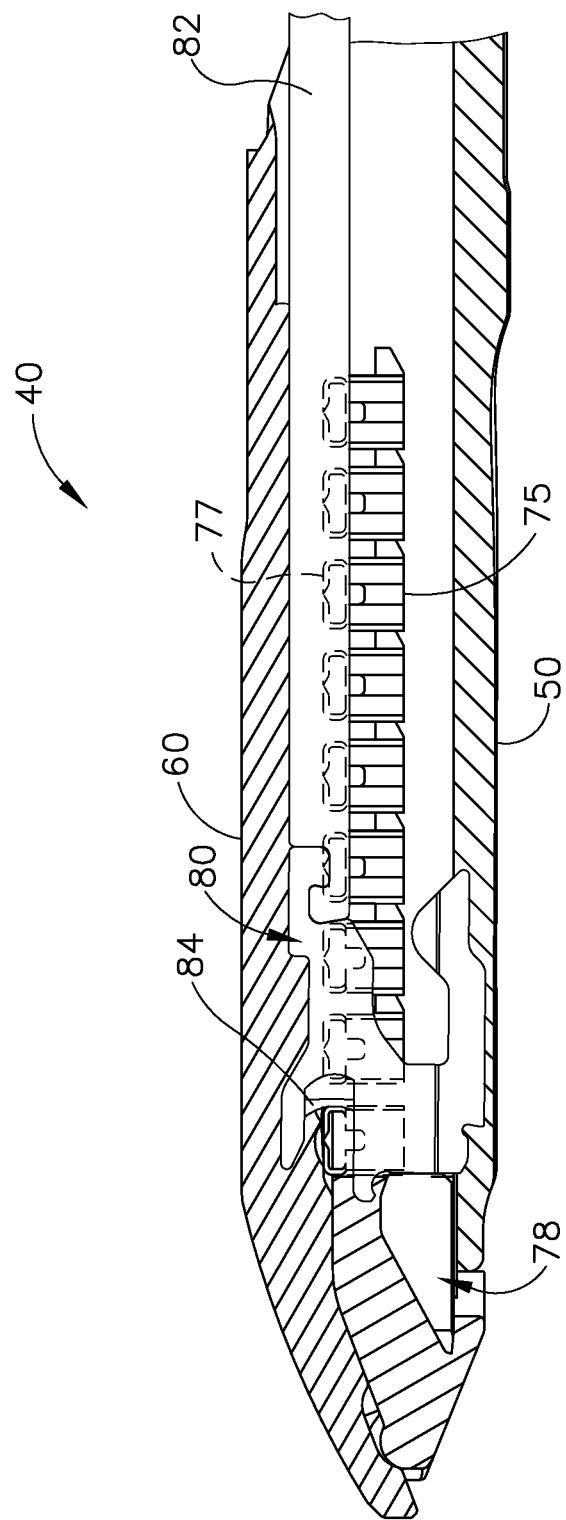
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to cut tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (74) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. patent application Ser. No. 13/780,082, entitled "Lockout Feature for Movable Cutting Member of Surgical Instrument," filed Feb. 28, 2013, issued as U.S. Pat. No. 9,717,497 on Aug. 1, 2017 the disclosure of which is incorporated by reference herein; and/or at least some of the teachings below. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017, the disclosure of which is incorporated by reference herein; and/or in accordance with at least some of the teachings of U.S. patent application Ser. No. 14/314,164, entitled "Jaw Opening Feature for Surgical Stapler," filed on even date herewith, published as U.S. Pub. No. 2015/0374361 on Dec. 31, 2015, issued as U.S. Pat. No. 10,456,132 on Oct. 29, 2019, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

Figure 9:
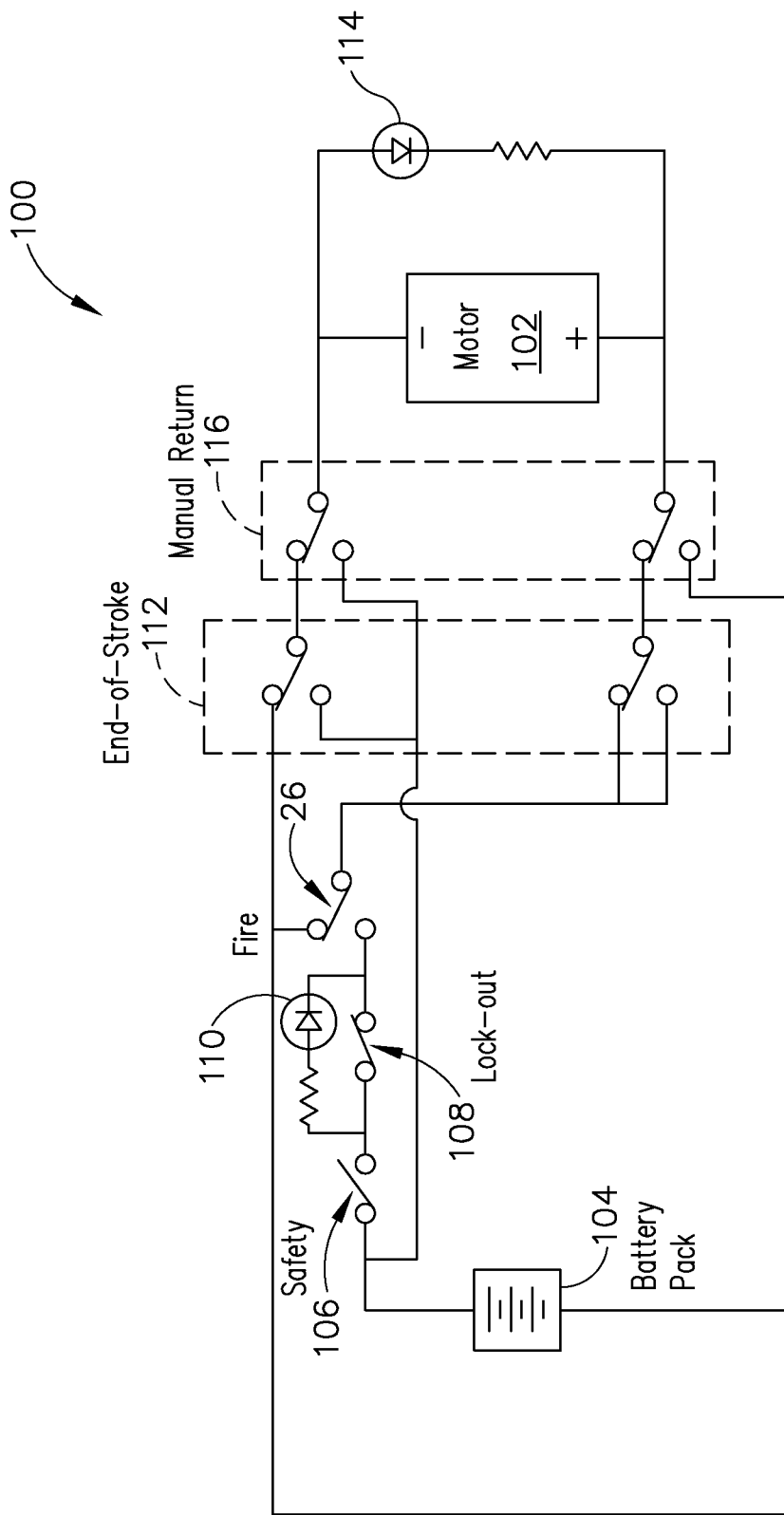
FIG. 9 depicts a schematic view of an exemplary control circuit for use in the instrument of FIG. 1.

In the present example, instrument (10) provides motorized control of firing beam (82). FIGS. 9-12 show exemplary components that may be used to provide motorized control of firing beam (82). In particular, FIG. 9 shows an exemplary control circuit (100) that may be used to power an electric motor (102) with electric power from a battery pack (28) (also shown in FIGS. 1-2). Electric motor (102) is operable to translate firing beam (82) longitudinally as will be described in greater detail below. It should be understood that the entire control circuit (100), including motor (102) and battery pack (28), may be housed within handle assembly (20). FIG. 9 shows firing trigger (26) as an open switch, though it should be understood that this switch is closed when firing trigger (26) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle assembly (20). Safety switch (106) may also provide a mechanical lockout of firing trigger (26), such that firing trigger (26) is mechanically blocked from actuation until safety switch (106) is actuated.

Circuit (100) of the present example also includes a lockout switch (108), which is configured to be closed by default but is automatically opened in response to a lockout condition. By way of example only, a lockout condition may include one or more of the following: the absence of a cartridge (70) in lower jaw (50), the presence of a spent (e.g., previously fired) cartridge (70) in lower jaw (50), an insufficiently closed anvil (60), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Figure 12:
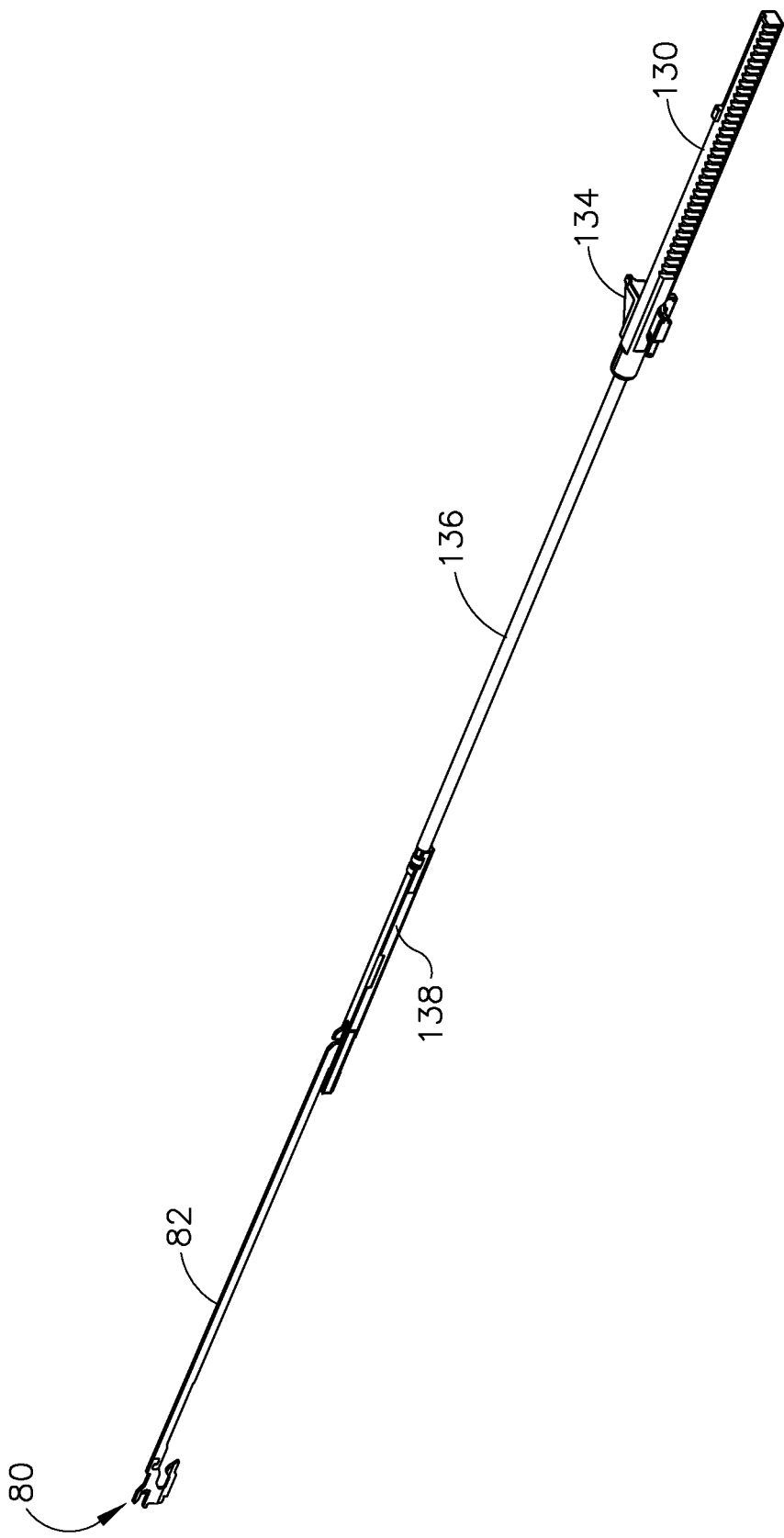
FIG. 12 depicts a perspective view of an elongate member from the drive assembly of FIG. 11, coupled with the firing beam.

Once firing beam (82) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (26) at this stage of operation. In this operational state, current flows through a reverse direction indicator (114) (e.g., an LED, etc.) to provide a visual indication to the operator that motor (102) rotation has been reversed. In the present example, and as best seen in FIG. 12, a switch actuation arm (134) extends laterally from rack member (130), and is positioned to engage end-of-stroke switch (112) when firing beam (82) reaches a distal-most position (e.g., after tissue (90) has been severed and staples (74) have been driven into tissue (90)). Various other suitable ways in which end-of-stroke switch (112) may be automatically switched to a closed position when firing beam (82) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle assembly (20) of the present example also includes a manual return switch (116), which is also shown in circuit (100). In the present example, return switch is activated by actuating reverse switch (27), which is shown on handle assembly (20) in FIG. 1. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114). In some versions, handle assembly (20) further includes a mechanical return feature that enables the operator to manually reverse firing beam (82) and thereby retract firing beam (82) mechanically. In the present example, this manual return feature comprises a lever that is covered by a removable panel (21) as shown in FIG. 1. Manual return switch (116) and the mechanical return feature are each configured to act as a "bailout" feature, enabling the operator to quickly begin retracting firing beam (82) proximally during a firing stroke. In other words, manual return switch (116) or the mechanical return feature may be actuated when firing beam (82) has only been partially advanced distally.

In some versions, one or more of switches (26, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 10:
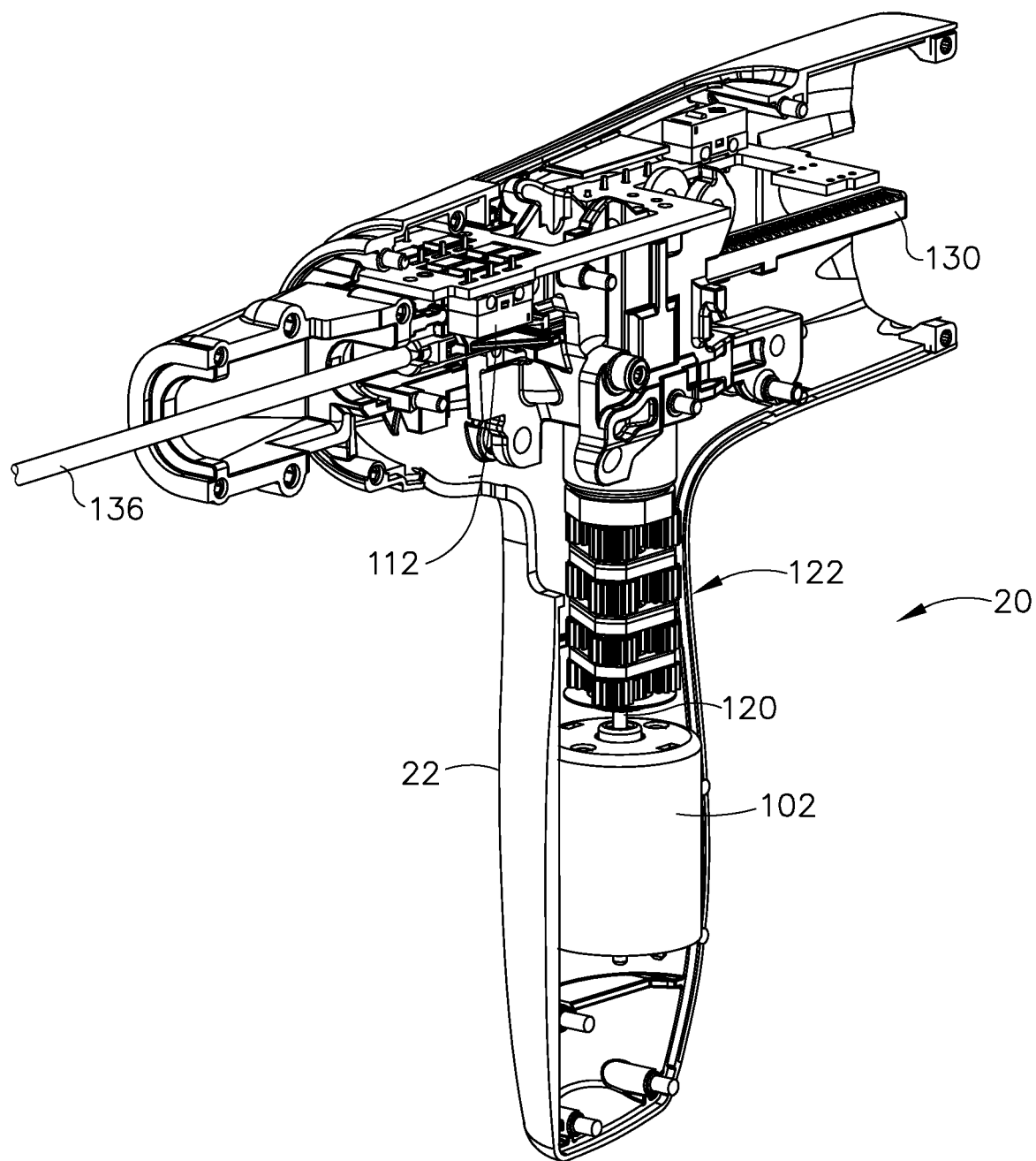
FIG. 10 depicts a perspective view of the handle assembly of the instrument of FIG. 1, with a housing half and some internal components removed.
Figure 11:
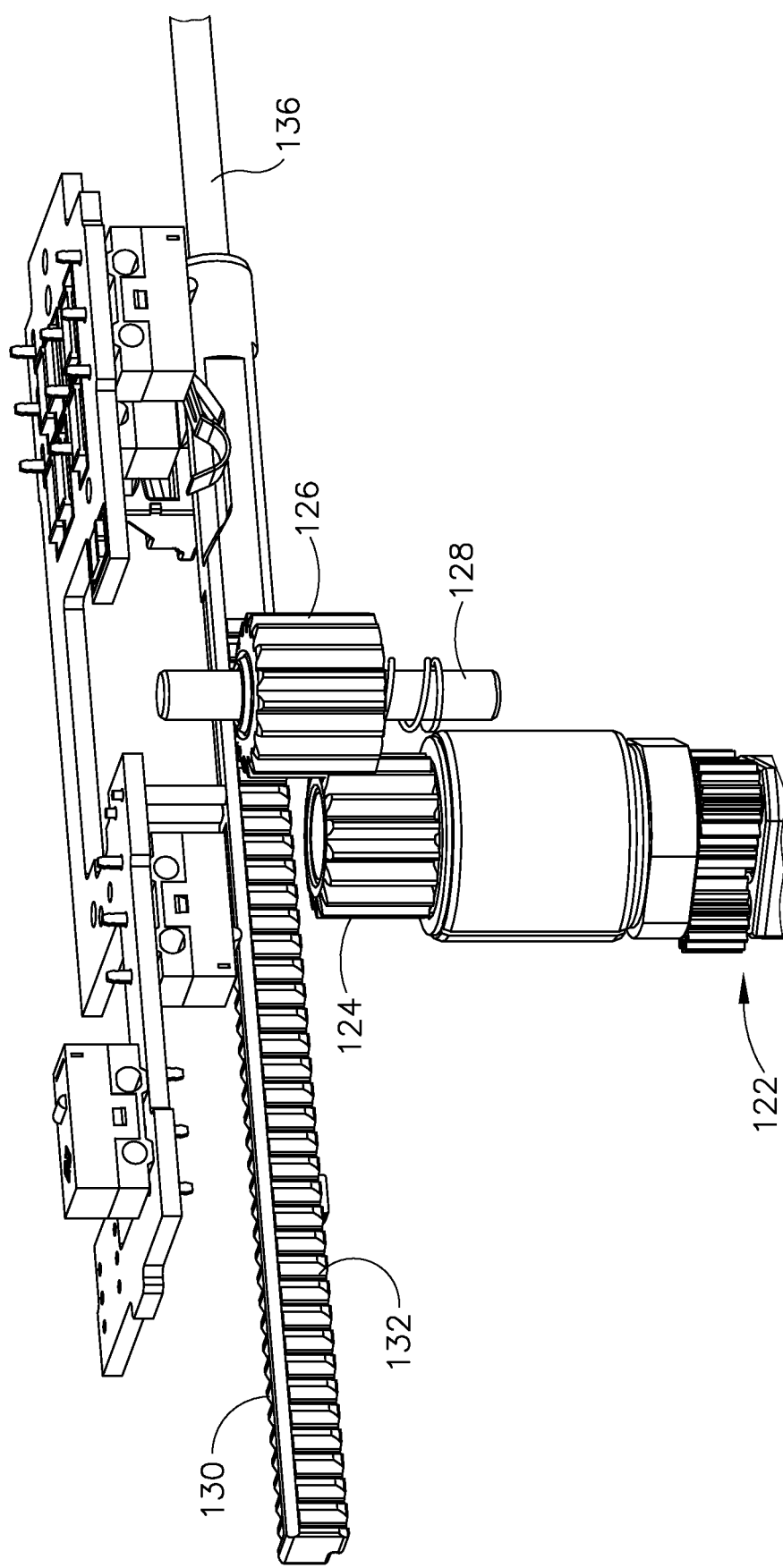
FIG. 11 depicts a perspective view of drive assembly components from the handle assembly of FIG. 10.

FIG. 10 shows motor (102) positioned within pistol grip (22) of handle assembly (20). Alternatively, motor (102) may be positioned elsewhere within handle assembly (20). Motor (102) has a drive shaft (120) that is coupled with a gear assembly (122). Thus, when motor (102) is activated, drive shaft (120) actuates gear assembly (122). As shown in FIG. 11, gear assembly (122) is in communication with a drive gear (124), which meshes with an idler pinion (126). Pinion (126) is disposed on a shaft (128) that is supported within handle assembly (20) and that is oriented parallel to drive shaft (120) of motor (102). Pinion (126) is further engaged with a rack member (130). In particular, pinion (126) meshes with teeth (132) at the proximal end of rack member (130). Rack member (130) is slidably supported in handle assembly (20). It should be understood from the foregoing that, when motor (102) is activated, the corresponding rotation of drive shaft (120) is communicated to pinion (126) via gear assembly (122), and the corresponding rotation of pinion (126) is converted to translation of rack member (130) by teeth (132). As shown in FIGS. 10-12, an elongate member (136) extends distally from rack member (130). As shown in FIG. 12, a coupling member (138) joins firing beam (82) with elongate member (136). Rack member (130), elongate member (136), coupling member (138), firing beam (82), and knife member (80) all translate together relative to handle assembly (20) in response to activation of motor (102). In other words, activation of motor (102) ultimately causes firing beam (82) to translate longitudinally, the direction of such translation depending on the direction of rotation of drive shaft (120).

It should be understood that a distal portion of elongate member (136), coupling member (138), and firing beam (82) extend through shaft assembly (130). A portion of firing beam (82) also extends through articulation section (34). In some versions, rack member (130), elongate member (136), and coupling member (138) are all substantially straight and rigid; while firing beam (82) has sufficient flexibility to bend at articulation section (34) and translate longitudinally through articulation section (34) when articulation section (34) is in a bent or articulated state.

In addition to or in lieu of the foregoing, the features operable to drive firing beam (82) may be configured in accordance with at least some of the teachings of U.S. Pat. No. 8,453,914, the disclosure of which is incorporated by reference herein. Other suitable components, features, and configurations for providing motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be actuated in accordance with at least some of the teachings of any other reference cited herein.

Figure 8:
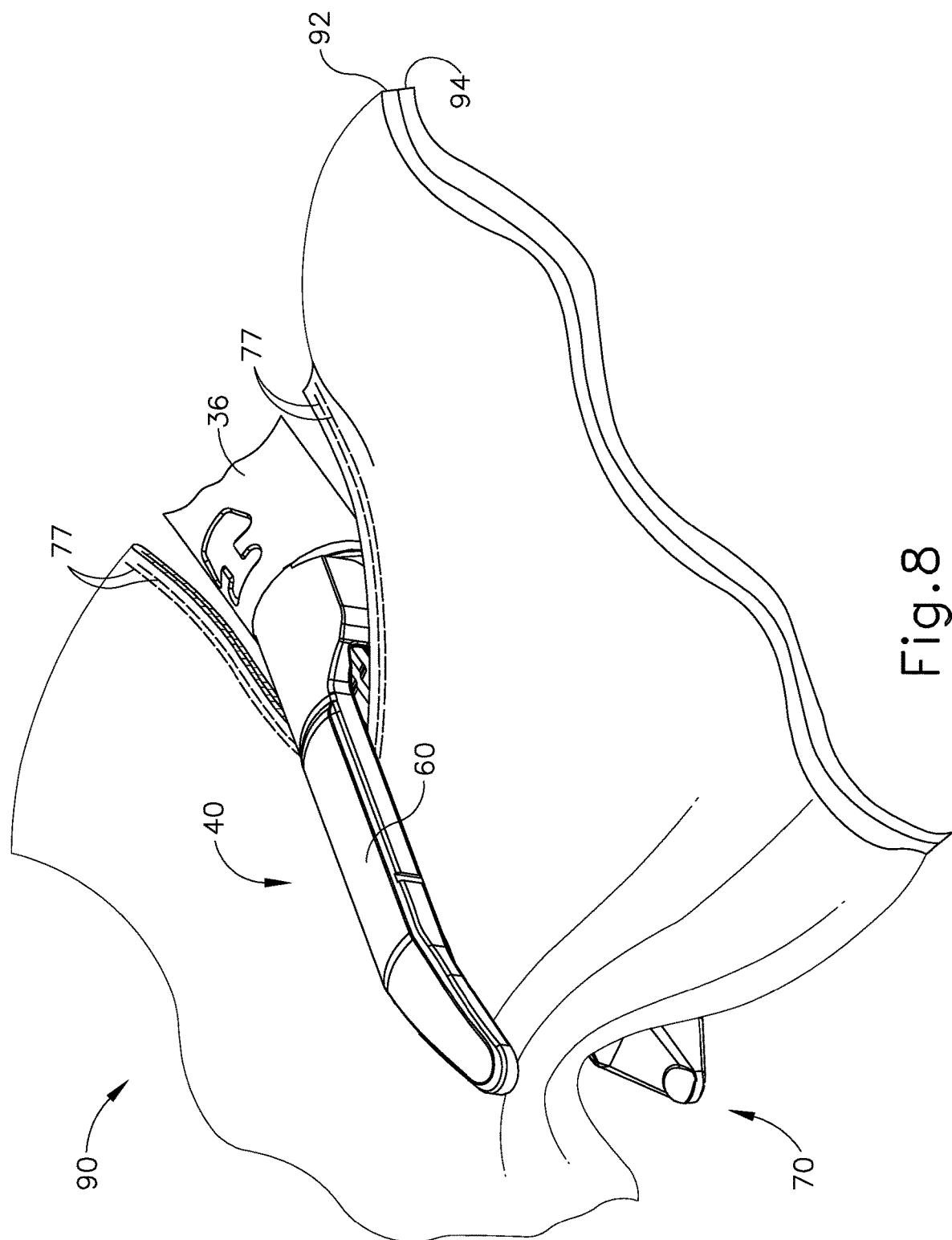
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector Lockout Features

In some instances, it may be desirable to provide a lockout feature for end effector (40) to prevent inadvertent firing (i.e. distal advancement) of firing beam (82) and cutting edge (84) so that tissue positioned between anvil (60) and lower jaw (50) is not severed without being stapled. For example, it may be desirable to prevent firing beam (82) and cutting edge (84) from firing if a staple cartridge (70) has not been loaded within end effector (40) or after staples (77) have been driven from staple cartridge (70). Accordingly, lockout features may be provided within end effector (40) to prevent inadvertent firing of firing beam (82) and cutting edge (84). The examples below include several merely illustrative versions of lockout features that may be readily introduced to an end effector (40).

FIG. 13 shows an exemplary end effector (240) that may be readily incorporated into instrument (10). End effector (240) comprises a lower jaw (250), a pivotable anvil (260), and a closure ring (236), which are similar to lower jaw (50), anvil (60), and closure ring (36) of end effector (40). A staple cartridge (270) may be removably installed into a channel of lower jaw (250). Staple cartridge (270) of the present example is similar to staple cartridge (70) of end effector (40). Staple cartridge (270) comprises a cartridge body (271) that is coupled with a lower cartridge tray (276). A wedge sled (278) and a plurality of staple drivers (275) are captured between cartridge body (271) and tray (276), with wedge sled (278) being located proximal to staple drivers (275). Wedge sled (278) is slidably disposed within a channel (269) of cartridge body (271). Although staples, similar to staples (47), have been omitted from FIG. 13 for clarity, it should be understood that staples (277) would be positioned directly above staple drivers (275). Wedge sled (278) and staple drivers (275) are similar to wedge sled (78) and staple drivers (75) of end effector (40) such that wedge sled (278) is configured to urge staple drivers (275) upwardly as wedge sled (278) is driven distally through channel (269) of staple cartridge (270) to drive staples (not shown in FIG. 13) vertically and into tissue positioned between anvil (260) and lower jaw (250). Wedge sled (278) of the present example is driven distally by a translating knife member (280), which is positioned proximally of wedge sled (278). A firing beam (282) is coupled to knife member (280) (e.g., by welding). Firing beam (282) is similar to firing beam (82) and is configured to drive knife member (280) distally and/or proximally. A resilient member (210) is proximal of knife member (280) and is configured to removably engage knife member (280). Knife member (280) and resilient member (210) are positioned within a frame member (238). Frame member (238) is positioned within closure ring (236) and coupled to a proximal end of lower jaw (250) such that frame member (238) couples with articulation section (234) of shaft assembly (230).

Articulation section (234) and shaft assembly (230) are similar to articulation section (34) and shaft assembly (30). By way of example only, articulation section (234) and/or shaft assembly (230) may be constructed in accordance with at least some of the teachings of U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015, the disclosure of which is incorporated by reference herein; and/or U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017, the disclosure of which is incorporated by reference herein. Alternatively, articulation section (234) and/or shaft assembly (230) may have any other suitable configurations.

Figure 14:
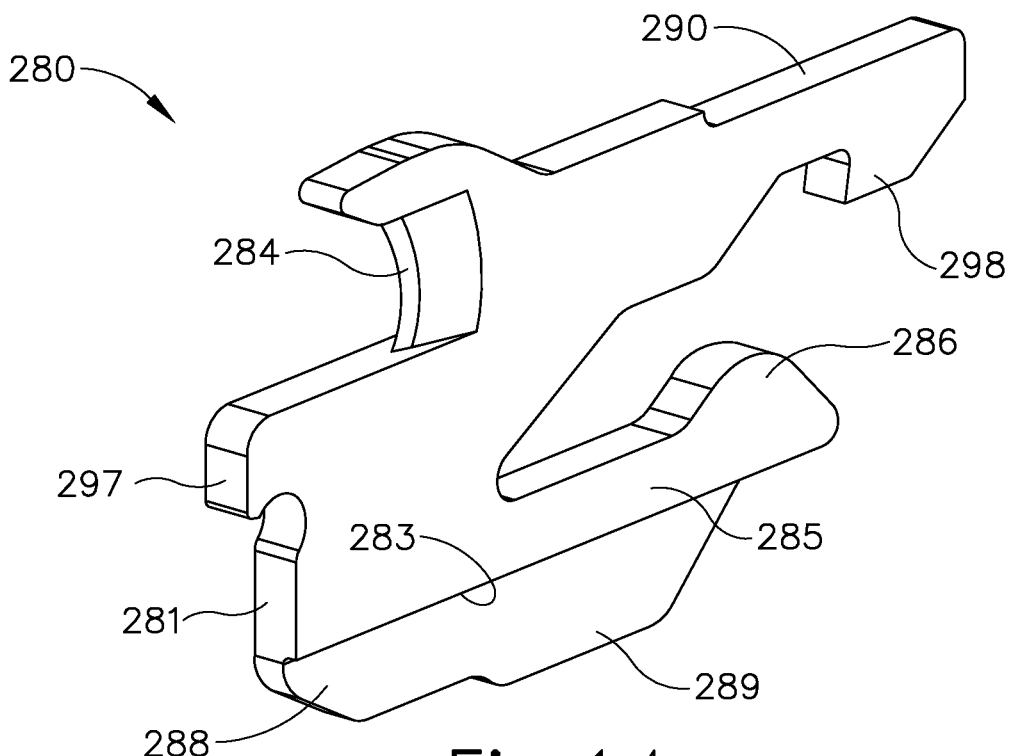
FIG. 14 depicts a perspective view of an exemplary blade of the end effector of FIG. 13.
Figure 15:
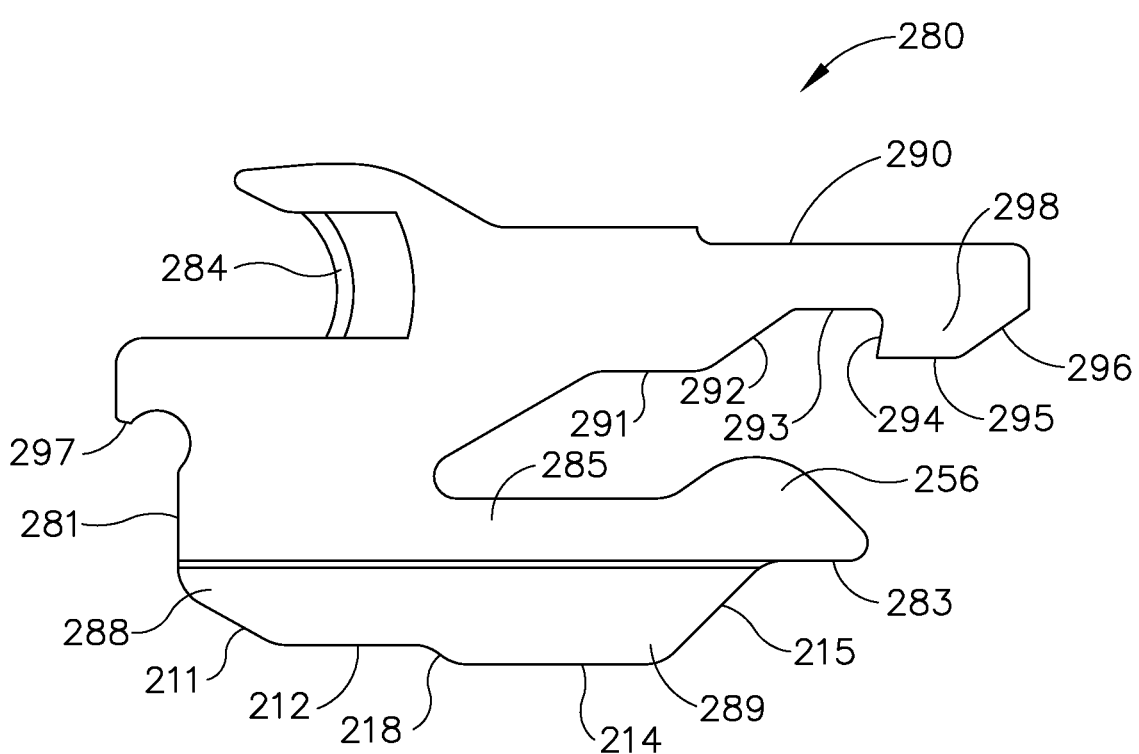
FIG. 15 depicts a side view of the blade of FIG. 14.

FIGS. 14-15 show knife member (280) in more detail. Knife member (280) comprises a cutting edge (284), an upper extension (290), and a lower extension (285). Cutting edge (284) is positioned on an upper distal portion of knife member (280) such that cutting edge (284) severs tissue as knife member (280) translates distally through lower jaw (250). Upper extension (290) extends proximally from cutting edge (284). Upper extension (290) comprises walls (291, 292, 293, 294, 295, 296) on a bottom surface of upper extension (290). Wall (291) extends proximally to wall (292). Wall (292) ramps upwardly to wall (293). Wall (293) extends proximally to wall (294), which extends downwardly to wall (295). Walls (292, 293, 294) together form a notch. Wall (295) extends proximally to wall (296), which ramps upwardly. Walls (294, 295, 296) form tab (298) that extends downwardly from upper extension (290). Tab (298) is configured to engage frame member (238) such that frame member (238) may prevent tab (298) and knife member (280) from advancing distally without a loaded staple cartridge (270), as will be described in greater detail below.

Lower extension (285) extends proximally from underneath cutting edge (284). A distal tip (297) and a distal wall (281) are positioned on a distal portion of lower extension (285). Distal tip (297) extends distally and downwardly from lower extension (285) such that distal tip (297) is configured to engage a top surface of wedge sled (278), as will be described in greater detail below. Distal wall (281) is vertically positioned on the distal portion of lower extension (285) beneath distal tip (297) such that distal wall (281) is configured to engage a proximal surface of wedge sled (278), as will also be described in greater detail below. Accordingly, distal tip (297) and distal wall (281) releasably engage wedge sled (278) when knife member (280) is translated distally within lower jaw (250) to thereby drive wedge sled (278) distally within lower jaw (250). A rounded tab (286) extends upwardly from a proximal portion of lower extension (285). Tab (286) is configured to engage resilient member (280) such that resilient member (280) may bias tab (286) and knife member (280) downwardly such that tab (286) of knife member (280) engages frame member (238) to prevent tab (286) and knife member (280) from advancing distally without a loaded staple cartridge (270).

Figure 17:
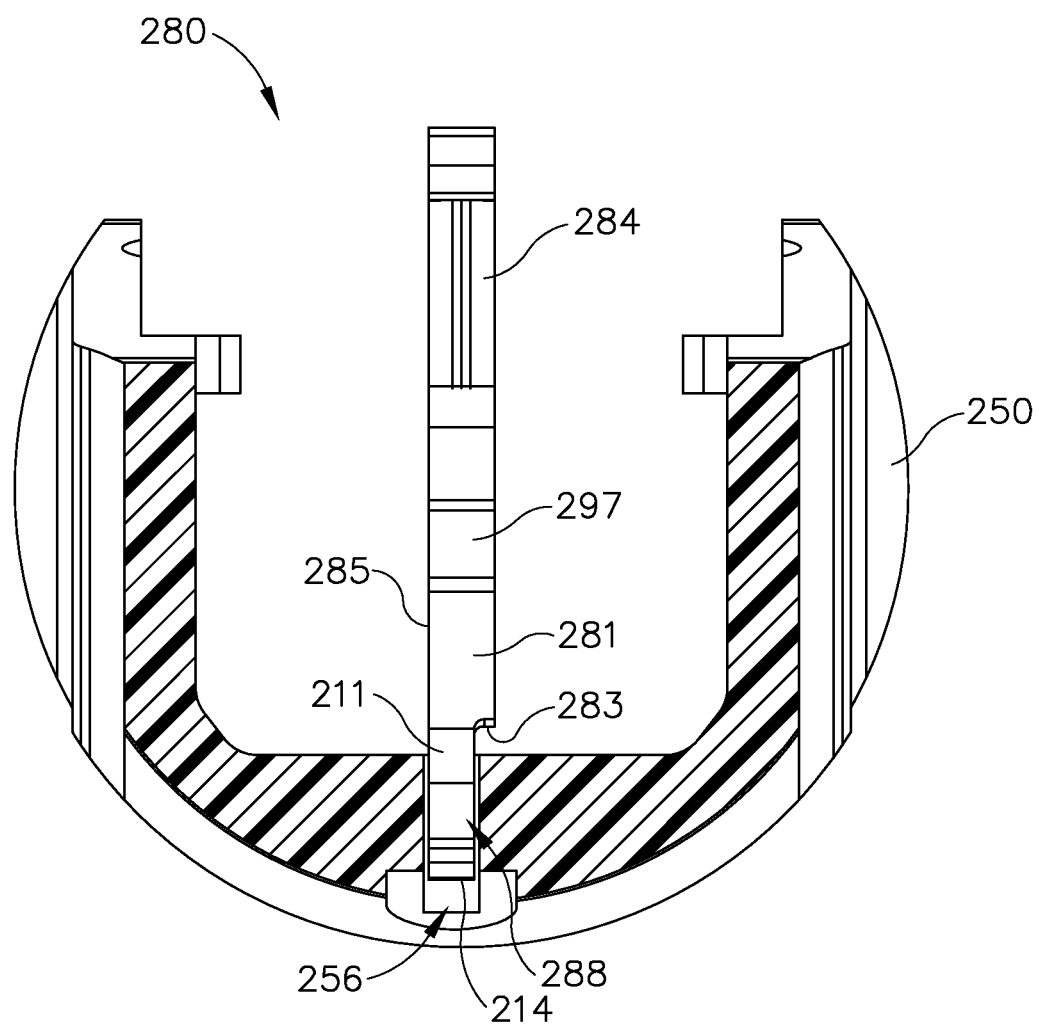
FIG. 17 depicts an end view of the blade of FIG. 14 positioned in a slot of the stationary jaw of FIG. 16.

A protrusion (288) extends downwardly from lower extension (285) and is configured to translate within a slot (256) of lower jaw (250). Protrusion (288) is not as wide as lower extension (285) such that a shelf (283) is formed between protrusion (288) and lower extension (285) on a bottom surface of lower extension (285). Accordingly, shelf (283) retains knife member (280) in a vertical position within slot (256) of lower jaw (250), as best seen in FIG. 17. Shelf (283) creates a retention method without the need for added or extended portions beyond the overall thickness of knife member (280). Protrusion (288) comprises a ramped wall (211) sloping toward wall (212). Wall (212) extends proximally to wall (218), which ramps downwardly to wall (214). Wall (214) extends proximally to wall (215) that ramps upwardly to lower extension (285). Walls (218, 214, 215) form tab (289) that extends downwardly from protrusion (288).

Figure 16:
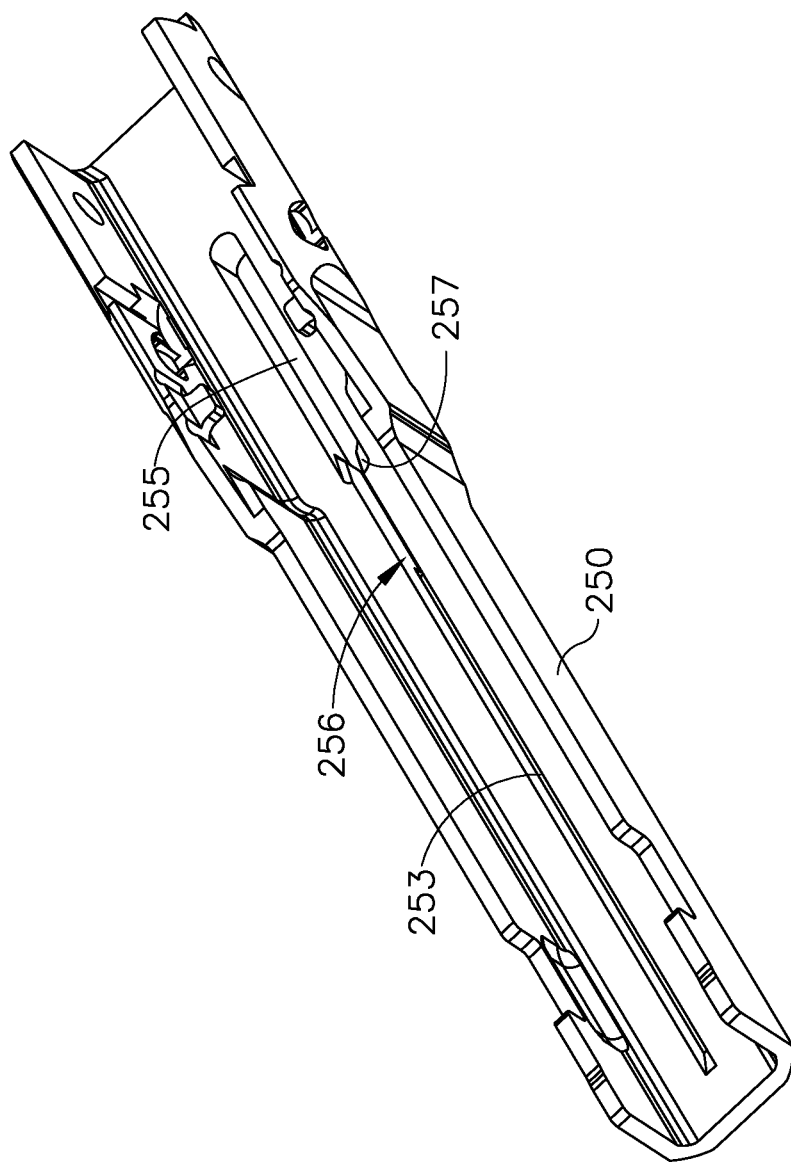
FIG. 16 depicts a perspective view of an exemplary stationary jaw of the end effector of FIG. 13.

Knife member (280) is configured to translate proximally and/or distally within lower jaw (250), based on the actuation of firing trigger (26) to drive motor (102) and firing beam (282). As shown in FIG. 16, lower jaw (250) comprises a slot (256) with a proximal portion (255) and a distal portion (253). Proximal portion (255) is wider than distal portion (253). Proximal portion (255) transitions to distal portion (253) via camming surface (257). FIG. 17 shows knife member (280) positioned within slot (256) of lower jaw (250) when knife member (280) is at a proximal, unfired position. Slot (256) receives protrusion (288) of knife member (280) such that protrusion (288) translates within slot (256) of lower jaw (250). Lower extension (285) is positioned above slot (256). Distal portion (253) of slot (256) has a lateral width sized to correspond to the lateral width of protrusion (288) such that shelf (283) extends laterally past distal portion (253) of slot (256) to maintain the vertical alignment or position of knife member (280) when knife member (280) is positioned within distal portion (253) of slot (256). Proximal portion (255) of slot (256) has a lateral width sized to correspond to the lateral width of lower extension (285) of knife member (280) such that protrusion (288) and lower extension (285) may fall within proximal portion (255) of slot (256) if knife member (280) is advanced without a loaded staple cartridge (270).

Figure 22:
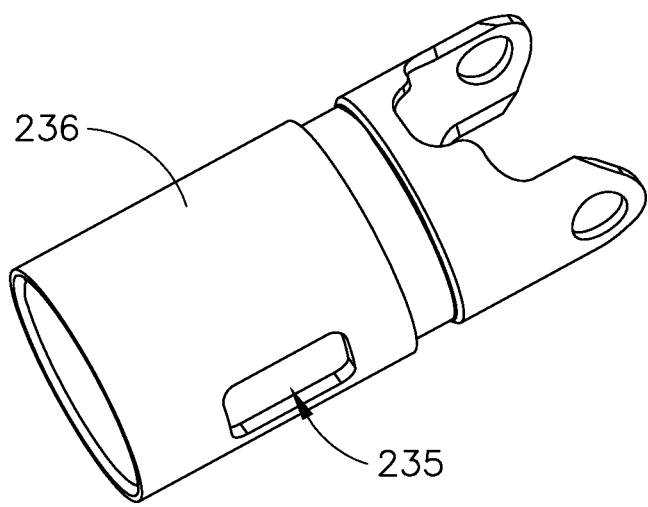
FIG. 22 depicts a perspective view of an exemplary closure ring of the end effector of FIG. 13.

Slot (256) extends continuously within lower jaw (250) to allow for the visualization of the position of knife member (280) within lower jaw (250) as knife member (280) translates proximally and/or distally. Closure ring (236) is coupled to lower jaw (250) to further allow for visualization of knife member (280). In the present example, closure ring (236) comprises an opening (235), as shown in FIG. 22. Closure ring (236) is slidably coupled with lower jaw (250) such that opening (235) is adjacent to proximal portion (255) of slot (256) when closure ring (236) is advanced to a distal position to close anvil (260) against lower jaw (250). Opening (235) is sized to correspond to tab (289) of knife member (280) such that closure ring (236) allows for visualization of tab (289) if protrusion (288) and lower extension (285) fall within proximal portion (255) of slot (256).

Figure 18:
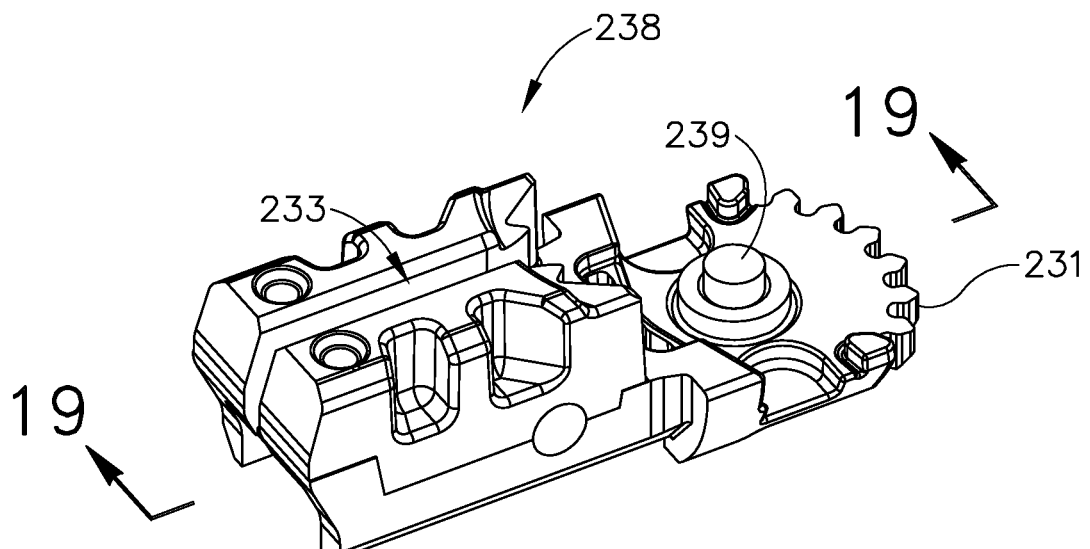
FIG. 18 depicts a perspective view of an exemplary lockout feature of the end effector of FIG. 13.
Figure 19:
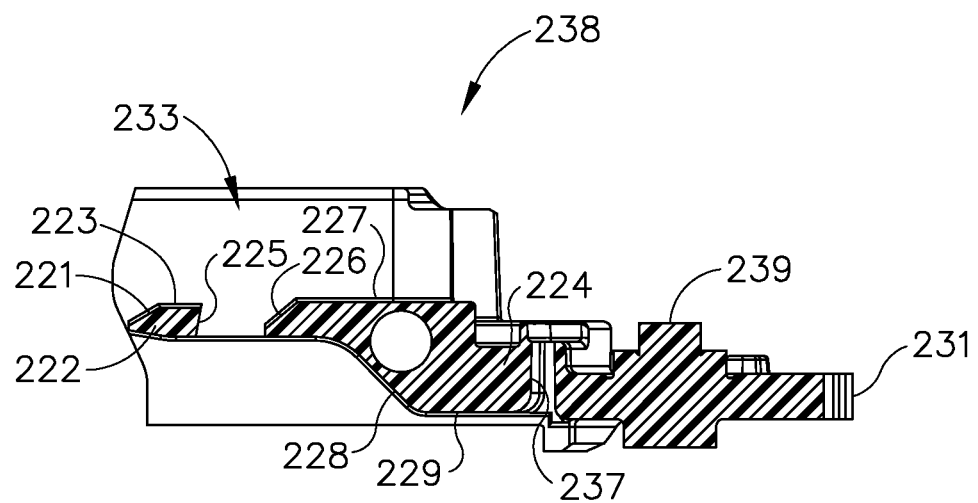
FIG. 19 depicts a cross sectional view of the lockout of feature of FIG. 18 taken along line 19-19 of FIG. 18.
Figure 23A:
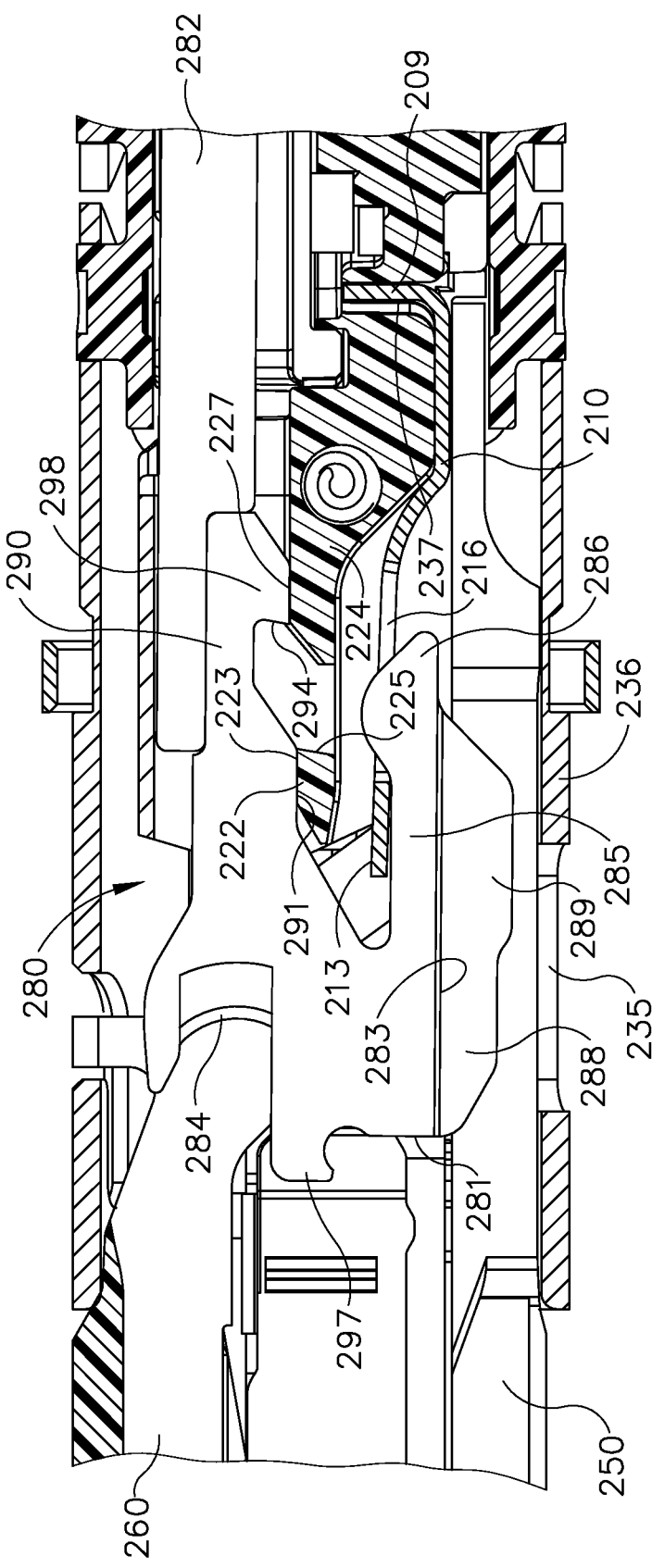
FIG. 23A depicts a side cross sectional view of the end effector of FIG. 13 in an initial position.

The proximal end of lower jaw (250) is coupled with frame member (238), shown in FIGS. 18-19. Frame member (238) comprises a channel (233), a pivot (239), and gear (231). A first engagement feature (222) and a second engagement feature (224) are positioned within channel (233), as shown in FIG. 19. Engagement features (222, 224) are configured to engage upper extension (290) of knife member (280). First engagement feature (222) comprises a wall (225) extending upwardly within channel (233). Wall (225) transitions to wall (223), which extends distally to wall (221). Wall (221) slopes downwardly in the distal direction. Second engagement feature (224) is proximal to first engagement feature (222). The top surface of second engagement feature (224) comprises a wall (227) extending distally to wall (226), which slopes downwardly in the distal direction. The bottom surface of second engagement feature (224) comprises a wall (228) sloping downwardly in the proximal direction to wall (229). Wall (229) extends proximally to wall (237), which extends upwardly from wall (229). The bottom surface of second engagement feature (224) is configured to engage resilient member (210), as shown in FIG. 23A. Gear (231) has teeth and is proximal to engagement feature (224). Pivot (239) extends upwardly from gear (231). Pivot (239) and gear (231) are configured to rotatably couple with articulation section (234) of shaft assembly (220) to allow end effector (240) to pivot to a desired angle (a) relative to shaft assembly (220). By way of example only, gear (231) and/or other features of articulation section (234) may be constructed in accordance with at least some of the teachings of U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015, the disclosure of which is incorporated by reference herein; and/or U.S. application Ser. No. 13/780,162, entitled "Surgical Instrument with Articulation Lock Having a Detenting Binary Spring," filed Feb. 28, 2013, issued as U.S. Pat. No. 9,867,615 on Jan. 16, 2018, the disclosure of which is incorporated by reference herein.

Figure 20:
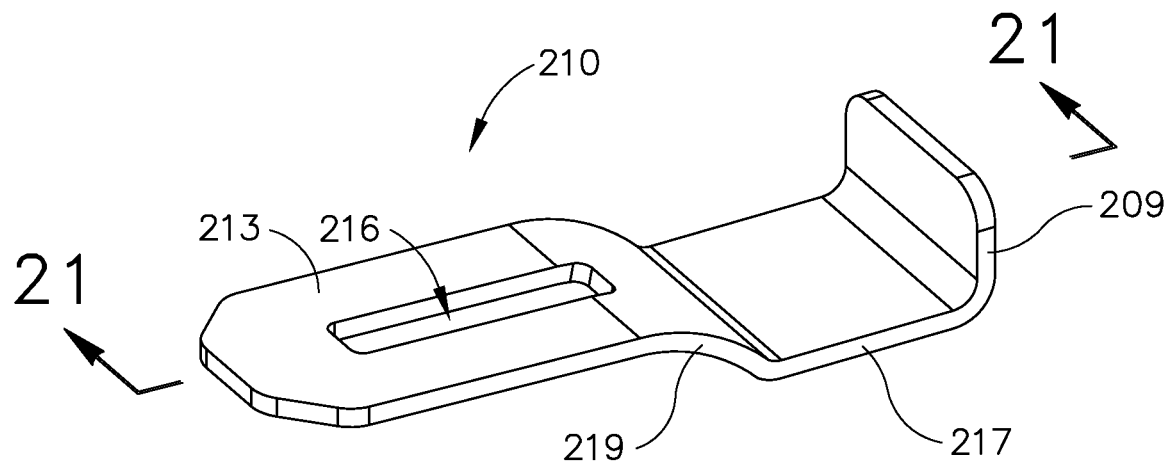
FIG. 20 depicts a perspective view of an exemplary spring of the end effector of FIG. 13.
Figure 21:
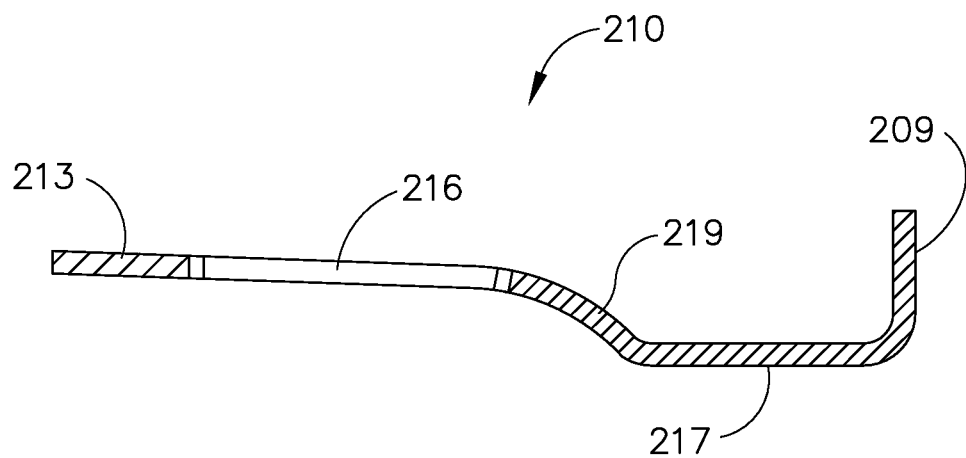
FIG. 21 depicts a cross sectional view of the spring of FIG. 20 taken along line 21-21 of FIG. 20.

FIGS. 20-21 show resilient member (210) in greater detail. Resilient member (210) comprises a distal portion (213) and a proximal portion (285). Distal portion (213) comprises an opening (216) that is configured to receive tab (286) of lower extension (285) of knife member (280). Distal portion (213) transitions to proximal portion (217) via ramped portion (219) that slopes downwardly in the proximal direction. Ramped portion (219) is compliant and is configured to resiliently bias distal portion (282) downwardly. A wall (209) extends upwardly from the proximal end of proximal portion (217). Wall (209) engages wall (237) of frame member (238) such that frame member (238) is configured to axially retain resilient member (210).

A. Exemplary Lockout Sequence

Figure 23B:
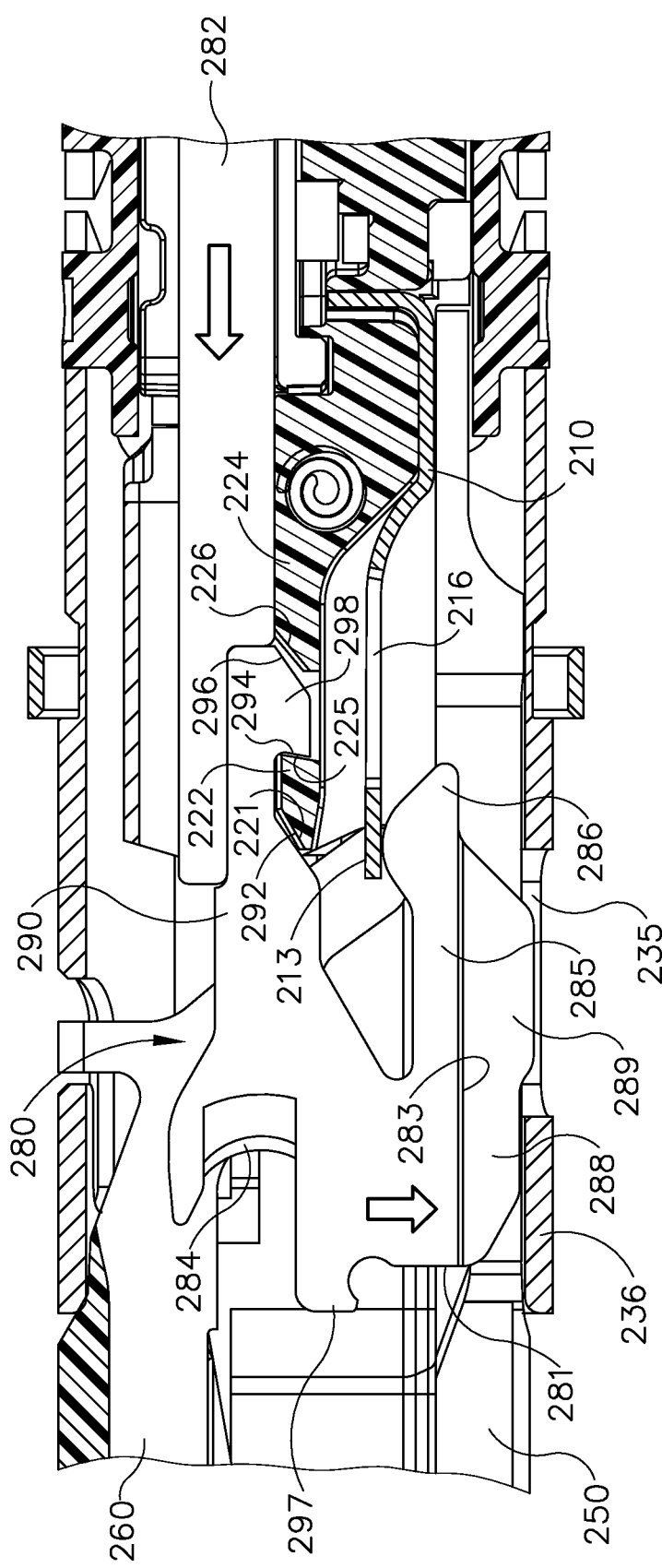
FIG. 23B depicts a side cross sectional view of the end effector of FIG. 13 in a lockout position.

FIGS. 23A-23B show an attempt at firing knife member (280) without a properly loaded staple cartridge (270). For instance, instrument (10) may be inserted to a surgical site in a nonarticulated state, with anvil (260) and lower jaw (250) closed. Once articulation section (234) and end effector (240) are inserted to the desired site within the patient, anvil (260) may be pivoted away from lower jaw (250) to the open end effector (240) such that anvil (260) and lower jaw (250) may be positioned about tissue. Articulation section (234) may be remotely articulated by articulation control knob (35), such that end effector (240) may be deflected to a desired angle (a). Closure trigger (24) may then be actuated toward pistol grip (22) to cause the closing of anvil (260) toward lower jaw (250). Such closing of anvil (260) is provided through a closure tube (32) and closure ring (236), which both longitudinally translate relative to handle portion (20) and lower jaw (250) in response to pivoting of closure trigger (24) relative to pistol grip (22). Articulation section (234) is operable to communicate longitudinal movement from closure tube (32) to closure ring (236).

FIG. 23A shows end effector (240) in an initial position just after anvil (260) and lower jaw (250) are closed, but without staple cartridge (270) in lower jaw (250). In the initial position, upper extension (290) of knife member (280) is positioned above engagement features (222, 224) of frame member (238). Wall (291) of upper extension (290) is resting on wall (223) of first engagement feature (222), while tab (298) of upper extension (290) is resting on wall (227) of second engagement feature (224). Resilient member (210) is positioned between lower jaw (250) and frame member (238). Wall (287) of resilient member (210) is engaged with wall (237) of frame member (238) such that wall (237) is configured to axially retain resilient member (210). Opening (216) of resilient member (210) is positioned above lower extension (285) of knife member (280) such that tab (286) of lower extension (285) is positioned within opening (216) of resilient member (210). Protrusion (288) of lower extension (285) is positioned within proximal portion (255) of slot (256) of lower jaw (250). Protrusion (288) is vertically aligned within slot (256) such that shelf (283) is positioned above slot (256). Accordingly, knife member (280) is ready to be fired in from the initial position.

However, in the present example, a staple cartridge (270) was not properly loaded in end effector (240). Accordingly, distal tip (297) and distal wall (281) are not engaged with a sled (278). When firing trigger (26) is actuated to drive firing beam (282) and knife member (280) distally without a properly loaded staple cartridge (270), knife member (280) falls downwardly within end effector (240) to engage engagement features (222, 224) of frame member (238) to prevent knife member (280) from travelling further distally within lower jaw (250), as shown in FIG. 23B. As knife member (280) is pushed distally without a properly loaded staple cartridge (270), tab (286) of lower extension (285) of knife member (280) translates distally from opening (216) of resilient member (210). Tab (286) then engages distal portion (213) of resilient member (210). Because distal portion (213) of resilient member (210) is biased downwardly, resilient member (210) pushes tab (286) of knife member (280) downward. This causes tab (298) of upper extension (290) of knife member (280) to fall downwardly between engagement features (222, 224). Accordingly, wall (294) of tab (298) engages wall (225) of first engagement feature (222) to prevent knife member (280) from travelling any further distally to lock knife member (280) within end effector (240). It should be understood that the foregoing lockout may also occur when an operator intends to advance firing beam (282) from a proximal position to a distal position when a spent staple cartridge (270) is loaded in end effector. The lockout features thus prevent advancement of firing beam (282) when no staple cartridge (270) is loaded in end effector (240); and when a cartridge (270) that is in end effector (240) has already been fired and firing beam (282) has been retracted back to a proximal position.

Figure 24A:
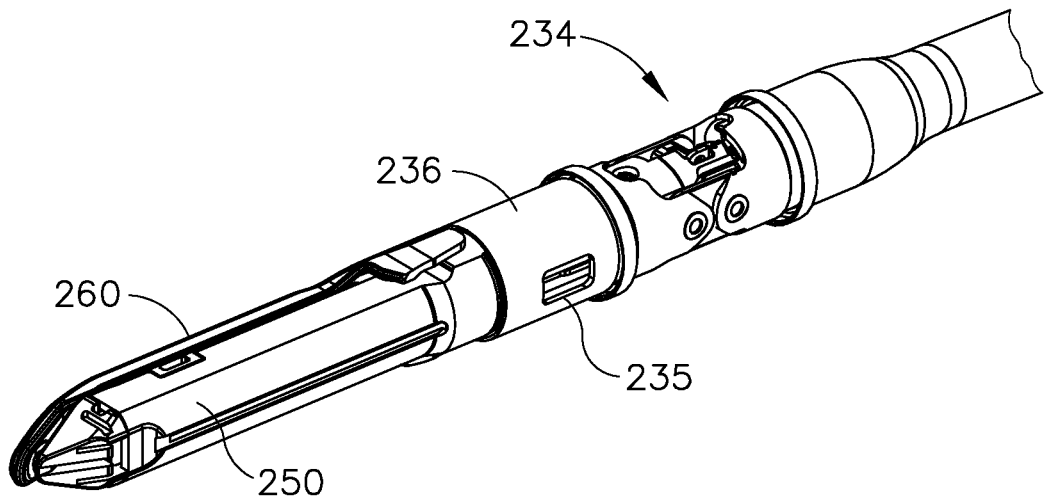
FIG. 24A depicts a bottom perspective view of the end effector of FIG. 13 in the initial position.
Figure 24B:
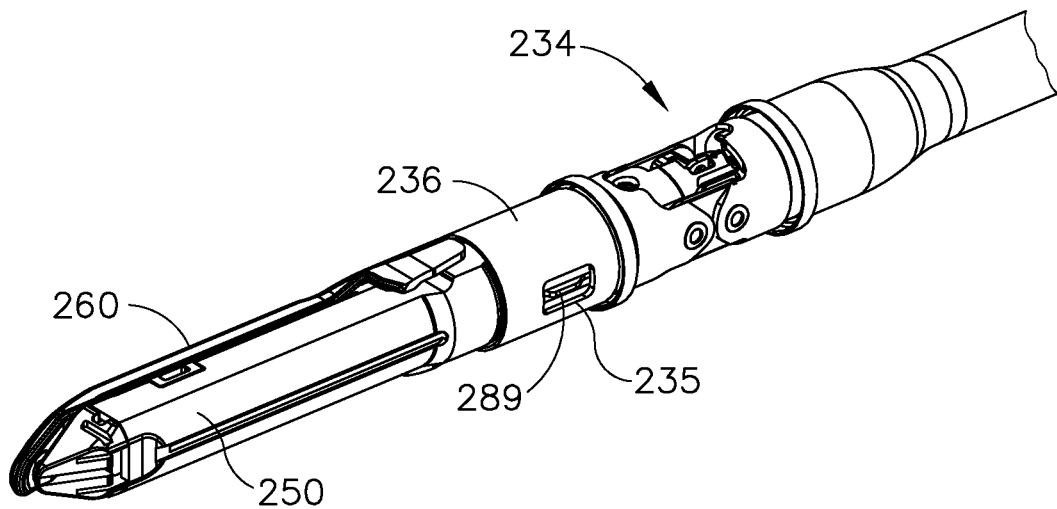
FIG. 24B depicts a bottom perspective view of the end effector of FIG. 13 in the lockout position.

As knife member (280) falls downwardly to the locked position shown in FIG. 23B, lower extension (285) and protrusion (288) of knife member (280) fall within proximal portion (255) of slot (256) of lower jaw (250). Accordingly, tab (289) of protrusion (288) extends through proximal portion (255) of slot (256) and through opening (235) of closure ring (236). This provides a visual indication that knife member (280) is in the lockout position, as shown in FIGS. 24A-24B. In FIG. 24A, knife member (280) is in the initial position such that tab (289) is positioned within slot (256) above opening (235) of closure ring (236). When knife member (280) falls downwardly to the lockout position, as shown in FIG. 24B, tab (289) extends through opening (235) of closure ring (236) to provide a visual indication of lockout. By providing lockout features and visual indications within the space of closure ring (236), the overall length of articulation section (234) may be minimized.

Knife member (280) may be returned to the initial position of FIG. 23A after knife member (280) is in the lockout position of FIG. 23B. For instance, motor (102) may be activated to pull firing beam (282) and knife member (280) proximally to return knife member (280) to the initial position of FIG. 23A. As knife member (280) translates proximally, ramped walls (292, 296) of upper extension (290) of knife member (280) slide proximally against ramped walls (221, 226) of engagement features (222, 224). As upper extension (290) translates proximally against engagement features (222, 224), walls (221, 226) of engagement features (222, 224) push upper extension (290) and knife member (280) upwardly through a camming action. Tab (286) of knife member (280) also travels upwardly to again be positioned within opening (216) of resilient member (210). This returns knife member (280) to the initial position, as shown in FIG. 23A.

B. Exemplary Firing Sequence

FIGS. 25A-25F show knife member (280) being fired with a properly loaded staple cartridge (270). For instance, instrument (10) may be inserted to a surgical site in a nonarticulated state, with anvil (260) and lower jaw (250) closed. Once articulation section (234) and end effector (240) are inserted to the desired site within the patient, anvil (260) may be pivoted away from lower jaw (250) to the open end effector (240) such that anvil (260) and lower jaw (250) may be positioned about tissue. Articulation section (234) may be remotely articulated by articulation control knob (35), such that end effector (240) may be deflected to a desired angle (a). Closure trigger (24) may then be actuated toward pistol grip (22) to cause the closing of anvil (260) toward lower jaw (250). Such closing of anvil is provided through closure tube (32) and closure ring (236), which both longitudinally translate relative to handle portion (20) and lower jaw (250) in response to pivoting of closure trigger (24) relative to pistol grip (22). Articulation section (234) is operable to communicate longitudinal movement from closure tube (32) to closure ring (236).

Figure 25A:
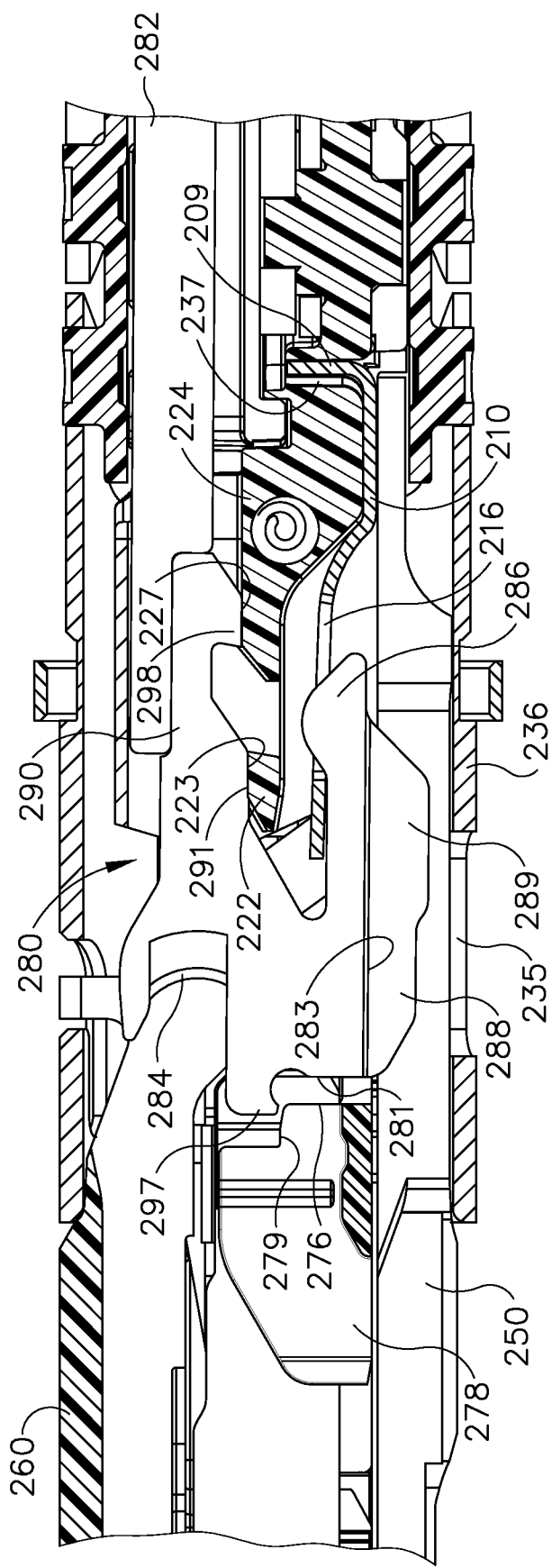
FIG. 25A depicts a side cross sectional view of the end effector of FIG. 13 in the initial position with a loaded cartridge.

FIG. 25A shows end effector (240) in an initial position just after anvil (260) and lower jaw (250) are closed with a properly loaded staple cartridge (270). In the initial position, upper extension (290) of knife member (280) is positioned above engagement features (222, 224) of frame member (238). Wall (291) of upper extension (290) is resting on wall (223) of first engagement feature (222), while tab (298) of upper extension (290) is resting on wall (227) of second engagement feature (224). Resilient member (210) is positioned between lower jaw (250) and frame member (238). Wall (209) of resilient member (210) is engaged with wall (237) of frame member (238) such that wall (237) is configured to axially retain resilient member (210). Opening (216) of resilient member is positioned above lower extension (285) of knife member (280) such that tab (286) of lower extension (285) is positioned within opening (216) of resilient member (210). Protrusion (288) of lower extension (285) is positioned within proximal portion (255) of slot (256) of lower jaw (250). Protrusion (288) is vertically aligned within slot (256) such that shelf (283) is positioned above slot (256). Distal tip (297) of knife member (280) is positioned above sled (278). Accordingly, knife member (280) is ready to be fired in from the initial position shown in FIG. 25A.

Figure 25B:
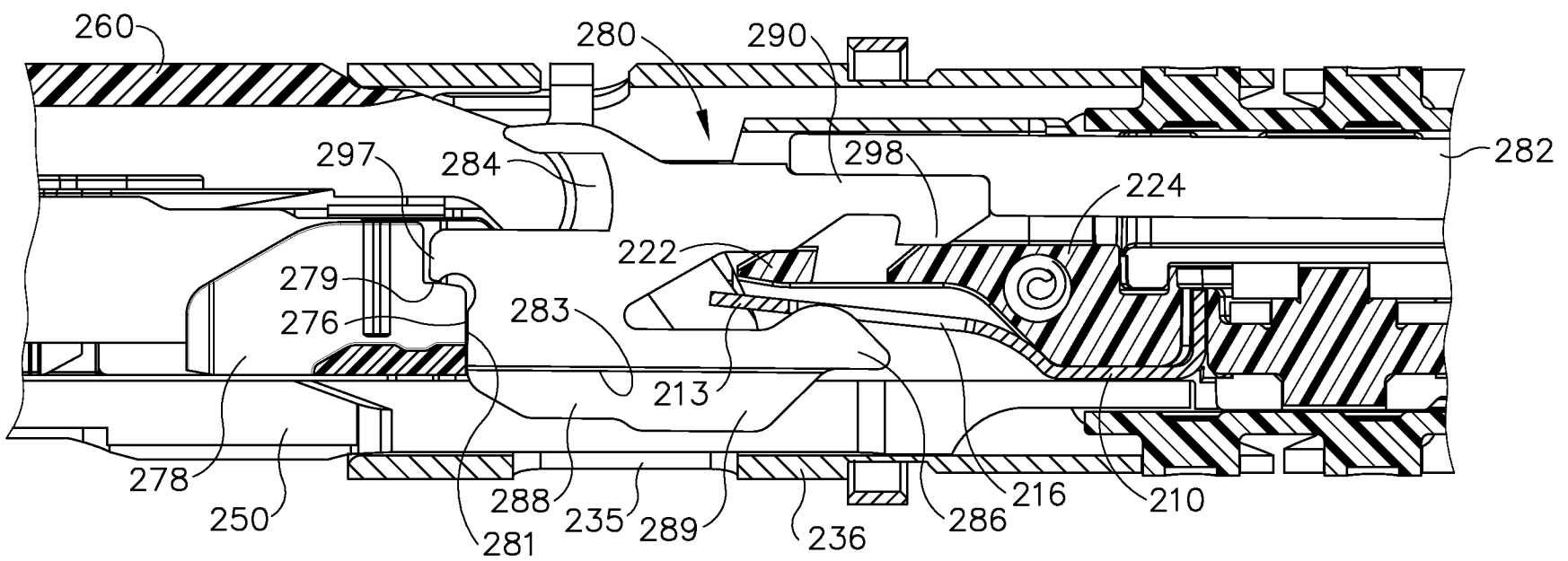
FIG. 25B depicts a side cross sectional view of the end effector of FIG. 13 in a first partially fired position with a loaded cartridge.
Figure 25C:
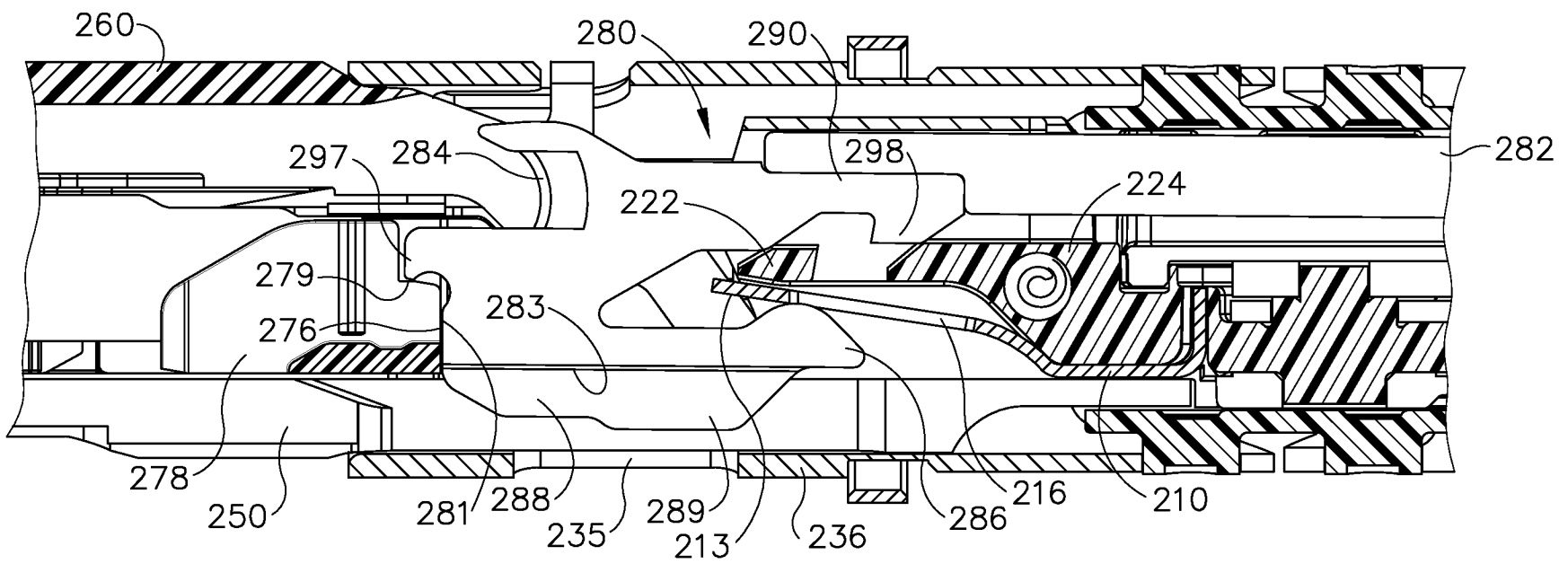
FIG. 25C depicts a side cross sectional view of the end effector of FIG. 13 in a second partially fired position with a loaded cartridge.
Figure 25D:
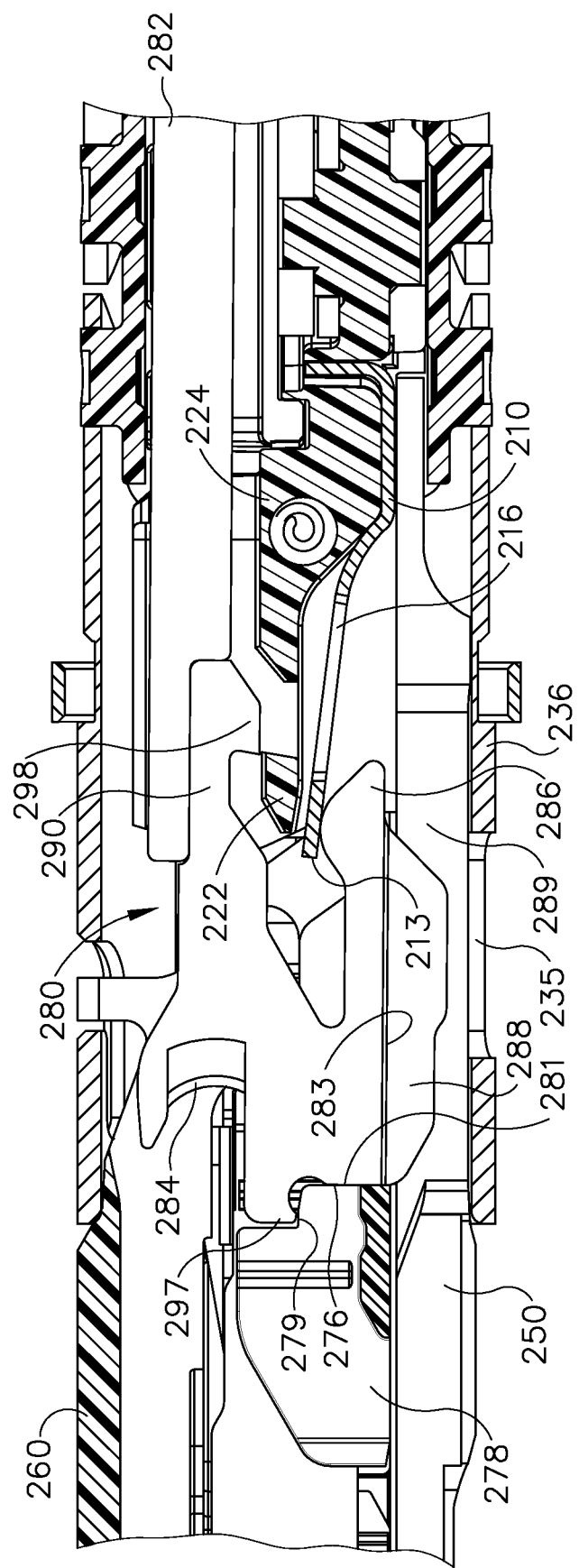
FIG. 25D depicts a side cross sectional view of the end effector of FIG. 13 in a third partially fired position with a loaded cartridge.
Figure 25E:
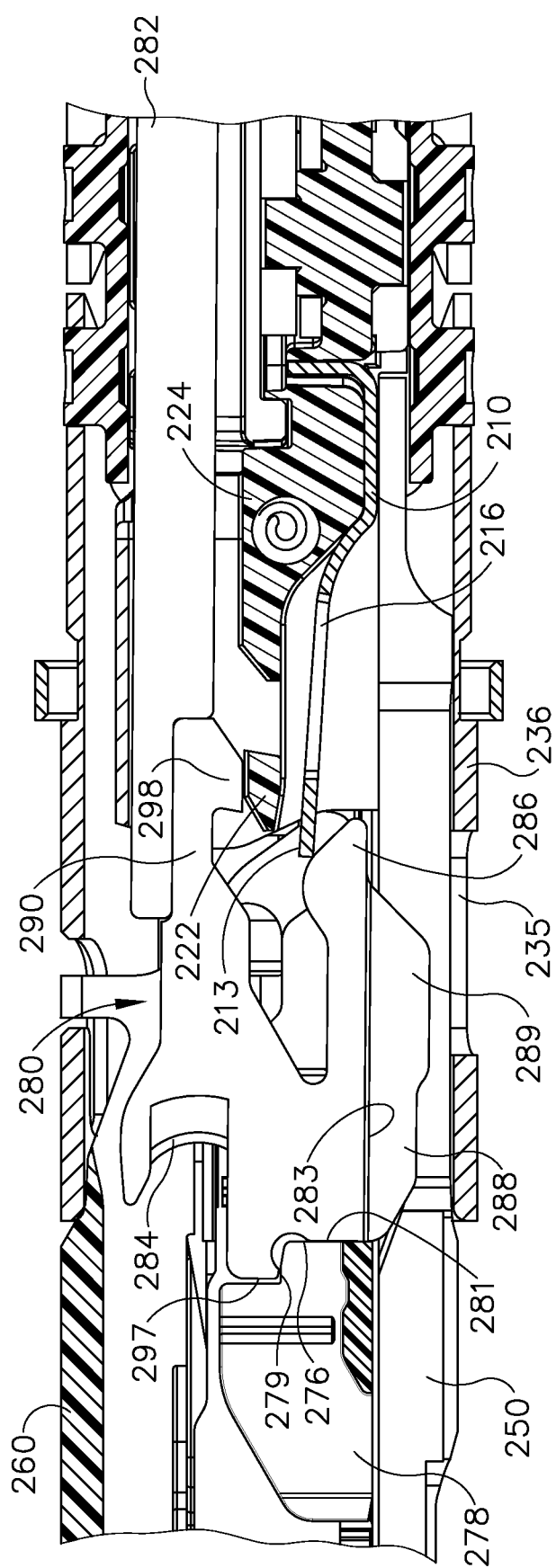
FIG. 25E depicts a side cross sectional view of the end effector of FIG. 13 in a fourth partially fired position with a loaded cartridge.
Figure 25F:
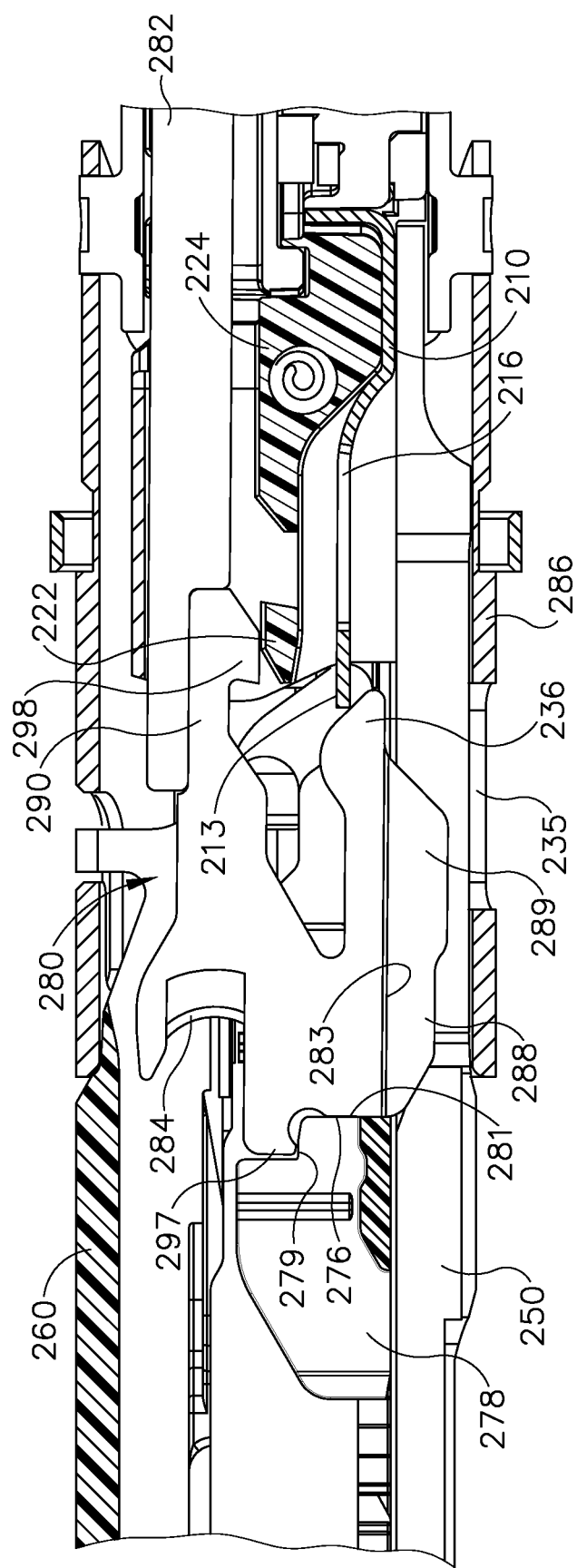
FIG. 25F depicts a side cross sectional view of the end effector of FIG. 13 in a fifth partially fired position with a loaded cartridge.
Figure 26:
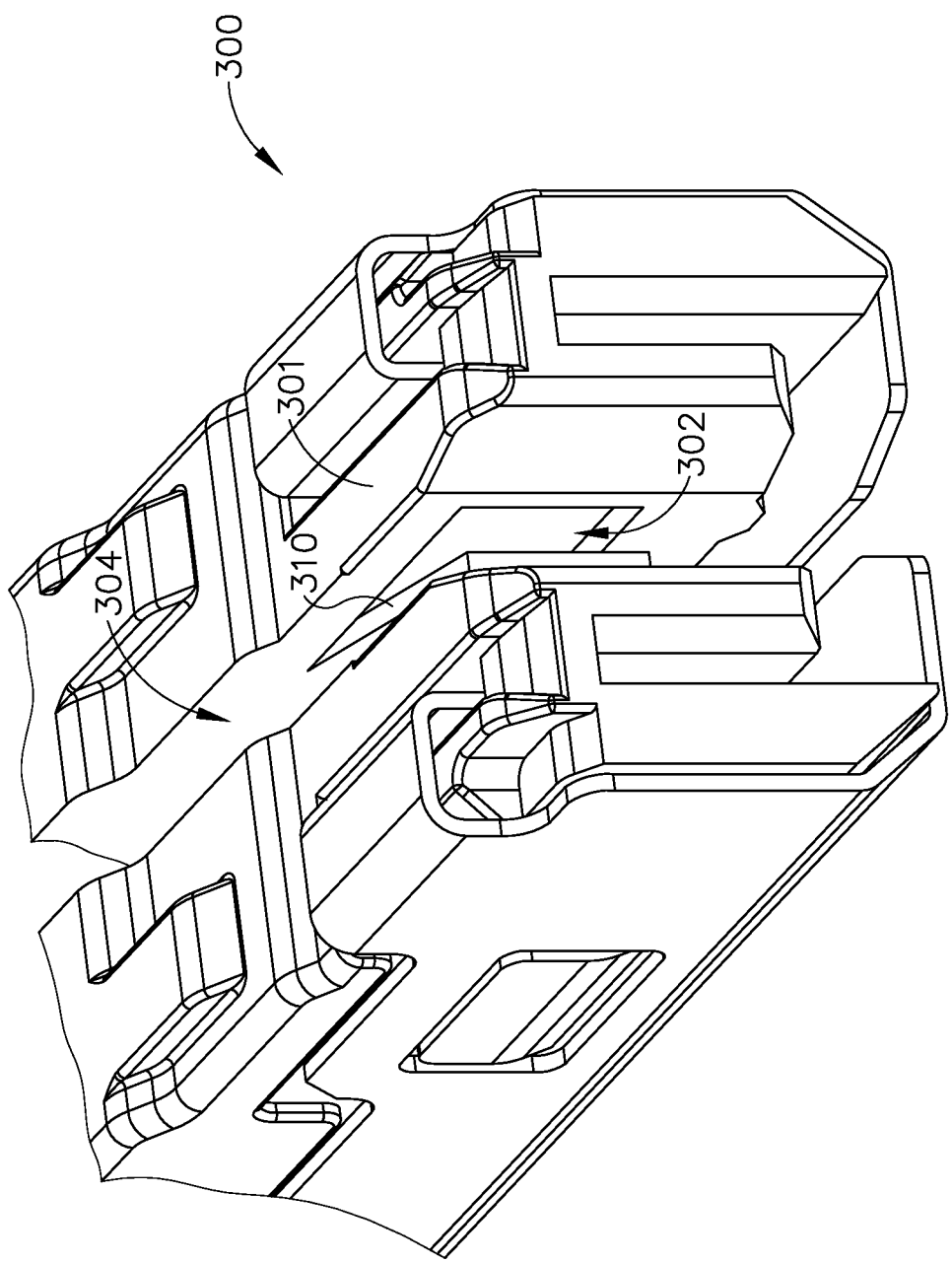
FIG. 26 depicts a perspective view of the proximal end of an exemplary alternative cartridge that may be incorporated into the end effector of FIG. 13.

Firing trigger (26) may be actuated to drive firing beam (282) and knife member (280). As knife member (280) is driven distally, distal tip (297) of knife member (280) engages a top surface (279) of sled (278) and distal wall (281) of knife member (280) engages a proximal end (276) of sled (278), as shown in FIG. 25B. This maintains the vertical position of knife member (280) when knife member is positioned within proximal portion (255) of slot (256) of lower jaw (250). As knife member (280) travels further distally, tab (286) of knife member (280) travels distally from opening (216) of resilient member (210) such that tab (286) engages distal portion (213) of resilient member (210). Tab (286) thereby pushes distal portion (213) of resilient member (210) upwardly, as shown in FIG. 25C. Because sled (278) maintains the vertical position of knife member (280), tab (298) of knife member (280) translates distally above engagement features (222, 224) of frame member (238) such that tab (298) does not fall between engagement features (222, 224) to prevent the distal movement of knife member (280), as shown in FIG. 25D. Knife member (280) thus overrides the lockout position at this stage. Distal portion (213) of resilient member (210) then biases downwardly to a nominal position, proximal of tab (286) of knife member (280), as tab (286) translates distally from resilient member (210), as shown in FIG. 25E. Protrusion (288) of knife member (280) then enters distal portion (253) of slot (256) of lower jaw (250), as shown in FIG. 25F. Shelf (283) of knife member (280) is then positioned above slot (256) and tab (298) of upper extension (290) is above first engagement feature (222). Knife member (280) is then further translated distally to cut and staple tissue positioned between anvil (260) and lower jaw (250).

After knife member (280) is fired distally, knife member (280) may be retracted proximally within lower jaw (250). For example, knife member (280) may be retracted by firing beam (282) by automatic reversal of motor (102) upon detected completion of a firing stroke, in response to a second actuation of firing trigger (26), and/or otherwise. When knife member (280) is retracted, knife member (280) disengages from sled (278). Without sled (280), knife member (280) may fall downwardly to the lockout position of FIG. 23B as knife member (280) is retracted after being fired. Knife member (280) may be returned to the initial position of FIG. 23A after knife member (280) is in the lockout position of FIG. 23B. As knife member (280) is driven proximally by motor (102), ramped walls (292, 296) of upper extension (290) of knife member (280) slide proximally against ramped walls (221, 226) of engagement features (222, 224). As upper extension (290) translates proximally against engagement features (222, 224), walls (221, 226) of engagement features (222, 224) push upper extension (290) and knife member (280) upwardly through a camming action. Tab (286) of knife member (280) also travels upwardly to again be positioned within opening (216) of resilient member (210). This returns knife member (280) to the initial position, as shown in FIG. 23A.

Once tissue positioned between anvil (260) and lower jaw (250) is cut and stapled, end effector (240) may be pivoted back to the nonarticulated position by articulation control knob (35) and removed from the surgical site, with anvil (260) and lower jaw (250) closed. Alternatively, anvil (260) and lower jaw (250) may be opened prior to pivoting end effector (240) to release any tissue between anvil (260) and lower jaw (250). Anvil (260) and lower jaw (250) may then be re-closed prior to removing end effector (240) from the surgical site. End effector (240) may then be opened to replace staple cartridge (270) with a new staple cartridge. To open end effector (240), closure trigger (24) may be released away from pistol grip (22). Staple cartridge (270) may be replaced with a new staple cartridge, and end effector (240) may be again inserted to the surgical site for further cutting and stapling.

In some variations, frame member (238) and knife member (280) are reconfigured such that wall (225) and wall (294) are located at or near the underside of the distal end of knife member (280). For instance, frame member (238) may include a feature that is substantially identical to first engagement feature (222) that is located near protrusion (288) of lower extension (285); and protrusion (288) of lower extension (285) may include a feature that is substantially identical to tab (298). Other suitable locations in which functional equivalents of walls (225, 294) may engage to provide a lockout against distal translation of knife member (280) will be apparent to those of ordinary skill in the art in view of the teachings herein.

III. Exemplary Alternative Spent Cartridge Lockout Features

In some instances, it may be desirable to provide features that prevent knife member (280) from being fired through the same staple cartridge (270) more than once, such that knife member (280) may not be fired through a "spent" staple cartridge (270). For example, such a feature may prevent knife member (280) from engaging the lockout features (222, 224) of frame member (238) discussed above upon being fired through a staple cartridge (270) a first time. However, upon subsequent attempts to fire knife member (280) such a feature would provide engagement between knife member (280) and lockout features (222, 224) of frame member (238) to thereby prevent firing of knife member (280) through the same staple cartridge (270) a second time. The examples below include several merely illustrative versions of spent staple cartridge (270) lockout features that may be readily introduced to an end effector such as end effector (240).

A. Exemplary Cartridge with Resilient Tab

Figure 27:
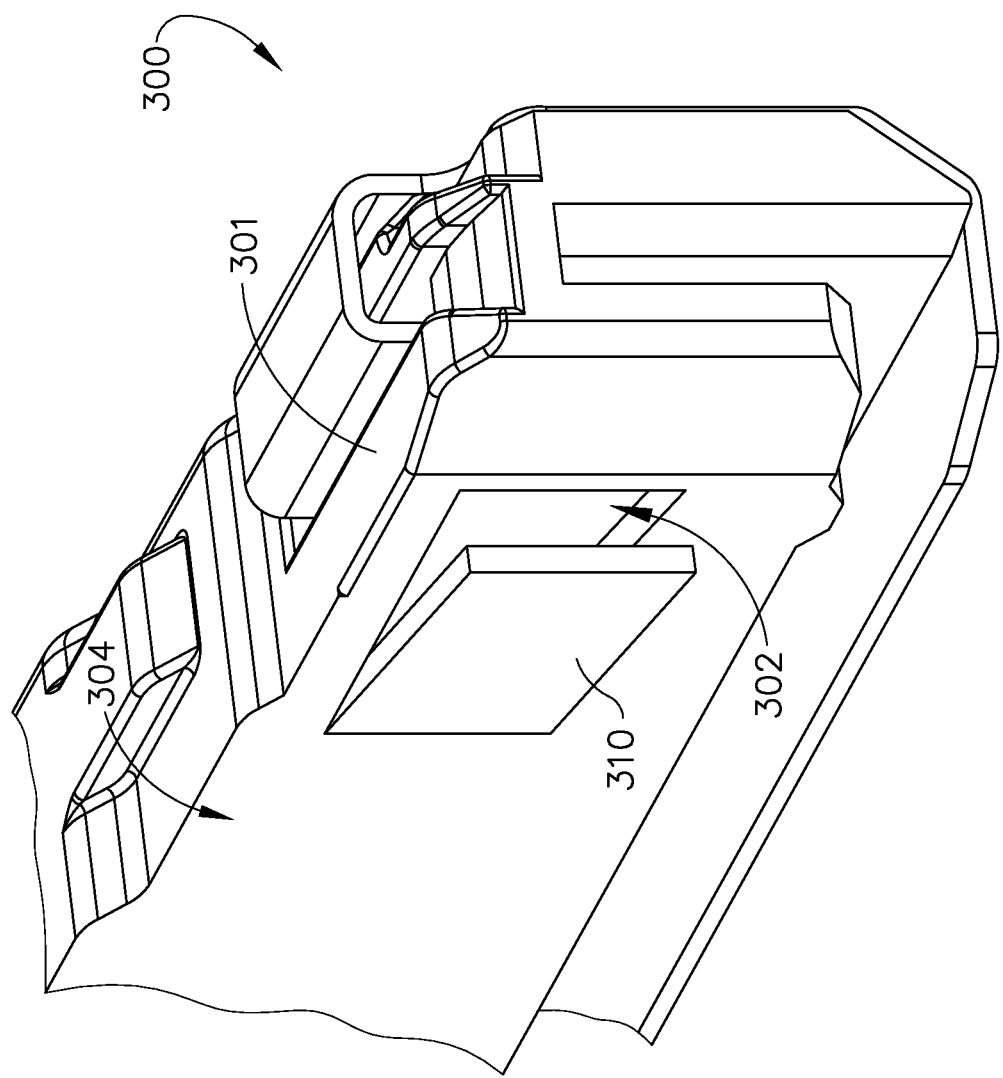
FIG. 27 depicts a cross-sectional perspective view of the proximal end of the cartridge of FIG. 26.

FIGS. 26-29D show an exemplary cartridge (300) having a spent cartridge lockout feature. It should be understood that cartridge (300) may be readily used in end effector (240) or in other end effectors. Cartridge (300) of the present example is configured to operate substantially similar to cartridges (70, 270) discussed above except for the differences discussed below. Cartridge (300) includes a cartridge body (301) having a longitudinal channel (304) through which wedge sled (278) and knife member (280) may be longitudinally translated. The spent cartridge lockout feature of the present example comprises a resilient tab (310). As best seen in FIG. 27, an interior surface of channel (304) of cartridge body (301) comprises a rectangular recess (302) within which resilient tab (310) is pivotably disposed. Resilient tab (310) is pivotably secured within rectangular recess (302) via a living hinge. Resilient tab (310) is pivotable between an unexposed position, in which resilient tab (310) is substantially completely disposed within rectangular recess (302); and an exposed position, in which resilient tab (310) extends from rectangular recess (302) into channel (304) and thus in the pathway of the distally translating knife member (280). Resilient tab (310) of the present example is biased toward the exposed position shown in FIGS. 26-27 and 29D. Resilient tab (310) is configured to allow for firing of knife member (280) when in the unexposed position and to prevent firing of knife member (280) when in the exposed position.

Figure 28:
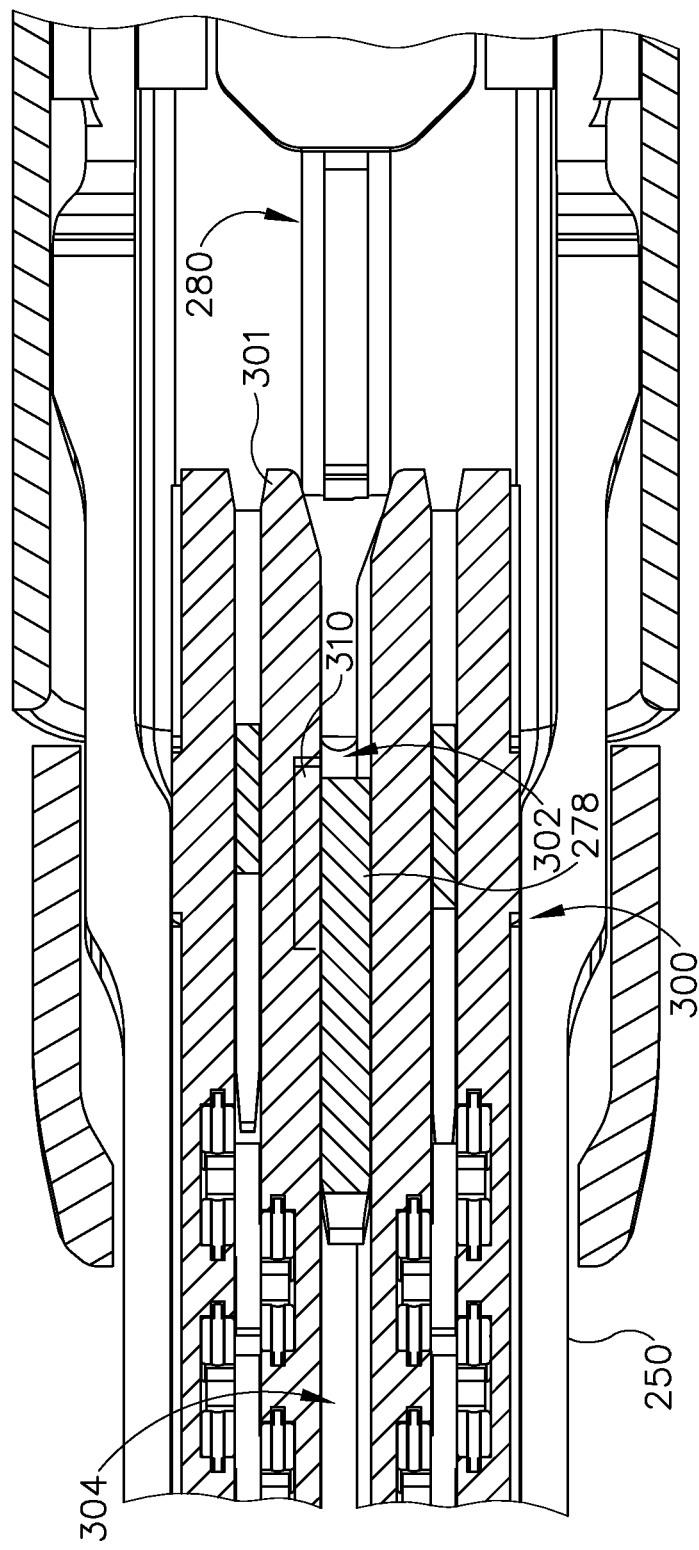
FIG. 28 depicts a cross-sectional top view of the proximal end of the cartridge of FIG. 26.
Figure 29A:
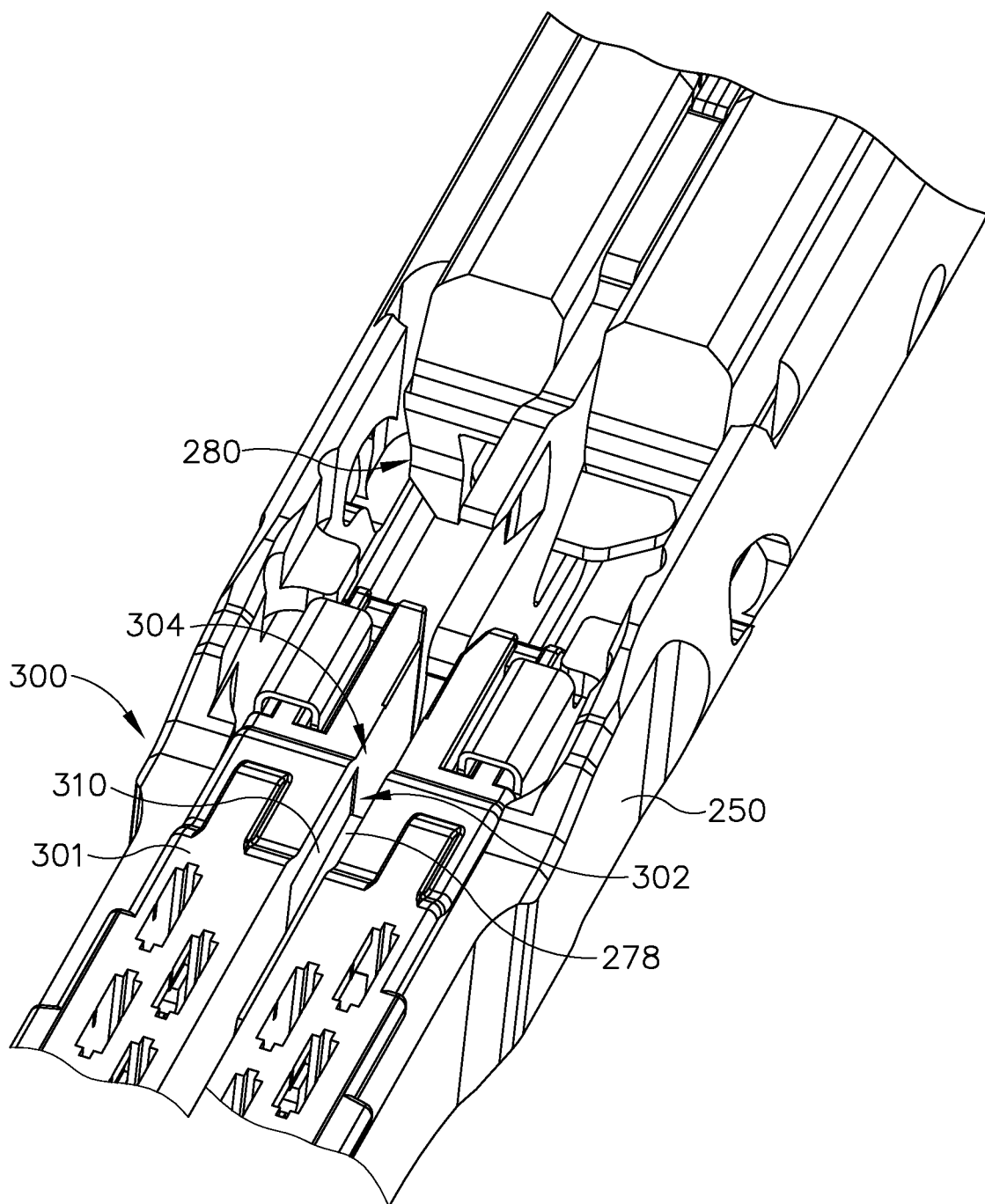
FIG. 29A depicts a perspective view of the proximal end of the cartridge of FIG. 26 engaged with the end effector of FIG. 13, with a resilient tab of the cartridge in a first rotational position, with a sled of the cartridge in a first longitudinal position, and with the knife of the end effector in a first longitudinal position.
Figure 29B:
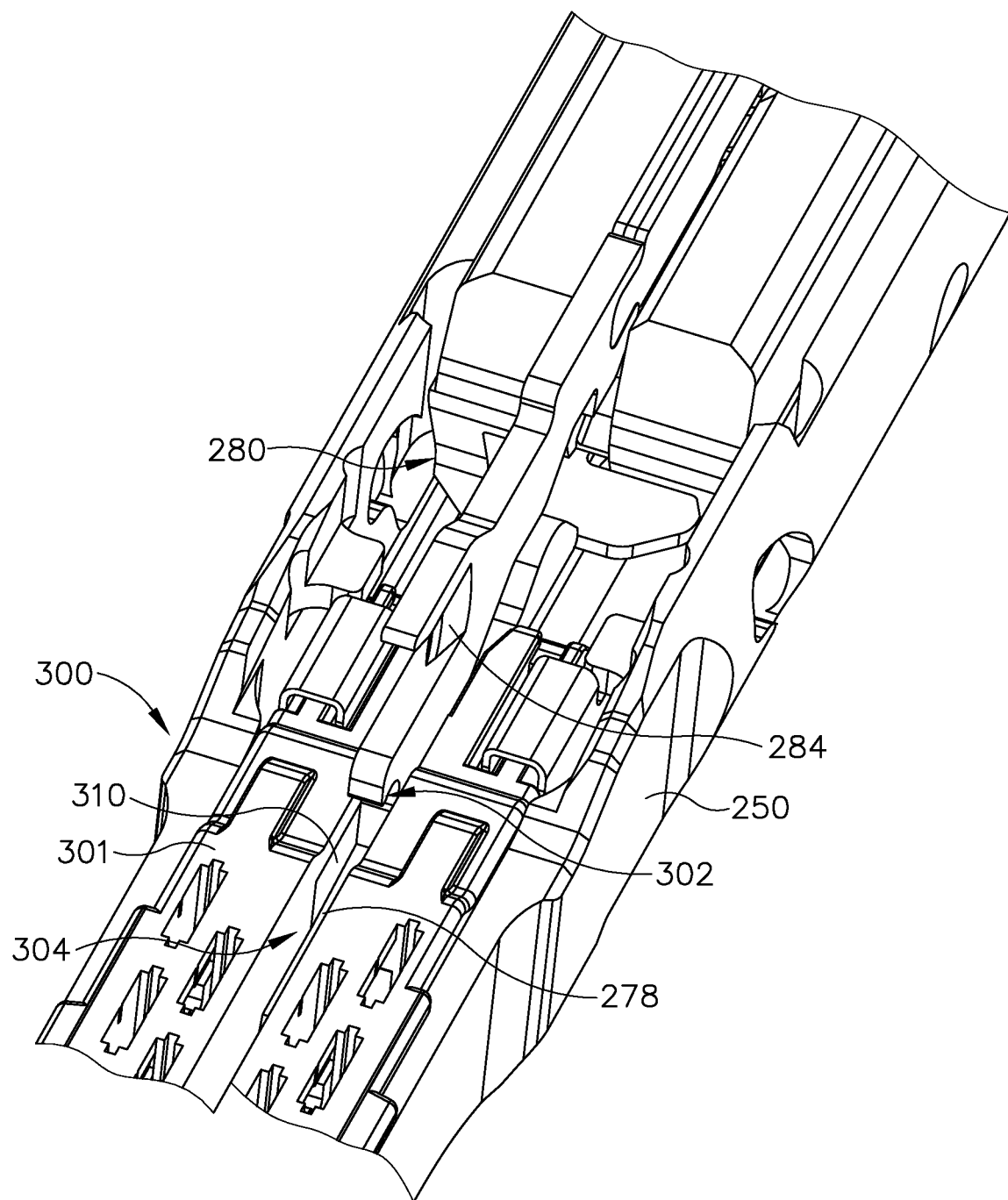
FIG. 29B depicts a perspective view of the proximal end of the cartridge of FIG. 26 engaged with the end effector of FIG. 13, with the resilient tab of the cartridge in the first rotational position, with the sled of the cartridge in the first longitudinal position, and with the knife of the end effector moved into a second longitudinal position.
Figure 29C:
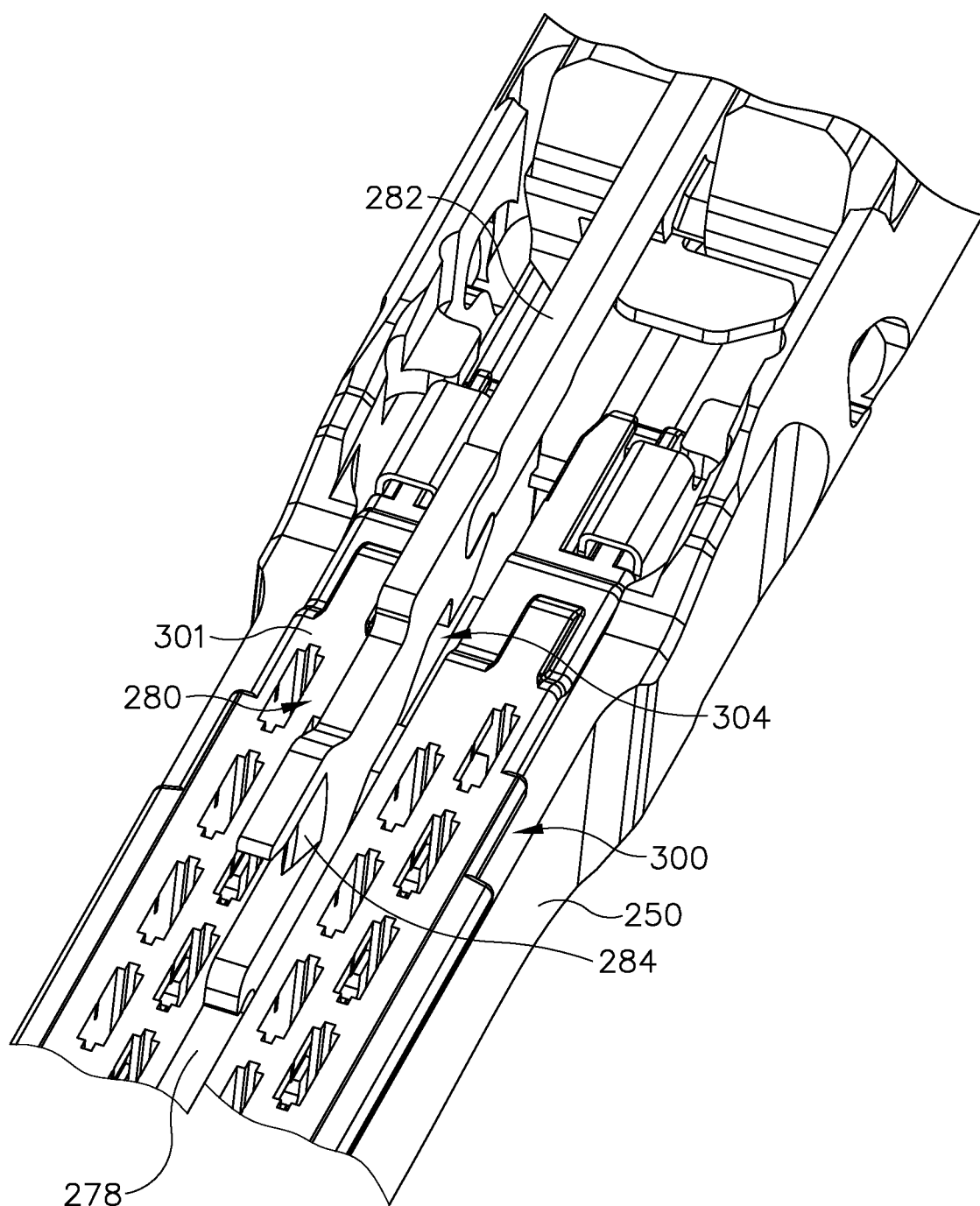
FIG. 29C depicts a perspective view of the proximal end of the cartridge of FIG. 26 engaged with the end effector of FIG. 13, with the resilient tab of the cartridge in the first rotational position, with the sled of the cartridge moved into a second longitudinal position by movement of the knife of the end effector into a third longitudinal position.
Figure 29D:
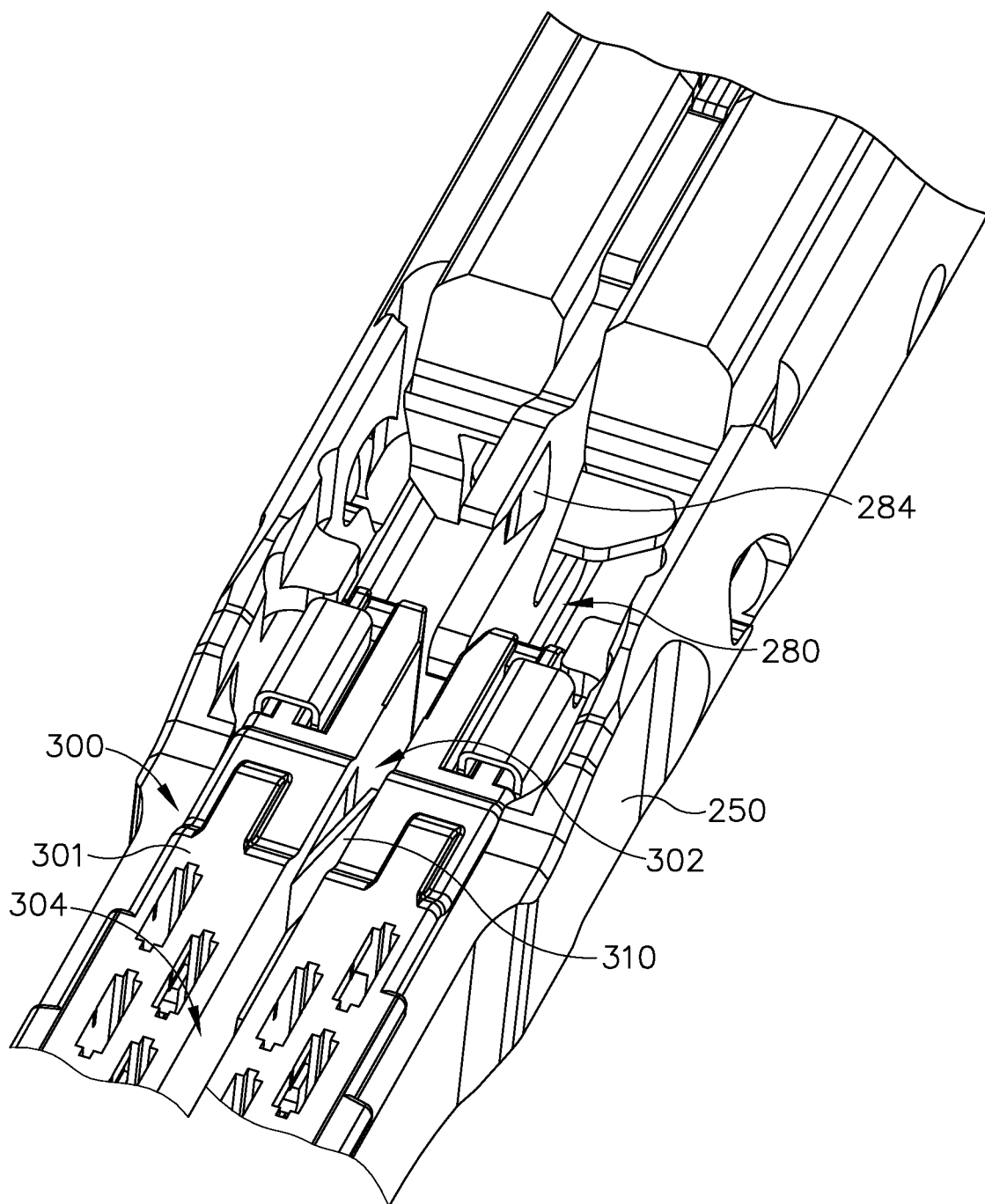
FIG. 29D depicts a perspective view of the proximal end of the cartridge of FIG. 26 engaged with the end effector of FIG. 13, with the resilient tab of the cartridge moved into a second rotational position by movement of the sled of the cartridge into the second longitudinal position and by movement of the knife of the end effector moved back into the first longitudinal position.
Figure 30:
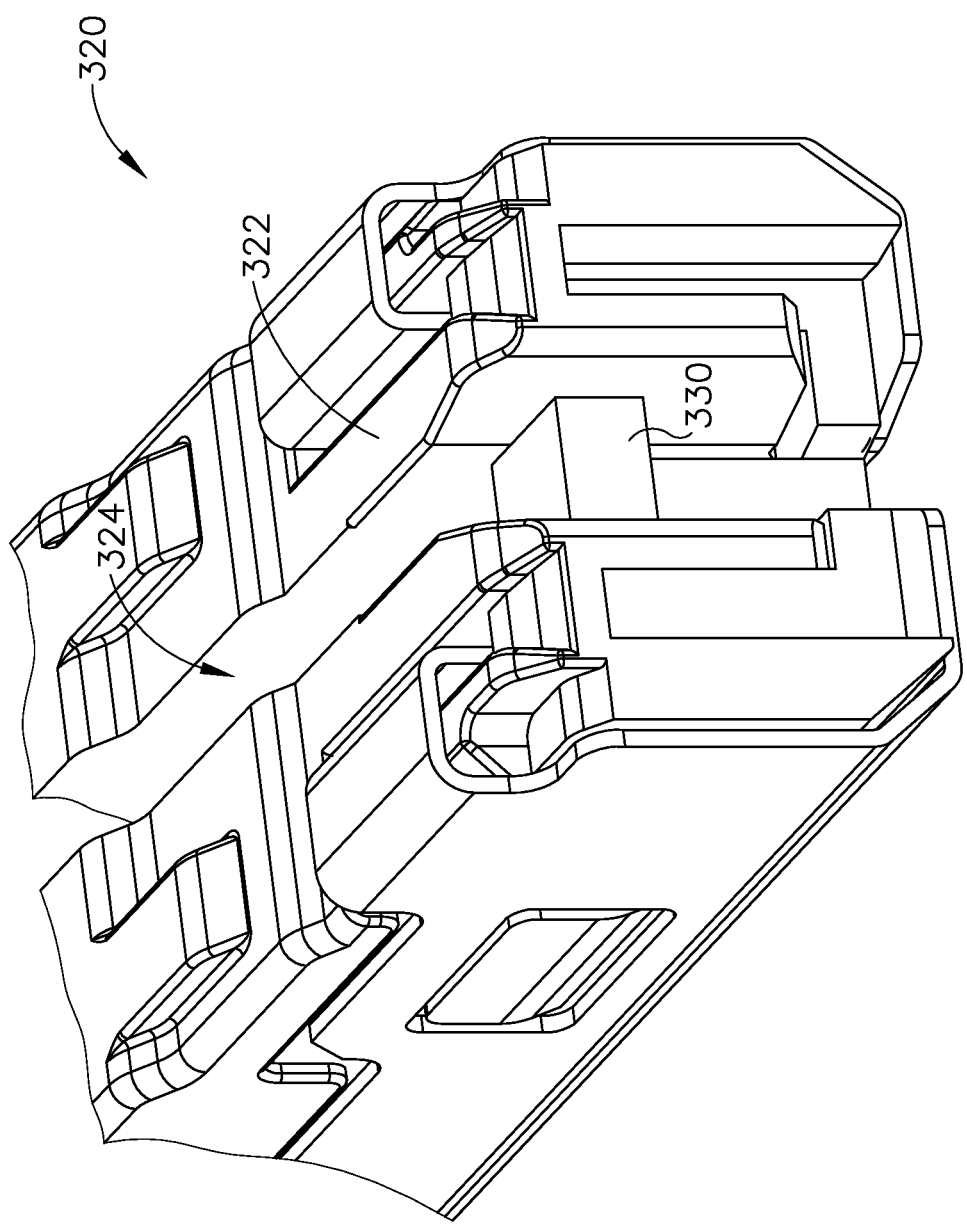
FIG. 30 depicts a perspective view of the proximal end of another exemplary alternative cartridge that may be incorporated into the end effector of FIG. 13.

As best seen in FIG. 28, wedge sled (278), is positioned within channel (304) of cartridge (300) and is operable to translate longitudinally through channel (304) of cartridge (300). In an initial position (FIGS. 28 and 29A), wedge sled (278) proximally is positioned so as to maintain resilient tab (310) in the unexposed position. As knife member (280) is fired a first time, knife member (280) engages wedge sled (278) (FIG. 29B) and drives wedge sled (278) distally as described above (FIG. 29C). As knife member (280) is being fired, knife member (280) and/or firing beam (282) are configured to maintain resilient tab (310) in the unexposed position. Once knife member (280) is retracted into the initial position, wedge sled (278), knife member (280), and/or firing beam (282) are no longer in a position to maintain resilient tab (310) in the unexposed position such that resilient tab (310) resiliently deflects into the exposed position (FIG. 29D). In the exposed position, resilient tab (310) will engage knife member (280) if the operator attempts to advance knife member (280) distally a second time, thereby preventing firing of knife member (280) a second time through cartridge (300).

B. Exemplary Cartridge with Bypass Beam

FIGS. 30-32E show another exemplary cartridge (320) having a spent cartridge lockout feature. It should be understood that cartridge (320) may be readily used in end effector (240) or in other end effectors. Cartridge (320) of the present example is configured to operate substantially similar to cartridges (70, 270) discussed above except for the differences discussed below. Cartridge (320) includes a cartridge body (322) having a longitudinal channel (324) through which wedge sled (278) and knife member (280) may be longitudinally translated. The spent cartridge lockout feature of the present example comprises a breakaway or cutaway beam (330) extending between opposing interior surfaces of channel (324). Beam (330) is positioned within channel (324) such that beam (330) is in the path of knife member (280). Beam (330) of the present example comprises a square cross-sectional profile, but may comprise any other appropriate shape. As will be discussed in more detail below, as knife member (280) is fired distally through channel (324), knife member (280) is configured to break and/or cut beam (330). Also as will be discussed in more detail below, beam (330) is configured to allow for firing of knife member (280) when beam (330) is present; and to prevent firing of knife member (280) when beam (330) is not present.

Figure 32A:
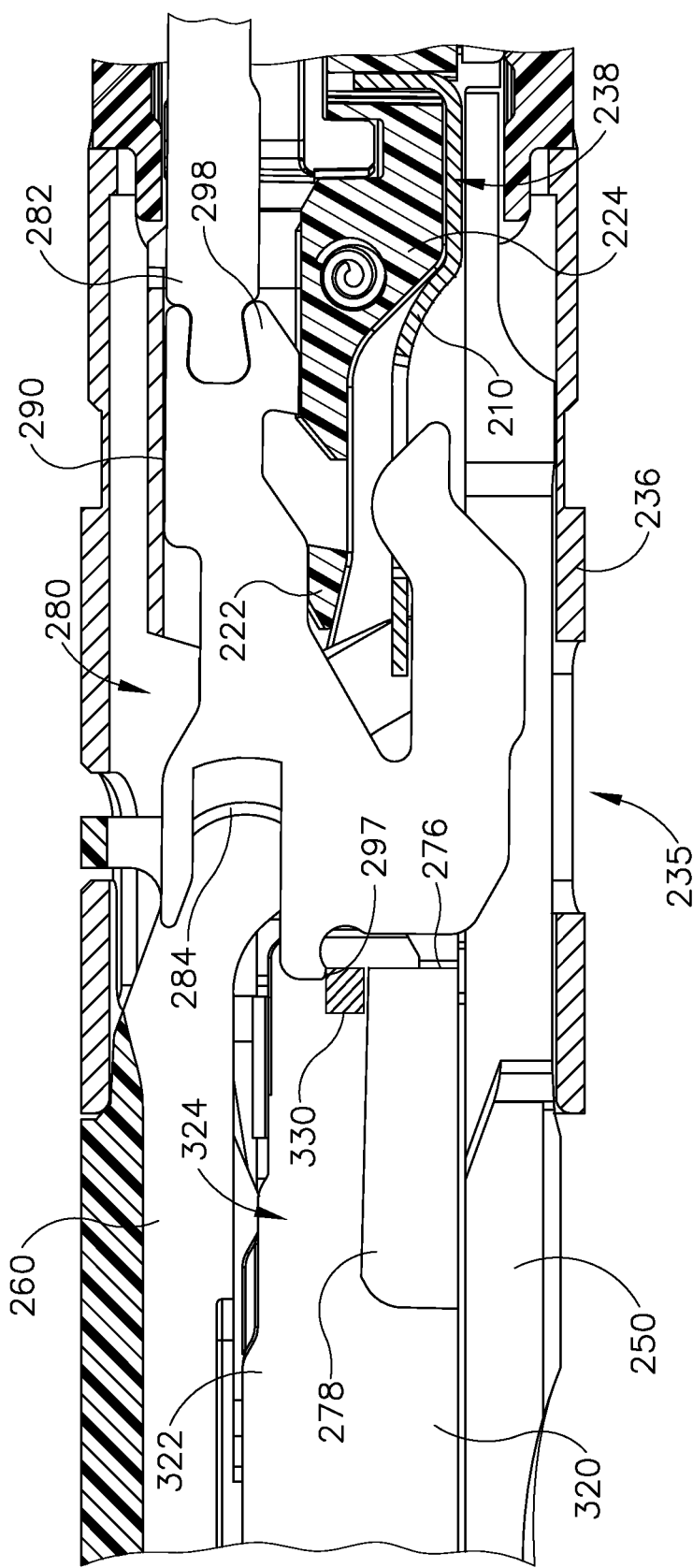
FIG. 32A depicts a cross-sectional view of the proximal end of the cartridge of FIG. 30 disposed within the end effector of FIG. 13, with a sled of the cartridge in a first longitudinal position and with a knife of the end effector in a first longitudinal position.
Figure 32B:
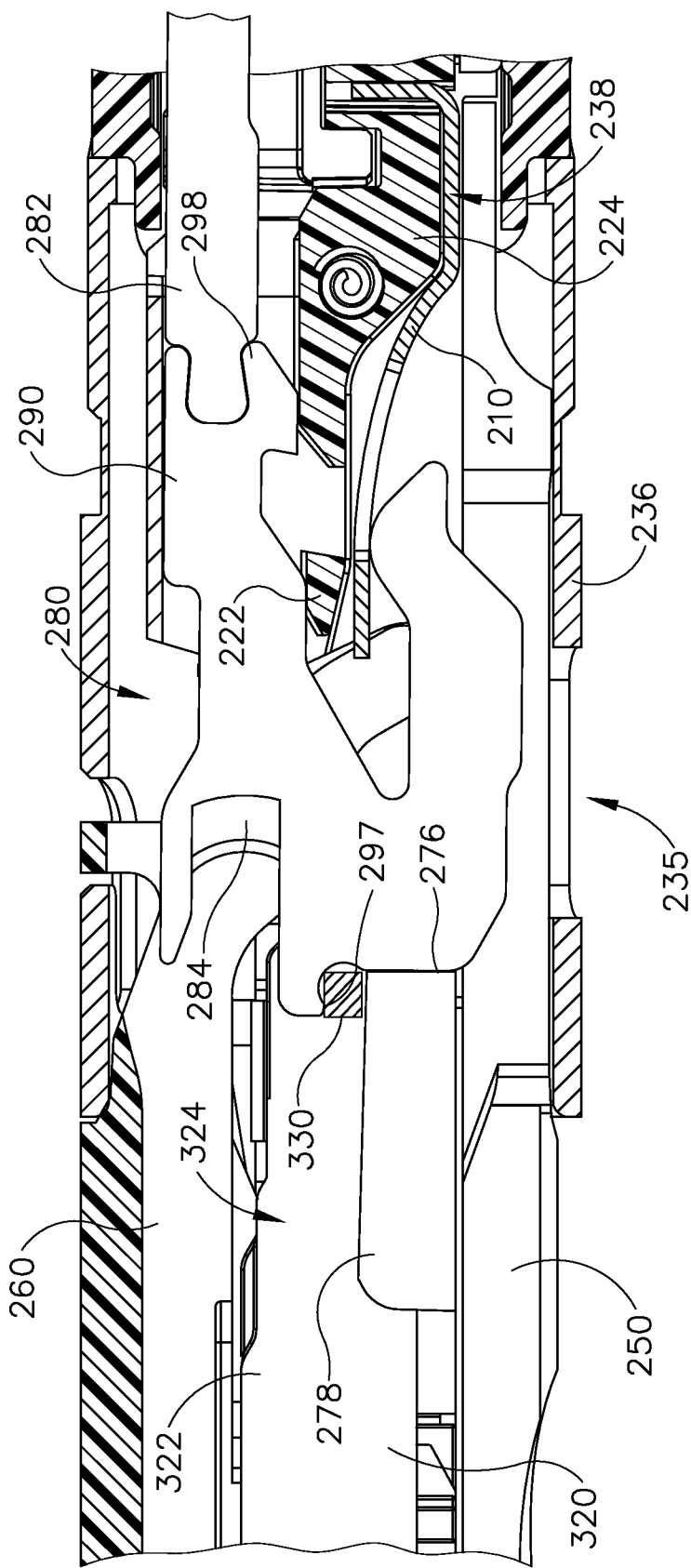
FIG. 32B depicts a cross-sectional view of the proximal end of the cartridge of FIG. 30 disposed within the end effector of FIG. 13, with the sled of the cartridge in the first longitudinal position and with the knife of the end effector moved into a second longitudinal position.
Figure 32C:
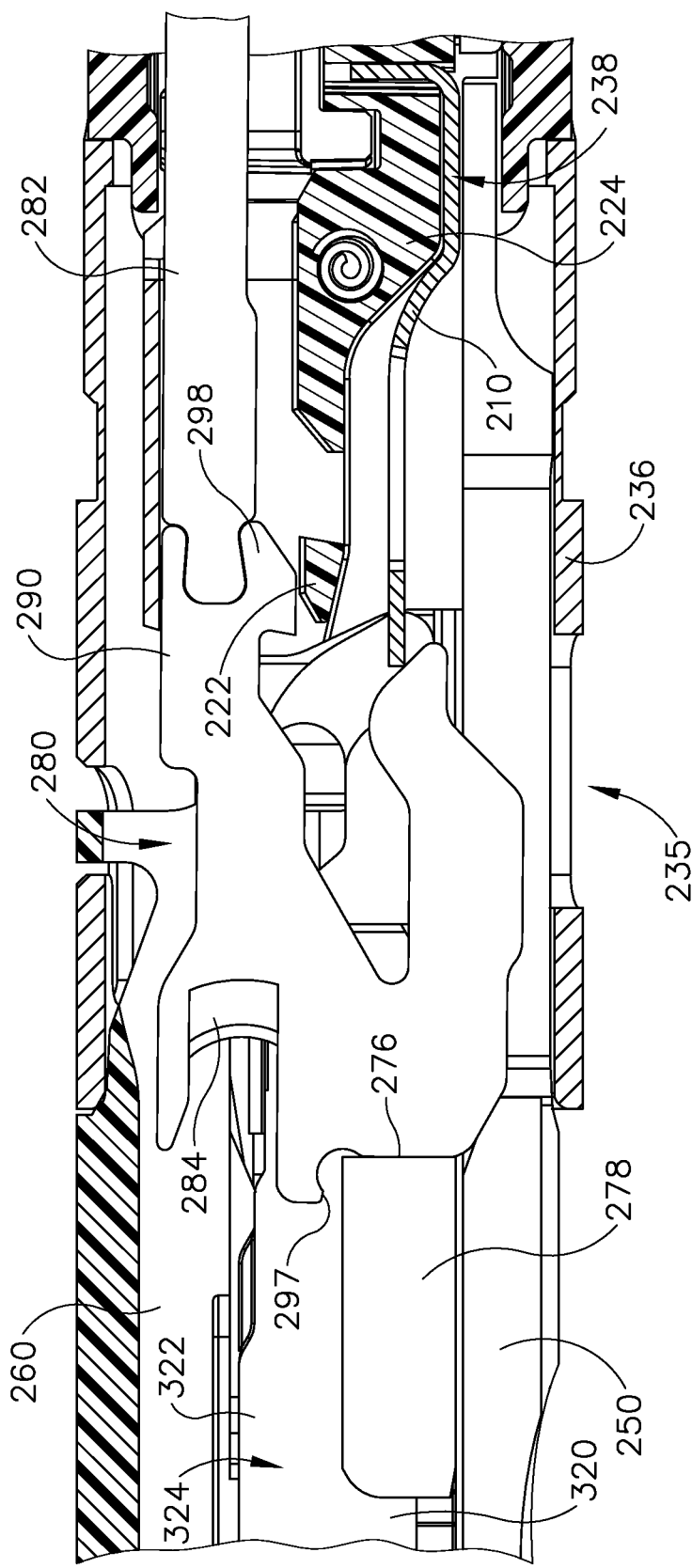
FIG. 32C depicts a cross-sectional view of the proximal end of the cartridge of FIG. 30 disposed within the end effector of FIG. 13, with the sled of the cartridge moved into a second longitudinal position by movement of the knife of the end effector into a third longitudinal position, with the knife breaking through the breakaway feature of the cartridge.
Figure 32D:
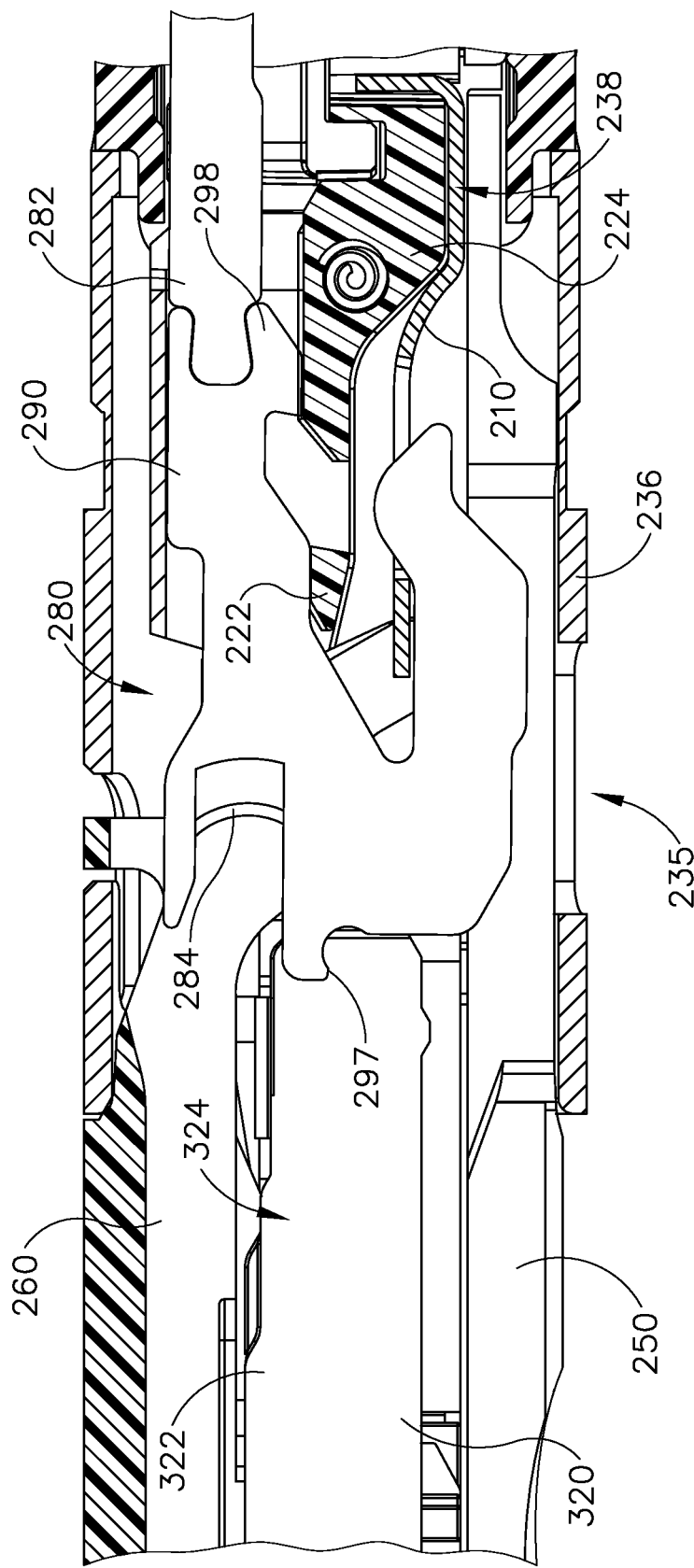
FIG. 32D depicts a cross-sectional view of the proximal end of the cartridge of FIG. 30 disposed within the end effector of FIG. 13, with the knife of the end effector moved back into the first longitudinal position and with the breakaway feature no longer present.
Figure 32E:
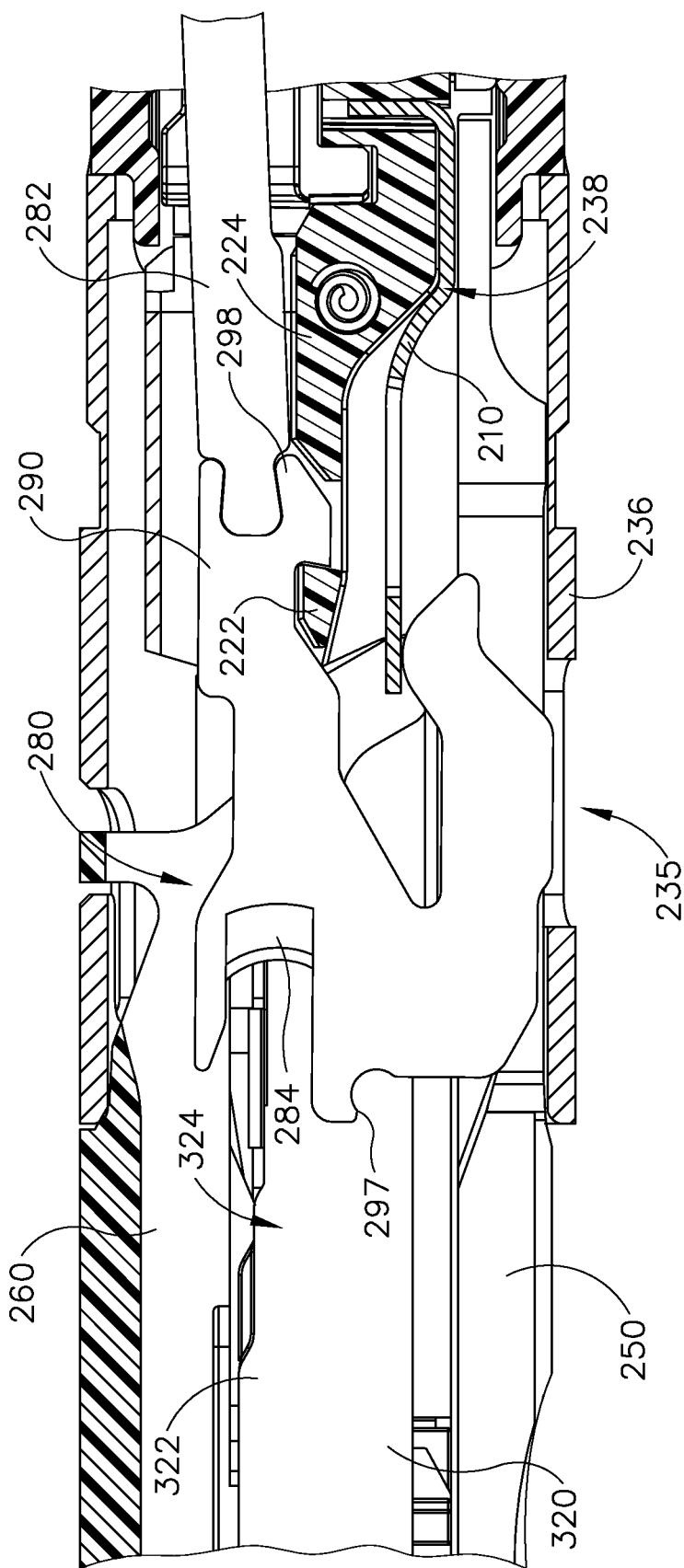
FIG. 32E depicts a cross-sectional view of the proximal end of the cartridge of FIG. 30 disposed within the end effector of FIG. 13, with the knife of the end effector moved into a lockout position upon being moved toward the second longitudinal position.
Figure 33:
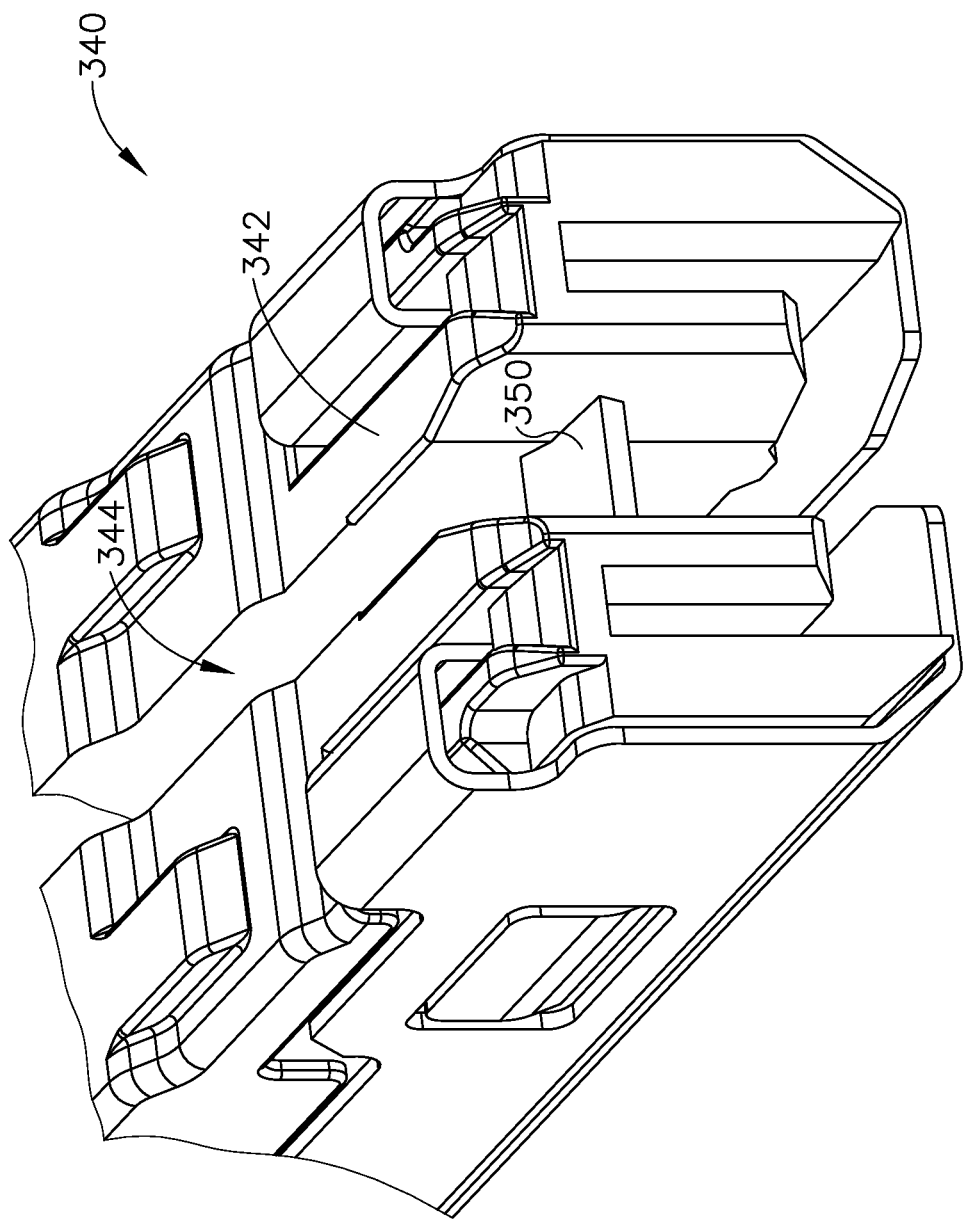
FIG. 33 depicts a perspective view of the proximal end of yet another exemplary alternative cartridge that may be incorporated into the end effector of FIG. 13.

FIG. 32A shows end effector (240) in an initial position. In the initial position, upper extension (290) of knife member (280) is positioned above engagement features (222, 224) of frame member (238). Also in the initial position, distal tip (297) of knife member (280) is in contact with a top surface of beam (330) of cartridge (320). As knife member (280) is fired distally, distal tip (297) of knife member (280) continues to engage the top surface of beam (330) as distal wall (281) of knife member (280) engages a proximal end (276) of sled (278), as shown in FIG. 32B. Engagement between distal tip (297) and the top surface of beam (330) maintains the vertical position of knife member (280). Because beam (330) maintains the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) breaks and/or cuts beam (330) as knife member (280) drives wedge sled (278) distally as described above (FIG. 32C). After knife member (280) is fired distally, knife member (280) may be retracted proximally within lower jaw (250) (FIG. 32D). If an operator attempts to fire knife member (280) a second time, without beam (330) to maintain the vertical position of knife member (280), resilient member (210) will resiliently drive knife member (280) downwardly to the lockout position as discussed above with reference to FIG. 23B and as shown in FIG. 32E.

C. Exemplary Cartridge with Bypass Ramp

Figure 34:
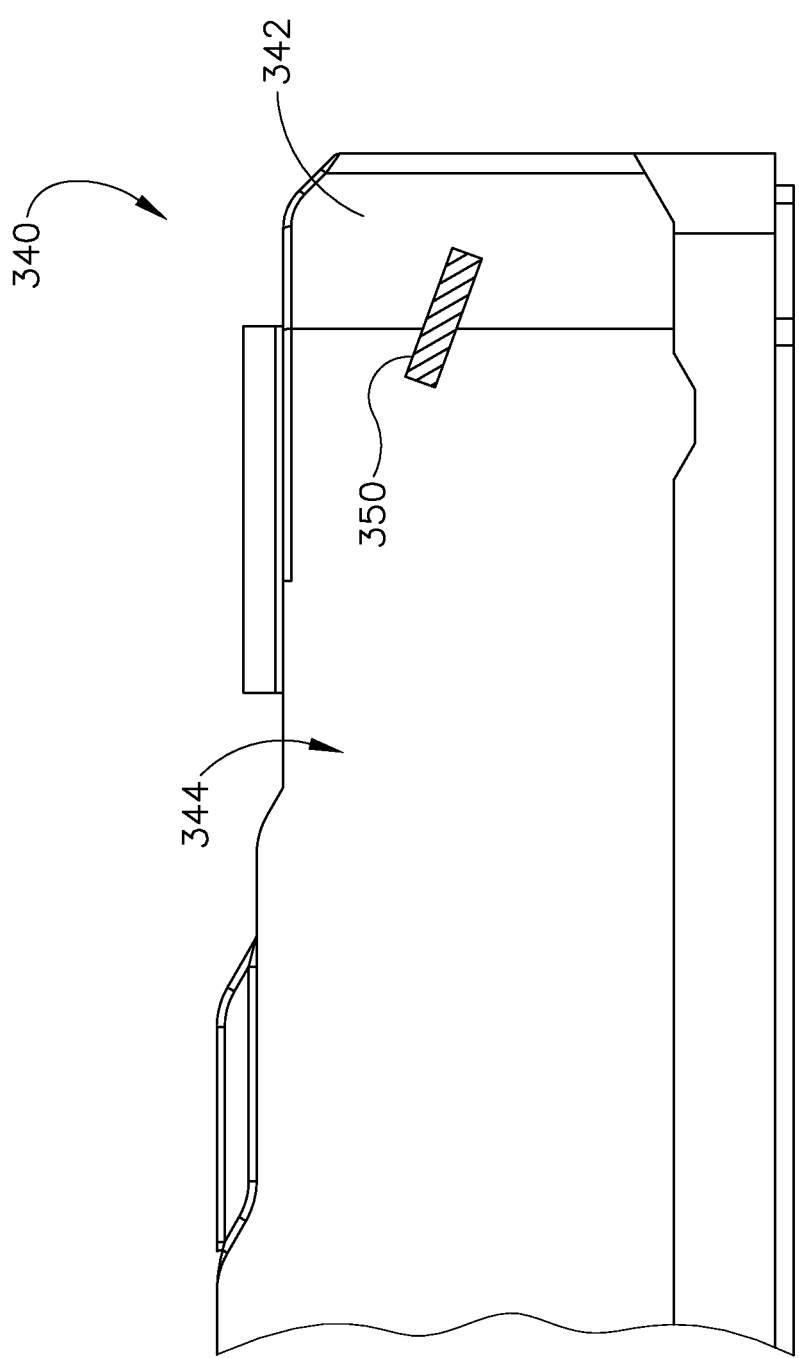
FIG. 34 depicts a cross-sectional side view of the proximal end of the cartridge of FIG. 33.
Figure 35:
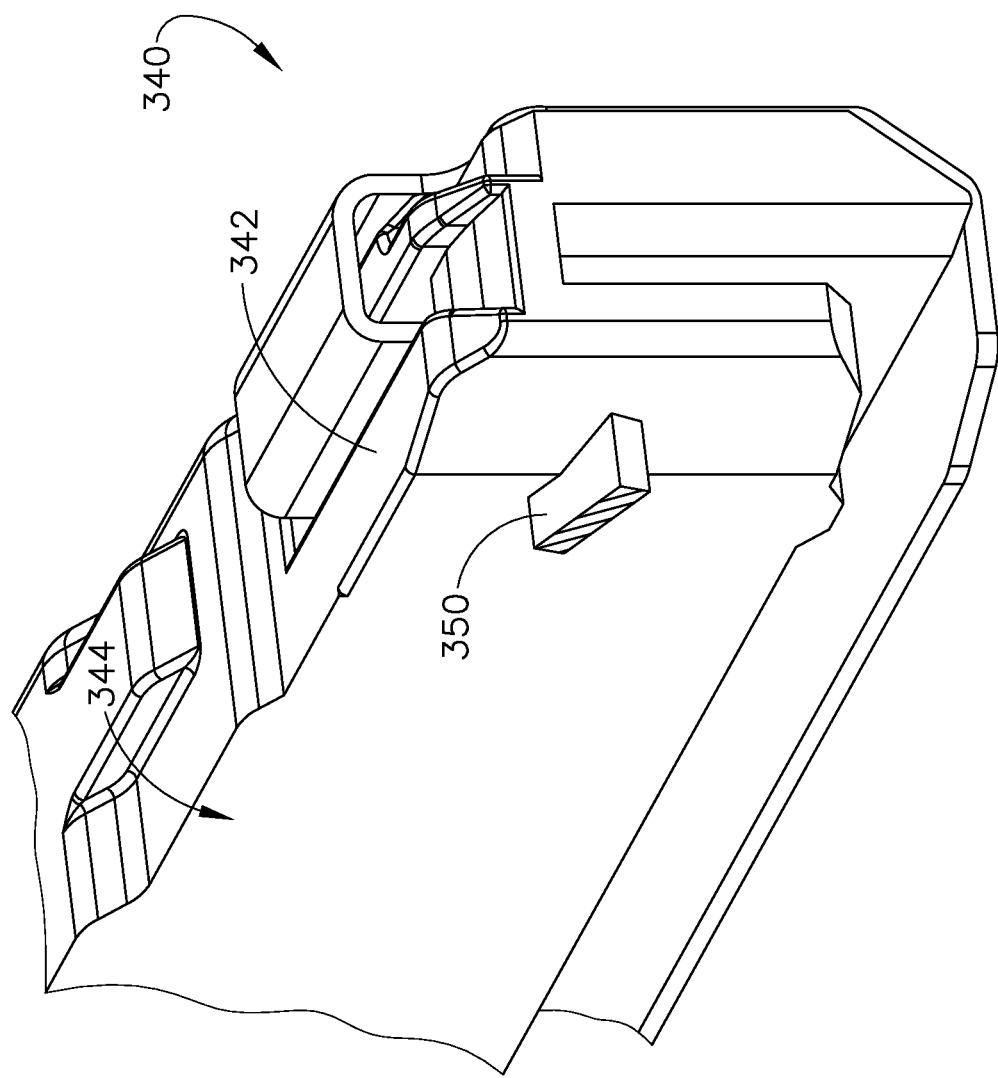
FIG. 35 depicts a cross-sectional perspective view of the proximal end of the cartridge of FIG. 33.

FIGS. 33-36E show another exemplary cartridge (340) having a spent cartridge lockout feature. It should be understood that cartridge (340) may be readily used in end effector (240) or in other end effectors. Cartridge (340) of the present example is configured to operate substantially similar to cartridges (70, 270) discussed above except for the differences discussed below. Cartridge (340) includes a cartridge body (342) having a longitudinal channel (344) through which wedge sled (278) and knife member (280) may be longitudinally translated. The spent cartridge lockout feature of the present example comprises a breakaway or cutaway ramp (350) extending between opposing interior surfaces of channel (344) of cartridge body (342). Ramp (350) is positioned within channel (344) such that ramp (350) is in the path of knife member (280). As best shown in FIG. 34, ramp (350) of the present example is angled upwardly-distally. As will be discussed in more detail below, as knife member (280) is fired distally through channel (344), knife member (280) is configured to break and/or cut ramp (350). Also as will be discussed in more detail below, ramp (350) is configured to allow for firing of knife member (280) when ramp (350) is present; and to prevent firing of knife member (280) when ramp (350) is not present.

Figure 36A:
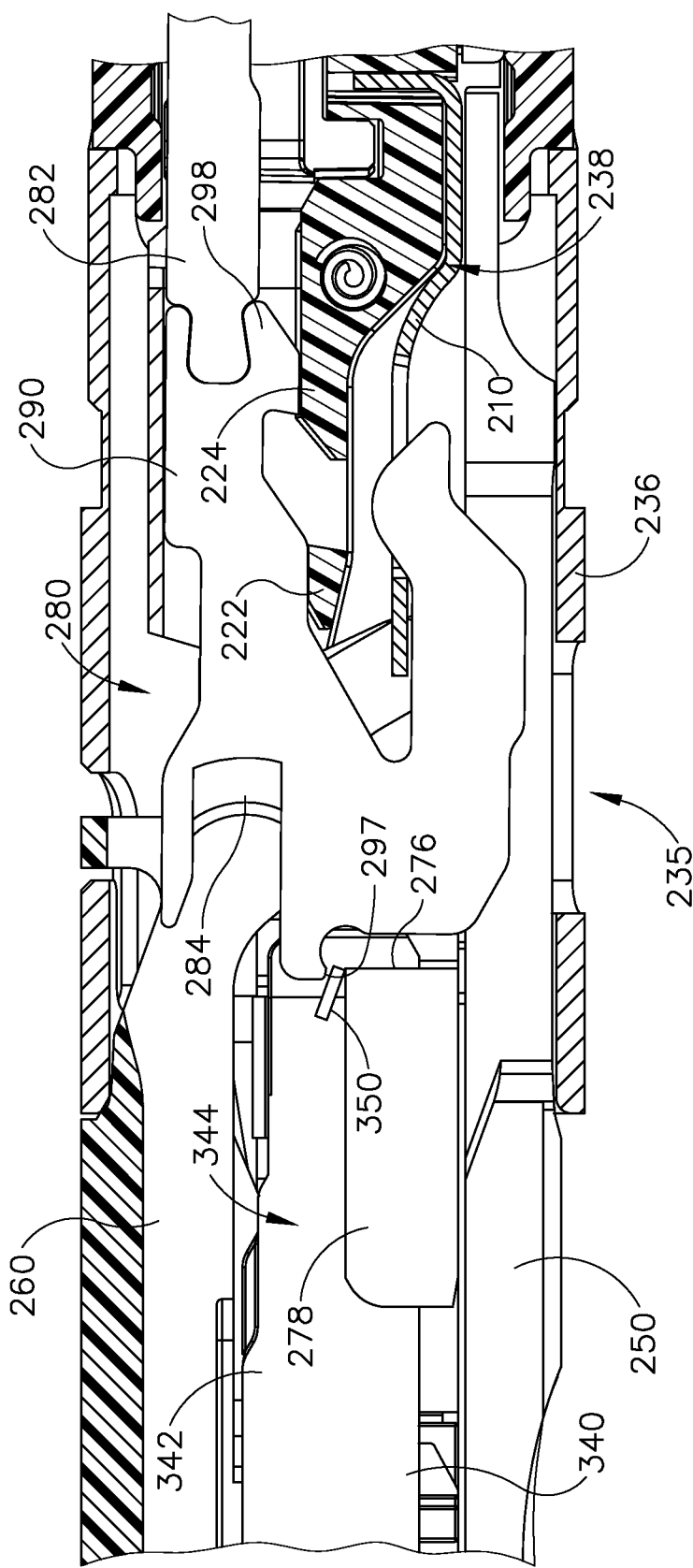
FIG. 36A depicts a cross-sectional view of the proximal end of the cartridge of FIG. 33 disposed within the end effector of FIG. 13, with a sled of the cartridge in a first longitudinal position and with a knife of the end effector in a first longitudinal position.
Figure 36B:
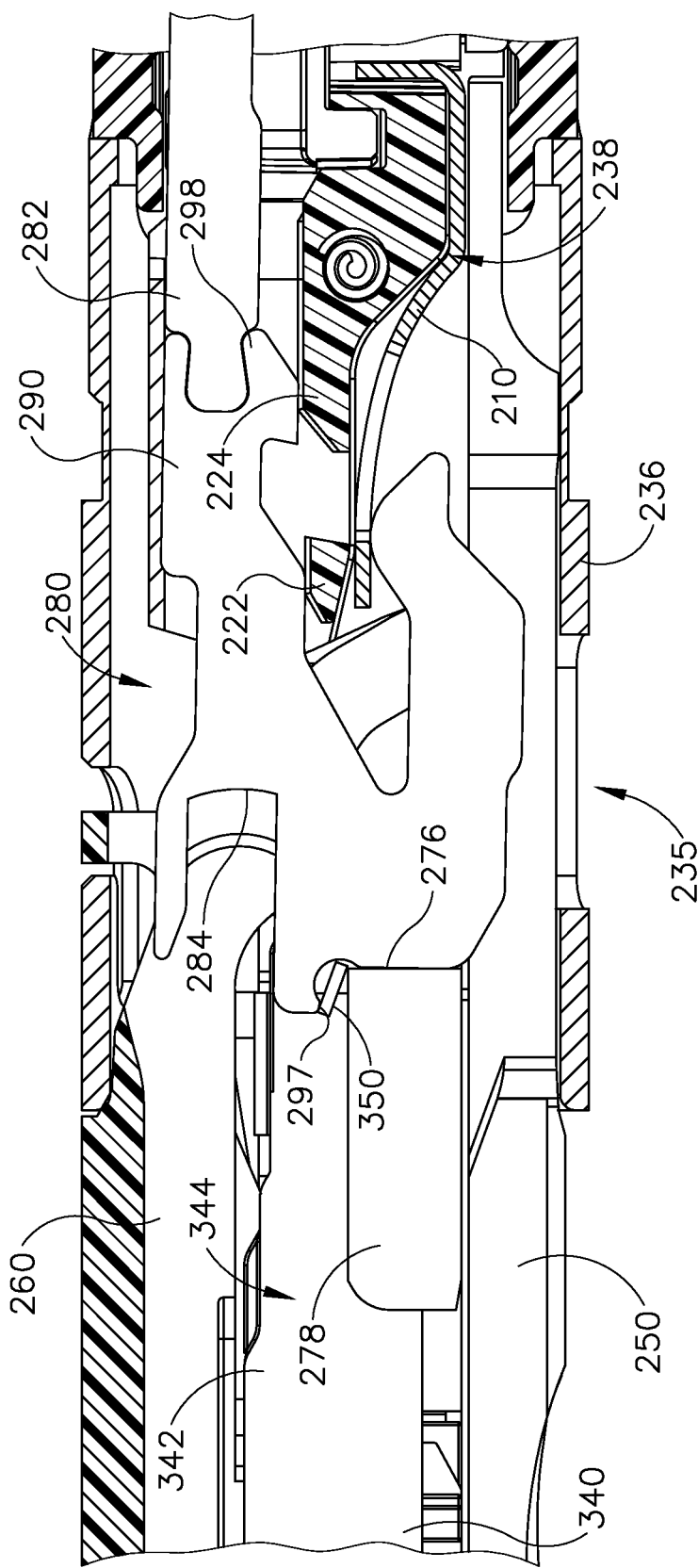
FIG. 36B depicts a cross-sectional view of the proximal end of the cartridge of FIG. 33 disposed within the end effector of FIG. 13, with the sled of the cartridge in the first longitudinal position and with the knife of the end effector moved into a second longitudinal position.
Figure 36C:
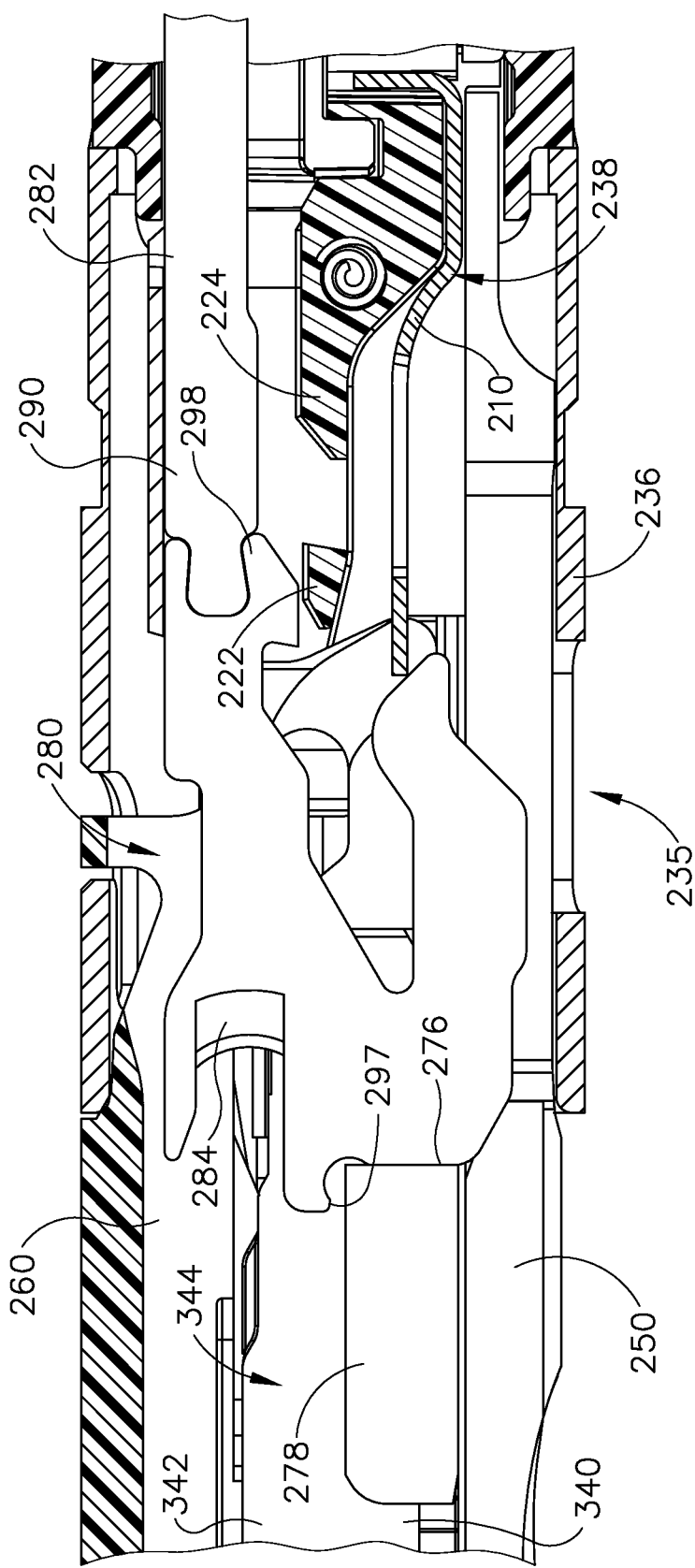
FIG. 36C depicts a cross-sectional view of the proximal end of the cartridge of FIG. 33 disposed within the end effector of FIG. 13, with the sled of the cartridge moved into a second longitudinal position by movement of the knife of the end effector into a third longitudinal position, with the knife breaking through the breakaway feature of the cartridge.
Figure 36D:
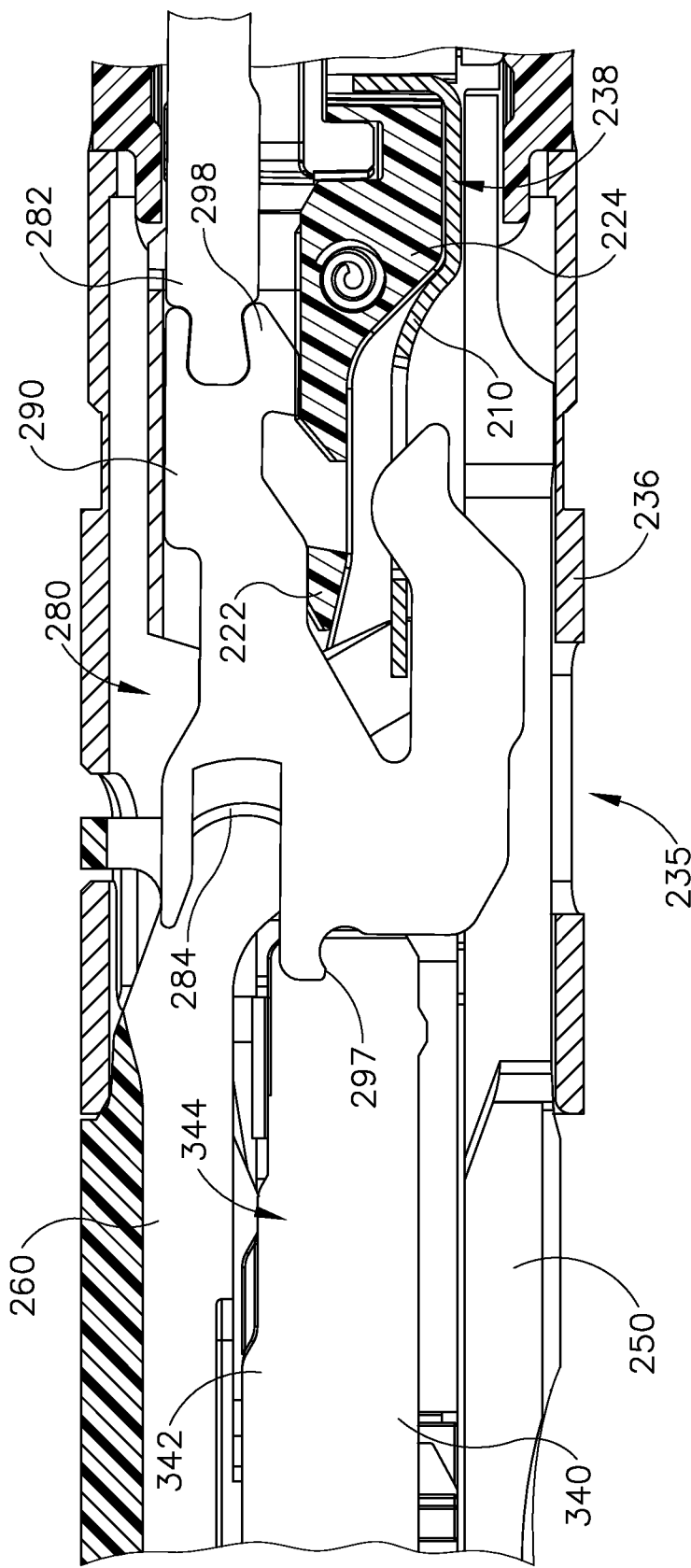
FIG. 36D depicts a cross-sectional view of the proximal end of the cartridge of FIG. 33 disposed within the end effector of FIG. 13, with the knife of the end effector moved back into the first longitudinal position and with the breakaway feature no longer present.
Figure 36E:
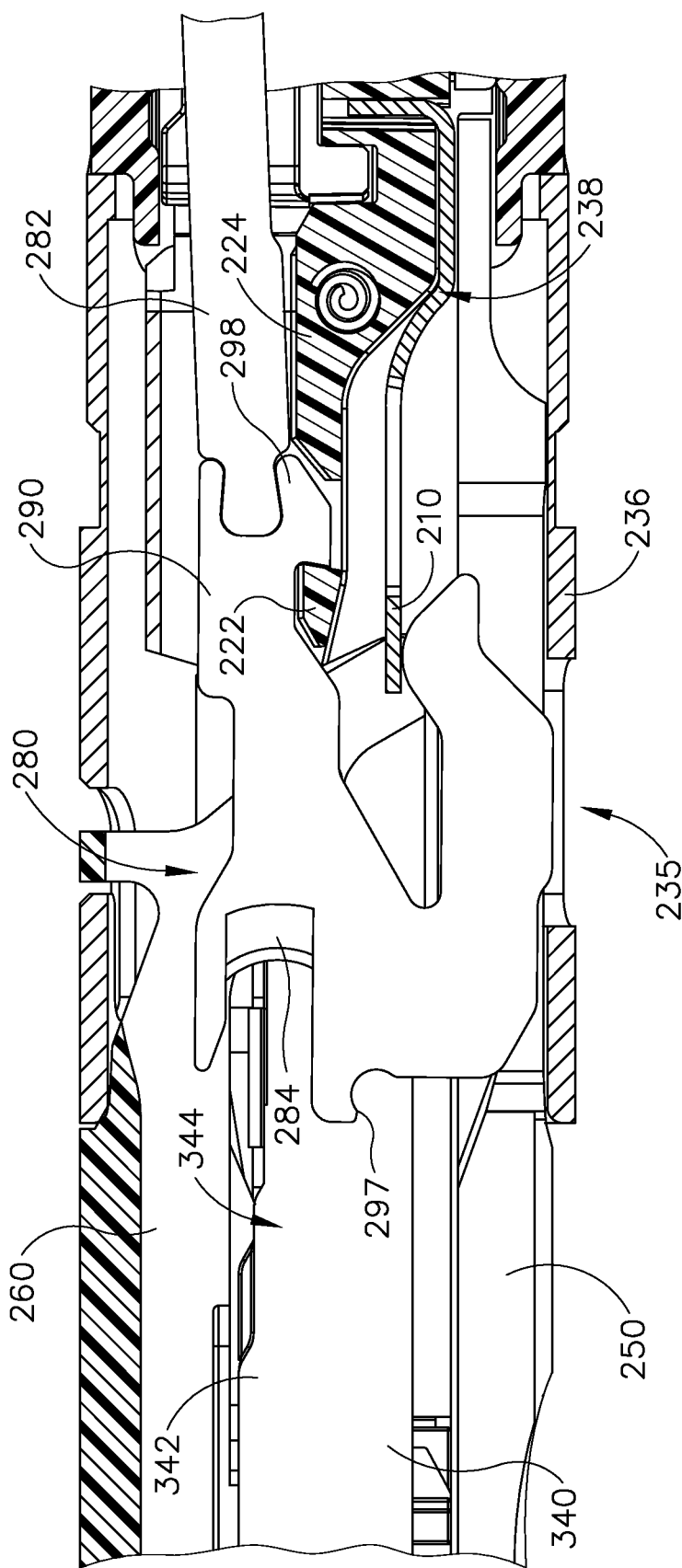
FIG. 36E depicts a cross-sectional view of the proximal end of the cartridge of FIG. 33 disposed within the end effector of FIG. 13, with the knife of the end effector moved into a lockout position upon being moved toward the second longitudinal position.
Figure 37:
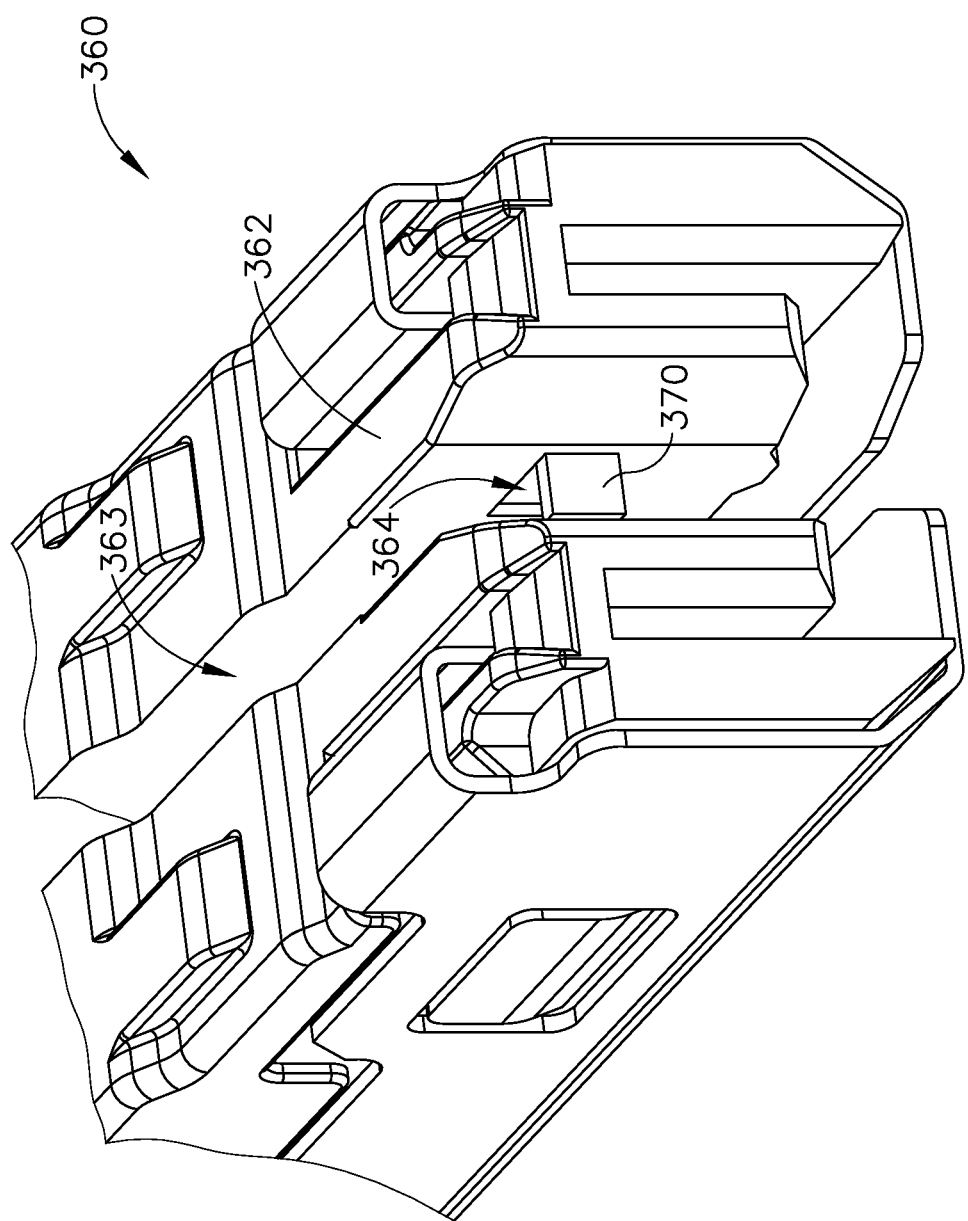
FIG. 37 depicts a perspective view of the proximal end of yet another exemplary alternative cartridge that may be incorporated into the end effector of FIG. 13.
Figure 38:
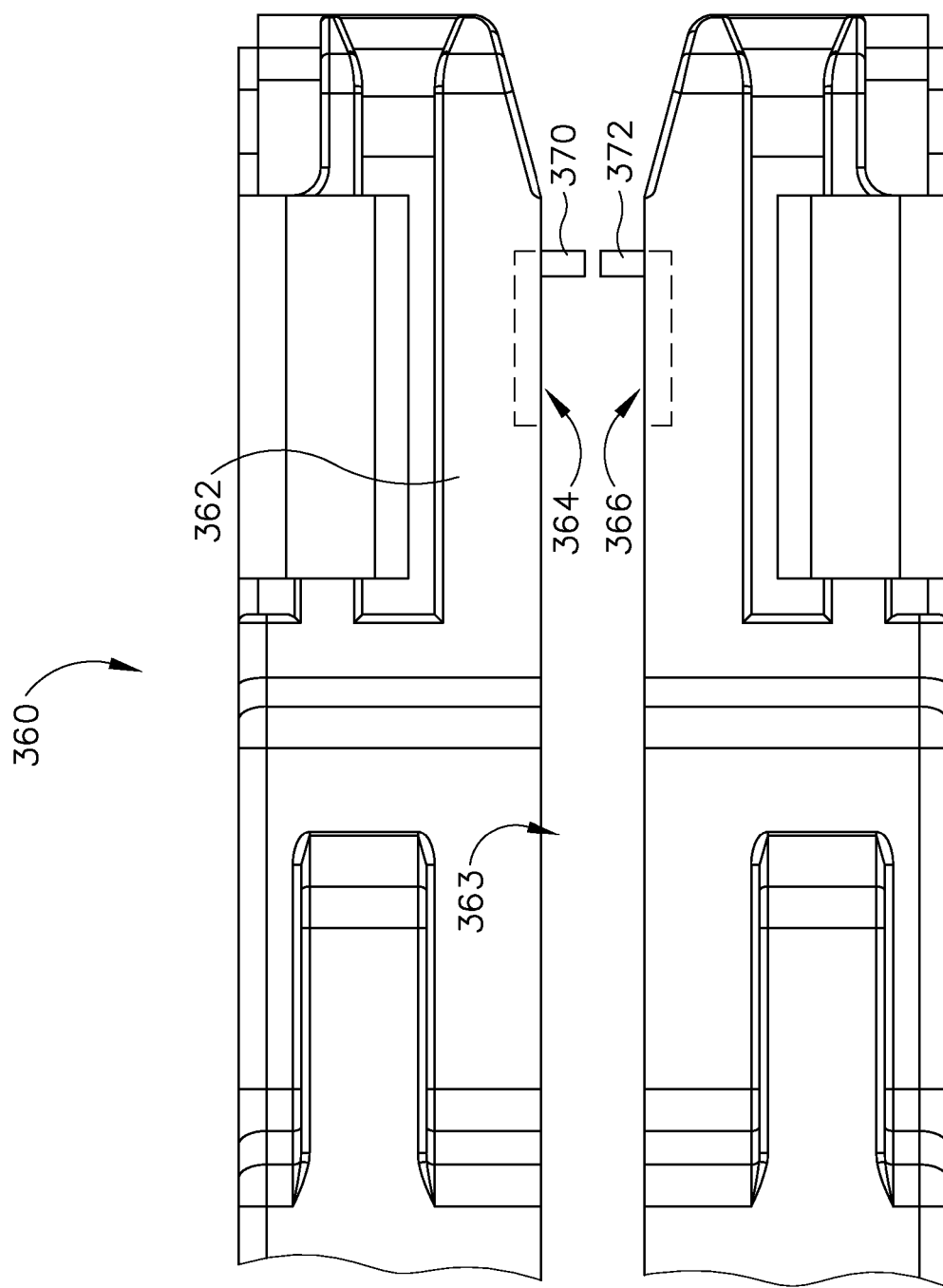
FIG. 38 depicts a top view of the proximal end of the cartridge of FIG. 37.
Figure 39:
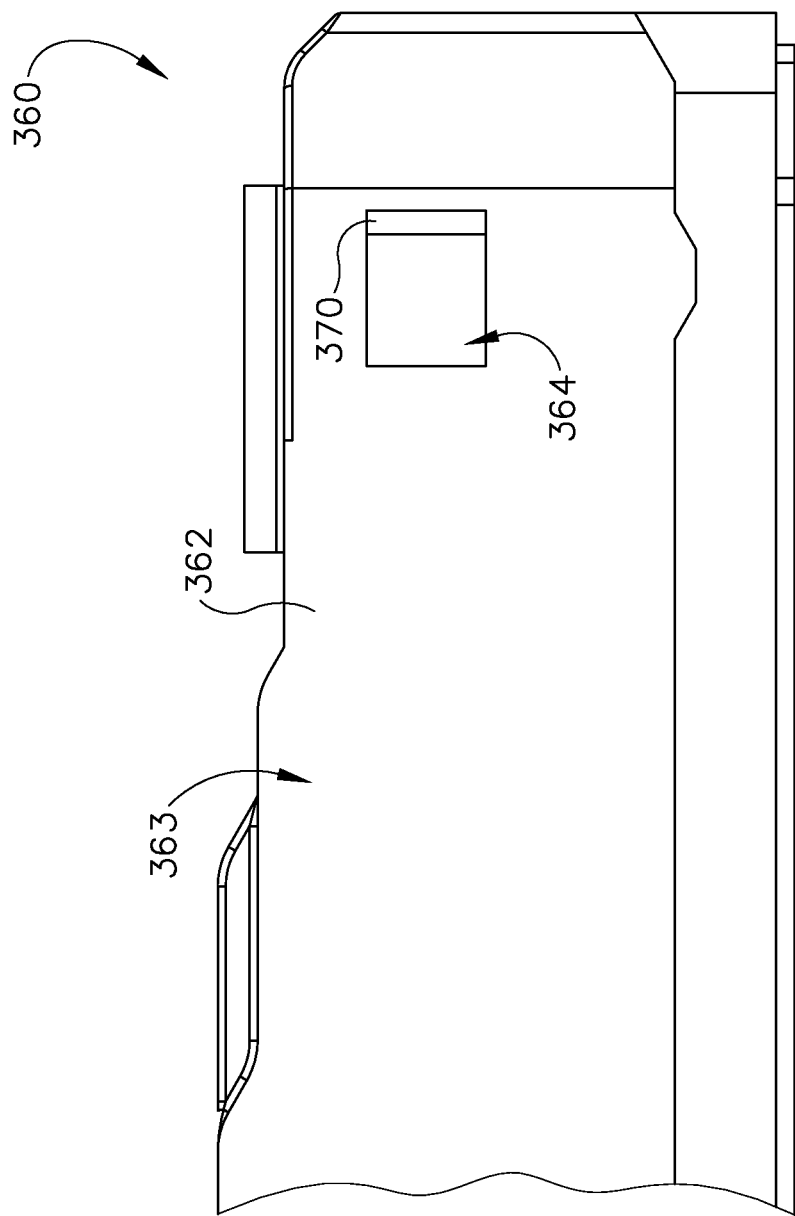
FIG. 39 depicts a cross-sectional side view of the proximal end of the cartridge of FIG. 37.
Figure 40:
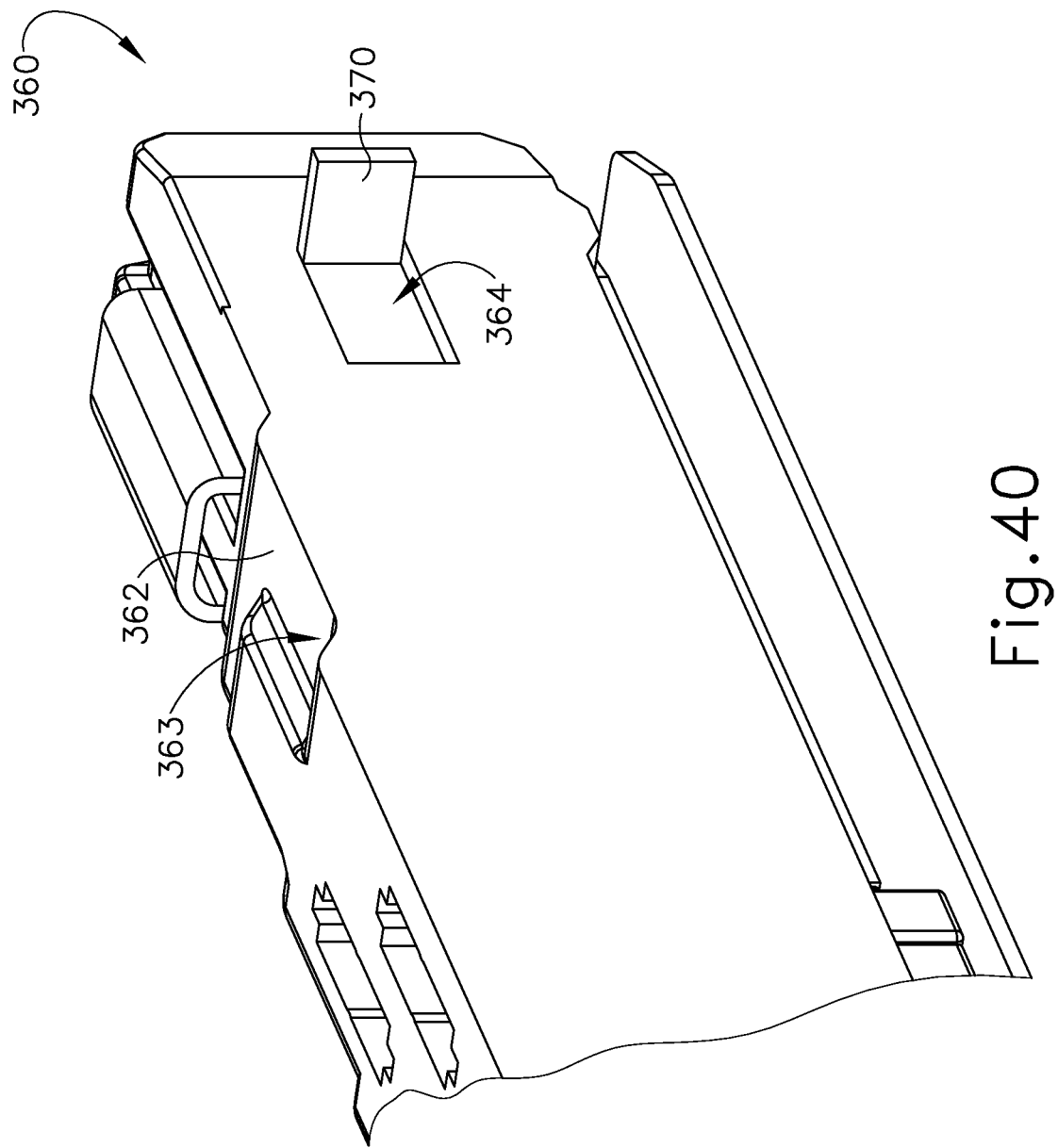
FIG. 40 depicts a cross-sectional perspective view of the proximal end of the cartridge of FIG. 37.

FIG. 36A shows end effector (240) in an initial position. In the initial position, upper extension (290) of knife member (280) is positioned above engagement features (222, 224) of frame member (238). Also in the initial position, distal tip (297) of knife member (280) is in contact with a top surface of ramp (350) of cartridge (340). As knife member (280) is fired distally, distal tip (297) of knife member (280) continues to engage the top surface of beam (330) as distal wall (281) of knife member (280) engages a proximal end (276) of sled (278), as shown in FIG. 36B. Engagement between distal tip (297) and the top surface of ramp (350) maintains the vertical position of knife member (280). Because ramp (350) maintains the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) breaks and/or cuts ramp (350) as knife member (280) drives wedge sled (278) distally as described above (FIG. 36C). After knife member (280) is fired distally, knife member (280) may be retracted proximally within lower jaw (250) (FIG. 36D). If an operator attempts to fire knife member (280) a second time, without ramp (350) to maintain the vertical position of knife member (280), resilient member (210) will resiliently drive knife member (280) downwardly to the lockout position as discussed above with reference to FIG. 23B and as shown in FIG. 36E.

D. Exemplary Cartridge with Bypass Tabs

FIGS. 37-41E show another exemplary cartridge (360) having a spent cartridge lockout feature. It should be understood that cartridge (360) may be readily used in end effector (240) or in other end effectors. Cartridge (360) of the present example is configured to operate substantially similar to cartridges (70, 270) discussed above except for the differences discussed below. Cartridge (360) includes a cartridge body (362) having a longitudinal channel (363) through which wedge sled (278) and knife member (280) may be longitudinally translated. The spent cartridge lockout feature of the present example comprises a pair of tabs (370, 372) extending from opposing interior surfaces of channel (363) of cartridge body (362). The interior surfaces of channel (364) of cartridge body (362) comprise a pair rectangular recesses (364, 366) within which tabs (370, 372) are pivotably disposed. Tabs (370) are pivotably secured within rectangular recesses (364, 366) via living hinges. Each tab (370, 372) is pivotable between an unexposed position, in which tabs (370, 372) are substantially completely disposed within rectangular recesses (364, 366); and an exposed position, in which tabs (370, 372) are substantially completely disposed outside of rectangular recesses (364, 366) and are positioned within channel (363), oriented substantially orthogonal to the respective interior surfaces of channel (363) of cartridge body (362). As will be discussed in more detail below, as knife member (280) is fired distally through channel (363), knife member (280) is configured to drive tabs (370, 372) from the exposed position toward the unexposed position. Tabs (370, 372) are configured to remain in the unexposed position once driven into the unexposed position. Also as will be discussed in more detail below, tabs (370, 372) are configured to allow for firing of knife member (280) when tabs (370, 372) are in the exposed position; and to prevent firing of knife member (280) when tabs (370, 372) are in the unexposed position.

Figure 41A:
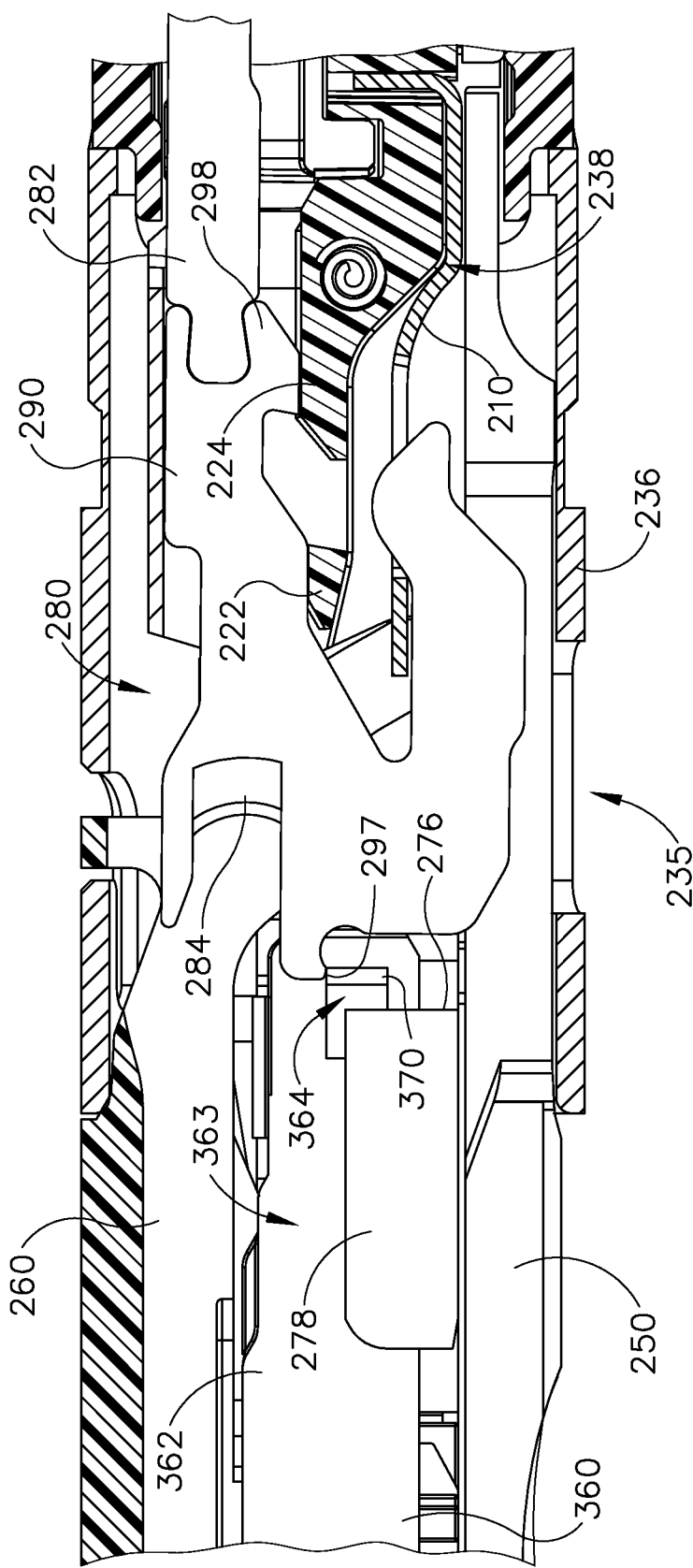
FIG. 41A depicts a cross-sectional view of the proximal end of the cartridge of FIG. 37 disposed within the end effector of FIG. 13, with the breakaway feature in a first rotational position, with a sled of the cartridge in a first longitudinal position, and with a knife of the end effector in a first longitudinal position.
Figure 41B:
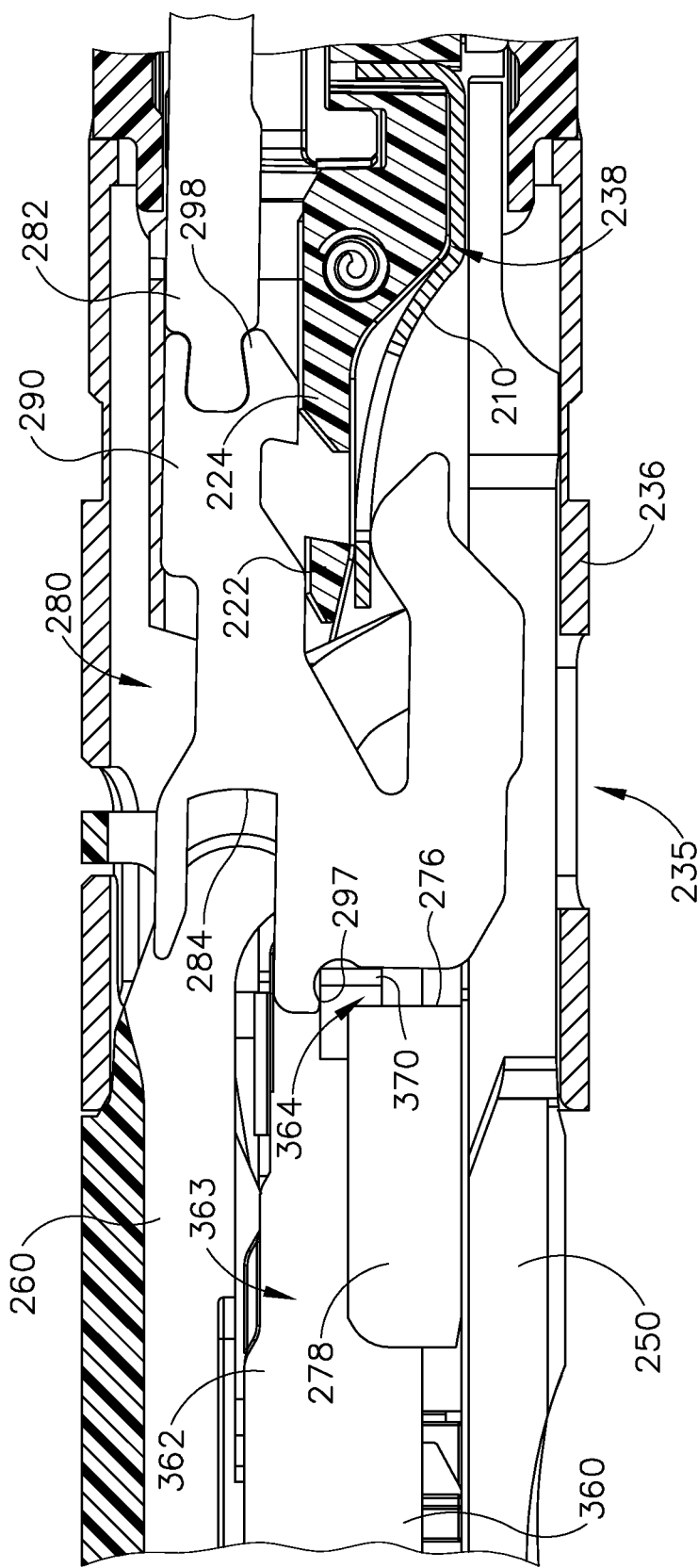
FIG. 41B depicts a cross-sectional view of the proximal end of the cartridge of FIG. 37 disposed within the end effector of FIG. 13, with the breakaway feature in the first rotational position, with the sled of the cartridge in the first longitudinal position, and with the knife of the end effector moved into a second longitudinal position.
Figure 41C:
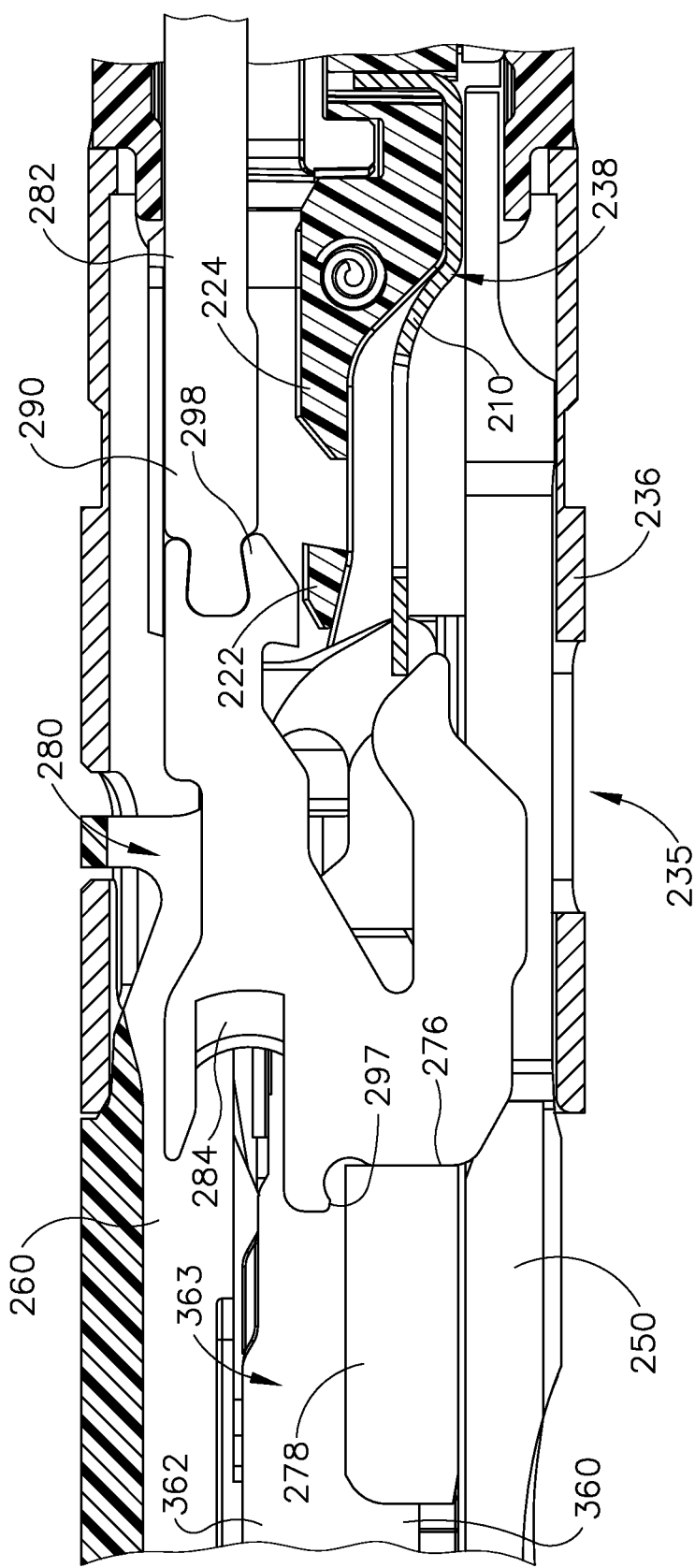
FIG. 41C depicts a cross-sectional view of the proximal end of the cartridge of FIG. 37 disposed within the end effector of FIG. 13, with the breakaway feature moved into a second rotational position and with the sled of the cartridge moved into a second longitudinal position both by movement of the knife of the end effector into a third longitudinal position.
Figure 41D:
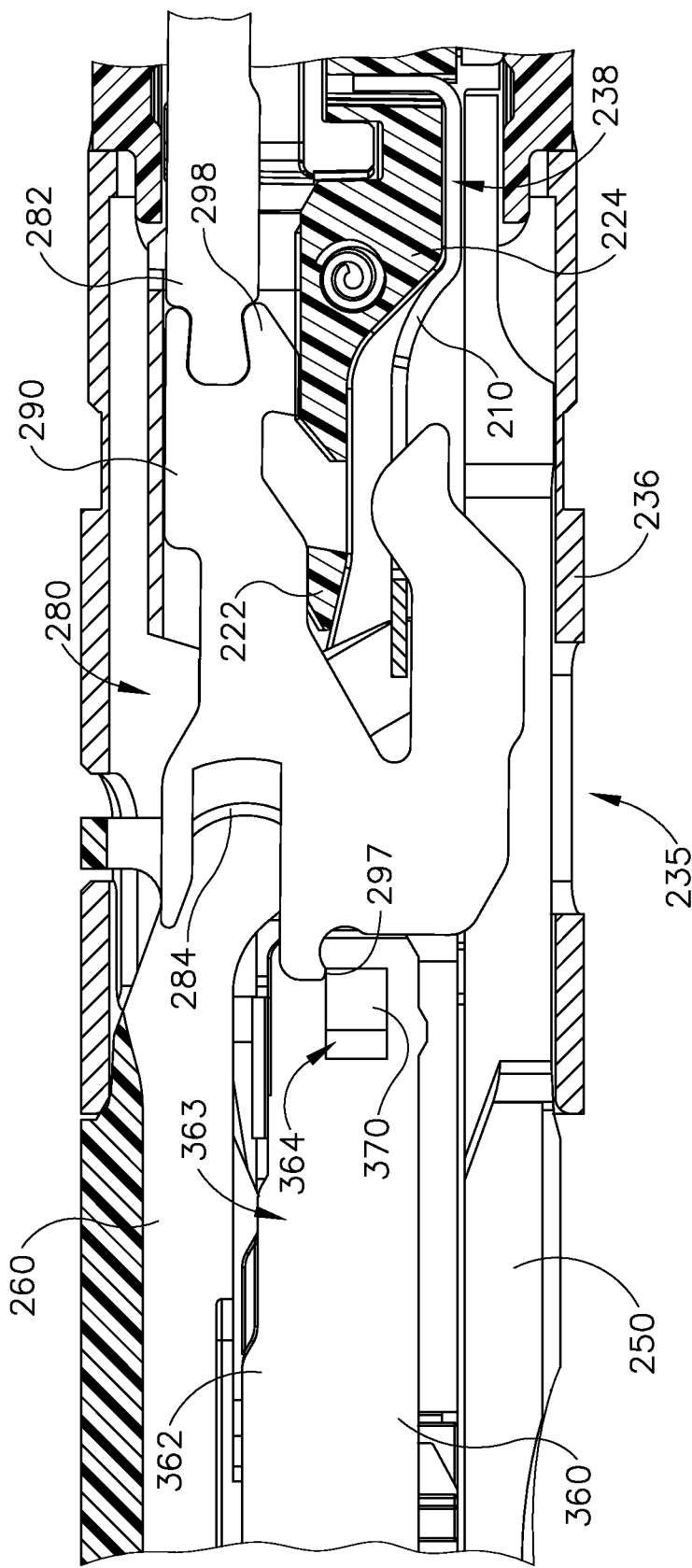
FIG. 41D depicts a cross-sectional view of the proximal end of the cartridge of FIG. 37 disposed within the end effector of FIG. 13, with the breakaway feature in the second rotational position and with the knife of the end effector moved back into the first longitudinal position.
Figure 41E:
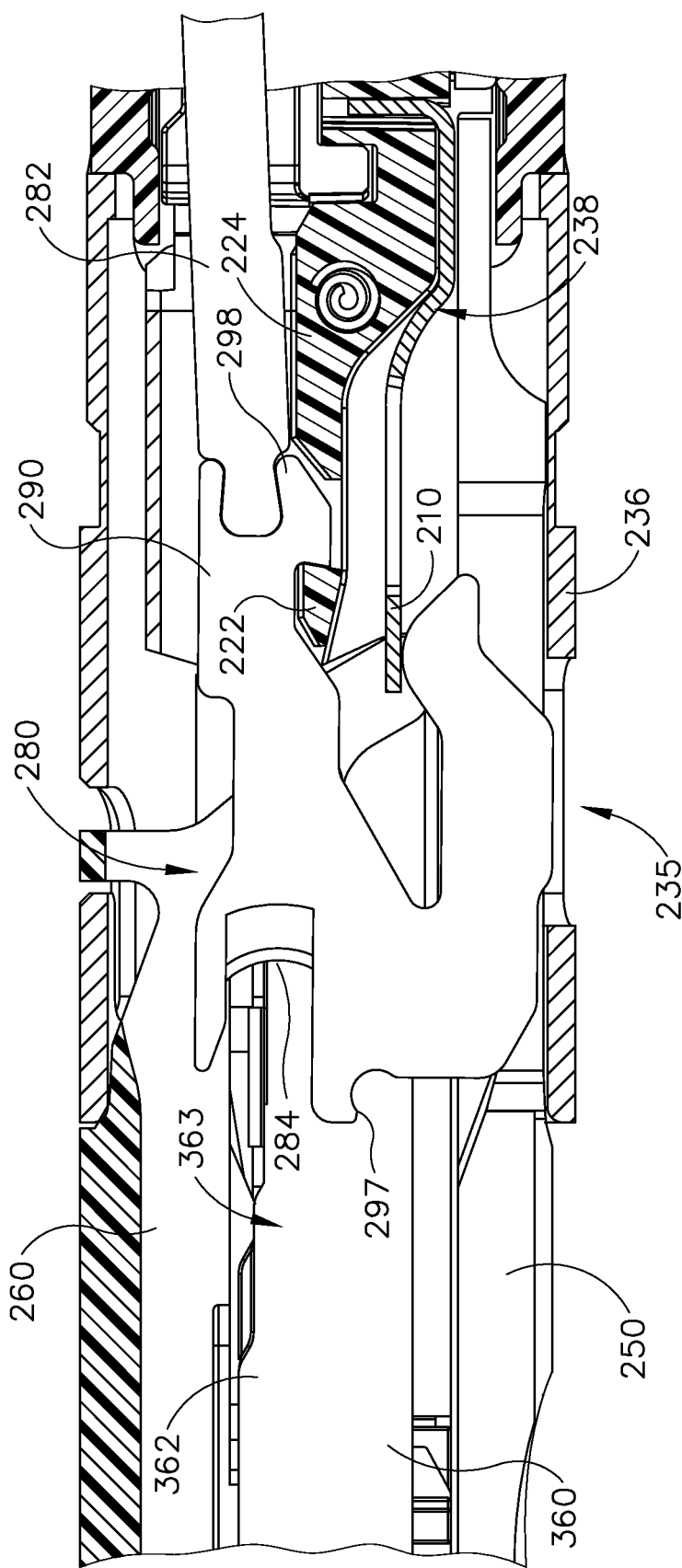
FIG. 41E depicts a cross-sectional view of the proximal end of the cartridge of FIG. 37 disposed within the end effector of FIG. 13, with the knife of the end effector moved into a lockout position upon being moved toward the second longitudinal position.

FIG. 41A shows end effector (240) in an initial position. In the initial position, upper extension (290) of knife member (280) is positioned above engagement features (222, 224) of frame member (238). Also in the initial position, tabs (370, 372) are in the exposed position and distal tip (297) of knife member (280) is in contact with a top surface of one or both tabs (370, 372) of cartridge (360). As knife member (280) is fired distally, distal tip (297) of knife member (280) continues to engage the top surface of one or both tabs (370, 372) as distal wall (281) of knife member (280) engages a proximal end (276) of sled (278), as shown in FIG. 41B. Engagement between distal tip (297) and of one or both tabs (370, 372) maintains the vertical position of knife member (280). Because one or both tabs (370, 372) maintain the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) drives tabs (370, 372) into the unexposed position as knife member (280) drives wedge sled (278) distally as described above (FIG. 41C). After knife member (280) is fired distally, knife member (280) may be retracted proximally within lower jaw (250) (FIG. 41D). If an operator attempts to fire knife member (280) a second time, with tabs (370, 372) in the unexposed position, tabs (370, 372) no longer maintain the vertical position of knife member (280), resilient member (210) will resiliently drive knife member (280) downwardly to the lockout position as discussed above with reference to FIG. 23B and as shown in FIG. 41E.

E. Exemplary Cartridges with Bypass Fins

Figure 42:
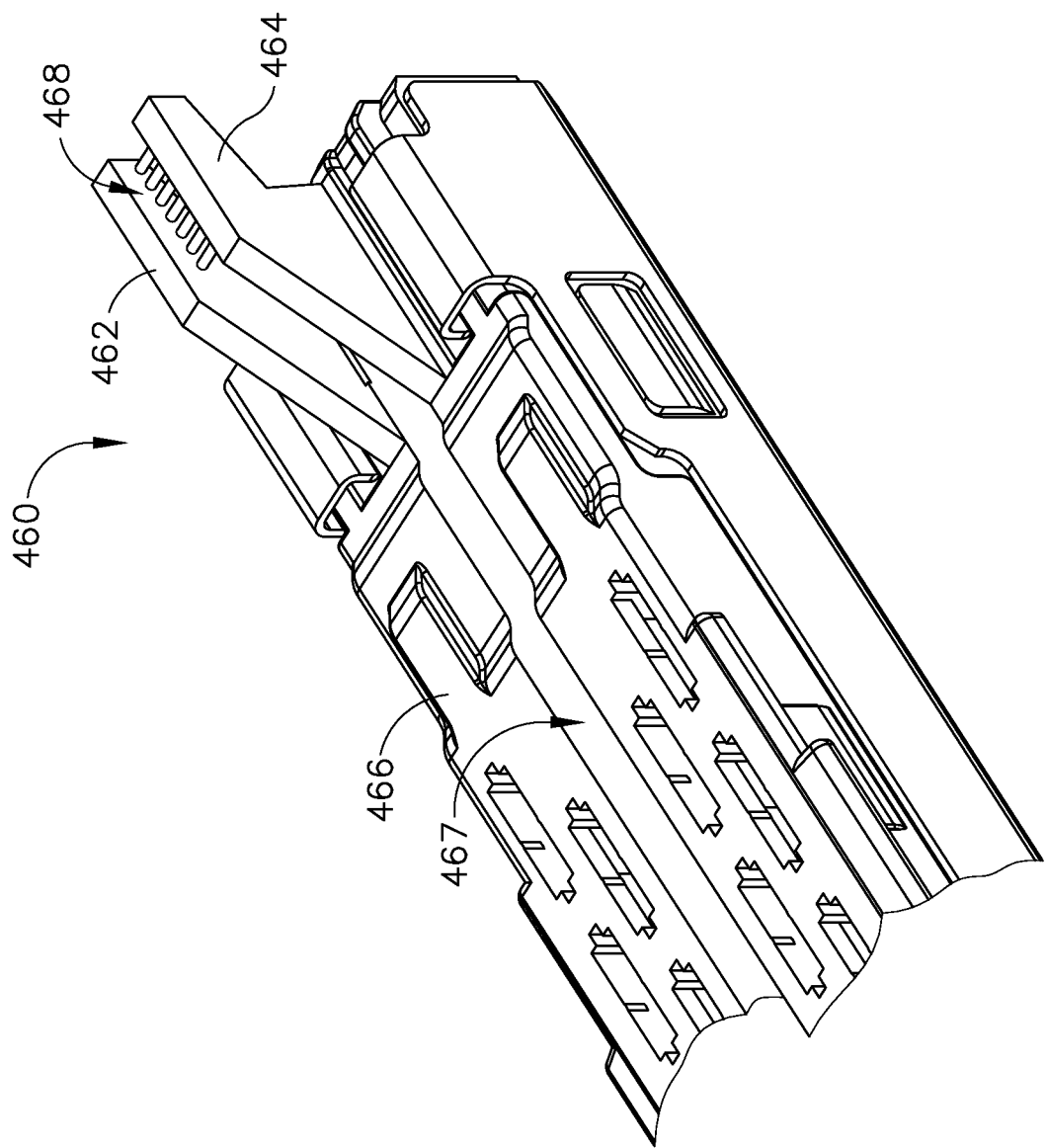
FIG. 42 depicts a perspective view of the proximal end of yet another exemplary alternative cartridge that may be incorporated into the end effector of FIG. 13.
Figure 43:
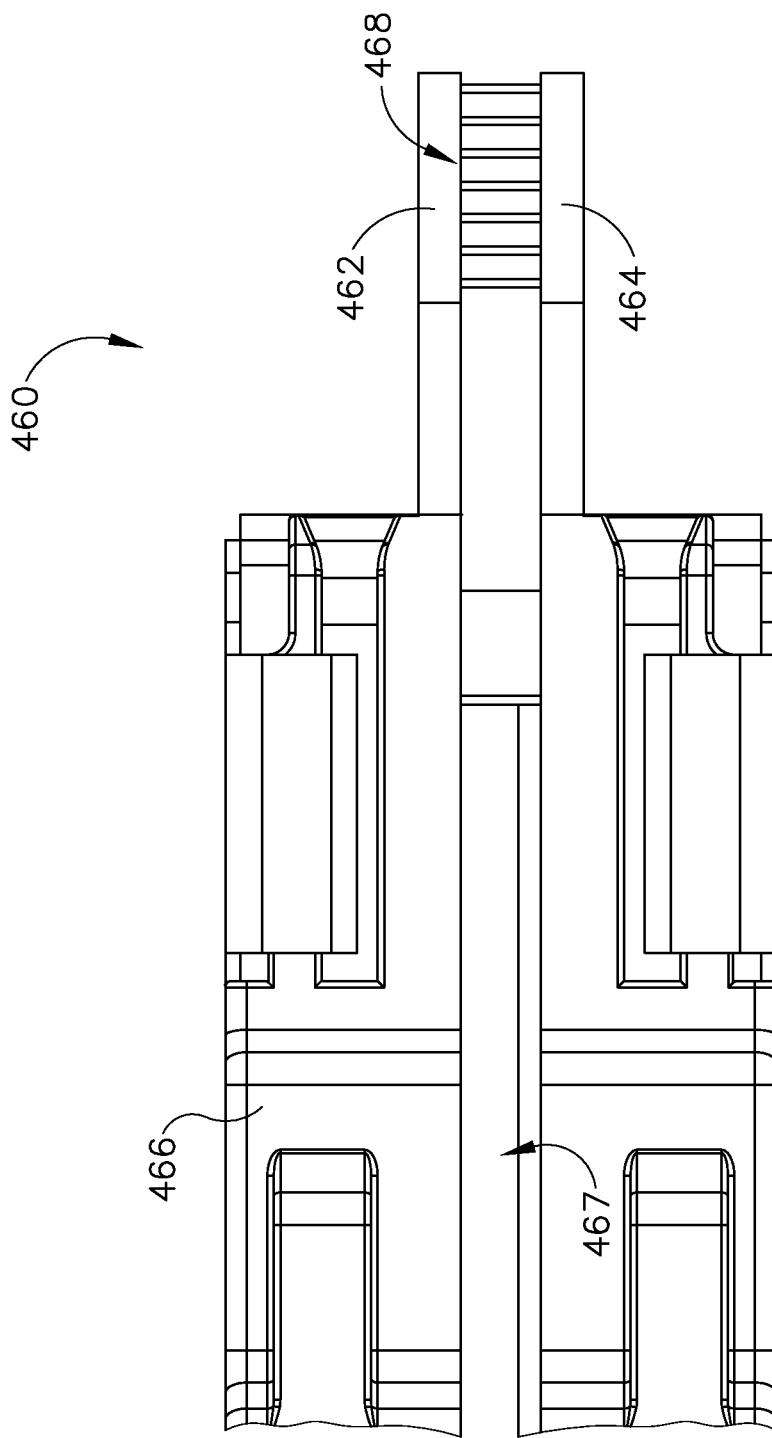
FIG. 43 depicts a top view of the proximal end of the cartridge of FIG. 42.

FIGS. 42 and 43 show another exemplary cartridge (460) having a spent cartridge lockout feature. It should be understood that cartridge (460) may be readily used in end effector (240) or in other end effectors. Cartridge (460) of the present example is configured to operate substantially similar to cartridges (70, 270) discussed above except for the differences discussed below. Cartridge (460) includes a cartridge body (466) having a longitudinal channel (467) through which wedge sled (278) and knife member (280) may be longitudinally translated. The spent cartridge lockout feature of the present example comprises a pair of fins (462, 464) extending upwardly and proximally from a cartridge body (466). A plurality of breakaway or cutaway pins (468) within a gap (463) defined between fins (462, 464). Gap (463) between fins (462, 464) is aligned with channel (467) of cartridge body (466) such that pins (468) are in the path of distally translating knife member (280). As will be discussed in more detail below, as knife member (280) is fired distally through channel (467) and gap (463), knife member (280) is configured to break and/or cut pins (468). Also as will be discussed in more detail below, pins (468) are configured to allow for firing of knife member (280) when pins (468) are present and to prevent firing of knife member (280) when pins (468) are not present.

Figure 44A:
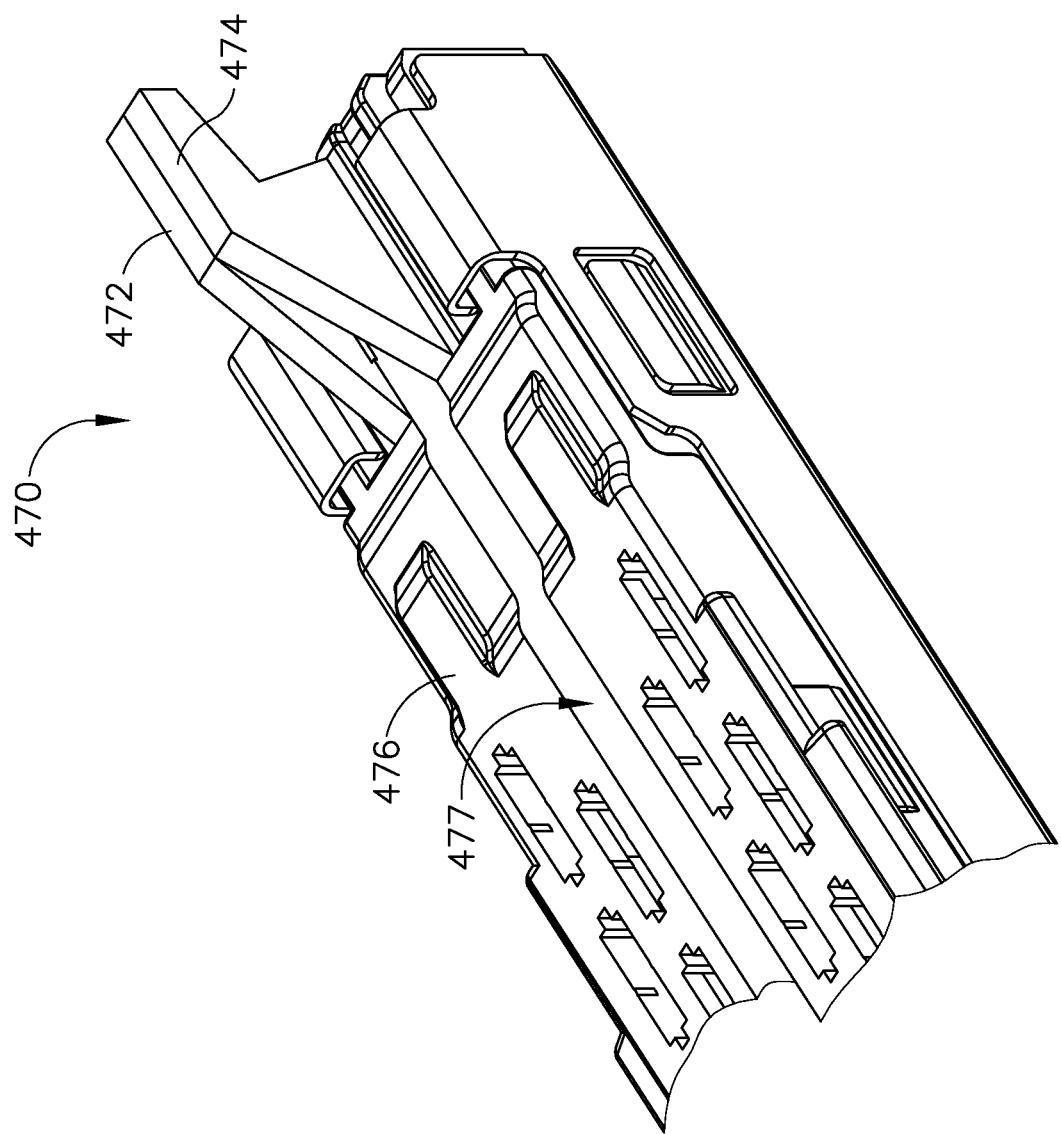
FIG. 44A depicts a perspective view of the proximal end of yet another exemplary alternative cartridge that may be incorporated into the end effector of FIG. 13.
Figure 44B:
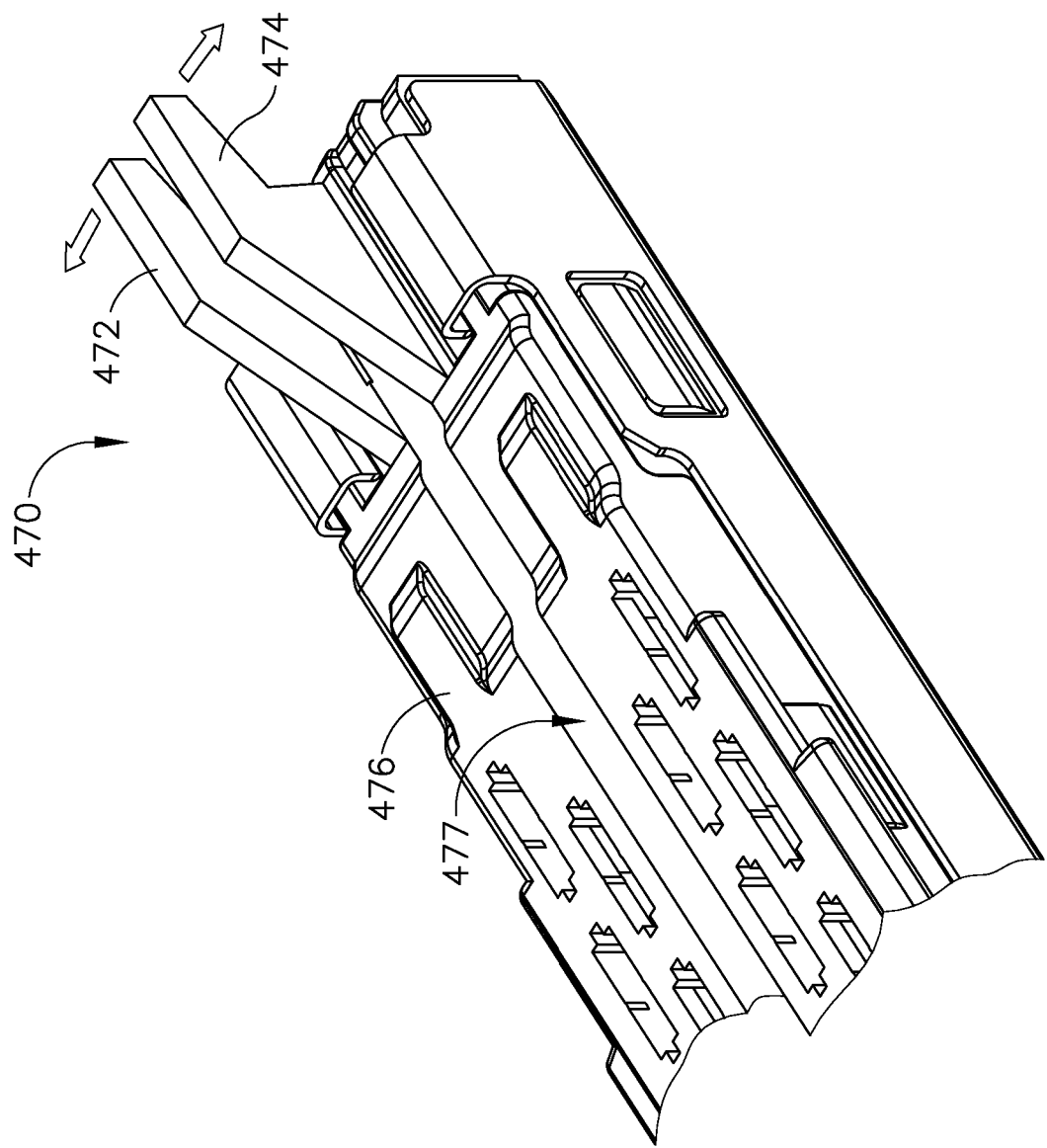
FIG. 44B depicts a perspective view of the proximal end of yet another exemplary alternative cartridge with the alternative pair of guide fins moved into an open position.
Figure 45A:
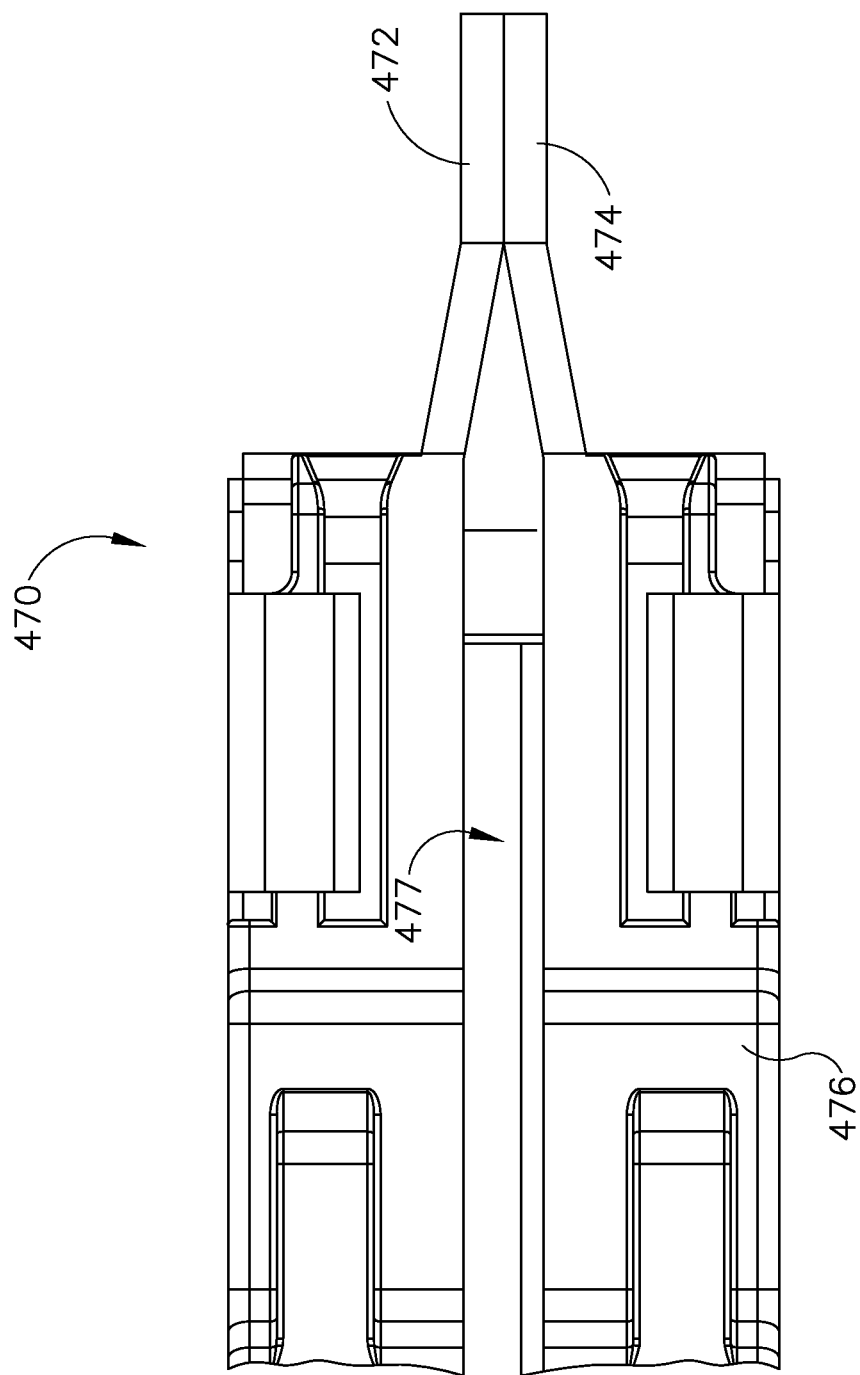
FIG. 45A depicts a top view of the proximal end of the cartridge of FIG. 44A with the guide fins in the closed position.

FIGS. 44A-45B show another exemplary cartridge (470) having a spent cartridge lockout feature. It should be understood that cartridge (470) may be readily used in end effector (240) or in other end effectors. Cartridge (470) of the present example is configured to operate substantially similar to cartridges (70, 270) discussed above except for the differences discussed below. Cartridge (470) includes a cartridge body (476) having a longitudinal channel (477) through which wedge sled (278) and knife member (280) may be longitudinally translated. The spent cartridge lockout feature of the present example comprises a pair of malleable fins (472, 474) extending upwardly and proximally from a cartridge body (476). Initially, fins (472, 474) are in a closed position as shown in FIGS. 44A and 45A. In the closed position, fins (472, 474) contact each other along a plane aligned with channel (477) of cartridge body (476), such that fins (472, 474) are in the path of distally translating knife (280). As will be discussed in more detail below, as knife member (280) is fired distally through channel (467), knife member (280) is configured to drive fins (472, 474) outwardly into an open position as shown in FIGS. 44B and 45B. Fins (472, 474) are configured to remain in the open position upon being driven into the open position by firing of knife member (280). As will be discussed in more detail below, fins (468) are configured to allow for firing of knife member (280) when fins (472, 474) are in the closed position; and to prevent firing of knife member (280) when fins (472, 474) in the open position.

Figure 46:
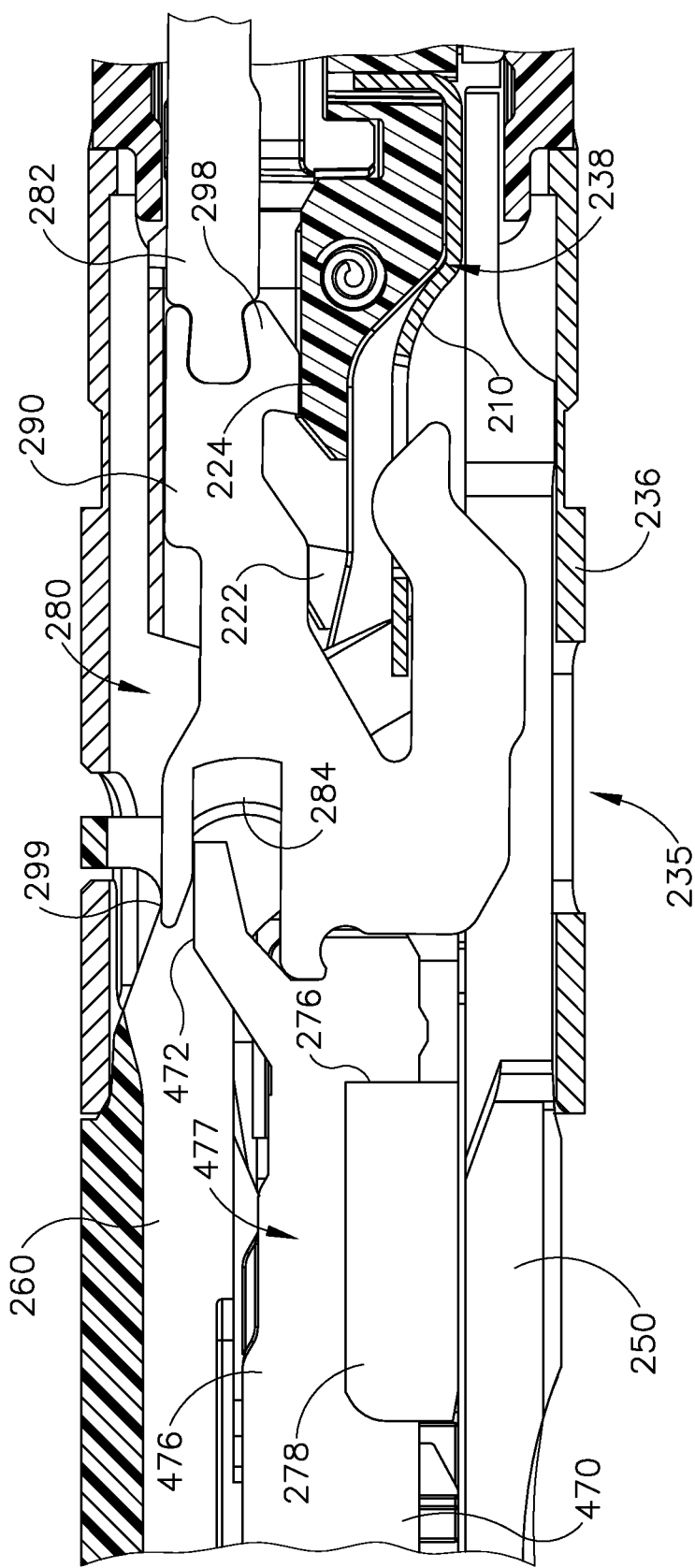
FIG. 46 depicts a cross-sectional side view of the proximal end of the cartridge of FIG. 44A disposed within the end effector of FIG. 13.
Figure 47:
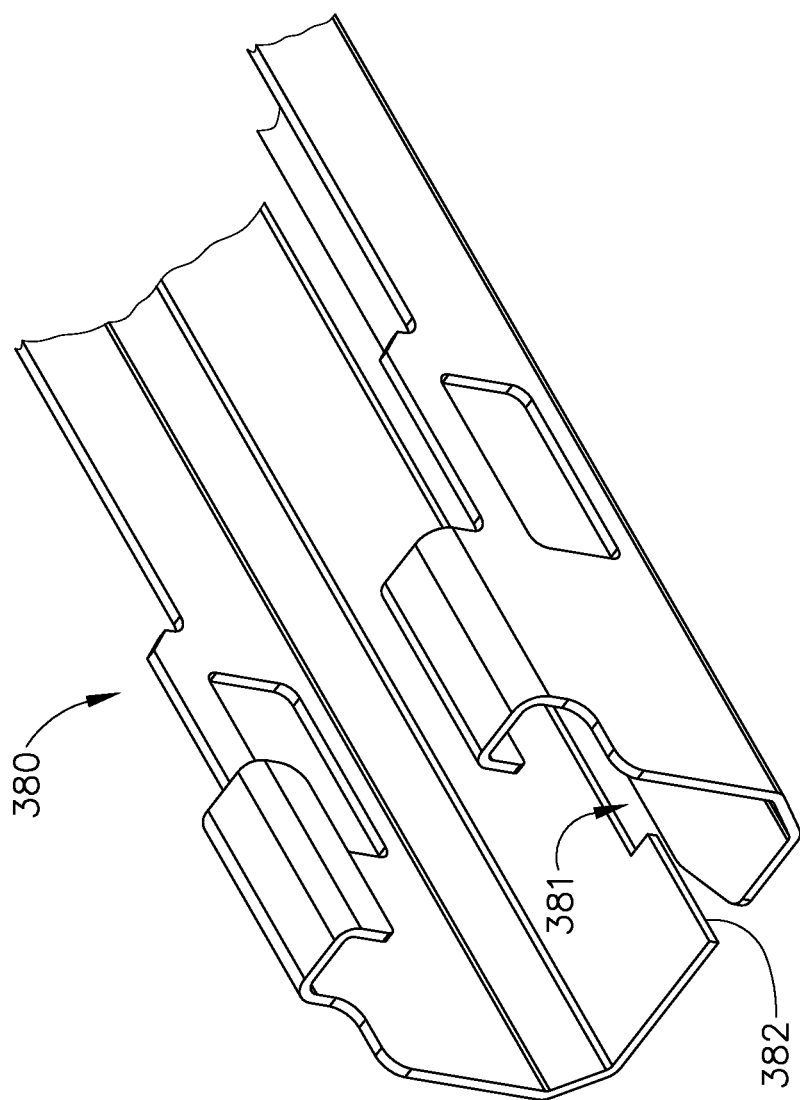
FIG. 47 depicts a perspective view of the proximal end of an exemplary cartridge tray that may be incorporated into a cartridge of the end effector of FIG. 13.
Figure 48:
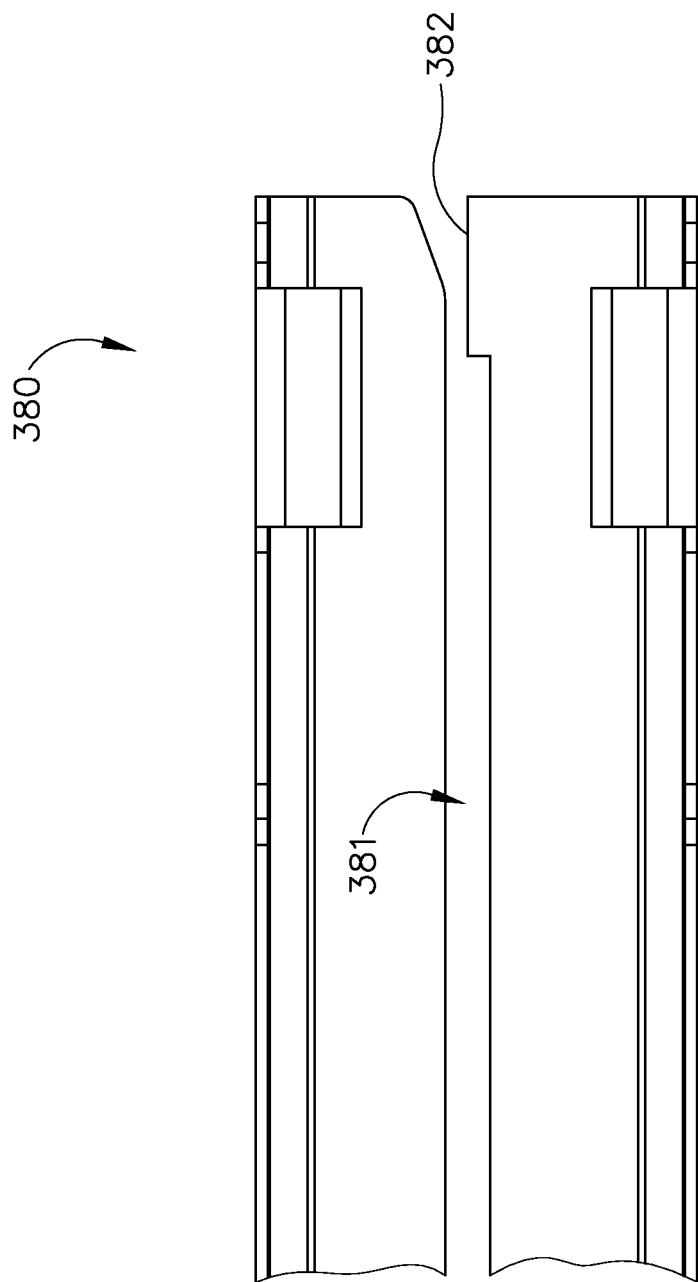
FIG. 48 depicts a top view of the proximal end of the cartridge tray of FIG. 47.

FIG. 46 shows end effector (240) in an initial position. In the initial position, upper extension (290) of knife member (280) is positioned above engagement features (222, 224) of frame member (238). Also in the initial position, a distal protrusion (299) of knife member (280) is in contact with a top surface of pins (468) of cartridge (460) or fins (472, 474) of cartridge (470). (Although cartridge (470) is being discussed in the present example, it should be appreciated that cartridge (460) may alternatively be used.) As knife member (280) is fired distally, distal protrusion (299) of knife member (280) continues to engage the top surface of pins (468) or fins (472, 474) so as to maintain the vertical position of knife member (280). Because pins (468) or fins (472, 474) maintain the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) breaks and/or cuts pins (468) or drives fins (472, 474) outwardly into the open position as knife member (280) drives wedge sled (278) distally as described above. After knife member (280) is fired distally, knife member (280) may be retracted proximally within lower jaw (250). If an operator attempts to fire knife member (280) a second time, without pins (468) or fins (472, 474) to maintain the vertical position of knife member (280), resilient member (210) will resiliently drive knife member (280) downwardly to the lockout position as discussed above with reference to FIG. 23B.

IV. Exemplary Permanent Lockout Bypass Features in Cartridge

In some instances, it may be desirable to provide other features in a staple cartridge (270) that enable the knife member (280) to bypass lockout features (222, 224) of frame member (238) discussed above to thereby allow continuous firing (i.e. distal advancement) of firing beam (282) and knife member (280) so that tissue positioned between anvil (260) and lower jaw (250) may be severed and stapled. For example, such a feature may prevent knife member (280) from engaging the lockout features of frame member (238) discussed above upon being fired. The examples below include several merely illustrative versions of lockout bypass features that may be readily incorporated into a staple cartridge (270) that is coupled with an end effector such as end effector (240). The examples discussed below provide a lockout bypass in lieu of having wedge sled (278) provide a lockout bypass as discussed above. The examples discussed below are also permanent, permitting re-firing of firing beam (282) and knife member (280) through a spent staple cartridge (270).

A. Exemplary Cartridge Tray with Projection

FIGS. 47-49B show an exemplary cartridge tray (380) having a lockout bypass feature. It should be understood that cartridge tray (380) may be readily used in staple cartridge (270) or in other staple cartridges. Cartridge tray (380) of the present example is configured to operate substantially similar to cartridge trays (76, 276) discussed above except for the differences discussed below. Cartridge tray (380) includes a longitudinal slot (381) through which protrusion (288) of knife member (280) may be longitudinally translated. Slot (381) is substantially aligned with channel (269) of cartridge (270). The lockout bypass feature of the present example comprises an inwardly extending projection (382). Projection (382) extends transversely inwardly within the proximal end of slot (381). Projection (382) is configured to engage shelf (283) of knife member (280) as knife member (280) is fired; yet projection (382) provides enough clearance for protrusion (288) of knife member (280) to traverse longitudinally through channel (269) of cartridge (270). As will be discussed in more detail below, projection (382) is configured to allow for firing of knife member (280) by preventing engagement of knife member (280) with the lockout features of frame member (238) as discussed above.

Figure 49A:
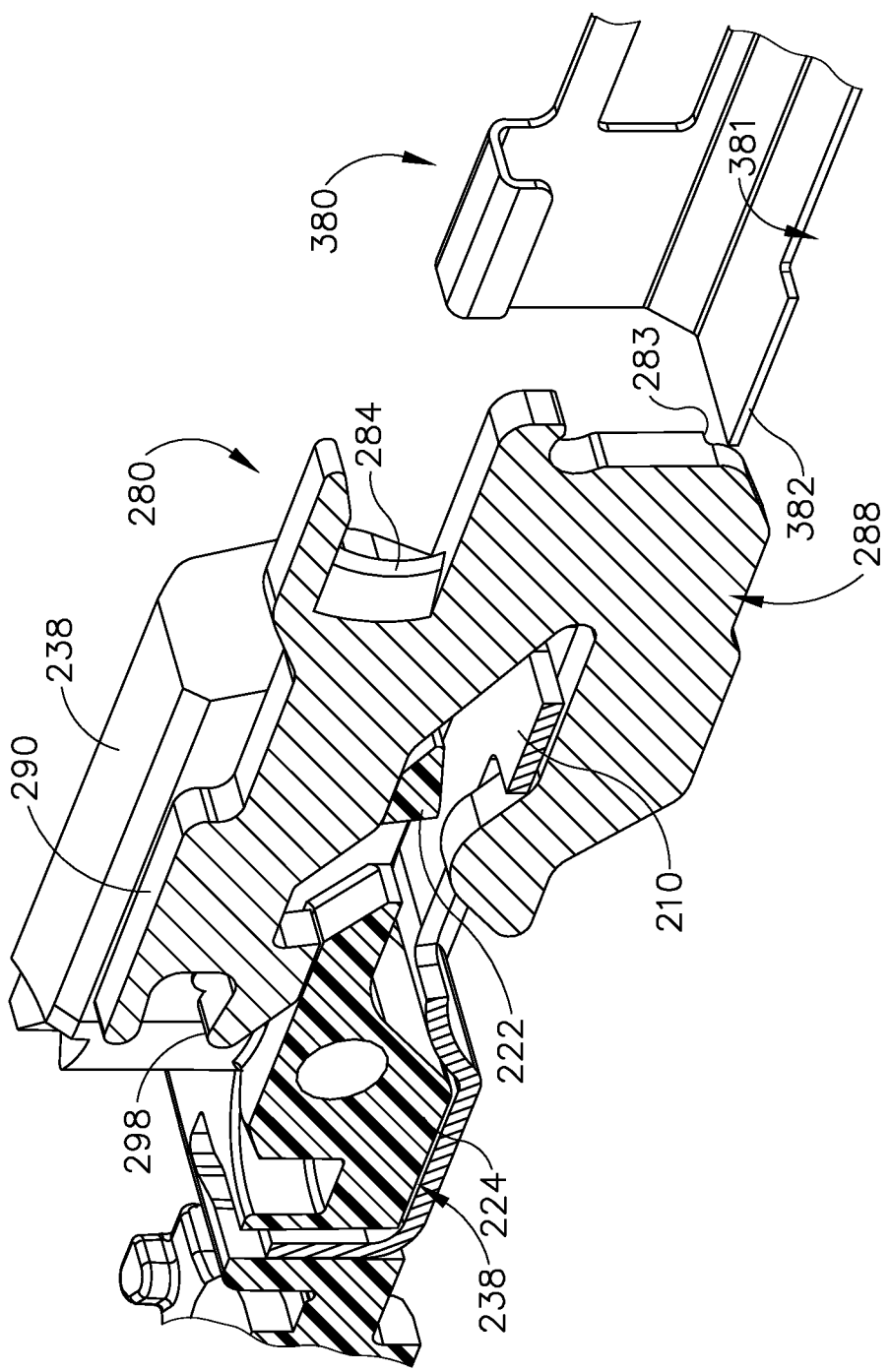
FIG. 49A depicts a cross-sectional perspective view of the proximal end of the cartridge tray of FIG. 47 with components of the end effector of FIG. 13, with a knife of the end effector in a first longitudinal position.
Figure 49B:
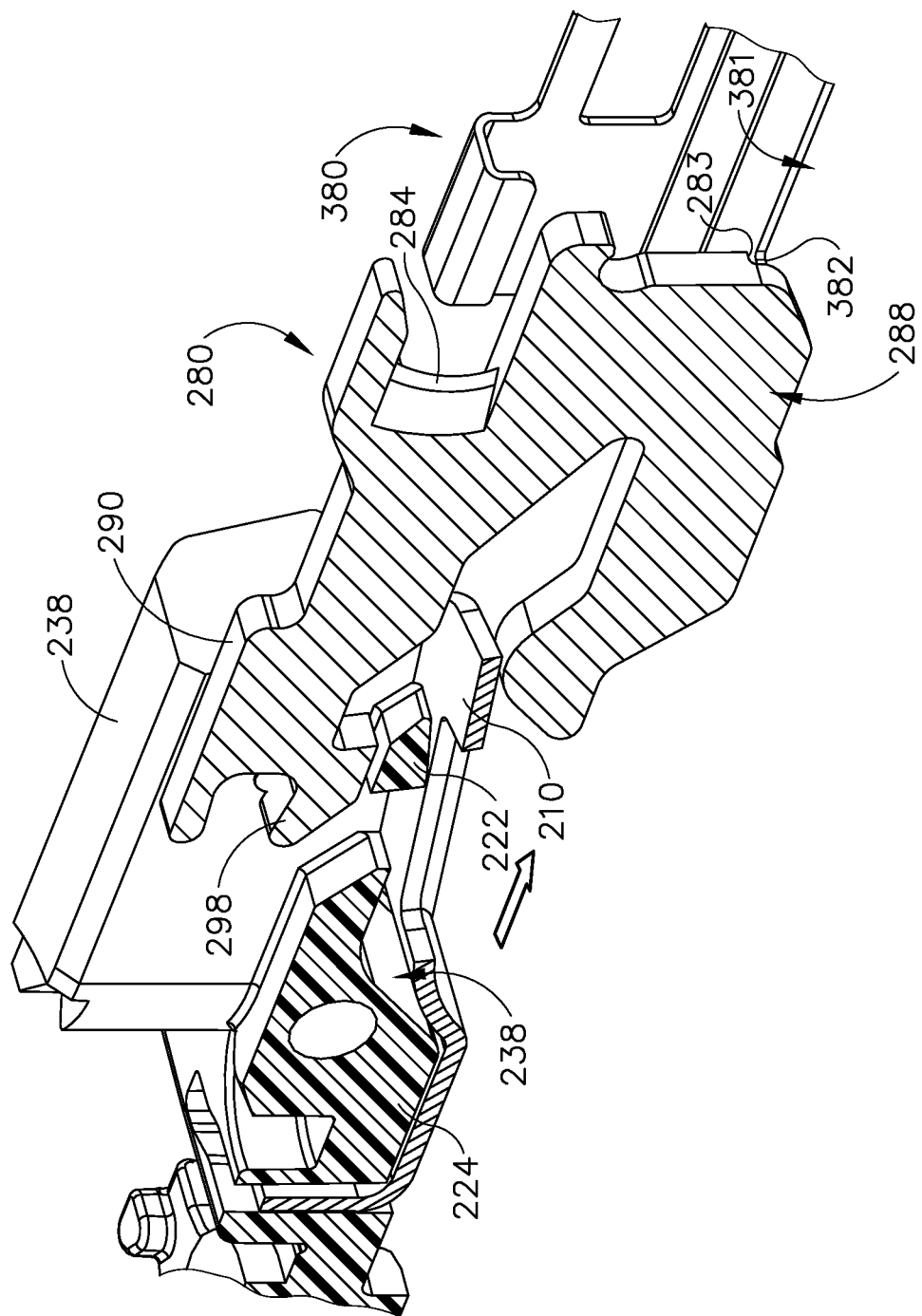
FIG. 49B depicts a cross-sectional perspective view of the proximal end of the cartridge tray of FIG. 47 with components of the end effector of FIG. 13, with the knife of the end effector moved into a second longitudinal position.
Figure 50:
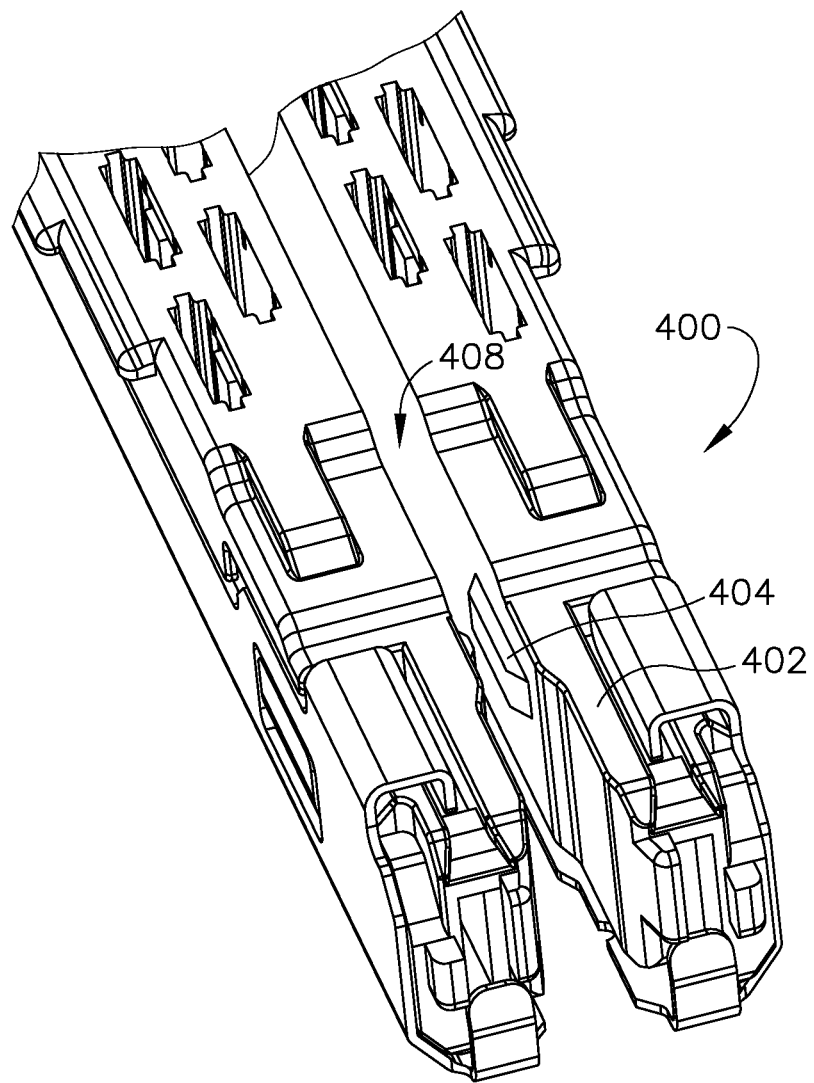
FIG. 50 depicts a perspective view of the proximal end of yet another exemplary alternative cartridge that may be incorporated into the end effector of FIG. 13.

FIG. 49A shows components of end effector (240) in an initial position. In the initial position, upper extension (290) of knife member (280) is positioned above engagement features (222, 224) of frame member (238). As knife member (280) is fired distally, shelf (283) of knife member (280) engages a top surface projection (382). Engagement between shelf (283) and projection (382) maintains the vertical position of knife member (280). Because projection (382) maintains the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280).

B. Exemplary Cartridge Body with Projections

FIGS. 50-52B show another exemplary staple cartridge (400) having a lockout bypass feature. It should be understood that cartridge (400) may be readily used in end effector (240) or in other end effectors. Cartridge (400) of the present example is configured to operate substantially similar to cartridges (70, 270) discussed above except for the differences discussed below. Cartridge (400) includes a cartridge body (402) having a longitudinal channel (408) through which wedge sled (278) and knife member (280) may be longitudinally translated. The lockout bypass feature of the present example comprises a pair of inwardly extending projections (404, 406) extending inwardly from opposing interior surfaces of channel (408) of cartridge body (402). Projections (404, 406) are configured to engage distal tip (297) of knife member (280) as knife member (280) is fired; yet projections (404, 406) provide enough clearance for knife member (280) to translate longitudinally through channel (408) of cartridge (400). As will be discussed in more detail below, projections (404, 406) are configured to allow for firing of knife member (280) by preventing engagement of knife member (280) with the lockout features of frame member (238) as discussed above.

Figure 52A:
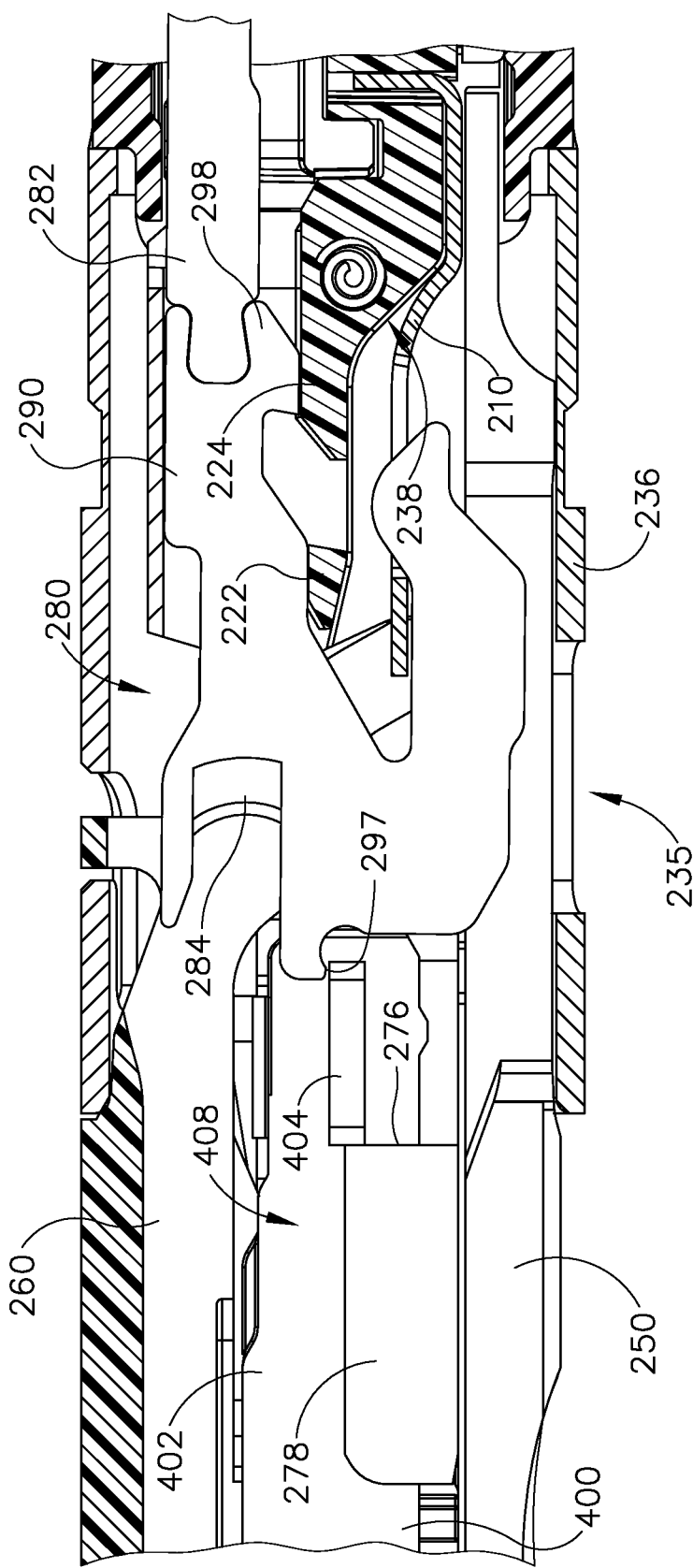
FIG. 52A depicts a cross-sectional view of the proximal end of the cartridge of FIG. 50 disposed within the end effector of FIG. 13, with a knife of the end effector in a first longitudinal position.
Figure 52B:
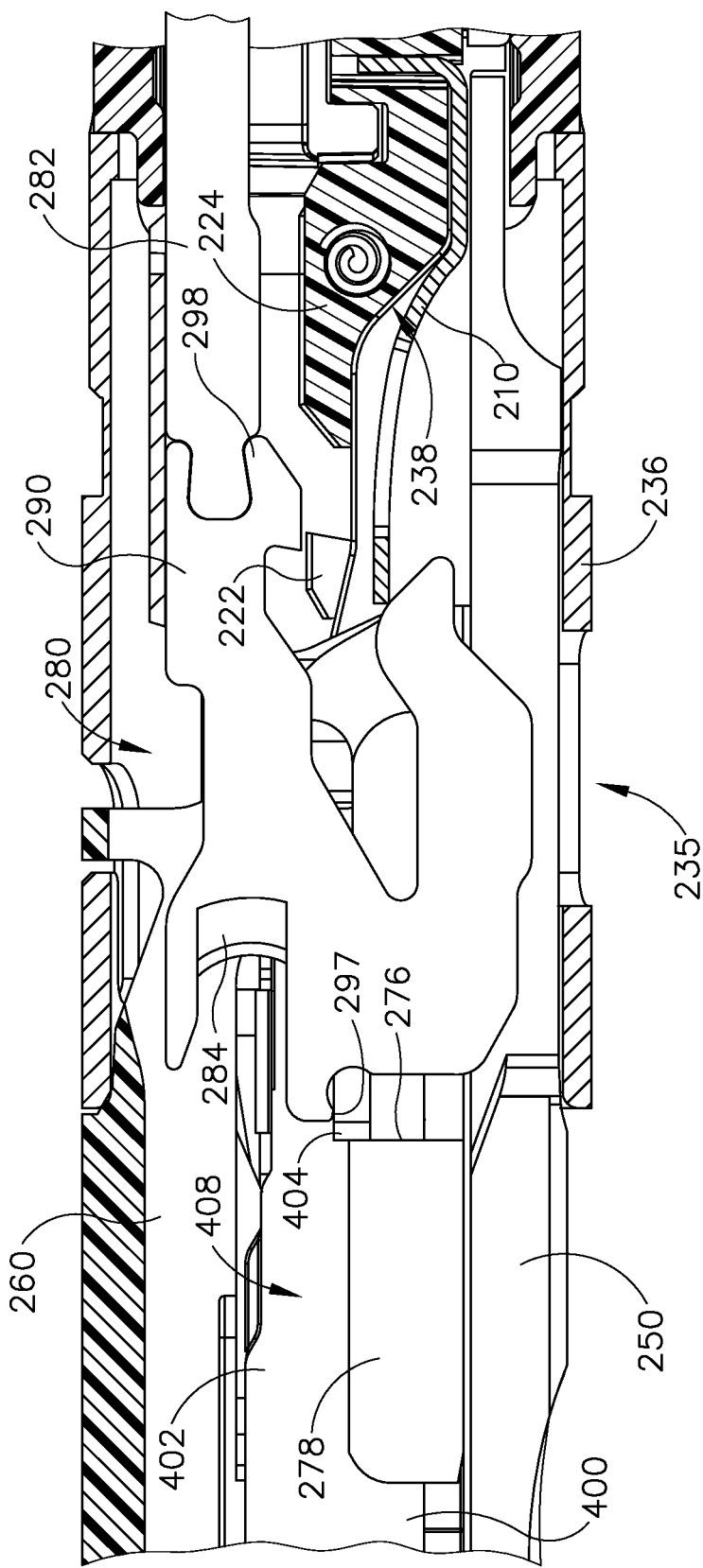
FIG. 52B depicts a cross-sectional view of the proximal end of the cartridge of FIG. 50 disposed within the end effector of FIG. 13, with the knife of the end effector moved into a second longitudinal position.
Figure 53:
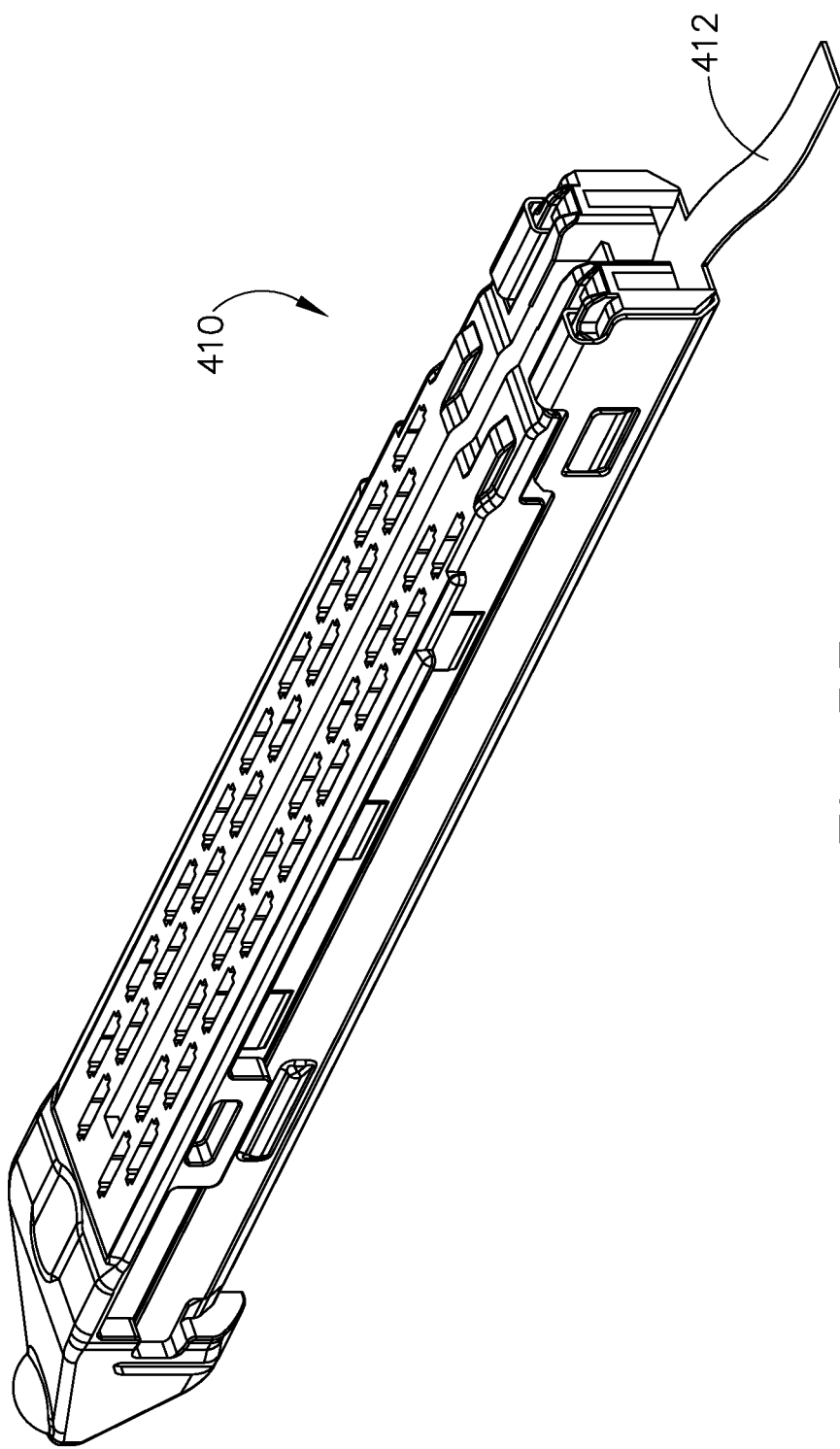
FIG. 53 depicts a perspective view of yet another exemplary alternative cartridge that may be incorporated into the end effector of FIG. 13.
Figure 54:
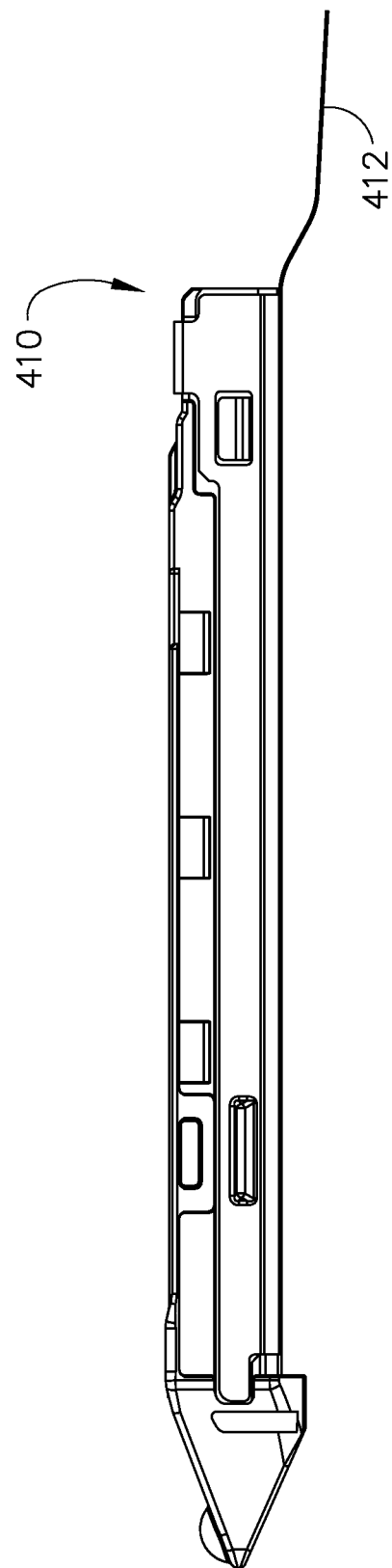
FIG. 54 depicts a side view of the cartridge of FIG. 53.
Figure 55:
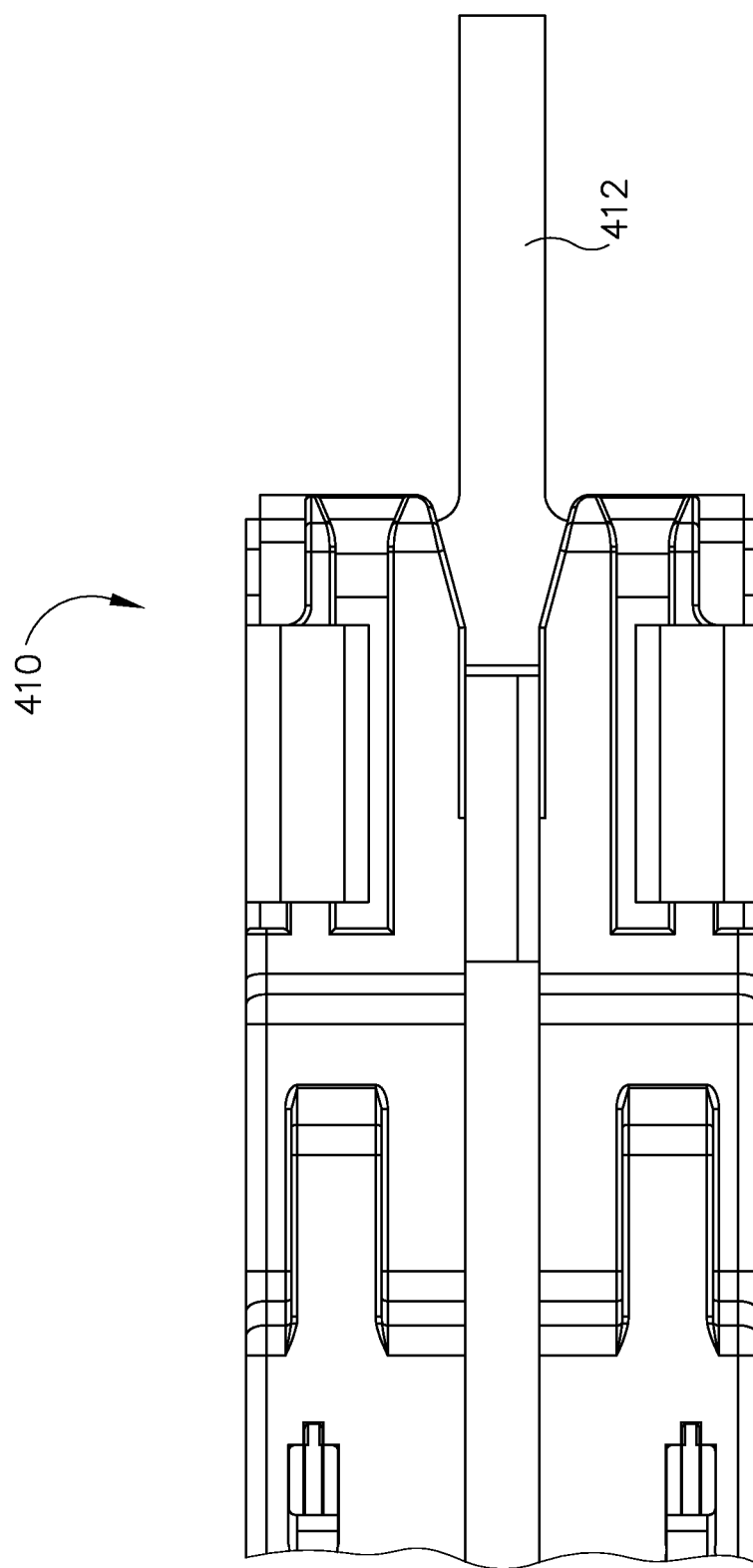
FIG. 55 depicts a top view of the proximal end of the cartridge of FIG. 53.

FIG. 52A shows end effector (240) in an initial position. In the initial position, upper extension (290) of knife member (280) is positioned above engagement features (222, 224) of frame member (238). As knife member (280) is fired distally to the position shown in FIG. 52B, distal tip (297) of knife member (280) engages a top surface of one or both projections (404, 406). Engagement between distal tip (297) and one or both projections (404, 406) maintains the vertical position of knife member (280). Because one or both projections (404, 406) maintain the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280).

C. Exemplary Cartridge with Proximal Ramp

Figure 56:
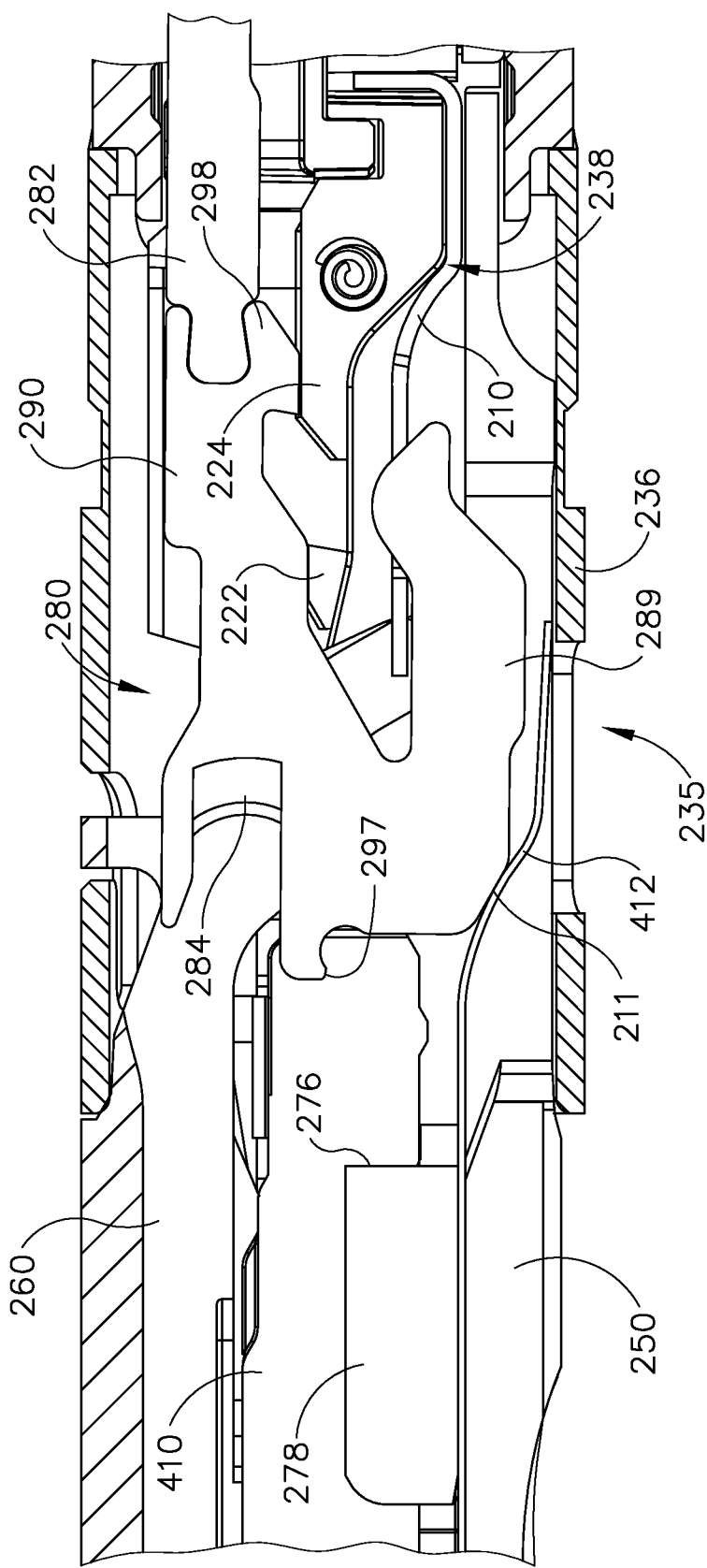
FIG. 56 depicts a cross-sectional view of the proximal end of the cartridge of FIG. 53 disposed within the end effector of FIG. 13.
Figure 57:
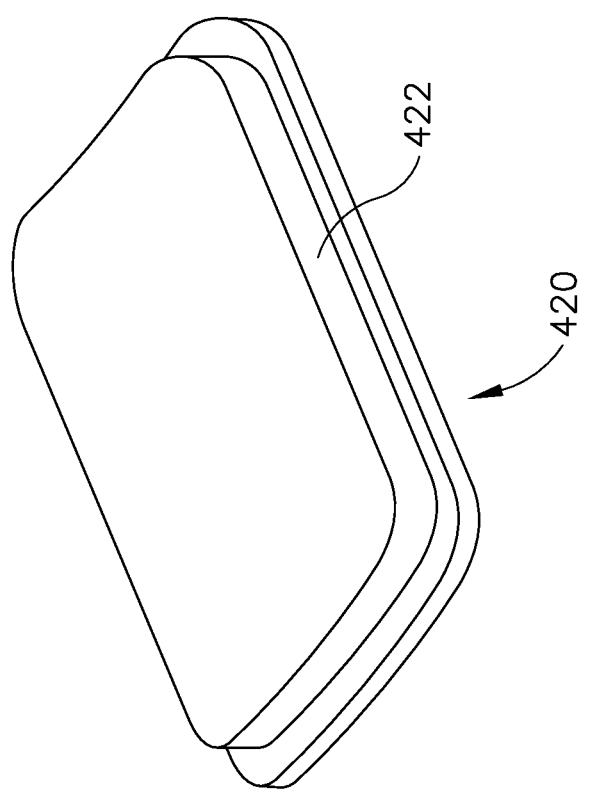
FIG. 57 depicts a perspective view of an exemplary tab insert.
Figure 58B:
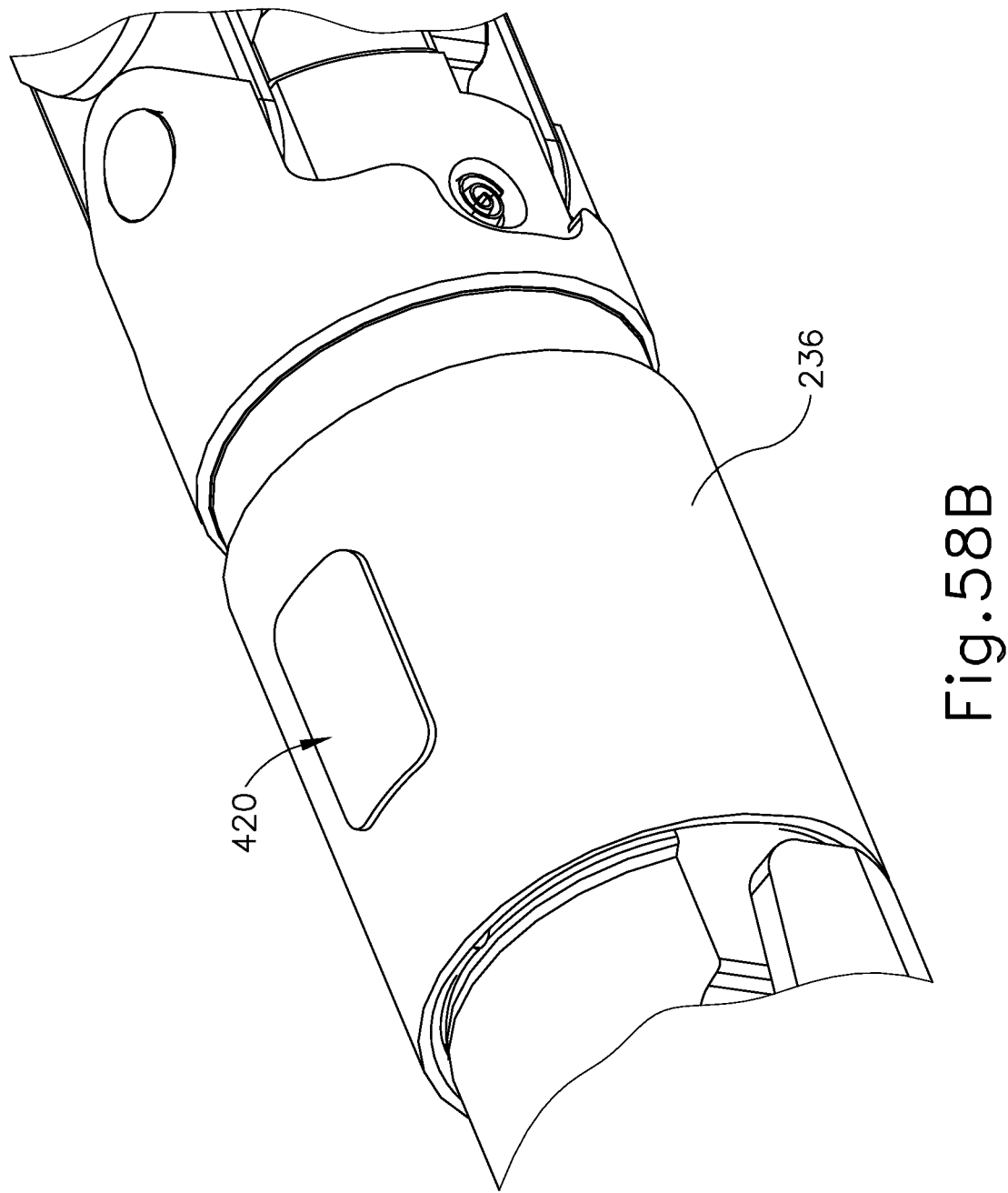
FIG. 58B depicts a perspective view of the end effector of FIG. 13, with the tab insert of FIG. 57 positioned within the end effector.

FIGS. 53-56 show another exemplary staple cartridge (410) having a lockout bypass feature. It should be understood that cartridge (410) may be readily used in end effector (240) or in other end effectors. Cartridge (410) of the present example is configured to operate substantially similar to cartridges (70, 270) discussed above except for the differences discussed below. The lockout bypass feature of the present example comprises a resilient ramp (412) extending proximally from a proximal end of cartridge (410). Ramp (412) is configured to engage ramped wall (211) and/or tab (289) of knife member (280) as knife member (280) is fired distally. Ramp (412) is configured to allow for firing of knife member (280) by preventing engagement of knife member (280) with the lockout features of frame member (238) as discussed above upon being fired. In particular, as shown in FIG. 56, with cartridge (410) positioned within lower jaw (250), ramp (410) covers opening (235) of closure ring (236) and provides a surface operable to engage ramped wall (211) and/or tab (289) of knife member (280) as knife member (280) is fired. As knife member (280) is fired distally, ramped wall (211) and/or tab (289) of knife member (280) engages a top surface of ramp (412). Engagement between ramped wall (211) and/or tab (289) and ramp (412) maintains the vertical position of knife member (280). Because ramp (412) maintains the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280).

It should also be understood that a variation of cartridge (410) may be used in other kinds of surgical staplers. By way of example only, a variation of cartridge (410) may be used in any of the various surgical staplers disclosed in U.S. Pat. No. 7,380,695, entitled "Surgical Stapling Instrument Having a Single Lockout Mechanism for Prevention of Firing," issued Jun. 3, 2008, the disclosure of which is incorporated by reference herein. For instance, ramp (412) may engage the "middle pin 46" of the "firing bar 14" of that stapler, such that the "middle pin 46" rides along the top surface of ramp (412). This may provide a bypass of a lockout assembly as taught in that reference, such that ramp (412) enables the "firing bar 14" to advance distally without being locked out. Various other suitable ways in which ramp (412) and other lockout bypass features described herein may be incorporated into other stapling instruments will be apparent to those of ordinary skill in the art in view of the teachings herein.

D. Exemplary Snap-Fit Cover

Figure 59A:
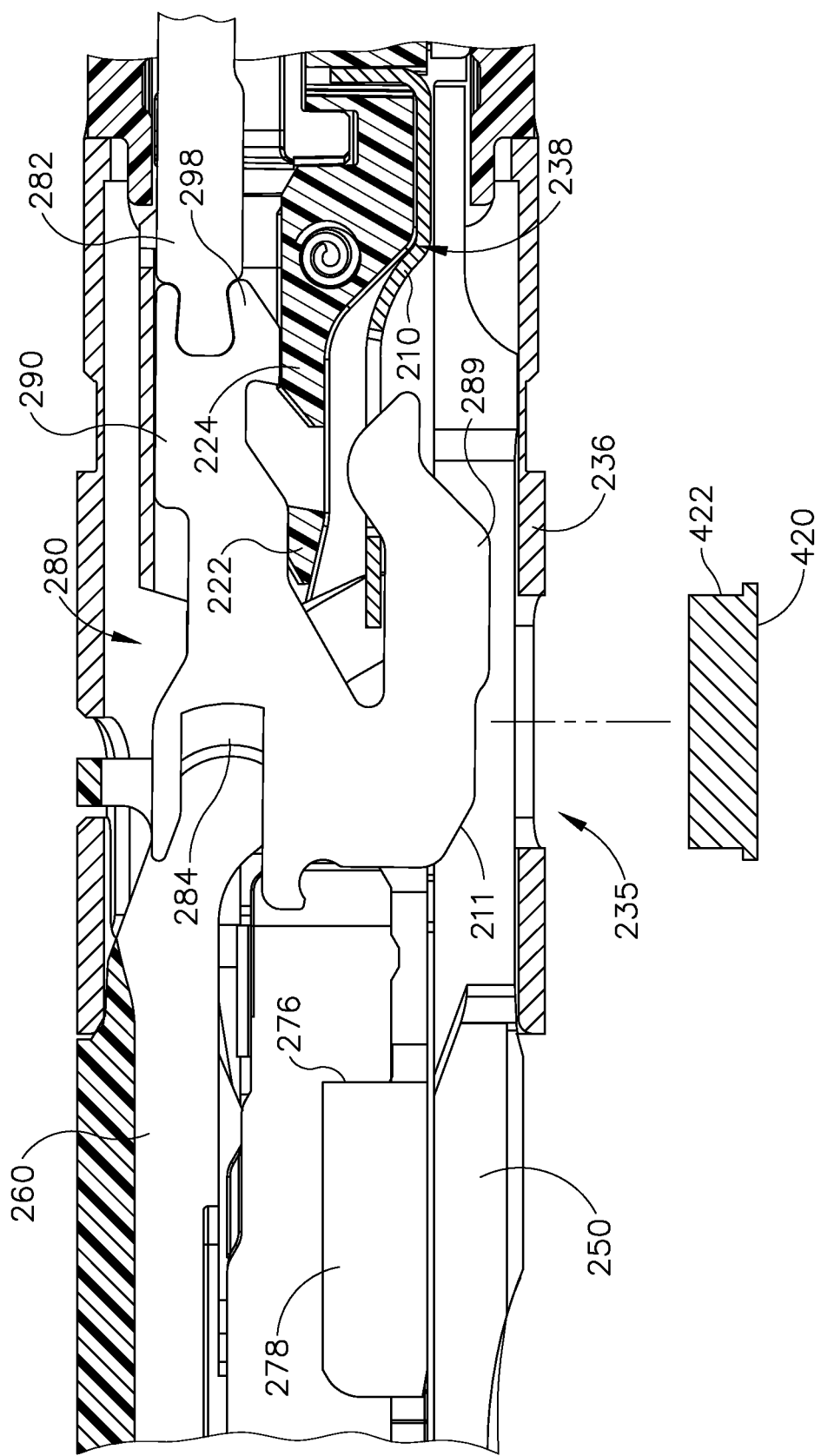
FIG. 59A depicts a cross-sectional side view of the end effector of FIG. 13, with the tab insert of FIG. 57 positioned to couple with the end effector.
Figure 59B:
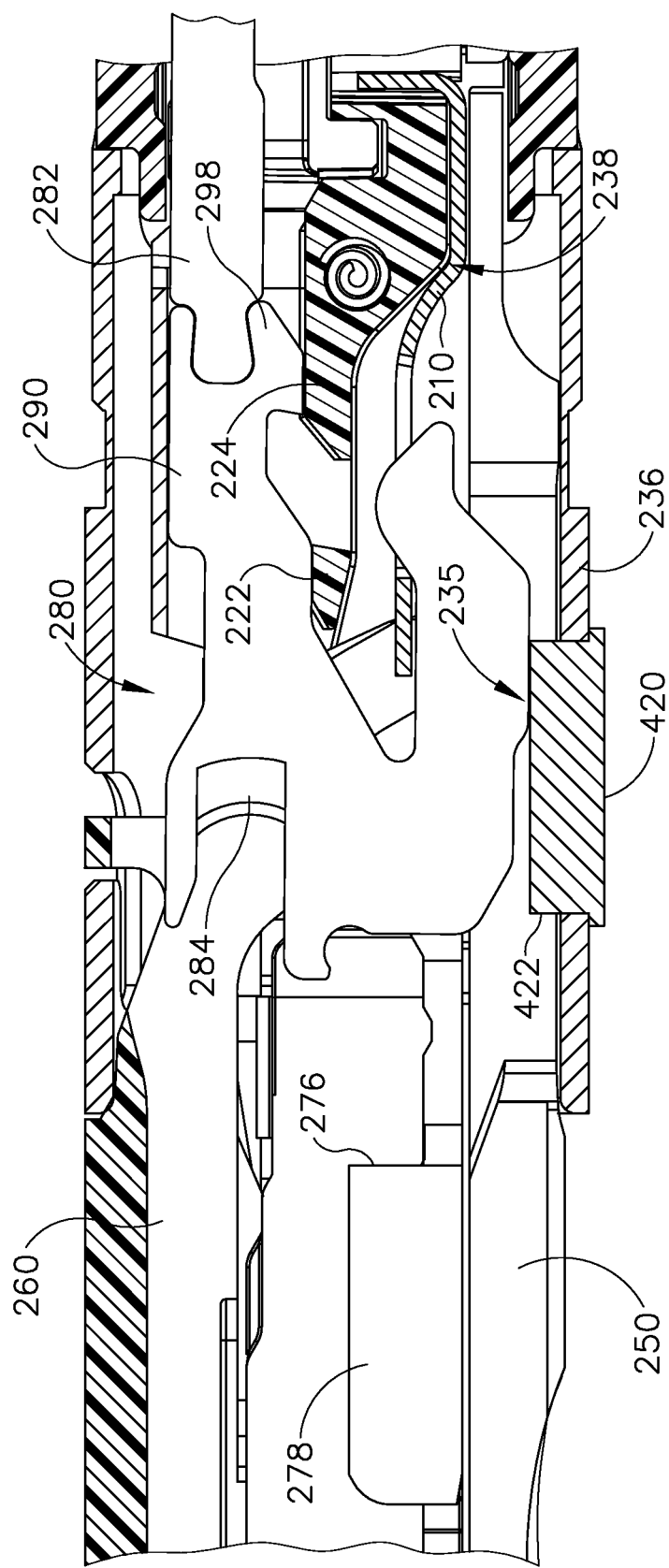
FIG. 59B depicts a cross-sectional side view of the end effector of FIG. 13, with the tab insert of FIG. 57 positioned within the end effector.

FIGS. 57-59B show another exemplary lockout bypass feature. The lockout bypass feature of the present example comprises a snap-fit cover (420). Cover (420) is configured to engage tab (289) of knife member (280) as knife member (280) is fired. Cover (420) is configured to allow for firing of knife member (280) by preventing engagement of knife member (280) with the lockout features of frame member (238) as discussed above upon firing of knife member (280). In particular, as best seen in FIGS. 59A and 59B, cover (420) is configured to be positioned within opening (235) of closure ring (236) such that a projection (422) of cover (420) extends inwardly within closure ring (236). As knife member (280) is fired distally, tab (289) of knife member (280) engages a top surface of projection (422) of cover (420). Engagement between tab (289) and projection (422) maintains the vertical position of knife member (280). Because projection (422) maintains the vertical position of knife member (280), tab (289) of knife member (280) translates distally above engagement features (222, 224) of frame member (238) such that resilient member (210) does not drive tab (298) downwardly between engagement features (222, 224) to prevent the distal movement of knife member (280). It should be understood that cover (420) may be readily used in end effector (240) or in other end effectors.

E. Exemplary Snap-Fit Ramp

Figure 60:
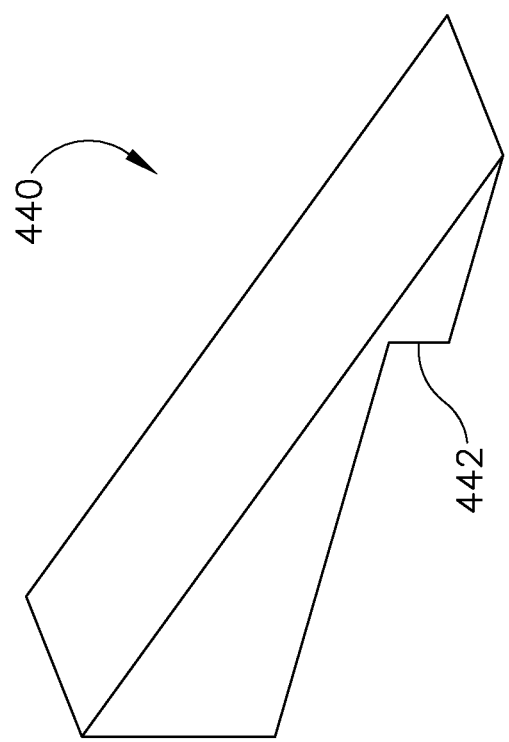
FIG. 60 depicts a perspective view of an exemplary ramp insert.
Figure 61:
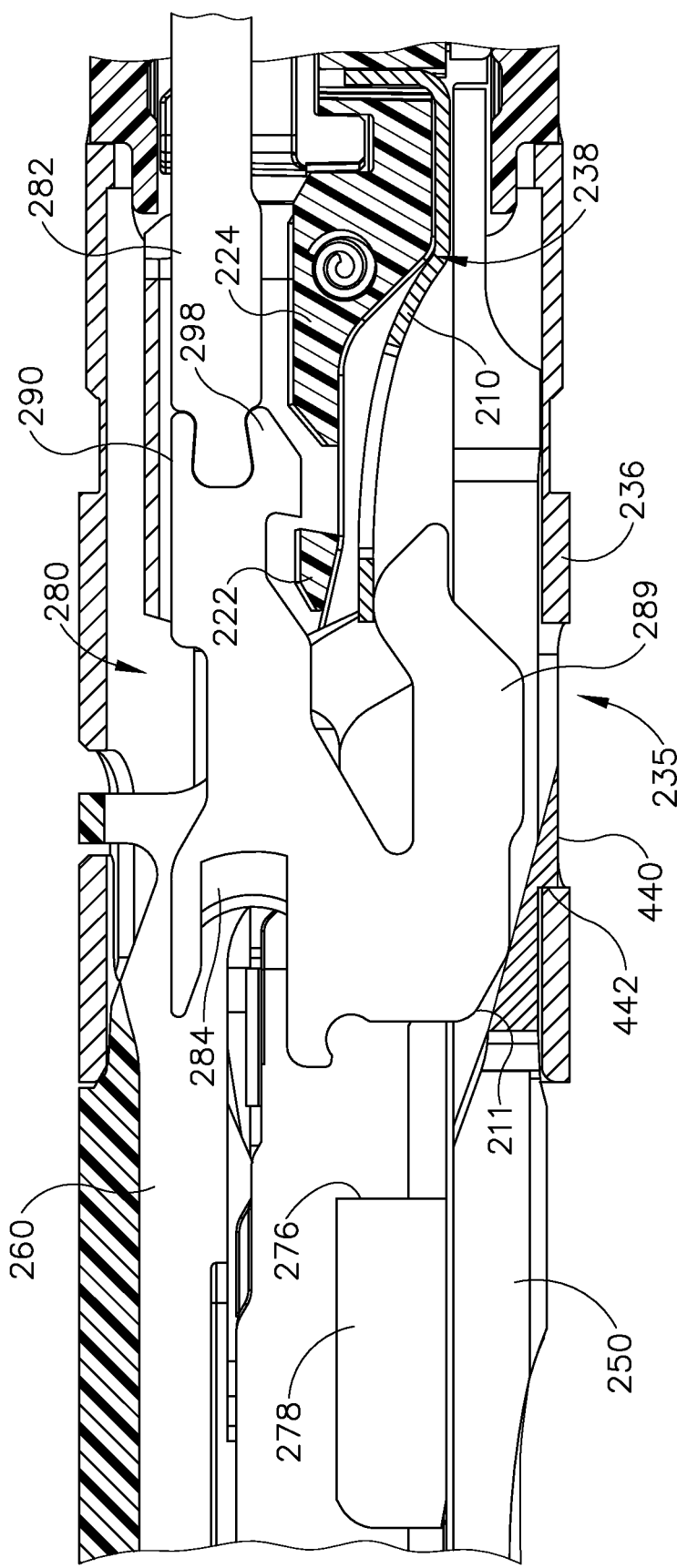
FIG. 61 depicts a cross-sectional side view of the end effector of FIG. 13 with the ramp insert of FIG. 60 positioned within the end effector.
Figure 62:
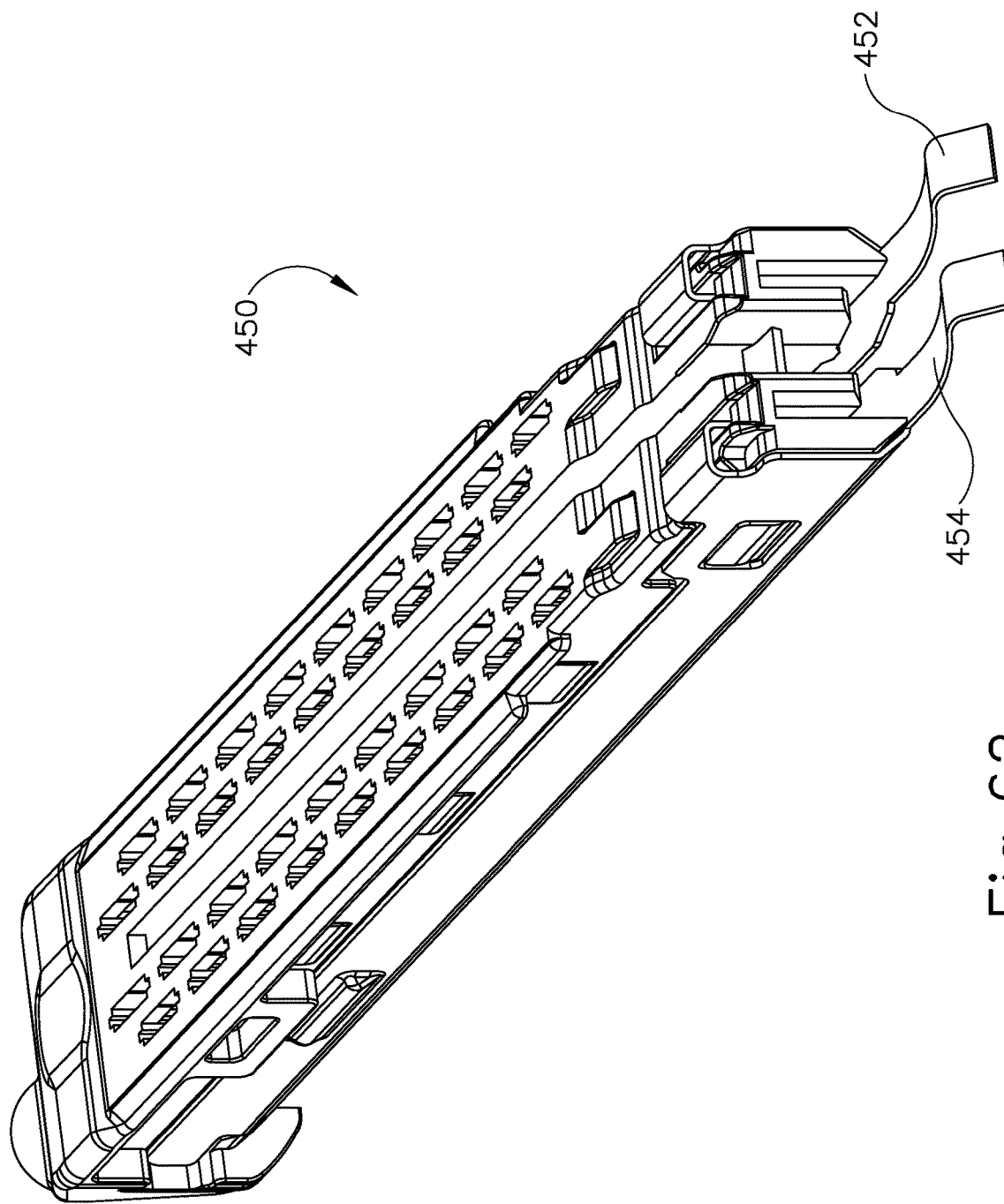
FIG. 62 depicts a perspective view of yet another exemplary alternative cartridge that may be incorporated into the end effector of FIG. 13.
Figure 63:
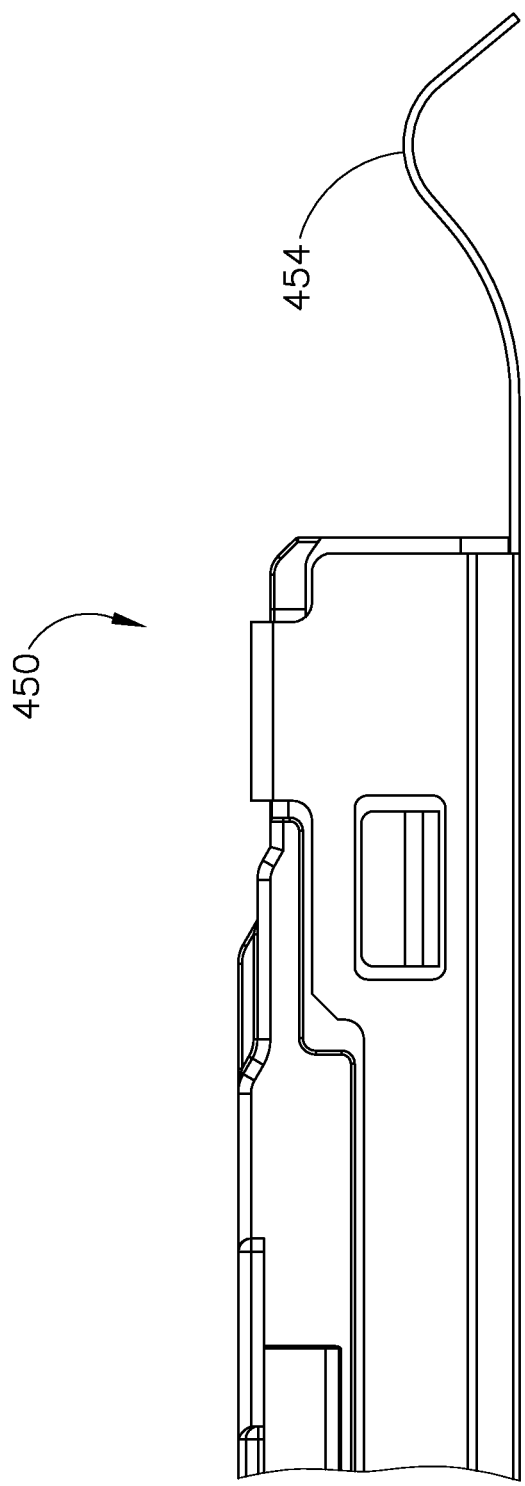
FIG. 63 depicts a side view of the proximal end of the cartridge of FIG. 62.

FIGS. 60 and 61 show another exemplary lockout bypass feature. The lockout bypass feature of the present example comprises a snap-fit ramp (440). Ramp (440) is configured to engage ramped wall (211) and/or tab (289) of knife member (280) as knife member (280) is fired. Ramp (440) is configured to allow for firing of knife member (280) by preventing engagement of knife member (280) with the lockout features of frame member (238) as discussed above upon being fired. In particular, as best seen in FIG. 61, ramp (440) is configured to be positioned within opening (235) of closure ring (236) such that ramp (440) extends inwardly within closure ring (236). A step (442) of ramp (440) engages a distal edge of opening (235) to maintain the position of ramp (440) during firing of knife member (280). As knife member (280) is fired distally, ramped wall (211) and/or tab (289) of knife member (280) engages a top surface of ramp (440). Engagement between ramped wall (211) and/or tab (289) and ramp (440) maintains the vertical position of knife member (280). Because ramp (440) maintains the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280). It should be understood that ramp (440) may be readily used in end effector (240) or in other end effectors.

F. Exemplary Cartridge Body with Proximal Supports

Figure 64A:
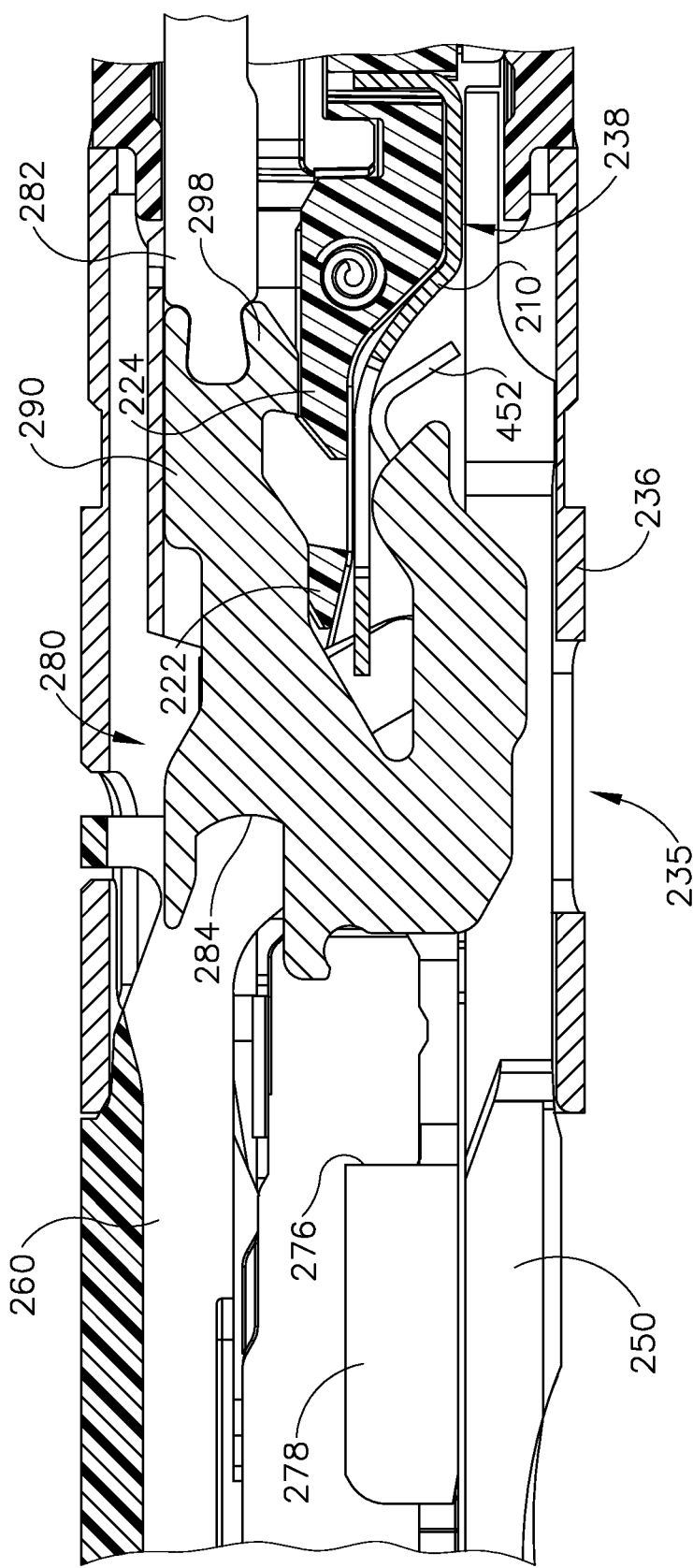
FIG. 64A depicts a cross-sectional view of the proximal end of the cartridge of FIG. 62 disposed within the end effector of FIG. 13, with a knife of the end effector in a first longitudinal position.
Figure 64B:
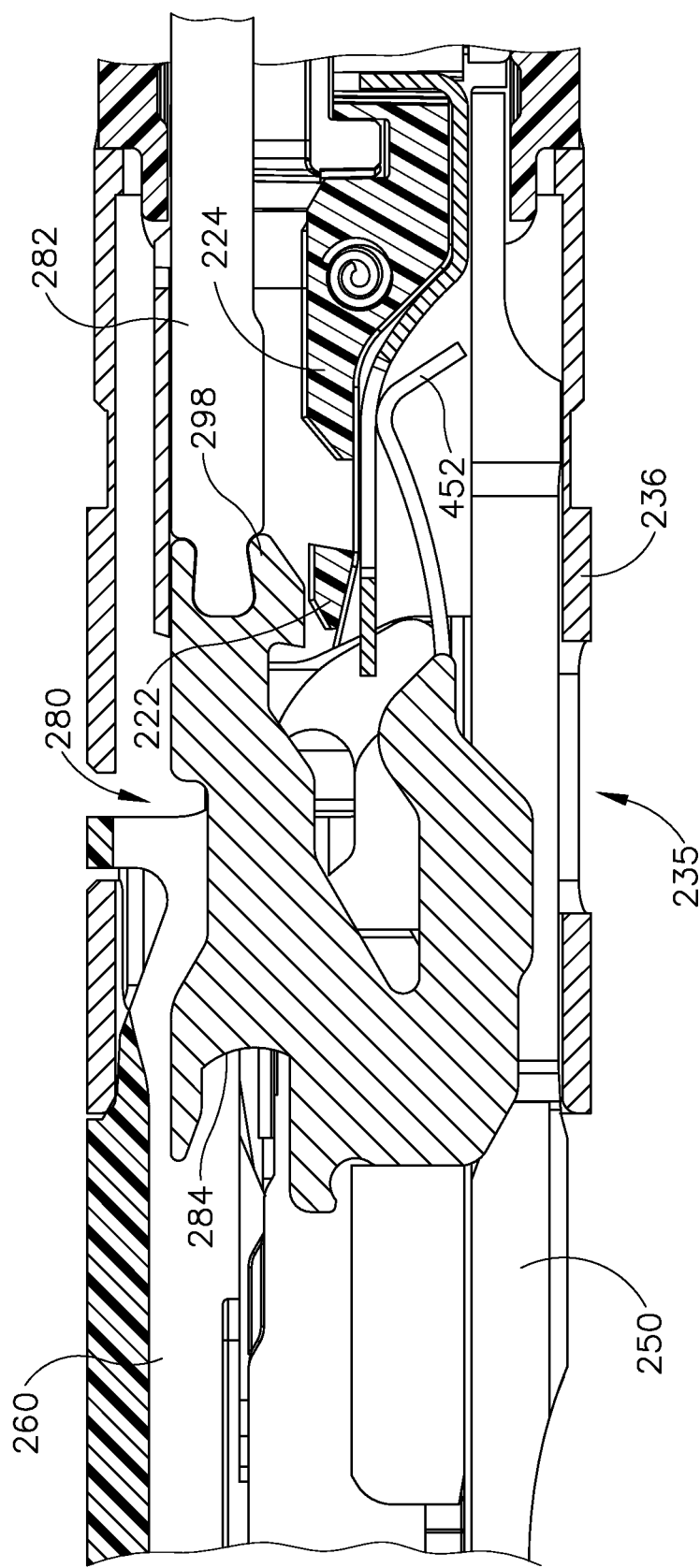
FIG. 64B depicts a cross-sectional view of the proximal end of the cartridge of FIG. 62 disposed within the end effector of FIG. 13, with the knife of the end effector moved into a second longitudinal position.
Figure 65:
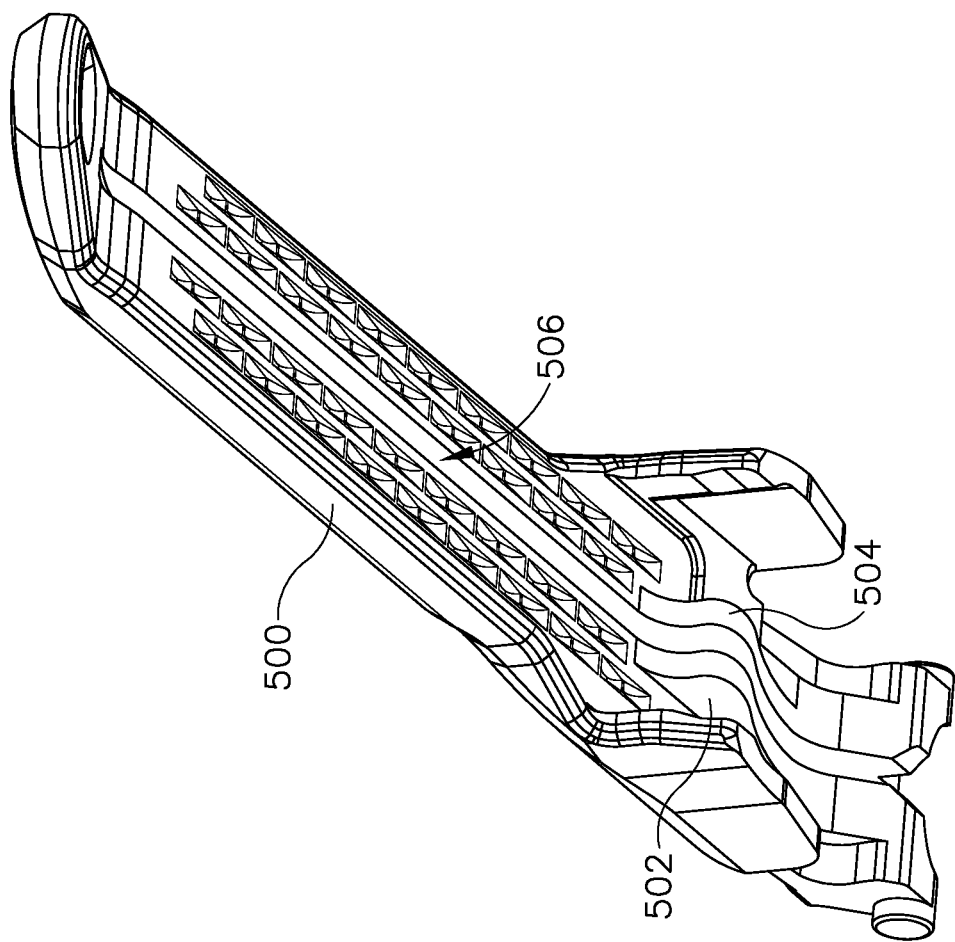
FIG. 65 depicts a perspective view of an exemplary alternative anvil that may be incorporated into the end effector of FIG. 3.
Figure 66:
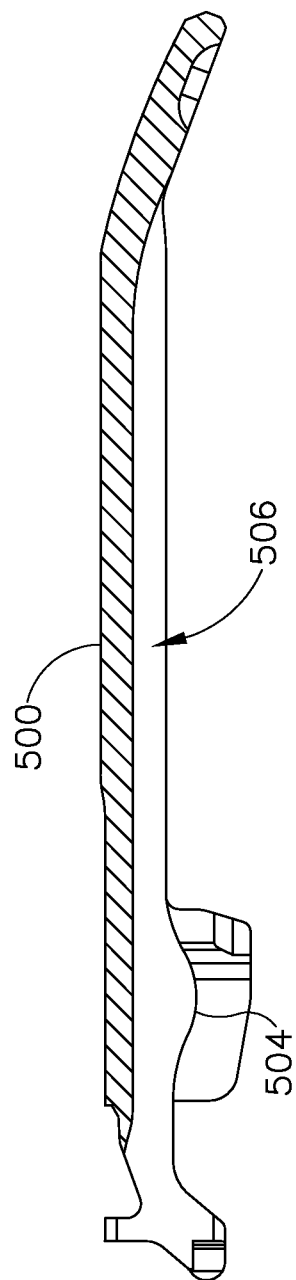
FIG. 66 depicts a cross-sectional side view of the anvil of FIG. 65.

FIGS. 62-64B show another exemplary staple cartridge (450) having a lockout bypass feature. It should be understood that cartridge (450) may be readily used in end effector (240) or in other end effectors. Cartridge (450) of the present example is configured to operate substantially similar to cartridges (70, 270) discussed above except for the differences discussed below. The lockout bypass feature of the present example comprises a pair of proximally extending resilient supports (452, 454). Supports (452, 454) are configured to engage resilient member (210) to prevent resilient member (210) from bearing upon knife member (280). By preventing resilient member (210) from bearing upon knife member (280), supports (452, 454) are configured to allow for firing of knife member (280) by preventing engagement of knife member (280) with the lockout features of frame member (238) as discussed above. In particular, as shown in FIGS. 64A and 64B, with cartridge (450) positioned within lower jaw (250), supports (452, 454) engage resilient member (210) and drive resilient member (210) upwardly, thereby holding resilient member (210) in the upward position. FIG. 64A shows end effector (240) in an initial position. In the initial position, upper extension (290) of knife member (280) is positioned above engagement features (222, 224) of frame member (238). As knife member (280) is fired distally, because resilient member (210) is not bearing upon knife member (280), knife member (280) maintains its vertical position. Because knife member (280) maintains its vertical position, tab (298) of knife member (280) translates distally above engagement features (222, 224) of frame member (238) such that resilient member (210) does not drive tab (298) downwardly between engagement features (222, 224) to prevent the distal movement of knife member (280).

V. Exemplary Cartridge Seating Features

In some instances, it may be desirable to provide features that promote proper seating of a staple cartridge (70, 270) within lower jaws (50, 250). For example, such a feature may provide for proper engagement of the cartridge staple cartridge (70, 270) within lower jaws (50, 250) and/or proper alignment of the staple cartridge (70, 270) relative to lower jaws (50, 250). Further, such a feature may be configured to retain a position of the staple cartridge (70, 270) within lower jaws (50, 250) during operation. The examples described below include several merely illustrative versions of seating features that may be readily introduced to end effectors (40, 240) and/or staple cartridges (70, 270). The examples described below may be viewed as "poka-yoke" features that represent exemplary alternatives to the "poka-yoke" features disclosed in U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017 the disclosure of which is incorporated by reference herein.

A. Exemplary Anvil with Engagement Features

FIGS. 65-67B show an exemplary alternative anvil (500) having a seating feature. Anvil (500) may be readily incorporated into end effectors (40, 240) in place of anvils (60, 260). Anvil (500) of the present example is configured to operate substantially similar to anvils (60, 260) discussed above except for the differences discussed below. The seating feature of the present example comprises a pair of protrusions (502, 504). Protrusions (502, 504) of the present example extend downwardly from a proximal portion of an underside of anvil (500) but may extend from any other appropriate portion of anvil (500). Protrusions (502, 504) are positioned on opposite lateral sides adjacent to a channel (506) formed in anvil (500). Channel (506) is substantially identical to channel (62) described above.

Figure 67A:
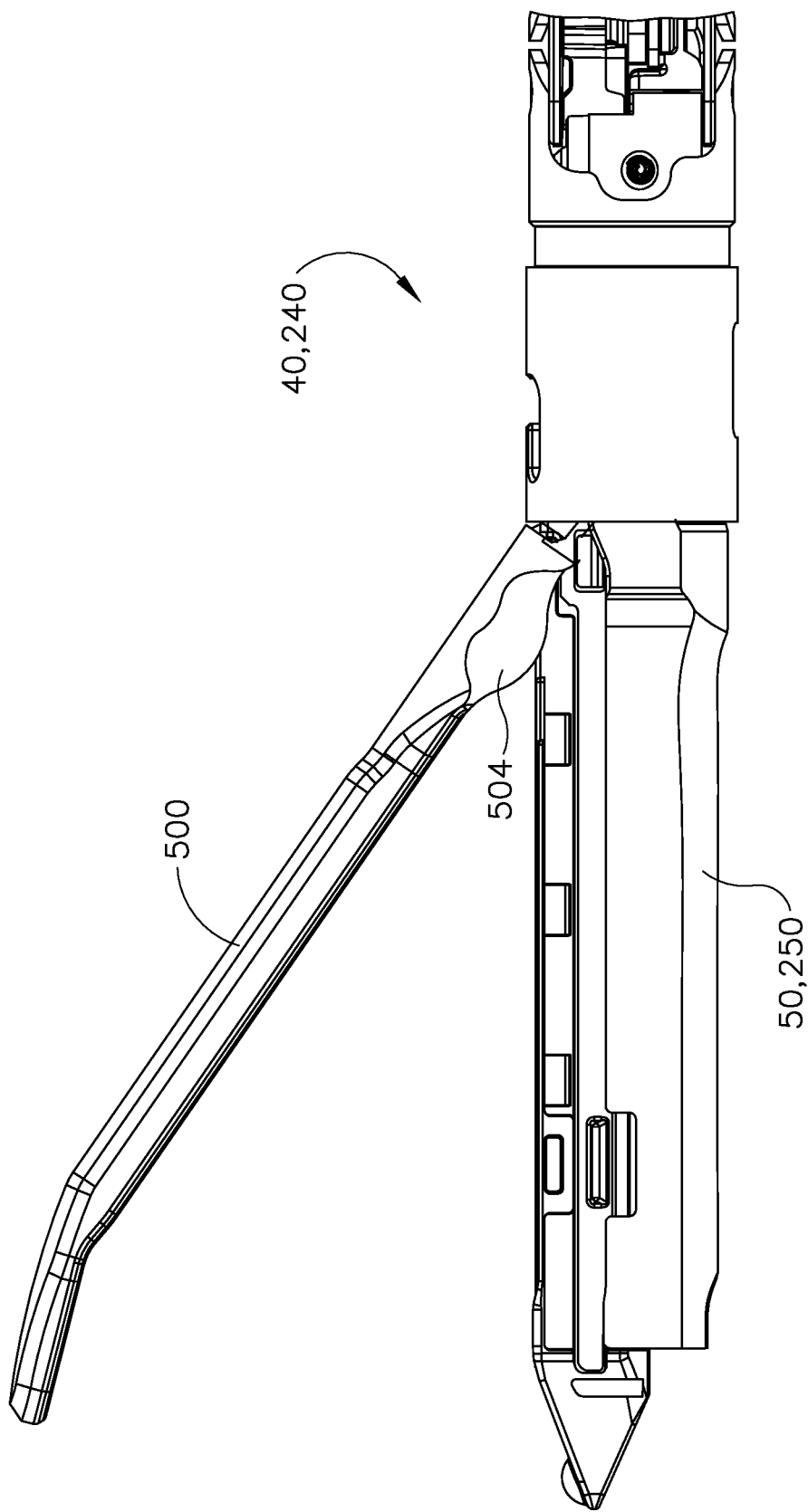
FIG. 67A depicts a partial cross-sectional side elevational view of the end effector of FIG. 3 with the anvil of FIG. 65 in a first rotational position.
Figure 67B:
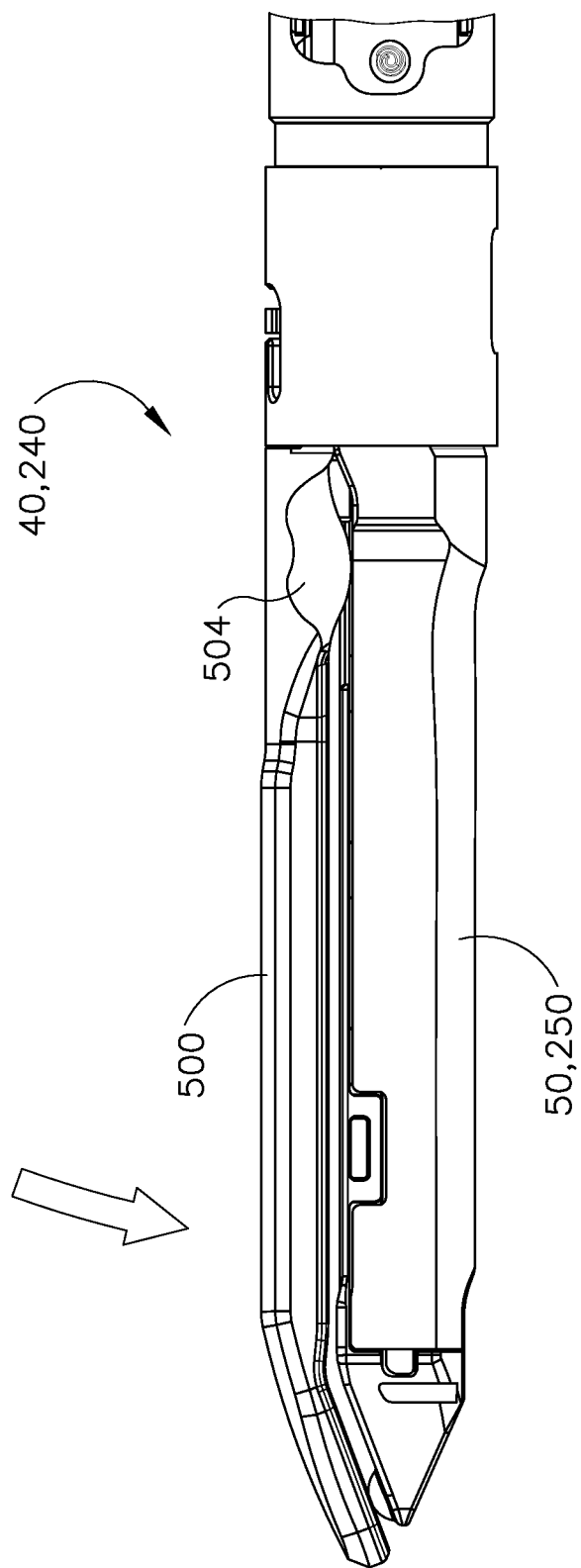
FIG. 67B depicts a partial cross-sectional side elevational view of the end effector of FIG. 3 with the anvil of FIG. 65 moved into a second rotational position.

Protrusions (502, 504) of the present example each define a parabolic shape. Although protrusions (502, 504) of the present example comprise a parabolic shape, protrusions (502, 504) may comprise any other appropriate shape. With anvil (500) in an open position as shown in FIG. 67A, cartridge (70) may be received within lower jaw (50, 250). As anvil (500) is pivoted toward lower jaw (50, 250) into a closed position as shown in FIG. 67B, protrusions (502, 504) are configured to bear against a top surface of a proximal portion of cartridge (70) so as to drive cartridge (70) downwardly into lower jaw (50, 250) to thereby provide for proper seating of cartridge (70) within lower jaw (50, 250). It should therefore be appreciated that if an operator fails to fully press cartridge (70) into lower jaw (50, 250) when the operator places cartridge (70) in lower jaw (50, 250), anvil (500) will fully press cartridge (70) into lower jaw (50, 250) during closure of anvil (500). Thus, before positioning tissue between anvil (500) and lower jaw (50, 250), the operator may close anvil (500) to ensure proper seating of cartridge (70), then open anvil (500) such that end effector (40, 240) is able to capture tissue. Although anvil (500) is shown and described as being used with cartridge (70) in the present example, it should be understood that anvil (500) may also be used with any cartridge (270, 300, 320, 340, 360, 400, 410, 450, 460, 470) discussed herein.

B. Exemplary Anvil and Cartridge with Alignment Features

Figure 68:
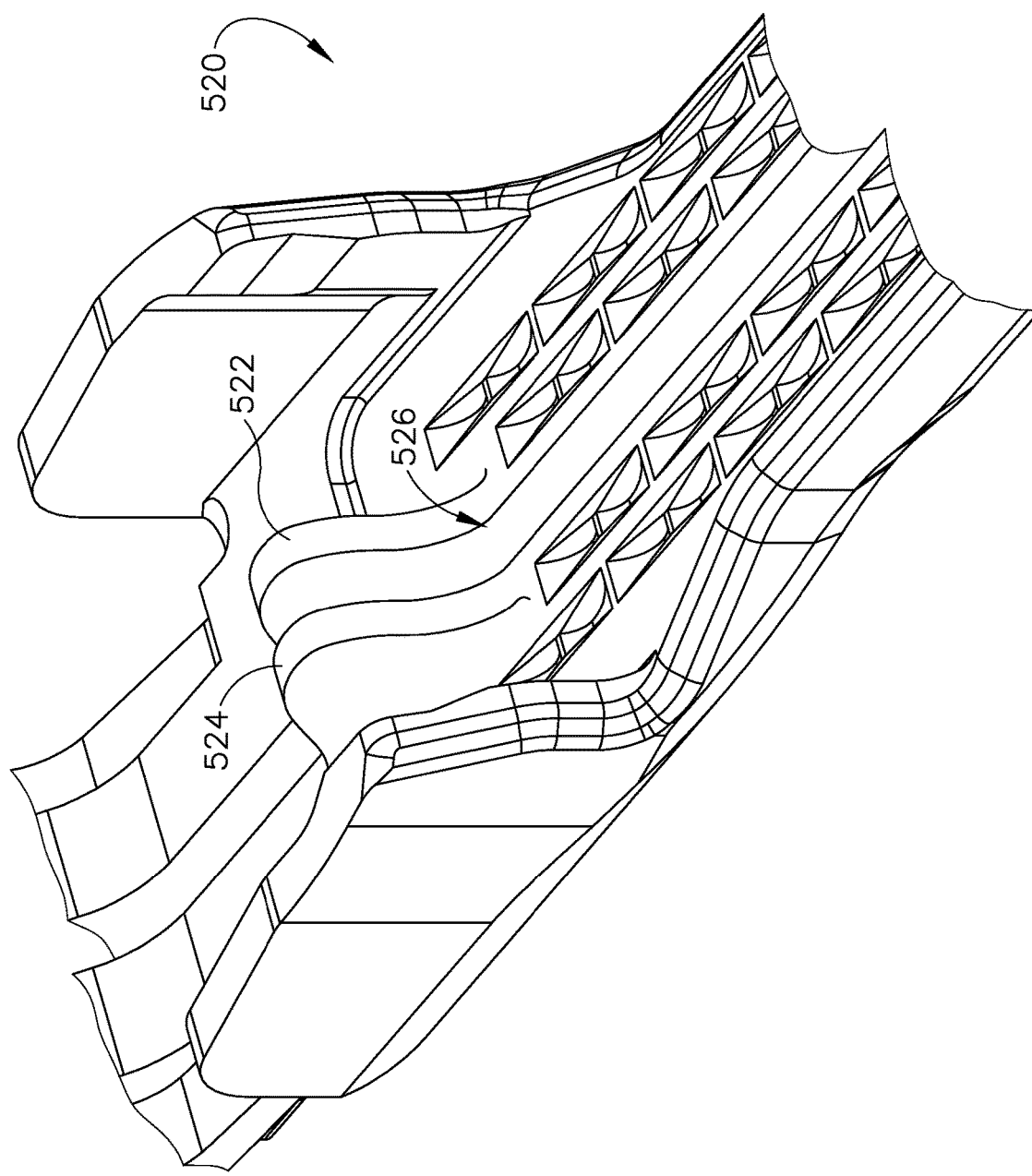
FIG. 68 depicts a perspective view of an underside region of another exemplary alternative anvil that may be incorporated into the end effector of FIG. 3.

FIGS. 68-71 show another exemplary alternative anvil (520) and staple cartridge (530) having mating seating features. Anvil (520) and cartridge (530) may be readily incorporated into end effectors (40, 240) in place of anvils (60, 260) and/or cartridges (270, 300, 320, 340, 360, 400, 410, 450, 460, 470). Anvil (520) of the present example is configured to operate substantially similar to anvils (60, 260) discussed above except for the differences discussed below. Cartridge (530) of the present example is configured to operate substantially similar to cartridges (70, 270) discussed above except for the differences discussed below. As best seen in FIG. 68, the seating features of anvil (520) of the present example comprise a pair of protrusions (522, 524). Protrusions (522, 524) of the present example extend downwardly from a proximal portion of an underside of anvil (520) but may extend from any other appropriate portion of anvil (520). Protrusions (522, 524) are positioned on opposite lateral sides adjacent to a channel (526) formed in anvil (520). Channel (526) is substantially identical to channel (62) described above.

Figure 69:
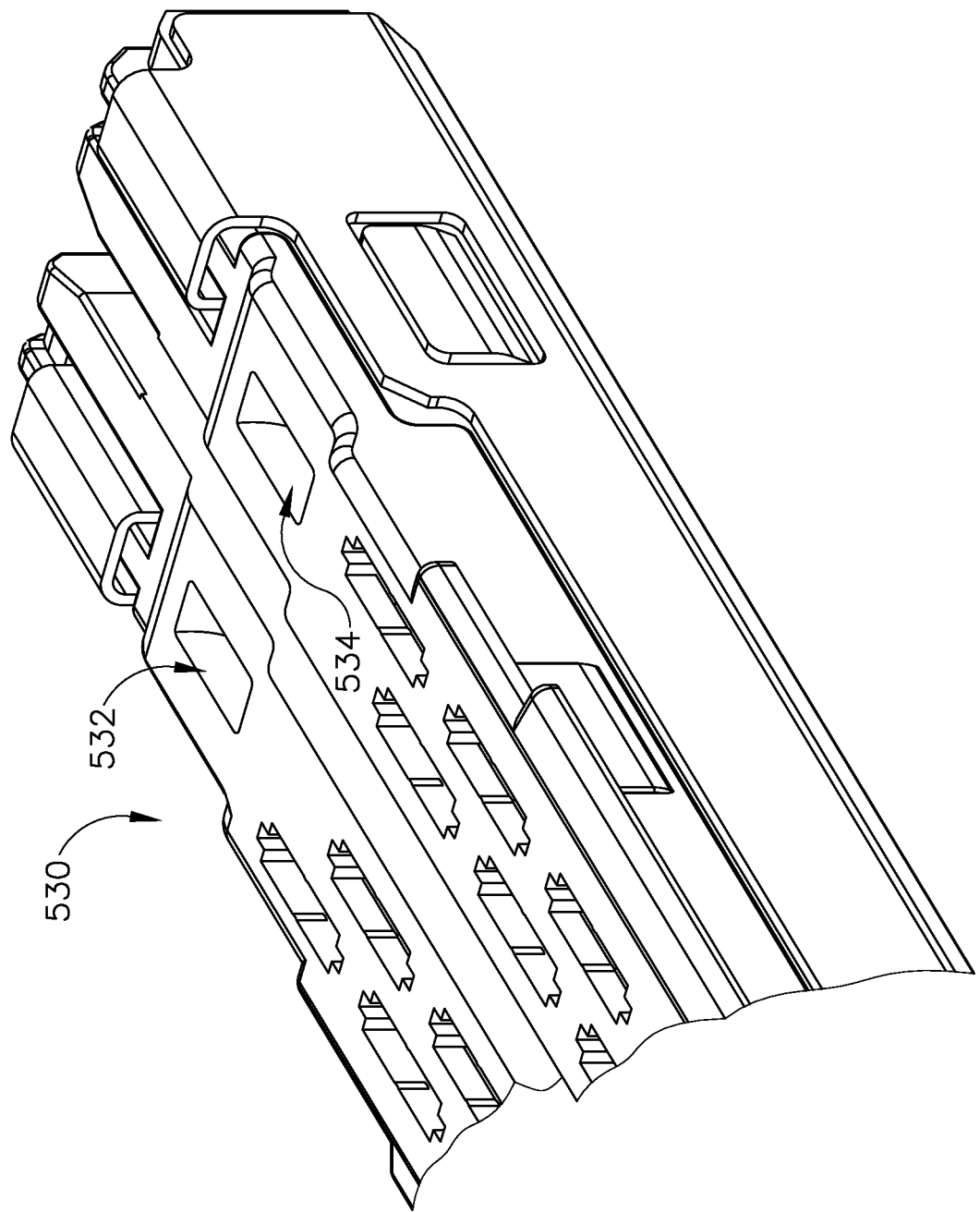
FIG. 69 depicts a perspective view of the proximal end of yet another exemplary alternative cartridge that may be incorporated into the end effector of FIG. 3.

As best seen in FIG. 69, the seating features of cartridge (530) of the present example comprise a pair of recesses (532, 534). Recesses (532, 534) of the present example are formed in a proximal portion of a top surface of cartridge (530) but may be formed in any other appropriate portion of cartridge (530). Recesses (532, 534) are positioned on opposite lateral sides adjacent to a channel (536) formed in cartridge (530). Channel (536) is substantially identical to channel (72) described above. Protrusions (522, 524) and recesses (532, 534) have complementary shapes such that recesses (532, 534) are configured to receive protrusions (522, 524). Protrusions (522, 524) and recesses (532, 534) of the present example each have a parabolic shape. Although protrusions (522, 524) and recesses (532, 534) of the present example comprise a parabolic shape, protrusions (522, 524) and recesses (532, 534) may comprise any other appropriate share.

Figure 70A:
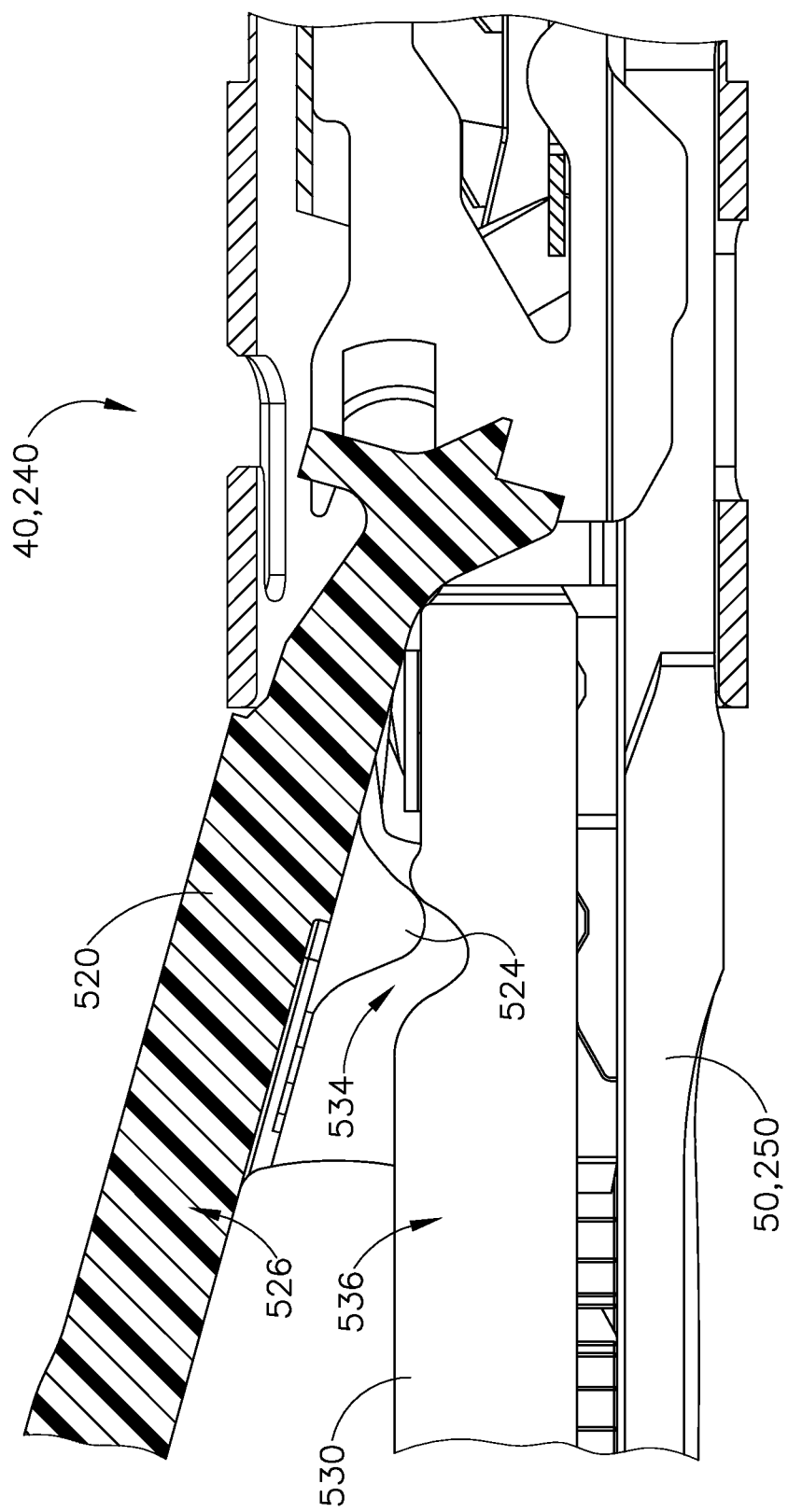
FIG. 70A depicts a cross-sectional side view of the end effector of FIG. 3 with the cartridge of FIG. 69 in a first longitudinal position and with the anvil of FIG. 68 in a first rotational position.
Figure 71:
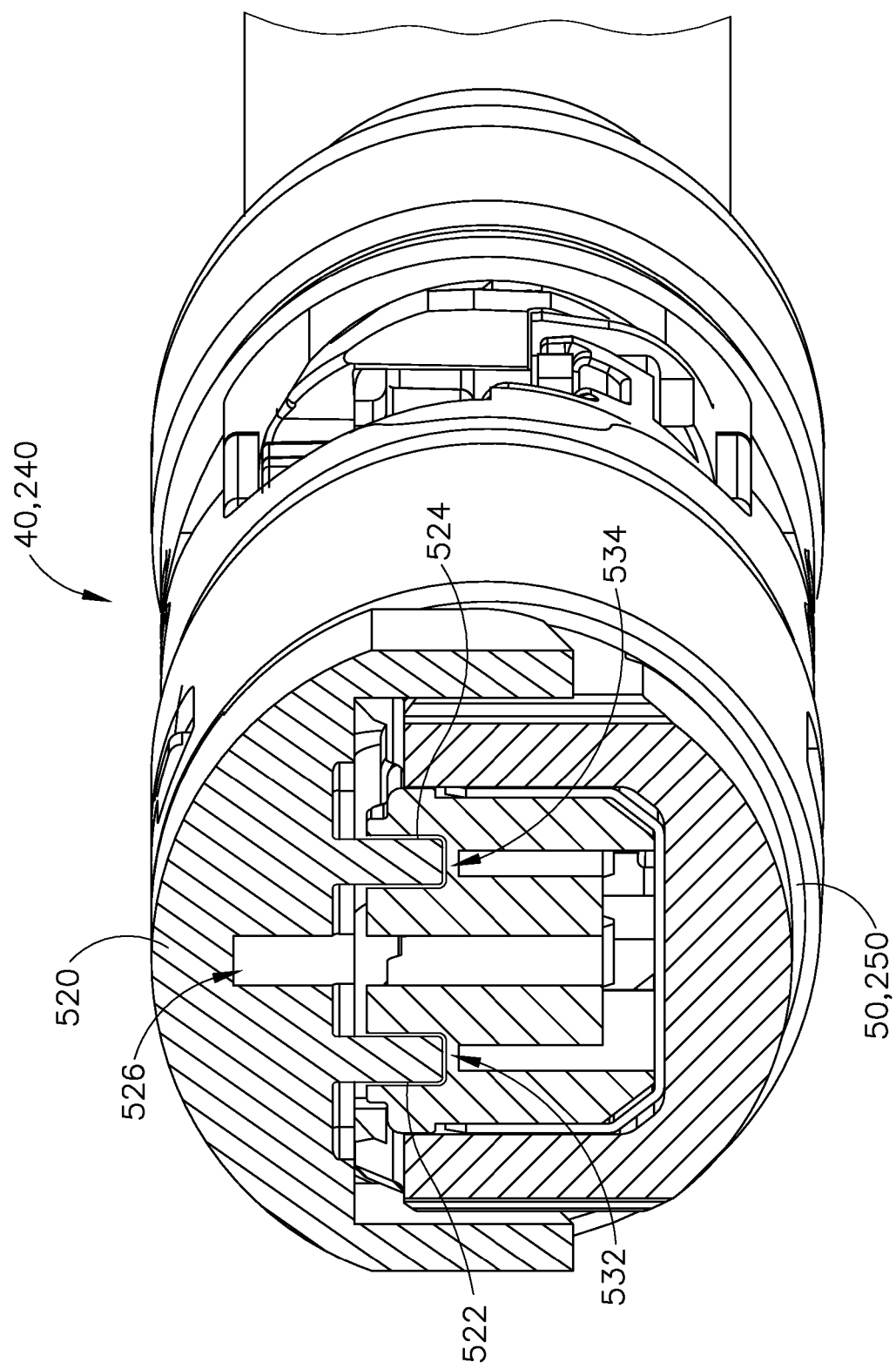
FIG. 71 depicts a cross-sectional perspective view of the end effector of FIG. 3 with the cartridge of FIG. 68 engaged with the anvil of FIG. 69.
Figure 72:
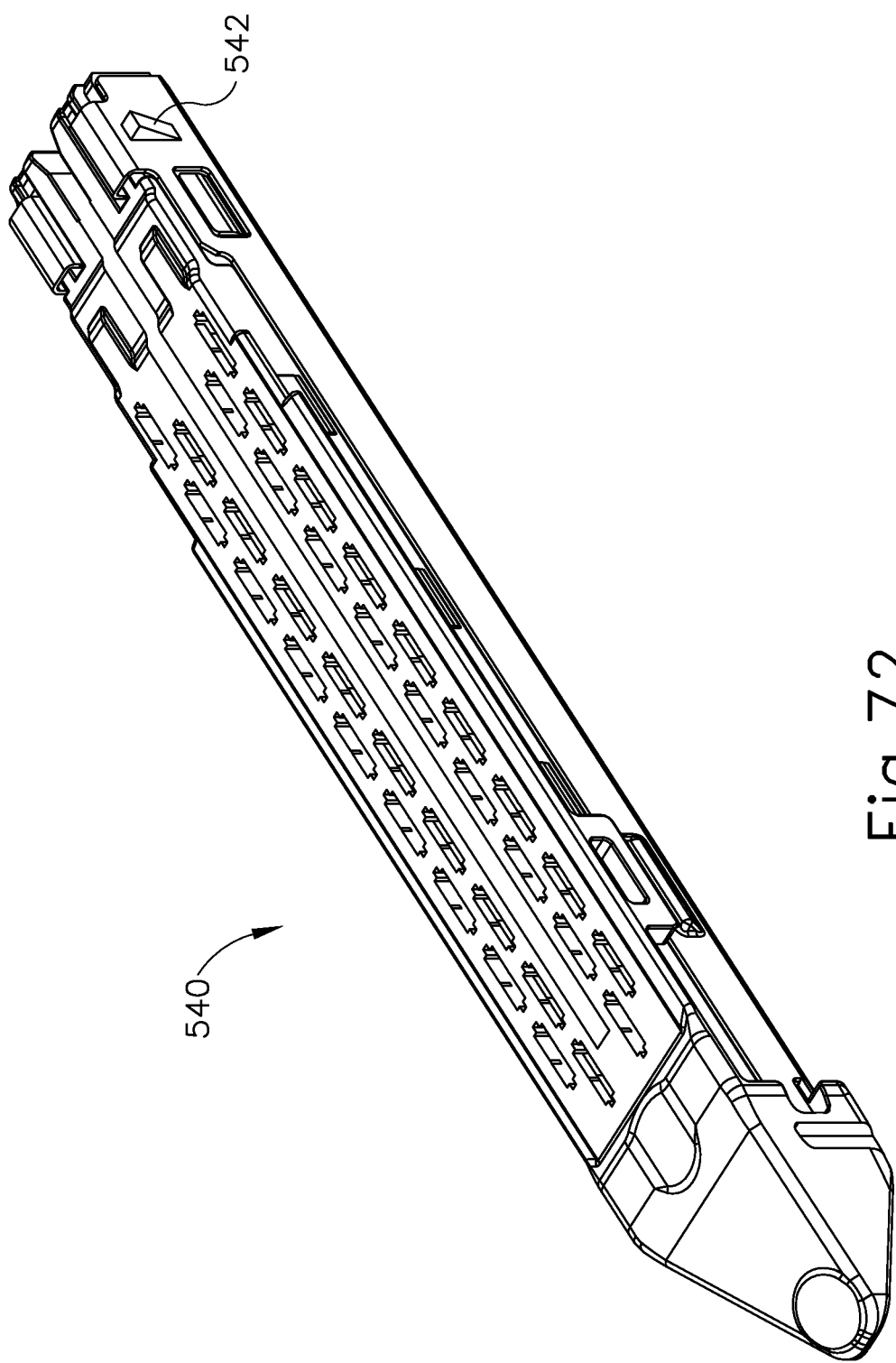
FIG. 72 depicts a perspective view of yet another exemplary alternative cartridge that may be incorporated into the end effector of FIG. 3.
Figure 73:
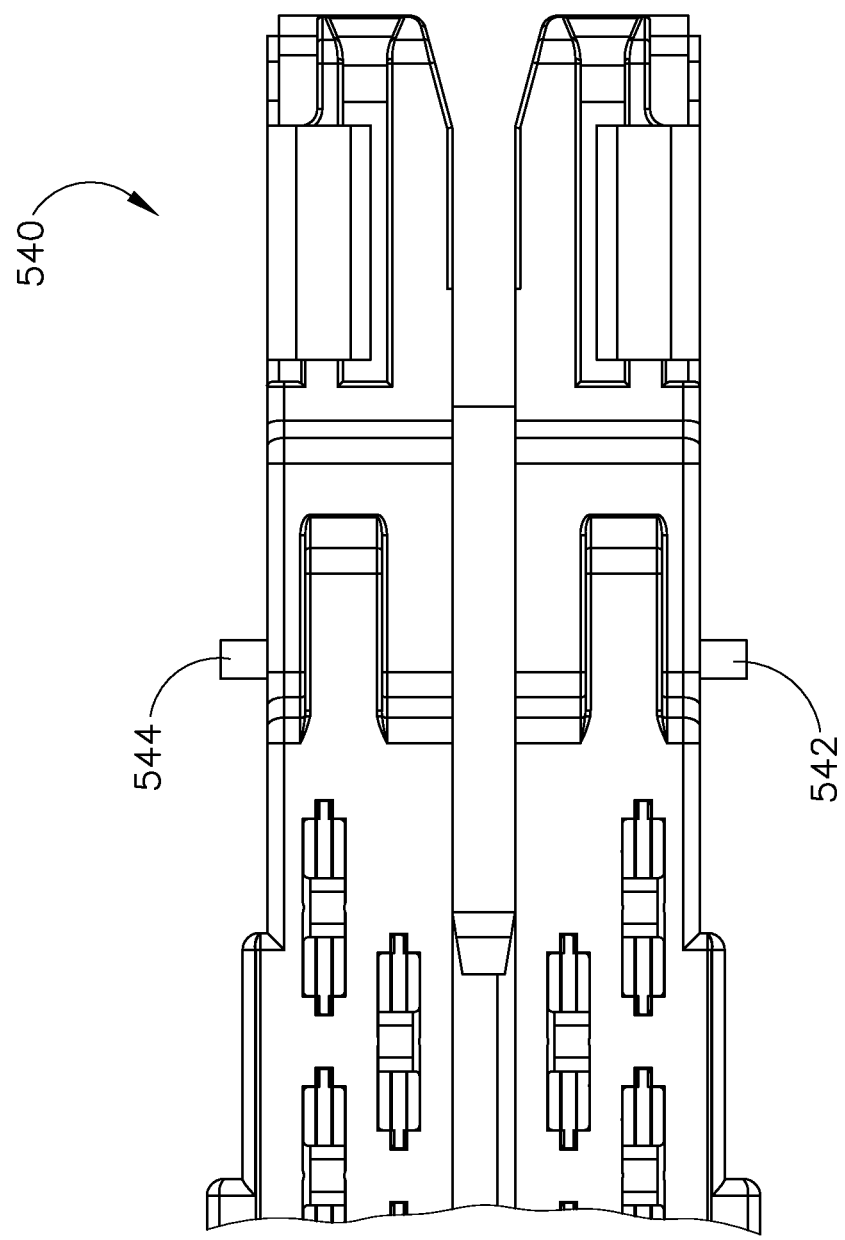
FIG. 73 depicts a top view of the proximal end of the cartridge of FIG. 72.
Figure 74:
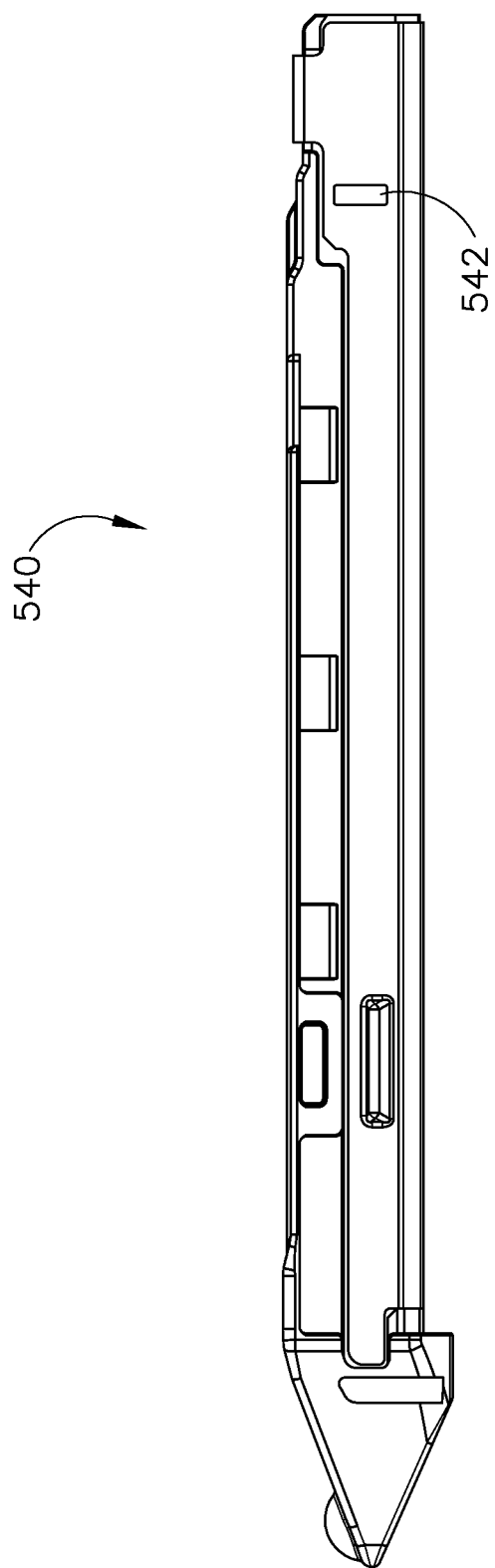
FIG. 74 depicts a side view of the cartridge of FIG. 72.
Figure 75:
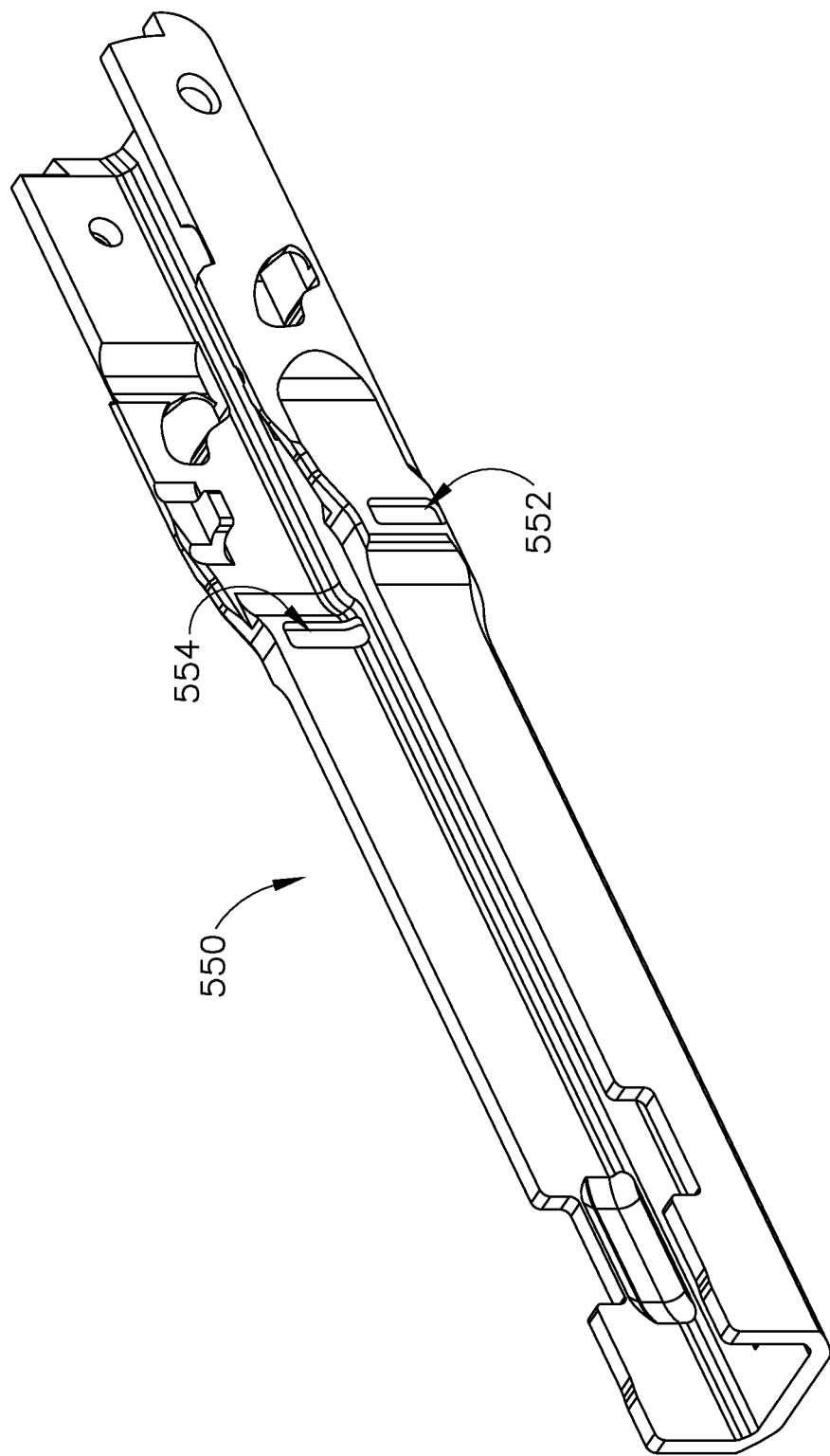
FIG. 75 depicts a perspective view of an exemplary lower jaw that may be incorporated into the end effector of FIG. 3.
Figure 76:
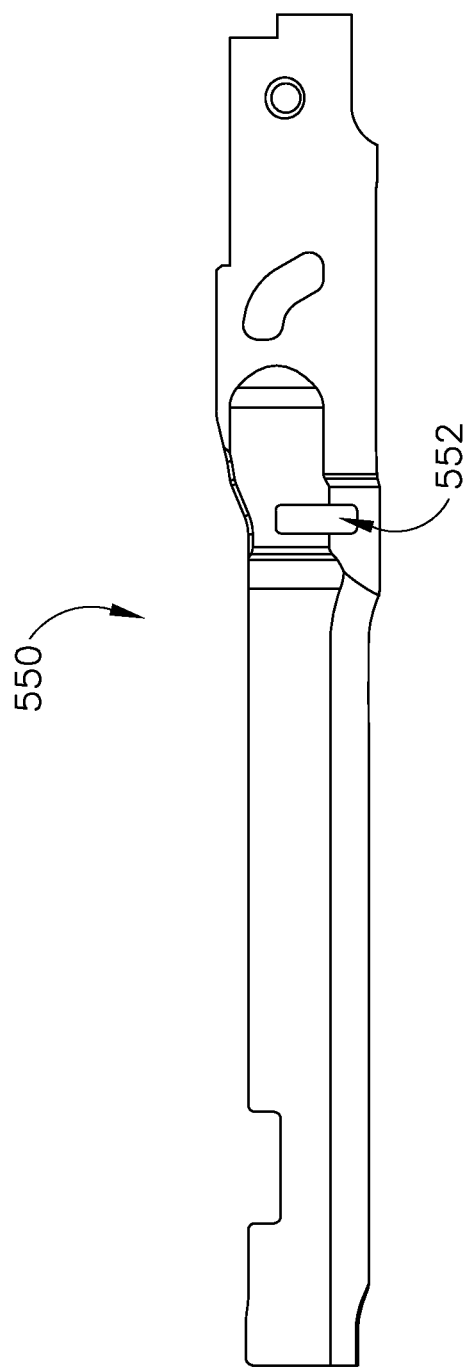
FIG. 76 depicts a side view of the lower jaw of FIG. 75.
Figure 77:
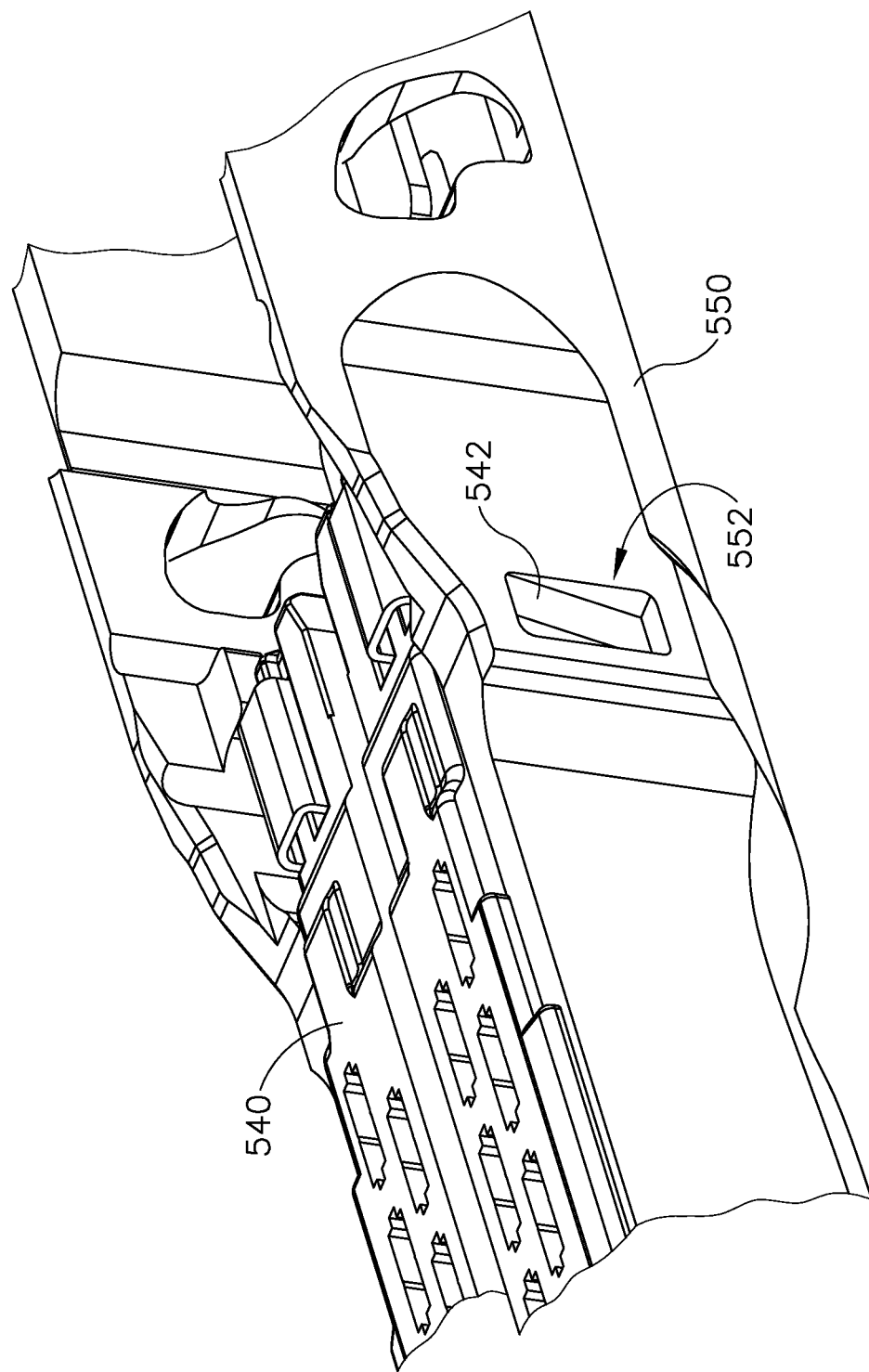
FIG. 77 depicts a perspective view of the proximal end of the cartridge of FIG. 72 engaged with the lower jaw of FIG. 75.

With anvil (520) in an open position, cartridge (530) may be received within lower jaw (50, 250). As anvil (520) is pivoted toward lower jaw (50, 250) into a partially closed position as shown in FIG. 70A, recesses (532, 534) of cartridge (530) initially receive protrusions (522, 524) of anvil (520). As anvil (520) is further pivoted toward lower jaw (50, 250) into a closed position as shown in FIGS. 70B and 71, recesses (532, 534) of cartridge (530) completely receive protrusions (522, 524) of anvil (520). As recesses (532, 534) receive protrusions (522, 524), engagement between recesses (532, 534) and protrusions (522, 524) will cause recesses (532, 534) to become aligned with protrusions (522, 524) to thereby laterally and longitudinally align cartridge (530) within lower jaw (50, 250). Thus, as anvil (520) is pivoted into the closed position, this motion will cause proper lateral and longitudinal alignment of cartridge (530). It should also be appreciated that protrusions (522, 524) and recesses (532, 534) cooperate to provide proper vertical positioning of cartridge (530) in lower jaw (50, 250) in addition to providing proper longitudinal and lateral positioning of cartridge (530) in lower jaw (50, 250). In particular, protrusions (522, 524) may further be configured to bear against a surface within recesses (532, 534) so as to drive cartridge (530) downwardly into lower jaw (50, 250) to thereby provide for proper seating of the cartridge within lower jaw (50, 250).

C. Exemplary Cartridge Body and Tray with Engagement Features

FIGS. 72-77 show an exemplary staple cartridge (540) and a lower jaw (550) having mating engagement features. Cartridge (540) and lower jaw (550) may be readily incorporated into end effectors (40, 240) in place of cartridges (270, 300, 320, 340, 360, 400, 410, 450, 460, 470) and/or lower jaws (50, 250) discussed above. Cartridge (540) of the present example is configured to operate substantially similar to cartridges (70, 270) discussed above except for the differences discussed below. Lower jaw (550) of the present example is configured to operate substantially similar to lower jaws (50, 250) discussed above except for the differences discussed below. The engagement features of cartridge (540) of the present example comprise a pair of angled protrusions (542, 544). Protrusions (542, 544) of the present example extend outwardly from a proximal portion of opposing exterior surfaces of cartridge (540) but may extend from any other appropriate portion of cartridge (540). The engagement features of lower jaw (550) of the present example comprise a pair of slots (552, 554). Slots (552, 554) are configured to matingly receive protrusions (542, 544) so as to provide for proper longitudinal alignment between cartridge (540) and lower jaw (550). Protrusions (542, 544) of the present example are angled upwardly and outwardly such that as cartridge (540) is inserted into lower jaw (550), lower jaw (550) will flare outwardly such that cartridge (540) may be received within lower jaw (550) and such that protrusions (542, 544) may be received within slots (552, 554). With protrusions (542, 544) engaged with slots (552, 554), cartridge (540) and lower jaw (550) are coupled together so as to ensure proper engagement between cartridge (540) and lower jaw (550).

D. Exemplary Cartridge and Lower Jaw with Alignment Features

Figure 78:
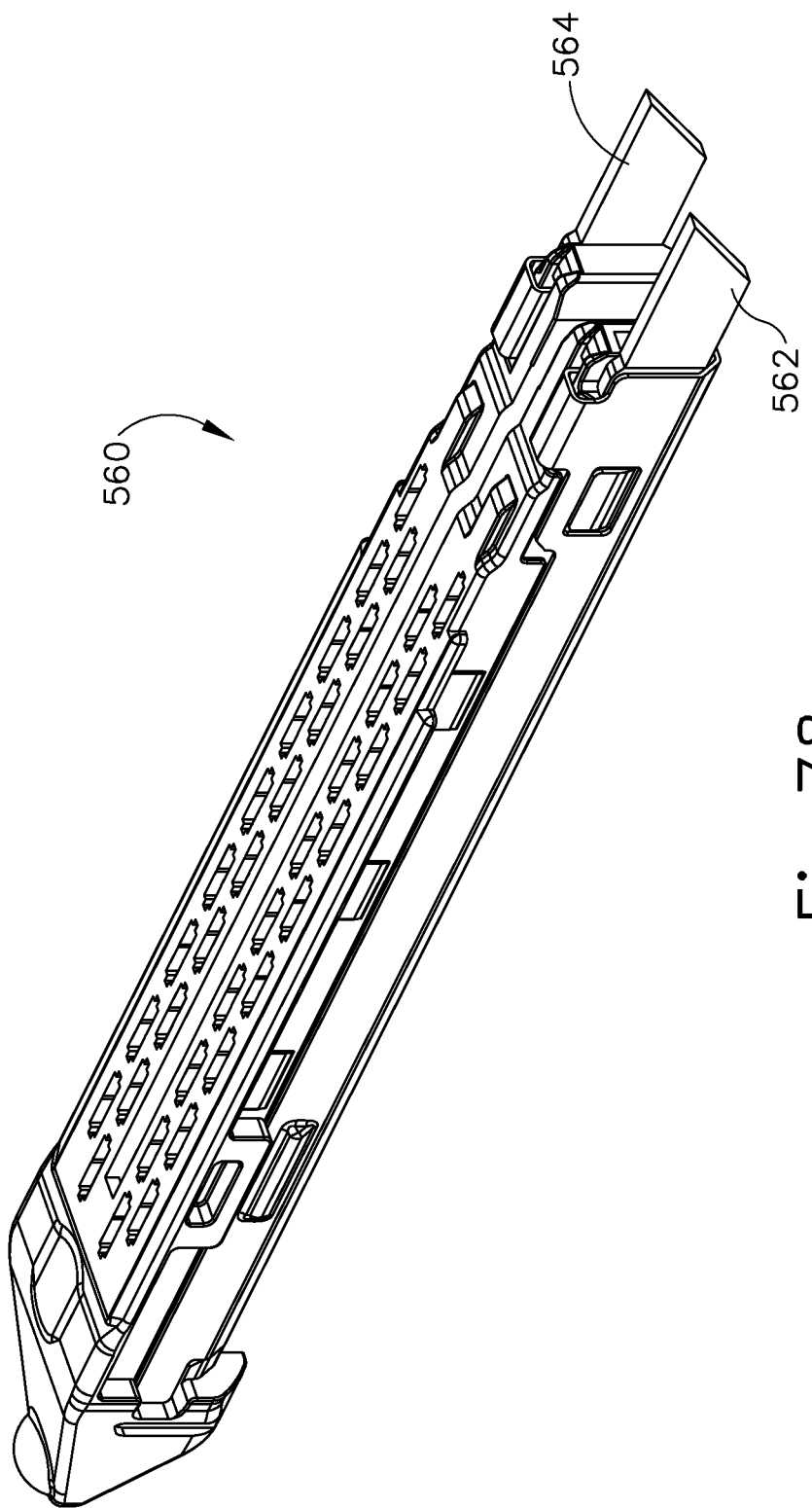
FIG. 78 depicts a perspective view of yet another exemplary alternative cartridge that may be incorporated into the end effector of FIG. 3.
Figure 79:
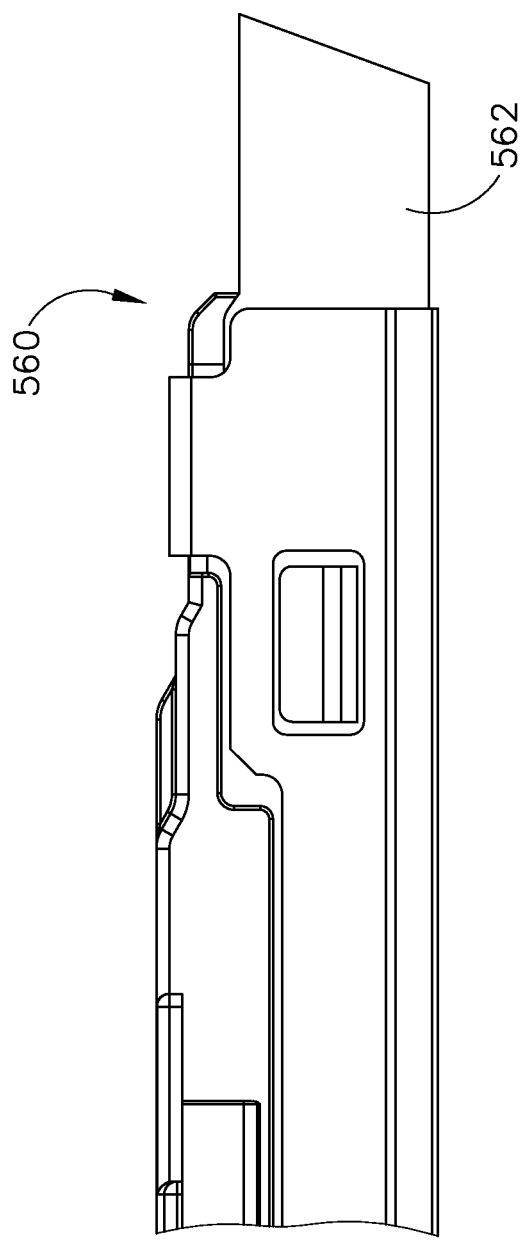
FIG. 79 depicts a side view of the proximal end of the cartridge of FIG. 78.
Figure 80:
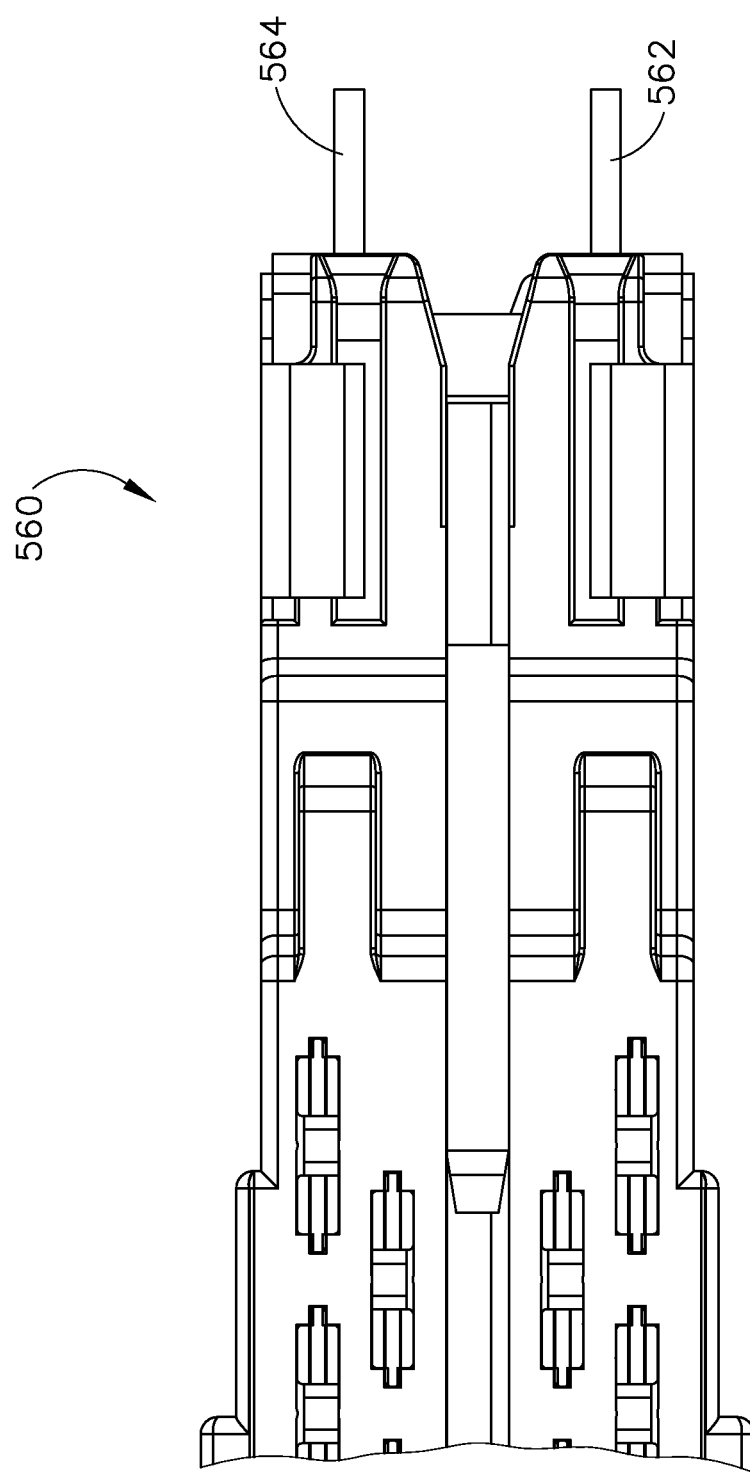
FIG. 80 depicts a top view of the proximal end of the cartridge of FIG. 78.
Figure 81:
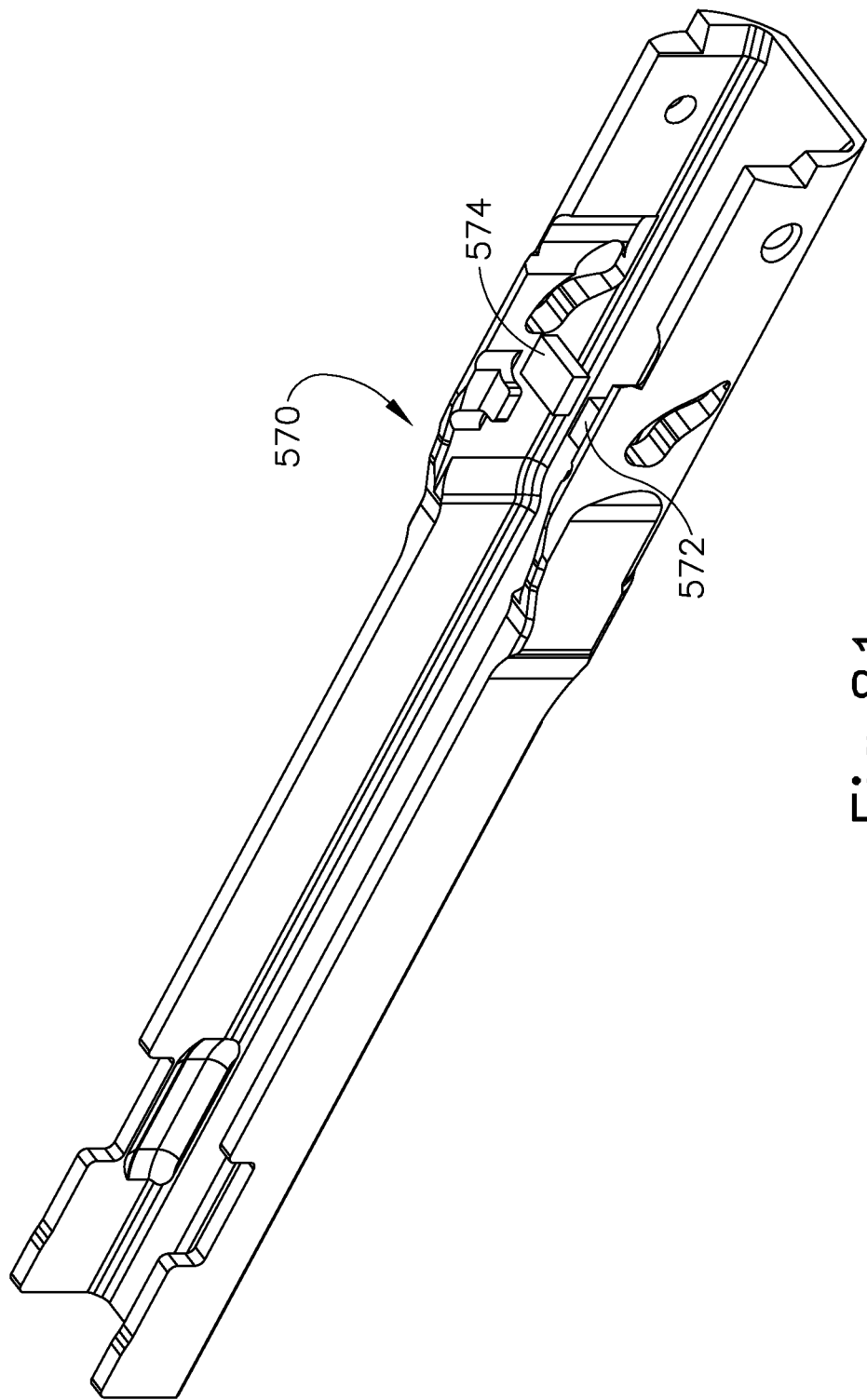
FIG. 81 depicts a perspective view of an exemplary alternative lower jaw that may be incorporated into the end effector of FIG. 3.
Figure 82:
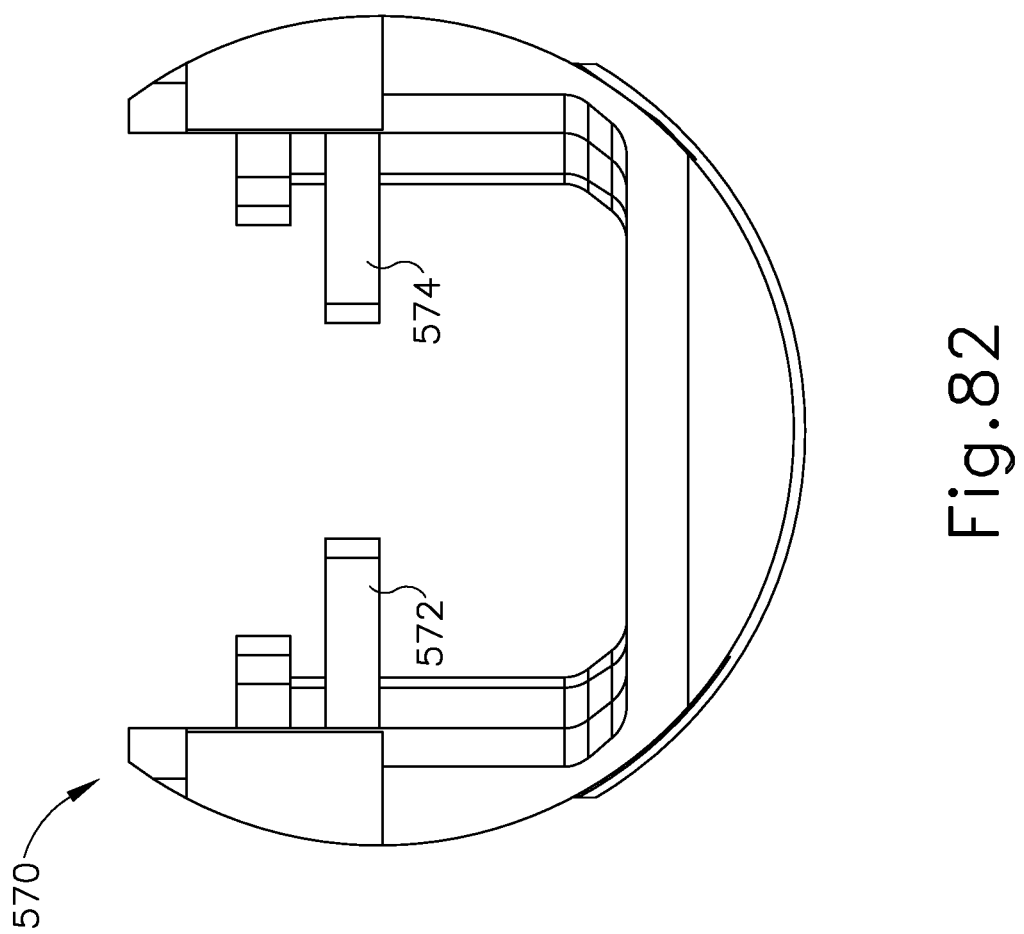
FIG. 82 depicts a rear view of the lower jaw of FIG. 81.
Figure 83:
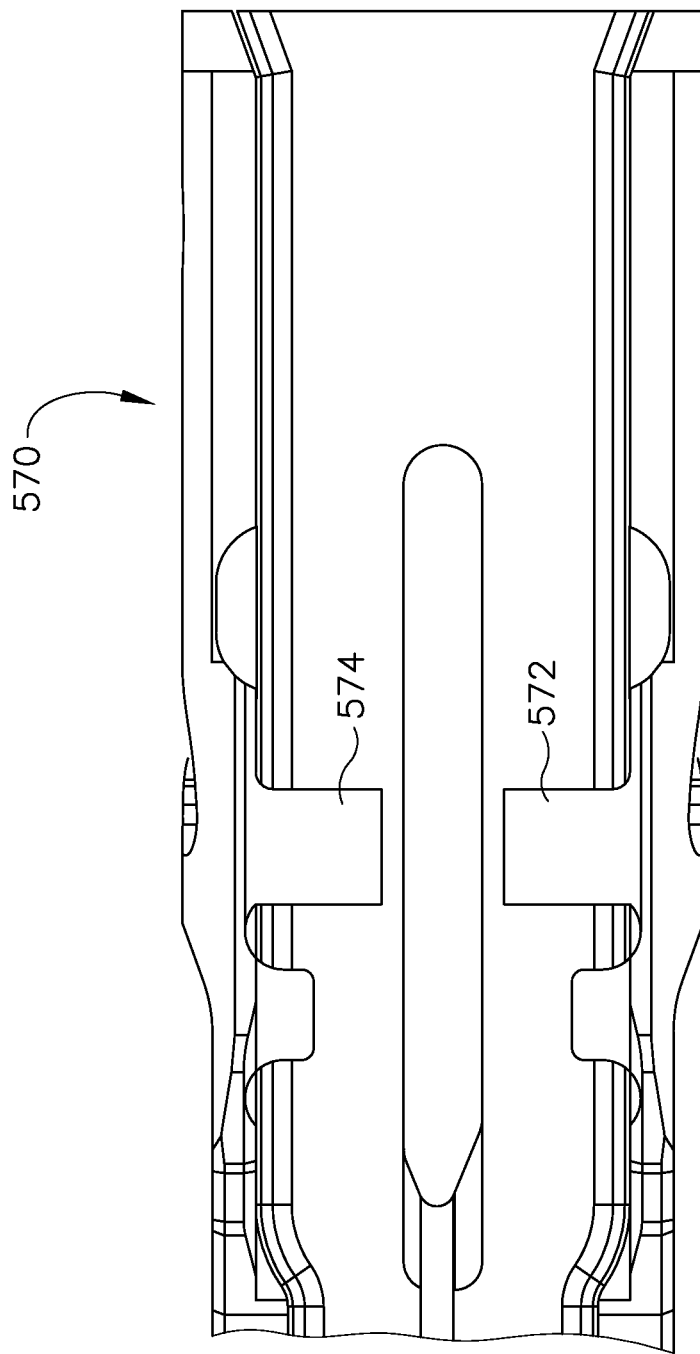
FIG. 83 depicts a top view of the proximal end of the lower jaw of FIG. 81.

FIGS. 78-86 show another exemplary alternative cartridge (560) and lower jaw (570) having mating alignment features. Cartridge (560) and lower jaw (570) may be readily incorporated into end effectors (40, 240) in place of cartridges (270, 300, 320, 340, 360, 400, 410, 450, 460, 470) and/or lower jaws (50, 250) discussed above. Cartridge (560) of the present example is configured to operate substantially similar to cartridges (70, 270) discussed above except for the differences discussed below. Lower jaw (570) of the present example is configured to operate substantially similar to lower jaws (50, 250) discussed above except for the differences discussed below. As best seen in FIGS. 78-80, the alignment features of cartridge (560) of the present example comprise a pair of rigid protrusions (562, 564) extending proximally from a proximal end of cartridge (560). As best seen in FIGS. 81-83, the alignment features of lower jaw (570) of the present example comprise a pair of rigid protrusions (572, 574) extending inwardly from opposing interior surfaces of cartridge (570). Lower jaw (570) is configured to receive cartridge (560).

Figure 84:
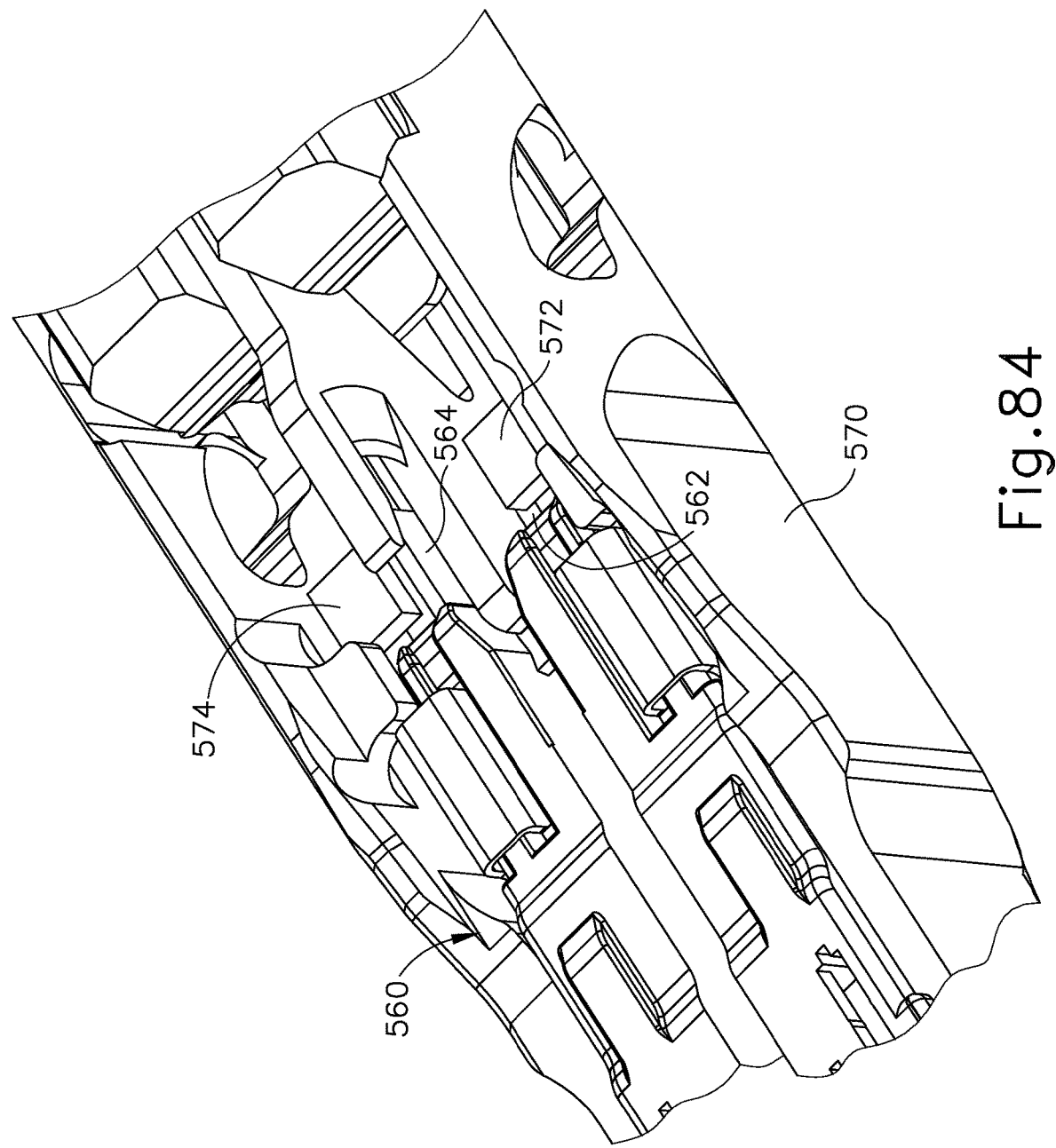
FIG. 84 depicts a perspective view of the proximal end of the cartridge of FIG. 78 engaged with the proximal end of the lower jaw of FIG. 81.
Figure 85:
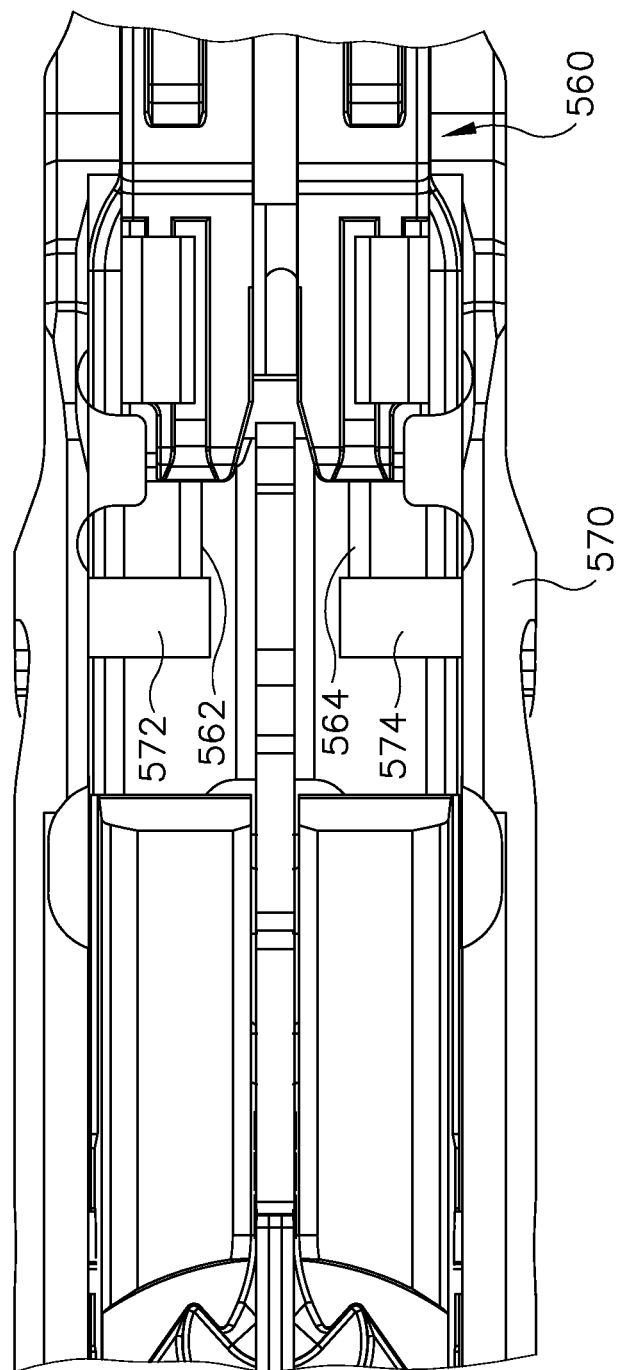
FIG. 85 depicts a top view of the proximal end of the cartridge of FIG. 78 engaged with the proximal end of the lower jaw of FIG. 81.
Figure 86:
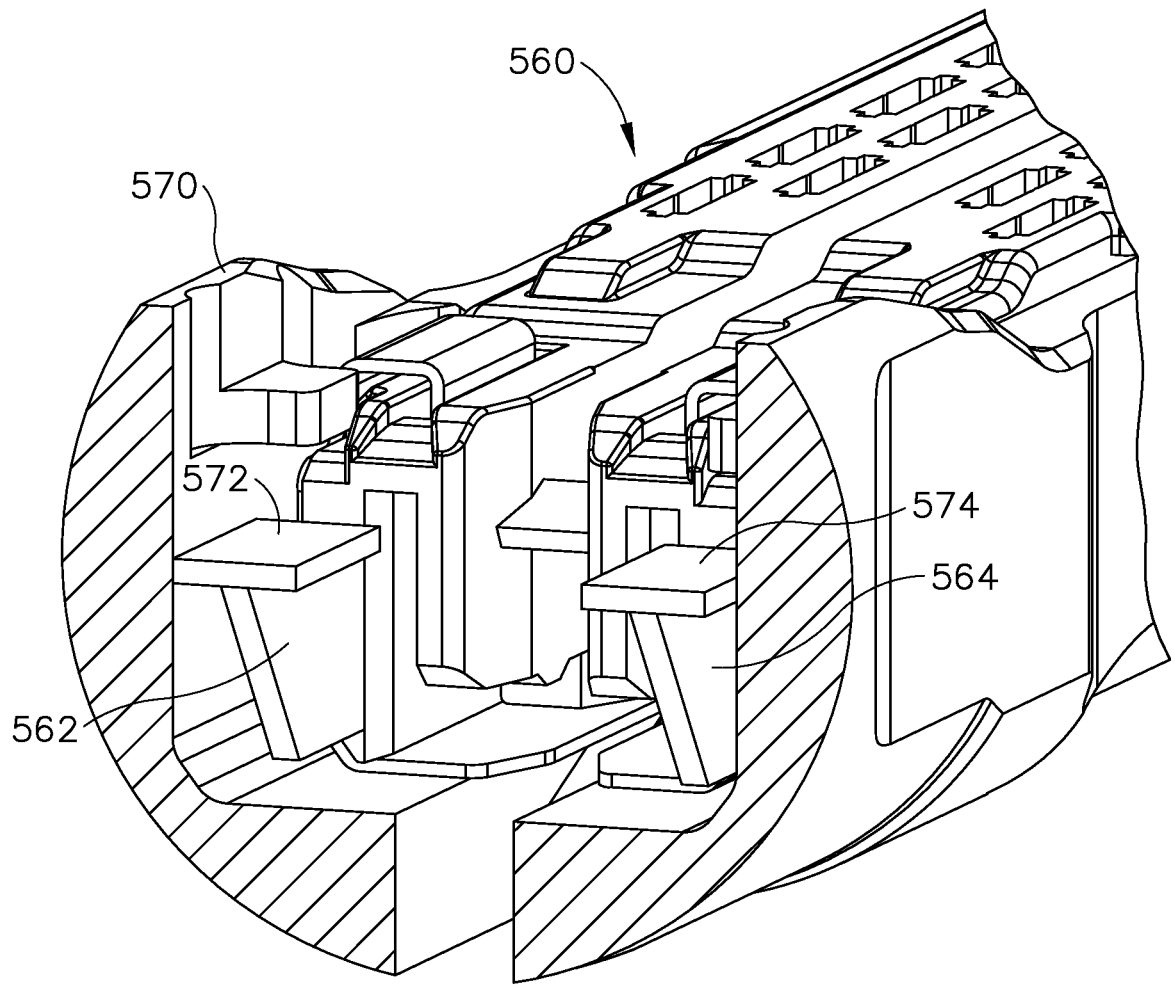
FIG. 86 depicts a cross-sectional perspective view of the proximal end of the cartridge of FIG. 78 engaged with the proximal end of the lower jaw of FIG. 81.

As shown in FIGS. 84-86, with cartridge (560) disposed within lower jaw (570), protrusions (562, 564) of cartridge (560) are aligned below protrusions (572, 574) of lower jaw (570) so as to ensure proper vertical alignment between cartridge (560) and lower jaw (570). As cartridge (560) is inserted into lower jaw (570), an operator first inserts the proximal end of cartridge (560) into lower jaw (570) such that protrusions (562, 564) are positioned below protrusions (572, 574) of lower jaw (570). At this point, the operator pivots a distal end of cartridge (560) into a distal end of lower jaw (570) such that cartridge (560) is completely engaged with lower jaw (570). As the distal end of cartridge (560) is pivoted into lower jaw (570), the positioning of protrusions (562, 564) of cartridge (560) below protrusions (572, 574) of lower jaw (570) will maintain the vertical alignment of the proximal end of cartridge (560). It should be understood that protrusions (572, 574) of lower jaw (570) may be downwardly biased so as to further provide for proper vertical alignment between cartridge (560) and lower jaw (570).

E. Exemplary Wedge Sled and Lower Jaw with Alignment Features

Figure 87:
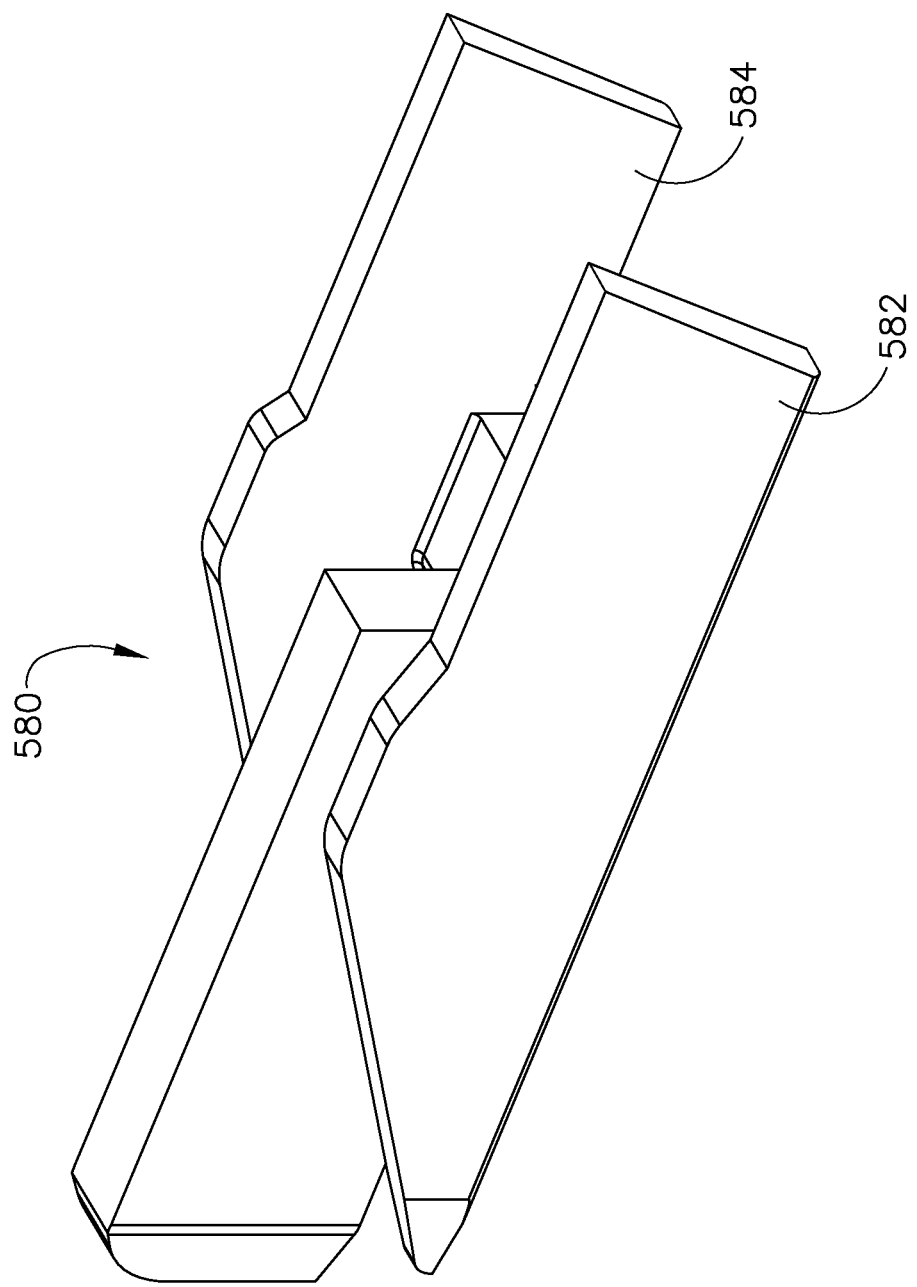
Figure 88:
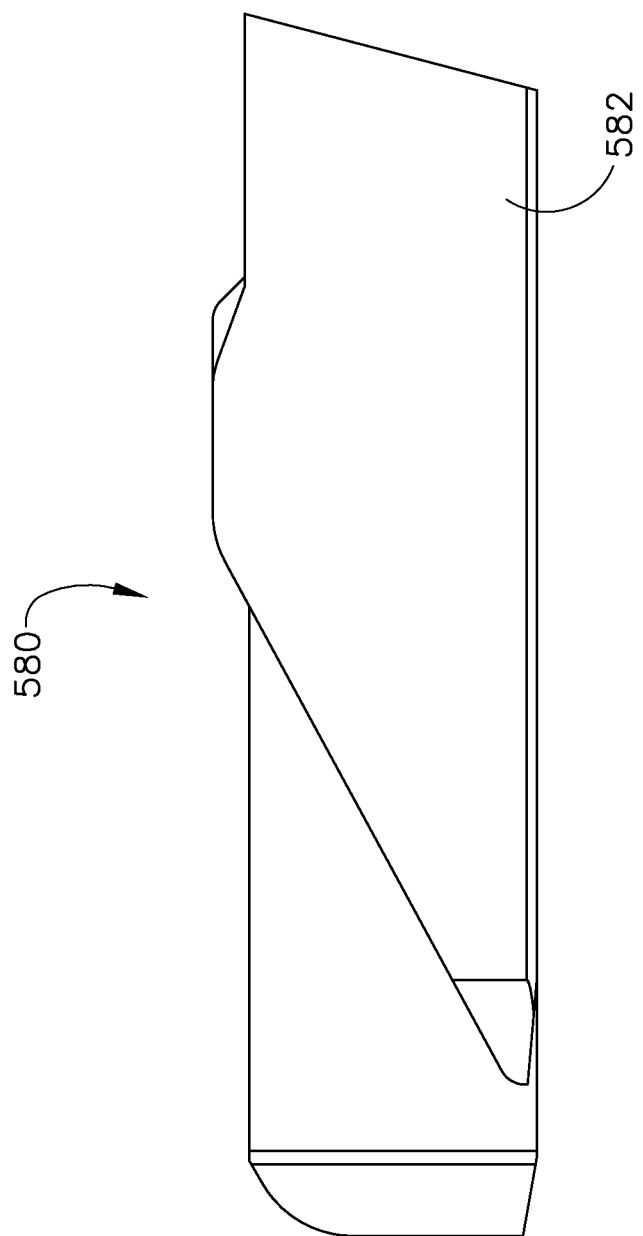
Figure 89:
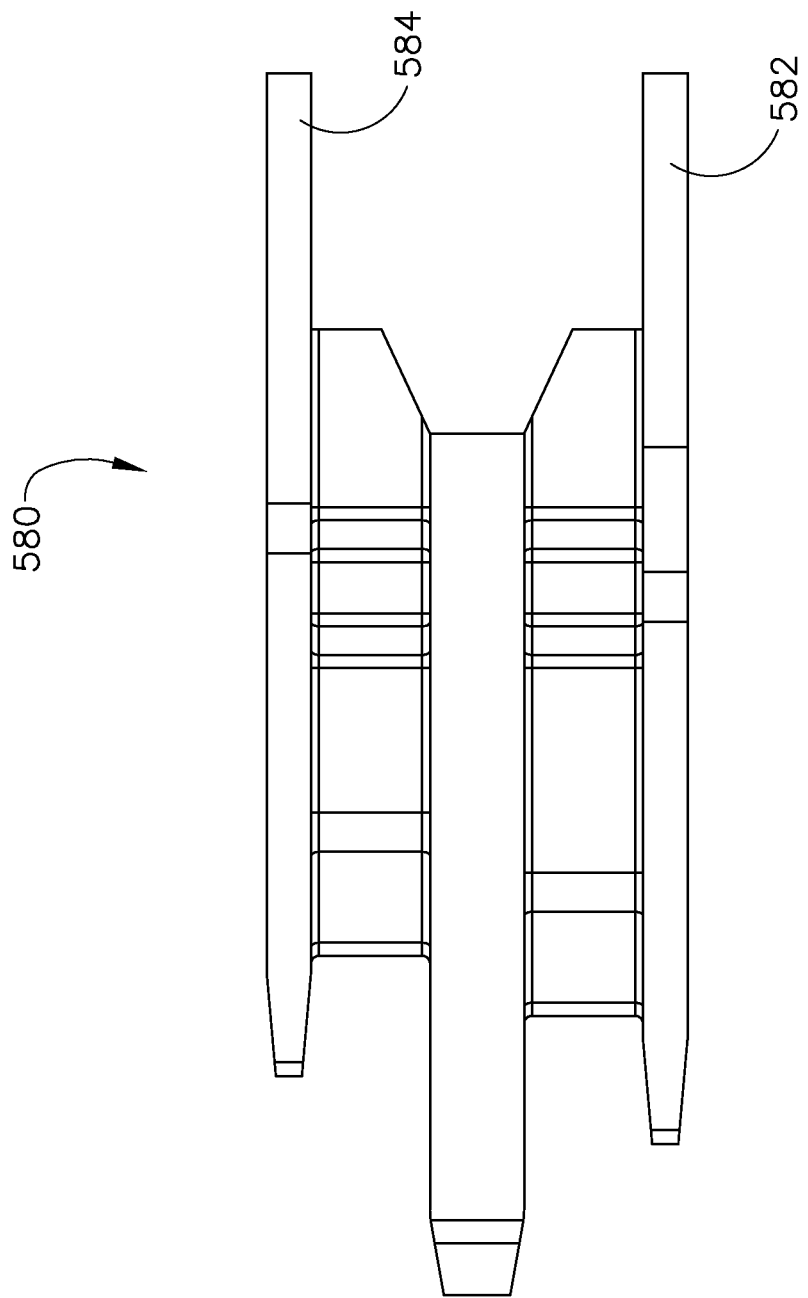
Figure 90:
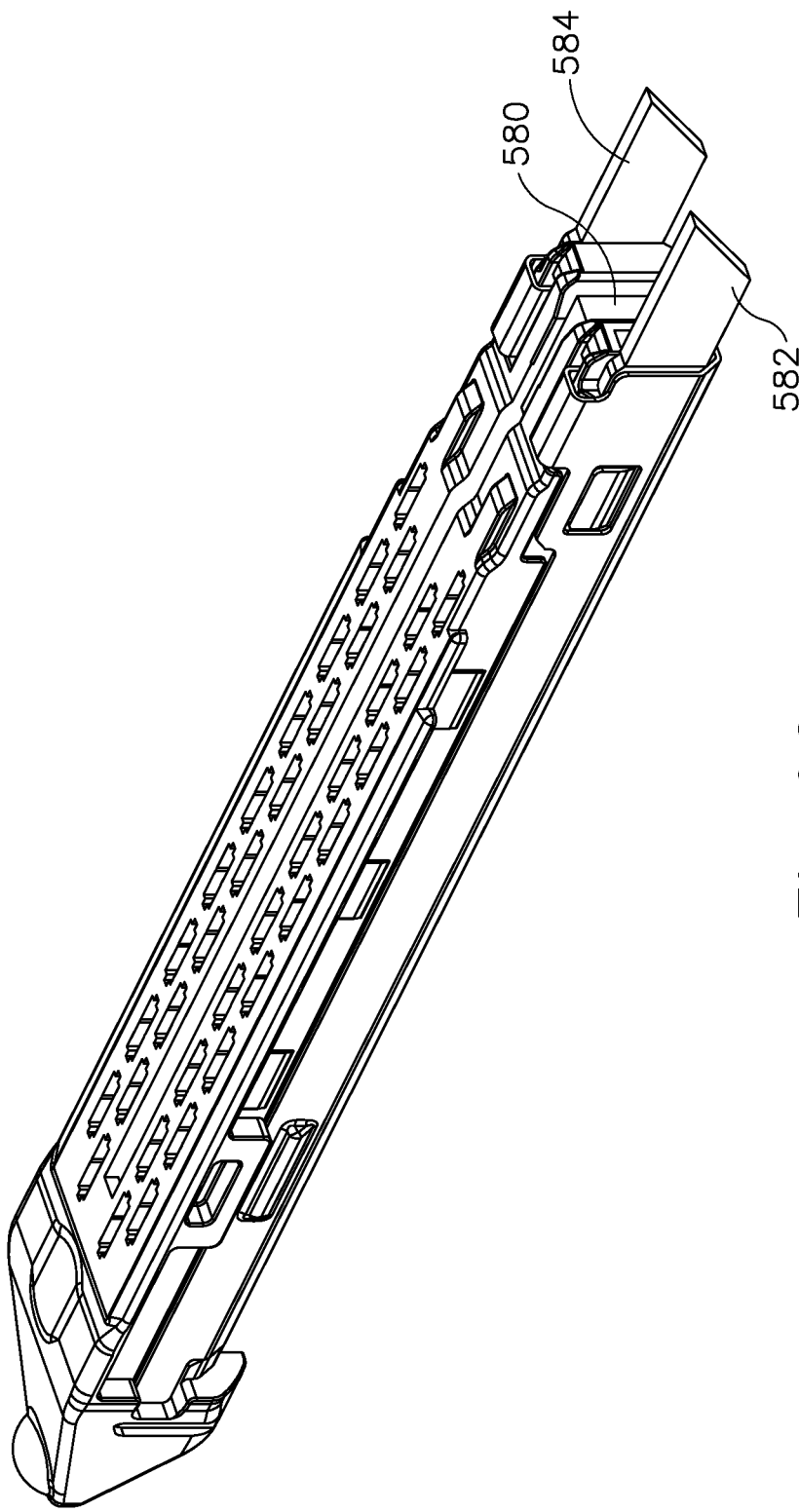
Figure 91:
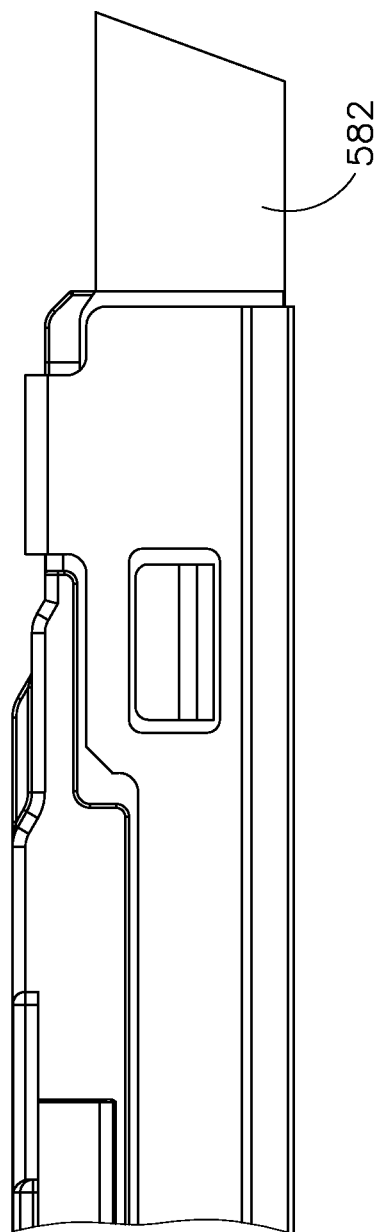
Figure 92:
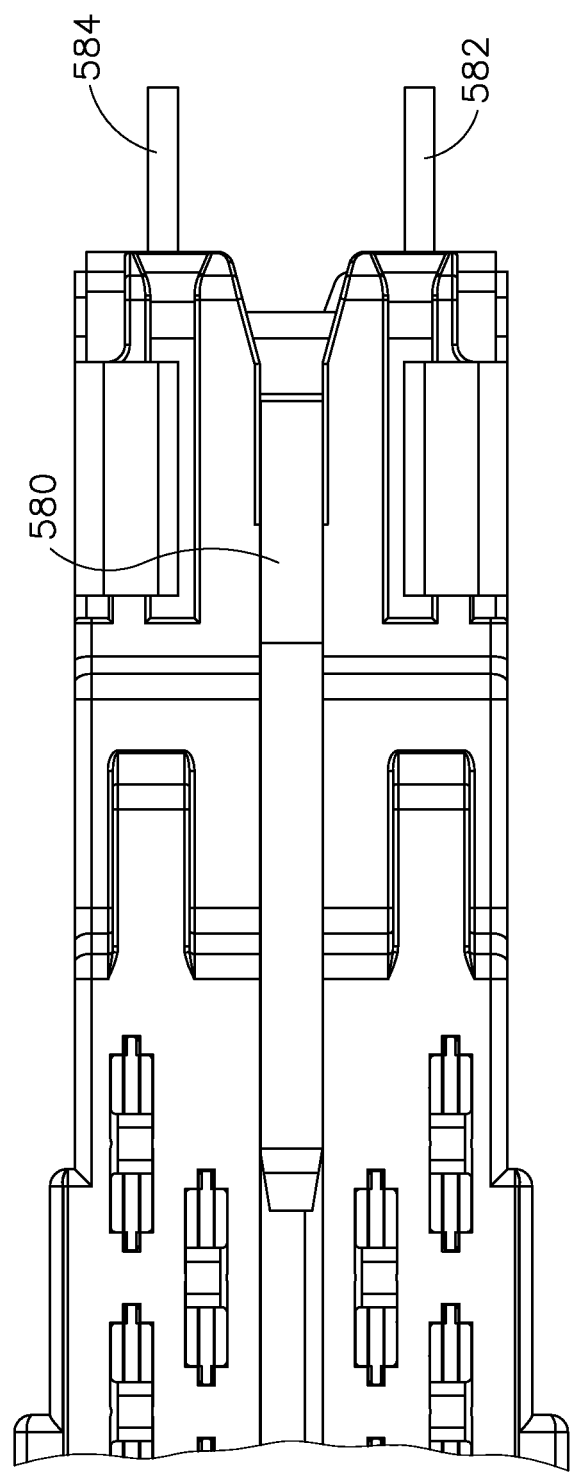
Figure 93:
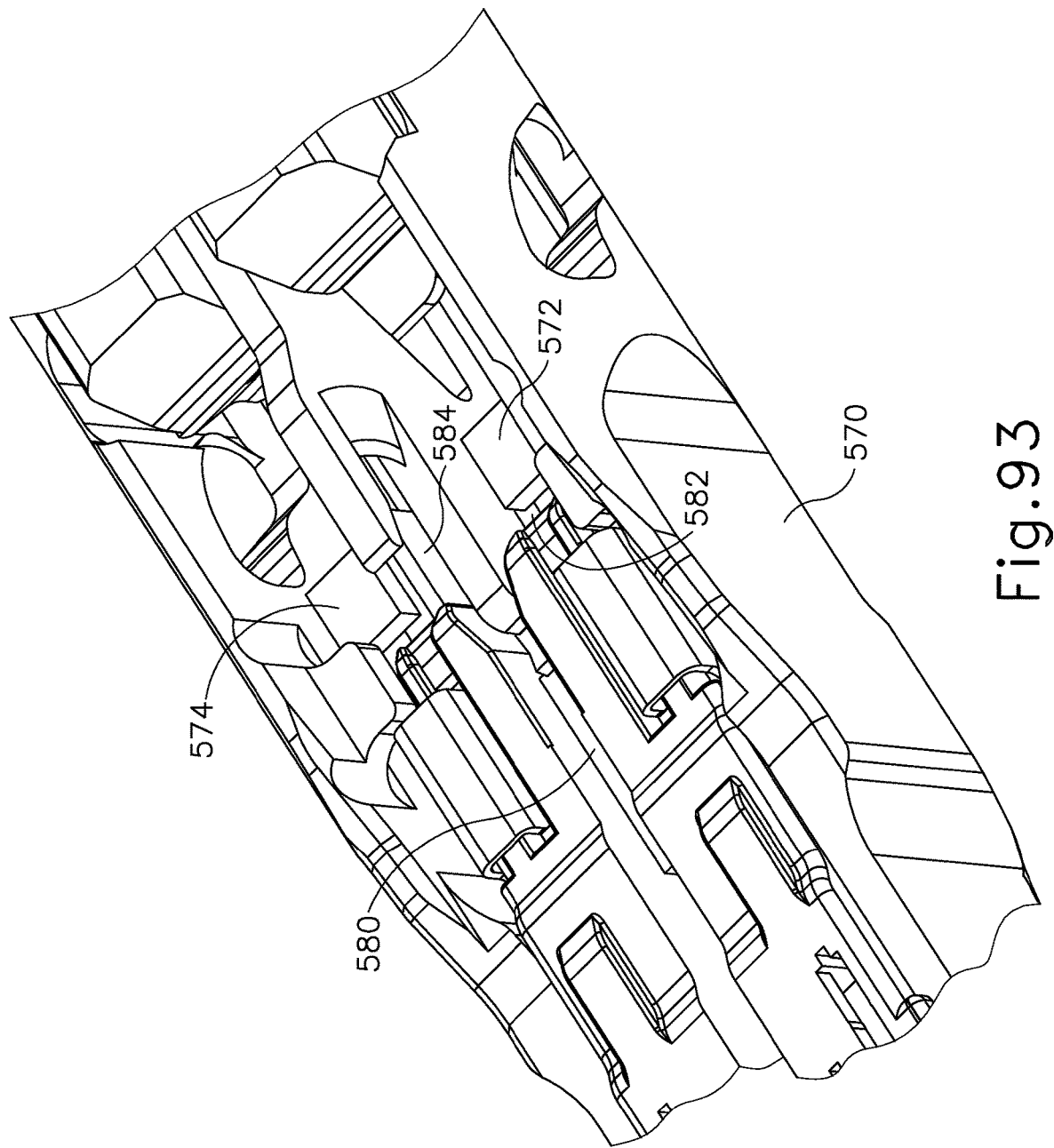
Figure 94:
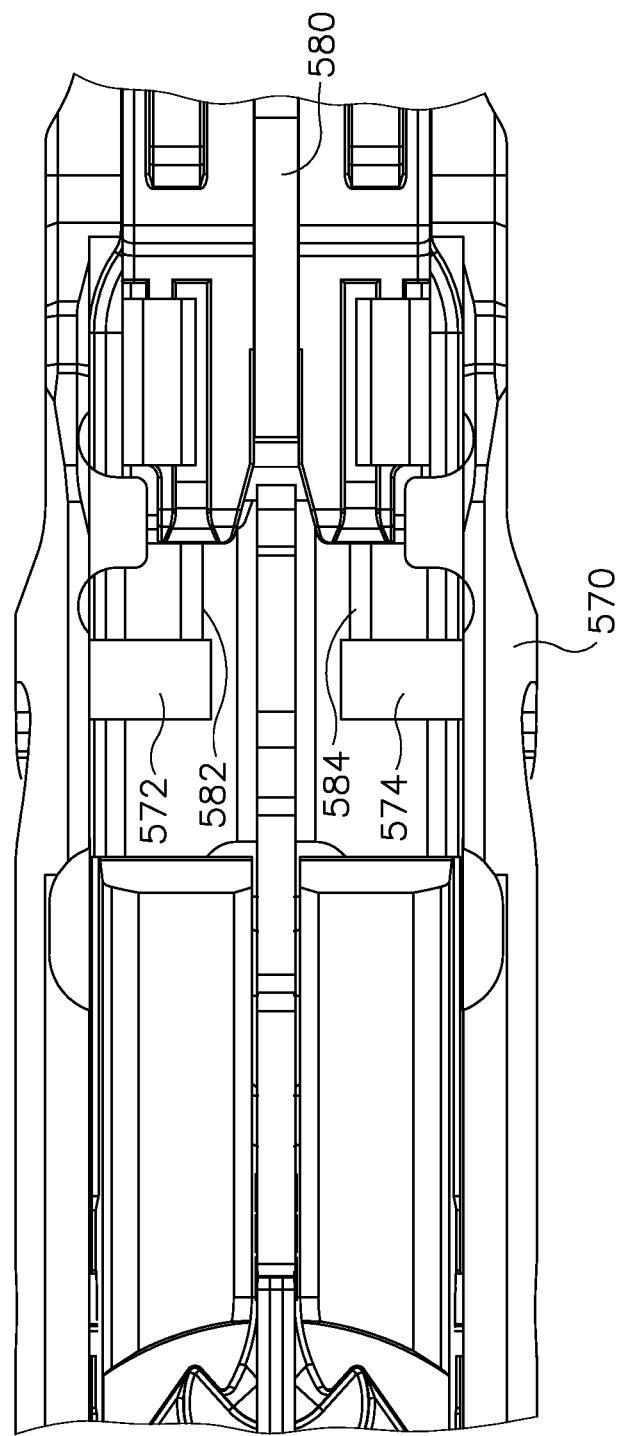
Figure 95:
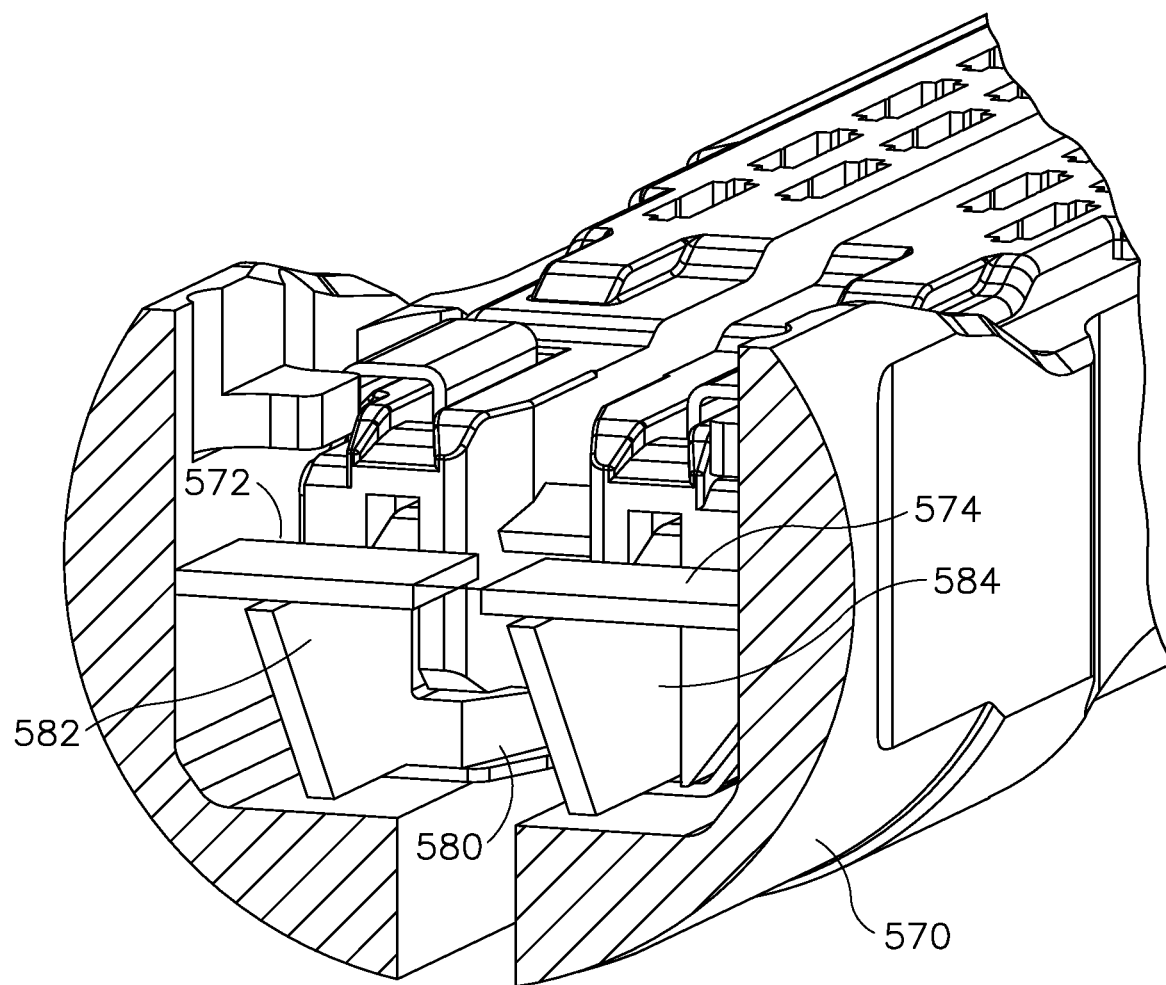

FIGS. 87-95 show an exemplary alternative wedge sled (580) having alignment features configured to matingly engage with lower jaw (570) discussed above. Sled (580) of the present example may be readily incorporated into staple cartridge (70) or any other staple cartridge described herein. Sled (580) of the present example is configured to operate substantially similar to sleds (78, 278) discussed above except for the differences discussed below. For instance, as with sleds (78, 278) discussed above, sled (580) of the present example is captured between a cartridge body and a cartridge tray of a cartridge and is operable to translate longitudinally the through cartridge body. It should be understood that sled (580) of the present example may be used with any appropriate cartridge discussed herein. As best seen in FIGS. 87-89, the alignment features of sled (580) of the present example comprise a pair of rigid protrusions (582, 584) extending proximally from a proximal end of sled (580). As shown in FIGS. 90-92, when sled (580) is in an initial position (a position prior to being fired distally), protrusions (582, 584) extend proximally from a proximal end of cartridge (70). As shown in FIGS. 93-95, with cartridge (70) disposed within lower jaw (570), protrusions (582, 584) of sled (580) are aligned below protrusions (572, 574) of lower jaw (570) so as to ensure proper vertical alignment between cartridge (70) and lower jaw (570). It should be understood that upon firing of sled (580) distally, protrusions (582, 584) would no longer be aligned with protrusions (572, 574) of lower jaw (570). As cartridge (70), with sled (580), is inserted into lower jaw (570), an operator first inserts the proximal end of cartridge (70) into lower jaw (570) such that protrusions (582, 584) are positioned below protrusions (572, 574) of lower jaw (570). At this point, the operator pivots a distal end of cartridge (70) into a distal end of lower jaw (570) such that cartridge (70) is completely engaged with lower jaw (570). As the distal end of cartridge (70) is pivoted into lower jaw (570), the positioning of protrusions (582, 584) of sled (580) below protrusions (572, 574) of lower jaw (570) will maintain the vertical alignment of the proximal end of cartridge (70). It should also be understood that protrusions (572, 574) of lower jaw (570) may be downwardly biased so as to further provide for proper vertical alignment between cartridge (70) and lower jaw (570).

F. Exemplary Cartridge Tray with Resilient Tab Engagement Features

Figure 96:
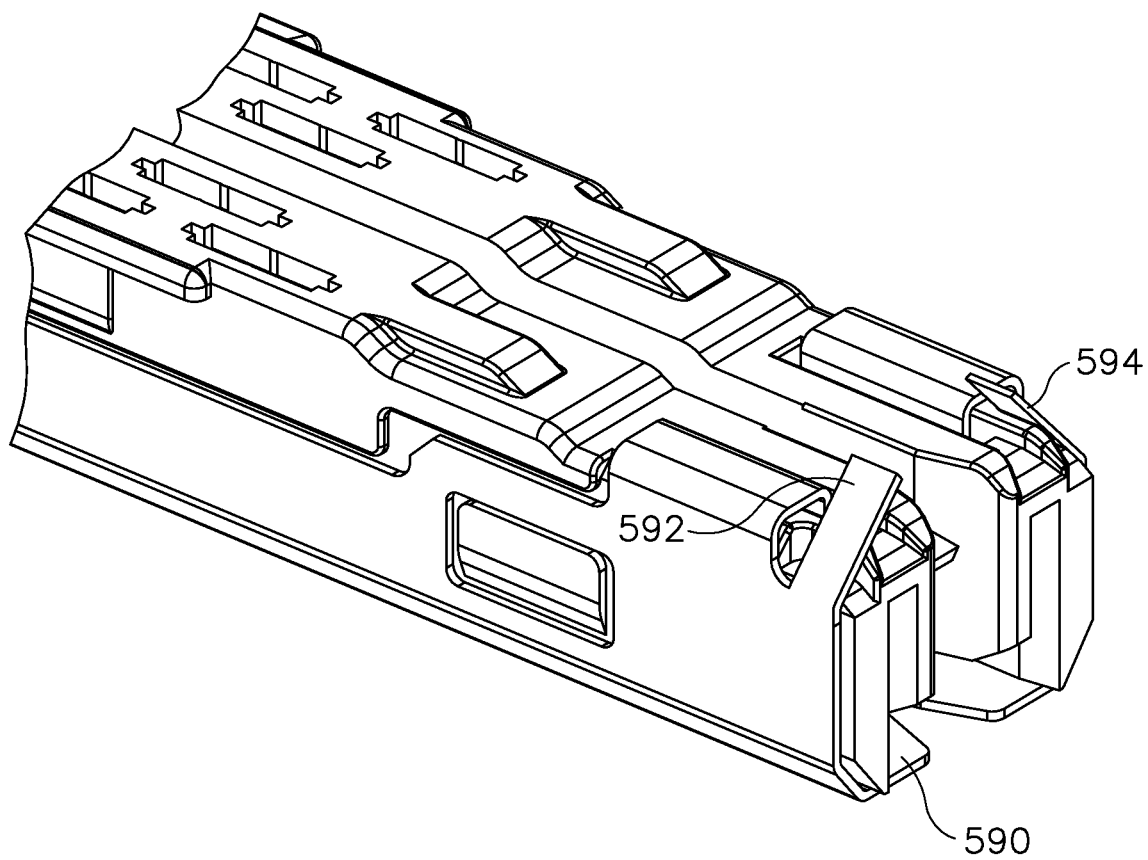
Figure 97:
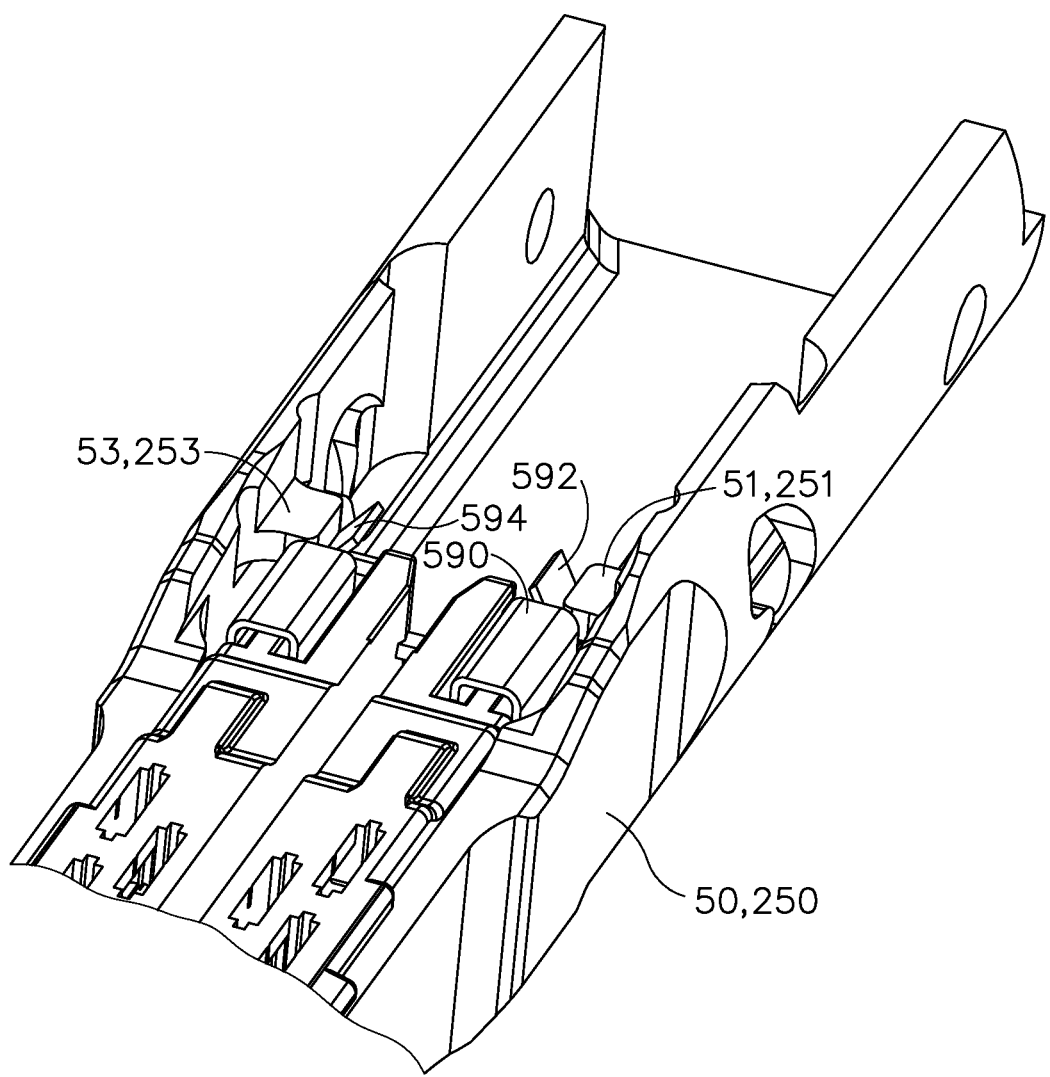
Figure 98:
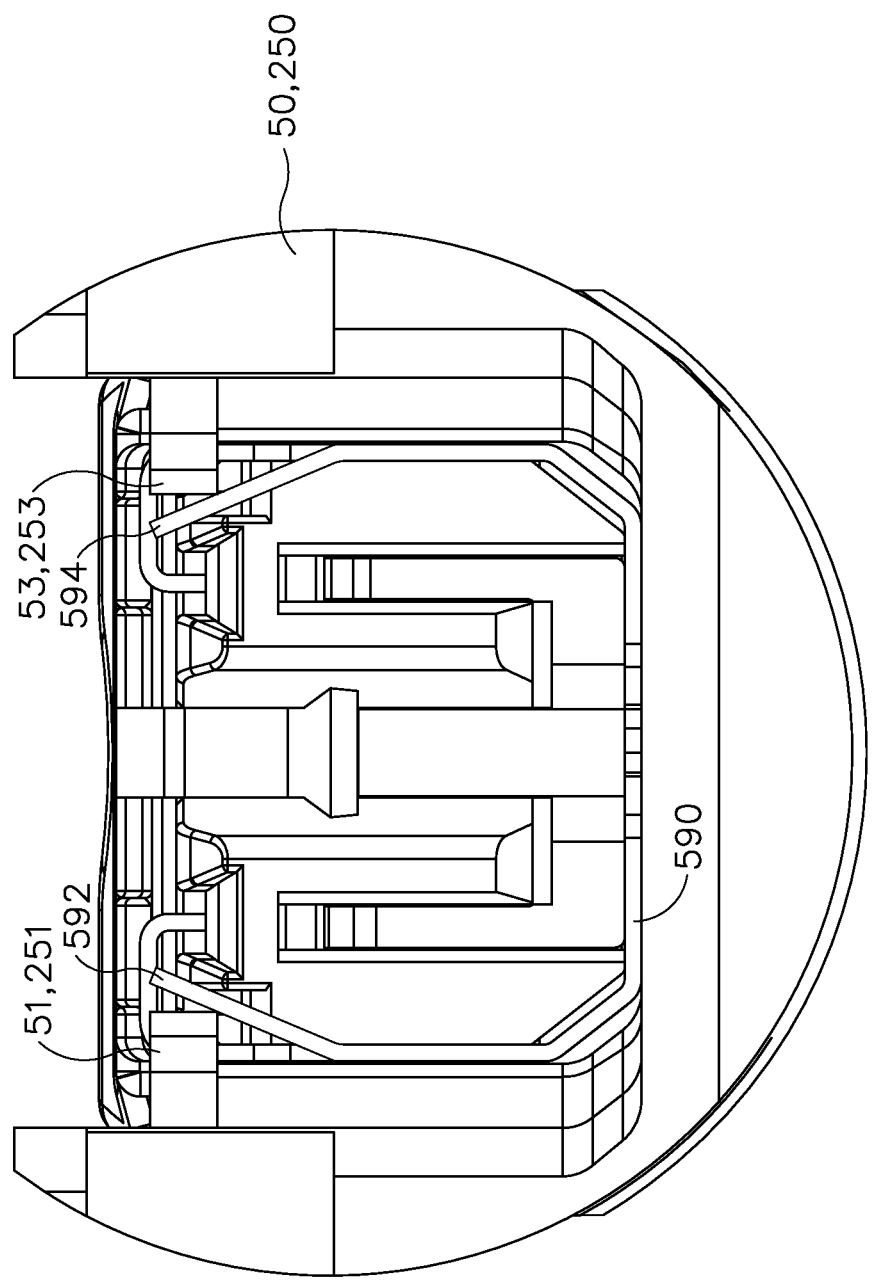

FIGS. 96-98 show another exemplary cartridge tray (590) with engagement features. Cartridge tray (590) of the present example may be readily incorporated into staple cartridge (70) or any other staple cartridge described herein. Cartridge tray (590) of the present example is configured to operate substantially similar to cartridge trays (76, 276) discussed above except for the differences discussed below. The engagement features of cartridge tray (590) of the present example comprise a pair of resilient tabs (592, 594) extending upwardly and inwardly from a proximal end of cartridge tray (590). It should be understood that cartridge tray (590) of the present example may be used with any appropriate cartridge discussed herein. As shown in FIGS. 97 and 98, with cartridge (70) having cartridge tray (590) disposed within lower jaw (50, 250), tabs (592, 594) of cartridge tray (590) engage a pair of inwardly extending tabs (51, 53, 251, 253) of lower jaw (50, 250). As best seen in FIG. 98, with cartridge (70) disposed within lower jaw (50, 250), tabs (51, 53, 251, 253) of lower jaw (50, 250) are configured to bear against a top surface of tabs (592, 294) of cartridge tray (590) to thereby drive cartridge (70) downwardly within lower jaw (50, 250) so as to ensure proper engagement between cartridge (70) and lower jaw (50, 250).

G. Exemplary Cartridge Tray with Leaf Spring Engagement Features

FIGS. 99-101 show another exemplary cartridge tray (600) with engagement features. Cartridge tray (600) of the present example may be readily incorporated into staple cartridge (70) or any other staple cartridge described herein. Cartridge tray (600) of the present example is configured to operate substantially similar to cartridge trays (76, 276) discussed above except for the differences discussed below. As shown in FIGS. 99 and 100, the engagement features of cartridge tray (600) of the present example comprise a pair of resilient members (602, 604) extending proximally from a proximal end of cartridge tray (600). Resilient members (602,604) are configured as leaf springs in the present example. It should be understood that cartridge tray (600) of the present example may be used with any appropriate cartridge discussed herein. As shown in FIG. 101, with cartridge (70) having cartridge tray (600) disposed within lower jaw (250), resilient members (602, 604) of cartridge tray (600) engage a bottom surface (241) of frame member (238). (It should be noted that the cross-sectional view of FIG. 101 is taken along a plane that is laterally offset from a longitudinal axis of end effector (240).) With cartridge (70) disposed within lower jaw (250), resilient members (602, 604) are configured to bear against the bottom surface (241) of frame member (238) to thereby drive cartridge (70) downwardly within lower jaw (250) so as to ensure proper engagement between cartridge (70) and lower jaw (250).

H. Exemplary Cartridge Tray with Resilient Engagement and Retaining Features

FIGS. 102-106 show an exemplary cartridge tray (610) with engagement and retaining features. Cartridge tray (610) of the present example may be readily incorporated into staple cartridge (70) or any other staple cartridge described herein. Cartridge tray (610) of the present example is configured to operate substantially similar to cartridge trays (76, 276) discussed above except for the differences discussed below. As best seen in FIGS. 102 and 103, the engagement and retaining features of cartridge tray (610) of the present example comprise a pair of resilient curved members (612, 614) curved upwardly and extending proximally from a proximal end of cartridge tray (590). It should be understood that cartridge tray (610) of the present example may be used with any appropriate cartridge discussed herein. As shown in FIGS. 104-106, with cartridge (70) having cartridge tray (610) disposed within lower jaw (50, 250), curved members (612, 614) of cartridge tray (610) engage inwardly extending tabs (51, 53, 251, 253) of lower jaw (50, 250). As best seen in FIGS. 104 and 105, as cartridge (70) is inserted into lower jaw (50, 250), this engagement is configured to bend curved members (612, 614) distally and fold curved members (612, 614) down upon a top surface of a proximal portion of cartridge (70) so as to ensure proper engagement between cartridge (70) and lower jaw (50, 250) and so as to retain engagement between cartridge (70) and lower jaw (50, 250).

VI. Anvil Alignment Features

In some instances, it may be desirable to provide alignment features that ensure that anvil (60, 260) will be clamped squarely relative to staple cartridge (70, 270). For instance, in some end effectors (40, 240), manufacturing tolerances may result in a tendency for anvil (60, 260) to be mis-aligned relative to staple cartridge (70, 270). Such mis-alignment may include a deflection of anvil (60, 260) laterally away from a vertical plane extending along the central longitudinal axis of staple cartridge (70, 270). Such mis-alignment may also include a roll deflection of anvil (60, 260) about the central longitudinal axis of staple cartridge (70, 270). In some cases, such mis-alignment may further include longitudinal mis-alignment of anvil (60, 260) relative to staple cartridge (70, 270). Alignment features may be used to address manufacturing tolerances to thereby correct lateral deflections, roll deflections, longitudinal deflections, and/or other deflections of anvil (60, 260) relative to staple cartridge (270).

It may also be desirable to provide alignment features that ensure that anvil (60, 260) will define an appropriate gap with staple cartridge (70, 270) when anvil (60, 260) is brought to the fully closed position. Such features may prevent anvil (60, 260) from being closed too firmly on tissue captured between anvil (60, 260) and staple cartridge (70, 270). Such features may also provide a consistent location for where pre-loading of anvil (60, 260) occurs against staple cartridge (70, 270) for each closure stroke of anvil (70, 270).

Various kinds of alignment and/or gap-setting features may be provided in anvil (60, 260), in cartridge (70, 270), or in both. Examples of such alignment or gap-setting features are disclosed in U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016, the disclosure of which is incorporated by reference herein. Further examples of alignment and/or gap-setting features may be provided in anvil (60, 260), in cartridge (70, 270) are described in greater detail below, while still other examples will be apparent to those of ordinary skill in the art in view of the teachings herein.

A. Exemplary Cartridge and Anvil with Cylindrical Alignment and Gap-Setting Features FIGS. 107-109 show an exemplary alternative cartridge (620) and anvil (630) having alignment and gap-setting features. Cartridge (620) and anvil (630) may be readily incorporated into end effectors (40, 240) in place of cartridges (270, 300, 320, 340, 360, 400, 410, 450, 460, 470) and/or anvils (60, 260). Cartridge (620) of the present example is configured to operate substantially similar to cartridges (70, 270) discussed above except for the differences discussed below. Anvil (630) of the present example is configured to operate substantially similar to anvils (60, 260) discussed above except for the differences discussed below. As best seen in FIG. 107, the alignment and gap-setting features of cartridge (620) of the present example comprise a pair of cylindrical protrusions (622, 624) extending upwardly from a top surface of a distal portion of cartridge (620). As best seen in FIG. 108, the alignment and gap-setting features of anvil (630) of the present example comprise a pair of cylindrical recesses (632, 634) formed in an underside of a distal portion of anvil (630). Recesses (632, 634) are sized and shaped to complement the size and shape of protrusions (622, 624). In some variations, recesses (632, 634) are formed in anvil (630) while protrusions (622, 624) are part of cartridge (620).

As shown in FIG. 109, upon closure of anvil (630), cylindrical recesses (632, 634) are configured to receive cylindrical protrusions (622, 624) to thereby ensure proper lateral, roll, and/or longitudinal alignment of anvil (630) relative to cartridge (620). Furthermore, a depth of cylindrical recesses (632, 634) and a height of cylindrical protrusions (622, 624) are such that upon proper closure, a top surface of cylindrical protrusions (622, 624) will contact a bottom surface of cylindrical recesses (632, 634) to thereby prevent further closure so as to maintain a proper distance between anvil (630) and cartridge (620) (i.e., protrusions (622, 624) and recesses (632, 634) establish a minimum gap distance between a top surface of cartridge (620) and anvil (630) so as to prevent over-compression of tissue). It should also be understood that protrusions (622, 624) may provide a depth stop to restrict insertion of the distal end of cartridge (620) in a catheter. Likewise, in versions where protrusions (622, 624) are part of anvil (630), protrusions (622, 624) may provide a depth stop to restrict insertion of the distal end of anvil (630) in a catheter. By way of example only, an operator may wish to position the end of a catheter on the distal end of anvil (630) or cartridge (620) in order to use anvil (630) or cartridge (620) to position the catheter in relation to an anatomical structure in the patient.

B. Exemplary Cartridge and Anvil with Conical Alignment and Gap-Setting Features FIGS. 110-113 show an exemplary alternative cartridge (640) and anvil (650) having alignment and gap-setting features. Cartridge (640) and anvil (650) may be readily incorporated into end effectors (40, 240) in place of cartridges (270, 300, 320, 340, 360, 400, 410, 450, 460, 470)

and/or anvils (60, 260). Cartridge (640) of the present example is configured to operate substantially similar to cartridges (70, 270) discussed above except for the differences discussed below. Anvil (650) of the present example is configured to operate substantially similar to anvils (60, 260) discussed above except for the differences discussed below. As best seen in FIGS. 110 and 111, the alignment and gap-setting features of cartridge (640) of the present example comprise a pair of rounded conical protrusions (642, 644) extending upwardly from a top surface of a distal portion of cartridge (640). As best seen in FIG. 112, the alignment and gap-setting features of anvil (650) of the present example comprise a pair of spherical recesses (652, 654) formed in an underside of a distal portion of anvil (650). Recesses (652, 654) are sized and shaped to complement the size and shape of protrusions (642, 644). In some variations, recesses (652, 654) are formed in anvil (630) while protrusions (642, 644) are part of cartridge (640).

As shown in FIG. 113, upon closure of anvil (650), spherical recesses (652, 654) are configured to receive conical protrusions (642, 644) to thereby ensure proper lateral, roll, and/or longitudinal alignment of anvil (650) relative to cartridge (640). Furthermore, a depth of spherical recesses (652, 654) and a height of conical protrusions (642, 644) are such that upon proper closure, a top surface of conical protrusions (642, 644) will contact a bottom surface of spherical recesses (652, 654) to thereby prevent further closure so as to maintain a proper distance between anvil (650) and cartridge (640) (i.e., protrusions (642, 644) and recesses (652, 654) establish a minimum gap distance between a top surface of cartridge (640) and anvil (650) so as to prevent over-compression of tissue). It should also be understood that protrusions (642, 644) may provide a depth stop to restrict insertion of the distal end of cartridge (640) in a catheter. Likewise, in versions where protrusions (642, 644) are part of anvil (650), protrusions (642, 644) may provide a depth stop to restrict insertion of the distal end of anvil (650) in a catheter. By way of example only, an operator may wish to position the end of a catheter on the distal end of anvil (650) or cartridge (640) in order to use anvil (650) or cartridge (640) to position the catheter in relation to an anatomical structure in the patient.

C. Exemplary Cartridge and Anvil with Rectangular Alignment and Gap-Setting Features FIGS. 114-117 show an exemplary alternative cartridge (660) and anvil (670) having alignment and gap-setting features. Cartridge (660) and anvil (670) may be readily incorporated into end effectors (40, 240) in place of cartridges (270, 300, 320, 340, 360, 400, 410, 450, 460, 470) and/or anvils (60, 260). Cartridge (660) of the present example is configured to operate substantially similar to cartridges (70, 270) discussed above except for the differences discussed below. Anvil (670) of the present example is configured to operate substantially similar to anvils (60, 260) discussed above except for the differences discussed below. As best seen in FIGS. 114 and 115, the alignment and gap-setting features of cartridge (660) of the present example comprise a pair of rectangular protrusions (662, 664) extending upwardly from a top surface of a distal portion of cartridge (660). As best seen in FIG. 116, the alignment and gap-setting features of anvil (670) of the present example comprise a pair of rectangular recesses (672, 674) formed in an underside of a distal portion of anvil (670). Recesses (672, 674) are sized and shaped to complement the size and shape of protrusions (662, 664). In some variations, recesses (672, 674) are formed in anvil (670) while protrusions (662, 664) are part of cartridge (660).

As shown in FIG. 113, upon closure of anvil (670), rectangular recesses (672, 674) are configured to receive rectangular protrusions (662, 664) to thereby ensure proper lateral, roll, and/or longitudinal alignment of anvil (670) relative to cartridge (660). Furthermore, a depth of rectangular recesses (672, 674) and a height of rectangular protrusions (662, 664) are such that upon proper closure, a top surface of rectangular protrusions (662, 664) will contact a bottom surface of rectangular recesses (672, 674) to thereby prevent further closure so as to maintain a proper distance between anvil (670) and cartridge (660) (i.e., protrusions (662, 664) and recesses (672, 674) establish a minimum gap distance between a top surface of cartridge (660) and anvil (670) so as to prevent over-compression of tissue). It should also be understood that protrusions (662, 664) may provide a depth stop to restrict insertion of the distal end of cartridge (660) in a catheter. Likewise, in versions where protrusions (662, 664) are part of anvil (670), protrusions (662, 664) may provide a depth stop to restrict insertion of the distal end of anvil (670) in a catheter. By way of example only, an operator may wish to position the end of a catheter on the distal end of anvil (670) or cartridge (660) in order to use anvil (670) or cartridge (660) to position the catheter in relation to an anatomical structure in the patient.

VII. Exemplary Features to Prevent Use of Staple Cartridge in Incorrect End Effector Various surgical stapling instruments are available for purchase and use. These various surgical stapling instruments may use different staple cartridges. In some instances, an operator may have difficulty in immediately discerning which staple cartridge corresponds to which surgical stapling instrument. An operator may therefore inadvertently place and attempt to use a staple cartridge in an incorrect surgical stapling device. Thus, it may be desirable to provide features that prevent a staple cartridge that is intended to be used in one particular surgical stapling instrument from being used in other, incorrect surgical stapling instruments. For instance, such features may prevent insertion of an improper staple cartridge and/or may prevent firing of a knife member or a firing beam in the presence of an incorrect staple cartridge. The example below includes merely illustrative versions of features that may be readily introduced to any of the cartridges (70, 270, 300, 320, 340, 360, 400, 410, 450, 460, 470) discussed above.

A. Exemplary End Effector with "E-Beam"

Some surgical stapling instruments may include an "E-Beam" type of knife member or firing beam, instead of including a structure like the combination of knife member (80, 280) and firing beam (82, 282) described above. An example of such a stapling instrument (710) is shown in FIGS. 118-128. Instrument (710) comprises an end effector (740) having an E-beam firing mechanism ("firing bar") (714) that controls the spacing of the end effector (740). In particular, a lower jaw (716) and a pivotally translatable anvil (760) are maintained at a spacing that assures effective stapling and cutting.

Instrument (710) includes a handle portion (720) connected to a shaft assembly (722), shaft assembly (722) comprising a shaft (723) distally terminating in end effector (740). Handle portion (720) includes a pistol grip (724) toward which a closure trigger (726) is pivotally drawn by the operator to cause clamping, or closing, of anvil (760) toward lower jaw (716) of end effector (740). A firing trigger (728) is farther outboard of closure trigger (726) and is pivotally drawn by the operator to cause the stapling and cutting of clamped tissue in end effector (740). A closure sleeve (732) encloses a frame (734), which in turn encloses a firing drive member (736) that is positioned by firing trigger (728). Frame (734) connects handle portion (720) to end effector (740). With closure sleeve (732) withdrawn proximally by closure trigger (726) as depicted, anvil (760) springedly opens, pivoting away from lower jaw (716) and translating proximally with closure sleeve (732).

As shown in FIGS. 119-121, firing bar (714) includes three vertically spaced pins (738, 744, 746) that control the spacing of end effector (740) during firing. In particular, an upper pin (738) is staged to enter an anvil pocket (716) near the pivot between anvil (760) and lower jaw (716). When fired with anvil (760) closed, the upper pin (738) advances distally within a longitudinal anvil slot (742) extending distally through anvil (760). Any minor upward deflection in anvil (760) is overcome by a downward force imparted by upper pin (738). Firing bar (714) also includes a lower most pin, or firing bar cap (744), that upwardly engages a channel slot (745) in lower jaw (716), thereby cooperating with upper pin (738) to draw anvil (760) and lower jaw (716) slightly closer together in the event of excess tissue clamped therebetween.

Firing bar (714) further includes a middle pin (746) that passes through a firing drive slot (747) formed in a lower surface of cartridge (770) and an upward surface of lower jaw (716), thereby driving the staples therein. Middle pin (746), by sliding against lower jaw (716), resists any tendency for end effector (740) to be pinched shut at its distal end. A distally presented cutting edge (748) between upper and middle pins (738, 746) on firing bar (714) traverses through a proximally presented, vertical slot (749) in cartridge (770) to cut clamped tissue. The affirmative positioning of firing bar (714) with regard to lower jaw (716) and anvil (760) assure that an effective cut is performed.

An exemplary use of instrument (710) is depicted in FIGS. 118, 119, and 122-128. In FIGS. 118 and 119, instrument (710) is in its start position, having had an unfired, fully loaded staple cartridge (770) snap-fitted into the distal end of lower jaw (716). Both triggers (726, 728) are forward and end effector (740) is open. Instrument (710) is then manipulated by the operator such that tissue to be stapled and severed is positioned between staple cartridge (770) and anvil (760), as depicted in FIG. 122. As shown in FIGS. 123 and 124, the operator moves closure trigger (726) proximally until positioned directly adjacent to pistol grip (724). With anvil (760) closed and clamped, firing bar (714) is aligned for firing through end effector (740). In particular, upper pin (738) is aligned with anvil slot (742) and lower jaw (716) is affirmatively engaged about channel slot (745) by middle pin (746) and firing bar cap (744).

As shown in FIGS. 125 and 126, after tissue clamping has occurred, the operator moves firing trigger (728) proximally causing firing bar (714) to move distally into end effector (740). In particular, middle pin (746) enters staple cartridge (770) through firing drive slot (747) to effect firing of staples (790) (not shown in FIGS. 125 and 126) via a wedge sled (778) toward anvil (760). Lower most pin, or firing bar cap (744), cooperates with middle pin (746) to slidingly position cutting edge (748) of firing bar (714) to cut tissue. The two pins (744, 746) also position upper pin (738) of firing bar (714) within longitudinal anvil slot (742) of anvil (760), affirmatively maintaining the spacing between anvil (760) and lower jaw (716) throughout its distal firing movement.

With reference to FIGS. 127 and 128, the operator continues moving firing trigger (728) until brought proximal to closure trigger (726) and pistol grip (724). Thereby, all of the ends of staples (790) are bent over as a result of their engagement with anvil (760). Firing bar cap (744) is arrested against a firing bar stop (792) projecting toward the distal end of channel slot (745). Cutting edge (748) has traversed completely through the tissue.

It should be understood that instrument (710) of the present example may be further constructed and/or operable in accordance with at least some of the teachings of U.S. Pat. No. 7,380,695, entitled "Surgical Stapling Instrument Having a Single Lockout Mechanism for Prevention of Firing," issued Jun. 3, 2008, the disclosure of which is incorporated by reference herein.

B. Exemplary Lockout to Prevent Use of Staple Cartridge in E-Beam End Effector

In some instances, it may be desirable to provide lockout features that prevent firing of firing bar (714) of instrument (710) if an inappropriate staple cartridge is inserted into end effector (740). Accordingly, lockout features may be provided on a staple cartridge that is not intended to be used with instrument (710) to thereby prevent firing of firing bar (714).

FIGS. 129-134 show an exemplary alternative cartridge tray (800) having lockout features. Cartridge tray (800) is incorporated into a staple cartridge (810) (FIG. 132) that is intended for use in end effector (40, 240) but not in end effector (740). Cartridge tray (800) of the present example is configured to operate substantially similar to cartridge trays (76, 276) discussed above except for the differences discussed below. As best seen in FIGS. 129-131, the lockout features of cartridge tray (800) of the present example comprise a pair of rigid tabs (802, 804) extending upwardly from a proximal end of a top surface of a base of cartridge tray (800). As shown in FIGS. 132 and 133, with a cartridge body (806) disposed within cartridge tray (800), tabs (802, 804) are positioned proximally of a proximal end of cartridge body (806). As shown in FIG. 134, tabs (802, 804) are configured to engage middle pin (746) so as to prevent distal firing of firing bar (714) in the event that cartridge (810) having cartridge tray (800) is inserted into lower jaw (716). Thus, tabs (802, 804) prevent cartridge (810) from being used in end effector (740). However, tabs (802, 804) do not prevent cartridge (810) from being used in end effectors (40, 240). End effectors (40, 240) include no moving components whose movement would be blocked by tabs (802, 804).

VIII. Exemplary Alternative Lockout Features

FIGS. 135-139 show features of an exemplary alternative end effector (1000) that may be used in place of any of the end effectors (40, 240) described herein. End effector (1000) of this example comprises an anvil (1010), a staple cartridge (1012), a lower jaw (1020), and a knife member (1040). Anvil (1010) of this example is identical to anvils (60, 260) described above. Similarly, staple cartridge (1012) of this example is identical to staple cartridges (70, 270) described above. It should be understood that end effector (1000) may be readily incorporated into instrument (10) in place of end effector (40, 240).

As best seen in FIGS. 135-136, knife member (1040) of the present example is substantially identical to knife members (80, 280) described above, except for the differences described below. Knife member (1040) of this example includes a distal cutting edge (1042), a distal tip (1044), a downwardly extending protrusion (1046), and a firing beam engagement feature (1052). Protrusion (1046) includes a distally facing lockout surface (1048), which will be described in greater detail below. An upwardly extending tab (1050) is located at the proximal end of protrusion (1046). As best seen in FIGS. 138-139, firing beam engagement feature (1052) is configured to couple with a complementary engaging feature (1062) of a firing beam (1060). Such coupling may be secured using welding (e.g., spot welds, etc.), adhesives, and/or any other suitable techniques/features/etc. It should also be understood that the combination of firing beam (1060) and knife member (1040) may be translated distally and proximally using the same features and techniques described above with respect to firing beam (82, 282). Other suitable ways in which the combination of firing beam (1060) and knife member (1040) may be translated distally and proximally will be apparent to those of ordinary skill in the art in view of the teachings herein.

FIG. 137 shows lower jaw (1020) of the present example in greater detail. Lower jaw (1020) is substantially identical to lower jaws (50, 250) described above, except for the differences described below. Lower jaw (1020) is configured to removably receive staple cartridge (1012) as shown in FIGS. 138-139. Lower jaw (1020) is also pivotably coupled with anvil (1010), such that anvil (1010) is operable to pivot toward and away from the combination of staple cartridge (1012) and lower jaw (1020), as described in other examples above. Turning back to FIG. 137, lower jaw (1020) of this example includes a proximal slot (1022). The distal end of slot (1022) terminates at a proximally facing lockout surface (1024). As will be described in greater detail below, lockout surface (1048) of knife member (1040) is configured to engage lockout surface (1024) of lower jaw (1020) in order to provide a lockout condition when either staple cartridge (1012) has already been fired once or staple cartridge (1012) is missing.

FIG. 138 shows end effector (1000) in a ready to fire state. In particular, staple cartridge (1012) is loaded in lower jaw (1020), anvil (1010) is in a closed position, and knife member (1040) is in a proximal position. In this state, knife member (1040) is also in an upper position. Knife member (1040) is positioned such that a portion of knife member (1040) is disposed in an opening (1084) of a resilient member (1080). Resilient member (1080) of this example is identical to resilient member (210) described above. In this state, a distal end (1082) is positioned above protrusion (1046) and distal to tab (1050). Resilient member (1080) resiliently bears downwardly on knife member (1040) in this state. However, distal tip (1044) of knife member (1040) engages an upwardly facing surface at the proximal end of a sled (1014) in staple cartridge (1012). Sled (1014) thus cooperates with distal tip (1044) to provide support for knife member (1040), holding knife member (1040) in the upper position despite the downward bias imposed by resilient member (1080). It should be noted that lockout surface (1048) of knife member (1040) is located at a vertical position that is higher than the vertical position of lockout surface (1024) in this state. Sled (1014) of this example is substantially identical to sleds (78, 278) described above.

As firing beam (1060) and knife member (1040) are advanced distally from the position shown in FIG. 138 to actuate end effector (1000), driving staples from staple cartridge (1012) into tissue and severing the tissue with edge (1042), sled (1014) continues to cooperate with distal tip (1044) to provide support for knife member (1040). Knife member (1040) thus maintains the vertical positioning shown in FIG. 138 as knife member (1040) translates from a proximal position to a distal position. It should therefore be understood that lockout surface (1048) of knife member (1040) passes over lockout surface (1024) of lower jaw (1020), such that lockout surface (1048) does not engage lockout surface (1024) during the distal translation of knife member (1040) when sled (1014) provides support for knife member (1040). It should also be understood that, in the present example, sled (1014) will only provide support for knife member (1040) when cartridge (1012) has been properly loaded in lower jaw (1020) and cartridge (1012) has not yet been fired.

In the event that cartridge (1012) is not loaded in lower jaw (1020), lockout surface (1048) of knife member (1040) will engage lockout surface (1024) of lower jaw (1020), thereby effectively locking knife member (1040) by preventing further distal translation of knife member (1040). Similarly, in the event that an operator attempts to drive knife member (1040) distally after cartridge (1012) has been fired (or even partially fired), lockout surface (1048) of knife member (1040) will engage lockout surface (1024) of lower jaw (1020), thereby effectively locking knife member (1040) by preventing further distal translation of knife member (1040). For instance, FIG. 139 shows end effector (1000) in a state where sled (1014) is positioned distally in relation to the position of sled (1014) in FIG. 138. Sled (1014) is thus spaced away from distal tip (1044), such that sled (1014) will not provide support for knife member (1040). Without the support of sled (1014), resilient member (1080) drives knife member (1040) downwardly as knife member (1040) is advanced distally. This causes lockout surface (1048) of knife member (1040) to engage lockout surface (1024) of lower jaw (1020), as shown in FIG. 139. With surfaces (1048, 1024) so engaged, knife member (1040) may not be translated any further distally.

If the operator subsequently retracts knife member (1040) proximally from the position shown in FIG. 139, a camming feature in end effector (1000) may drive knife member (1040) upwardly, such that knife member (1040) and resilient member (1080) return to the positions shown in FIG. 138. This may enable the operator to load an unfired staple cartridge (1012) in end effector (1000) and actuate end effector (1000) properly.

It should be understood from the foregoing that the lockout features of lower jaw (1020) and knife member (1040) may serve as a substitute for the lockout features of frame member (238) and knife member (280) described above. It should also be understood that the various kinds of lockout bypass features described above with reference to FIGS. 26-64B may also be readily incorporated into or otherwise combined with end effector (1000). Various suitable ways in which end effector (1000) may be combined with other teachings herein will be apparent to those of ordinary skill in the art.

IX. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013 the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of preventing use of an incompatible staple cartridge with a surgical stapling instrument, wherein the surgical stapling instrument includes a body that supports a motor, a shaft assembly extending distally from the body, an end effector at a distal end of the shaft assembly, and a firing assembly having a translating member configured to translate through the end effector, wherein the end effector includes a jaw configured to receive a staple cartridge and an anvil pivotable relative to the jaw, wherein one of the jaw or the anvil includes an elongate slot, wherein the translating member includes a guide element slidably disposed within the elongate slot and a cutting element configured to cut tissue, wherein the translating member is configured to translate distally through a compatible staple cartridge to thereby drive staples into tissue and cut the tissue with the cutting element, the method comprising:
   (a) receiving an unspent staple cartridge within the jaw, wherein the unspent staple cartridge includes a plurality of staples;
   (b) in response to a first user input, pivoting the anvil toward the unspent staple cartridge to thereby clamp tissue therebetween;
   (c) in response to a second user input, activating the motor to urge the translating member distally toward the unspent staple cartridge; and
   (d) engaging a first blocking feature of the translating member with a second blocking feature of the unspent staple cartridge to thereby inhibit distal translation of the translating member through the unspent staple cartridge.

2. The method claim 1, wherein the unspent staple cartridge is incompatible with the surgical stapling instrument such that the unspent staple cartridge is received by the end effector but not fired.

3. The method of claim 1, wherein the first blocking feature comprises a distally facing surface, wherein the second blocking feature comprises a proximally facing surface configured to directly contact the distally facing surface.

4. The method of claim 1, wherein the first blocking feature extends laterally relative to a longitudinal axis of the translating member.

5. The method of claim 1, wherein the unspent staple cartridge includes a cartridge body having a longitudinal slot and a plurality of staples housed within openings spaced along opposed lateral sides of the longitudinal slot, wherein the second blocking feature is disposed at a proximal end of the longitudinal slot and is configured to inhibit entry of the translating member into the longitudinal slot.

6. The method of claim 5, wherein the second blocking feature is laterally offset from the longitudinal axis.

7. The method of claim 5, wherein the second blocking feature comprises a tab.

8. The method of claim 5, wherein the unspent staple cartridge further includes a cartridge tray that extends along an underside of the cartridge body, wherein the cartridge tray provides the second blocking feature.

9. The method of claim 1, wherein the translating member is configured to drive a sled having a plurality of cam features distally through a compatible staple cartridge to thereby drive staples into tissue.

10. The method of claim 9, wherein the first blocking feature of the translating member is configured to engage and drive a sled of a compatible staple cartridge distally through the compatible staple cartridge.

11. The method of claim 1, wherein the guide element is translatable from a proximal end of the elongate slot to a distal end of the elongate slot, wherein the guide element is proximal to the distal end of the elongate slot when the first blocking feature engages the second blocking feature.

12. The method of claim 1, wherein the jaw includes a first elongate slot and the anvil includes a second elongate slot, wherein a lower portion of the translating member is configured to translate through the first elongate slot and an upper portion of the translating member is configured to translate through the second elongate slot during translation of the translating member through the end effector, wherein at least one of the upper portion or the lower portion comprises the guide element.

13. The method of claim 12, wherein at least a portion of at least one of the first elongate slot or the second elongate slot is configured to provide visualization of a portion of the translating member.

14. The method of claim 1, wherein the unspent staple cartridge comprises a first staple cartridge, wherein the method further comprises:
   (a) receiving an unspent second staple cartridge within the jaw in place of the first staple cartridge;
   (b) pivoting the anvil toward the second staple cartridge to thereby clamp tissue therebetween; and
   (c) activating the motor to actuate the translating member distally through the second staple cartridge and thereby drive staples from the second staple cartridge into the tissue and cut the tissue with the cutting element.

15. The method of claim 14, wherein the surgical stapling instrument further comprises a lockout feature configured to inhibit distal translation of the translating member in the presence of a spent staple cartridge and in the absence of a staple cartridge, wherein the method further comprises after receiving the unspent second staple cartridge within the jaw, bypassing the lockout feature with the translating member to thereby drive staples from the unspent second staple cartridge into tissue.

16. A method of preventing use of an incompatible staple cartridge with a surgical stapling instrument, wherein the surgical stapling instrument includes a body that supports a motor, a shaft assembly extending distally from the body, an end effector at a distal end of the shaft assembly, and a firing assembly having a translating member configured to translate through the end effector, wherein the end effector includes a jaw configured to receive a staple cartridge and an anvil pivotable relative to the jaw, wherein the translating member includes a cutting element and is configured to translate distally through a compatible staple cartridge to thereby drive staples into tissue and cut the tissue with the cutting element, the method comprising:
   (a) receiving an unspent staple cartridge within the jaw, wherein the unspent staple cartridge includes a longitudinal slot and a plurality of staples;
   (b) in response to a first user input, pivoting the anvil toward the unspent staple cartridge to thereby clamp tissue therebetween;
   (c) in response to a second user input, activating the motor to urge the translating member distally toward a proximal end of the unspent staple cartridge; and
   (d) inhibiting entry of the translating member into the longitudinal slot with a blocking feature disposed at the proximal end of the unspent staple cartridge, wherein the blocking feature is laterally offset from the longitudinal slot.

17. The method of claim 16, wherein at least one of the jaw or the anvil includes an elongate slot, wherein a portion of the translating member is slidable within the elongate slot, wherein the elongate slot is configured to provide visibility of the portion of the translating member during use of the surgical stapling instrument.

18. The method of claim 16, wherein the blocking member comprises a pair of tabs disposed at the proximal end of the unspent staple cartridge on opposed lateral sides of the longitudinal slot.

19. A method of operating a surgical stapling instrument including a body that supports a motor, a shaft assembly extending distally from the body, an end effector at a distal end of the shaft assembly, and a firing assembly having a translating member configured to translate through the end effector, wherein the end effector includes a jaw configured to receive a staple cartridge and an anvil pivotable relative to the jaw, wherein the translating member includes a cutting element and is configured to translate distally through the staple cartridge to thereby drive staples into tissue and cut the tissue with the cutting element, the method comprising:
  (a) receiving an unspent first staple cartridge within the jaw;
  (b) pivoting the anvil toward the first staple cartridge to thereby clamp tissue therebetween;
  (c) activating the motor to urge the translating member distally toward the first staple cartridge;
  (d) engaging a first blocking feature of the firing assembly with a second blocking feature of the first staple cartridge to thereby inhibit distal translation of the translating member through the first staple cartridge;
  (e) receiving an unspent second staple cartridge within the jaw in place of the first staple cartridge, wherein the second blocking feature is omitted from the second staple cartridge;
  (f) pivoting the anvil toward the second staple cartridge to thereby clamp tissue therebetween; and
  (g) activating the motor to actuate the translating member distally through the second staple cartridge and thereby drive staples from the second staple cartridge into the tissue and cut the tissue with the cutting element.

20. The method of claim 19, wherein the surgical stapling instrument further comprises a lockout feature configured to inhibit distal translation of the translating member in the presence of a spent staple cartridge and in the absence of a staple cartridge, wherein the method further comprises:
  after receiving the unspent second staple cartridge within the jaw, bypassing the lockout feature with the translating member to thereby drive staples from the second staple cartridge into tissue in response to activation of the motor.

* * * * *